(12) United States Patent
Maeda et al.

(10) Patent No.: US 7,807,701 B2
(45) Date of Patent: *Oct. 5, 2010

(54) DIBENZYLAMINE COMPOUNDS AND PHARMACEUTICAL USE THEREOF

(75) Inventors: Kimiya Maeda, Takatsuki (JP);
Hironobu Nagamori, Takatsuki (JP);
Hiroshi Nakamura, Takatsuki (JP);
Hisashi Shinkai, Takatsuki (JP);
Yasunori Suzuki, Takatsuki (JP);
Daisuke Takahashi, Takatsuki (JP);
Toshio Taniguchi, Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/939,359

(22) Filed: Nov. 13, 2007

(65) Prior Publication Data

US 2008/0146620 A1     Jun. 19, 2008

Related U.S. Application Data

(63) Continuation of application No. 10/503,185, filed as application No. PCT/JP03/11041 on Aug. 29, 2003, now Pat. No. 7,332,514.

(30) Foreign Application Priority Data

Aug. 30, 2002  (JP) .............................. 2002-255604
Apr. 10, 2003  (JP) .............................. 2003-107161

(51) Int. Cl.
*A61K 31/41*   (2006.01)
*A61K 31/42*   (2006.01)
*C07D 257/04*  (2006.01)
*C07D 263/30*  (2006.01)

(52) U.S. Cl. ...................................... 514/381; 548/250
(58) Field of Classification Search .................. 514/381; 548/250

See application file for complete search history.

(56) References Cited

U.S. PATENT DOCUMENTS

| | | | |
|---|---|---|---|
| 3,576,830 A | 4/1971 | Fukumaru et al. | |
| 4,064,125 A | 12/1977 | Krapcho | |
| 4,122,255 A | 10/1978 | Krapcho | |
| 4,127,606 A | 11/1978 | Krapcho | |
| 4,151,354 A | 4/1979 | Krapcho | |
| 4,473,579 A | 9/1984 | Devries et al. | |
| 4,623,662 A | 11/1986 | De Vries | |
| 5,834,514 A | 11/1998 | Dolle et al. | |
| 6,218,426 B1 | 4/2001 | Anderson et al. | |
| 6,747,049 B2 | 6/2004 | Brodbeck et al. | |
| 7,332,514 B2 * | 2/2008 | Maeda et al. ............... 514/374 |
| 2004/0006141 A1 | 1/2004 | Yanagisawa et al. | |

FOREIGN PATENT DOCUMENTS

| JP | 45-2730 B | 1/1970 |
|---|---|---|
| JP | 45-2731 B | 1/1970 |
| JP | 45-2891 B | 1/1970 |
| JP | 45-2892 B | 1/1970 |
| JP | 45-11132 B | 4/1970 |
| JP | 2001-106666 A | 4/2001 |
| WO | WO 95/06626 A1 | 3/1995 |
| WO | WO 95/29672 A1 | 11/1995 |
| WO | WO 96/10559 A1 | 4/1996 |
| WO | WO 97/24328 A1 | 7/1997 |
| WO | WO 98/04528 A2 | 2/1998 |
| WO | WO 99/18066 A1 | 4/1999 |
| WO | WO 99/44987 A1 | 9/1999 |
| WO | WO 99/67204 A1 | 12/1999 |
| WO | WO 00/17164 A1 | 3/2000 |
| WO | WO 00/17166 A1 | 3/2000 |
| WO | WO 00/18721 A1 | 4/2000 |
| WO | WO 00/18723 A1 | 4/2000 |
| WO | WO 00/18724 A1 | 4/2000 |
| WO | WO 00/69810 A1 | 11/2000 |
| WO | WO 01/10825 A1 | 2/2001 |
| WO | WO 01/40190 A1 | 6/2001 |

OTHER PUBLICATIONS

Patani et al., Chem Rev, 1996, vol. 96 (8), especially p. 3147.*

(Continued)

*Primary Examiner*—Susannah Chung
(74) *Attorney, Agent, or Firm*—Leydig, Voit & Mayer, Ltd.

(57) ABSTRACT

A dibenzylamine compound represented by the formula (1)

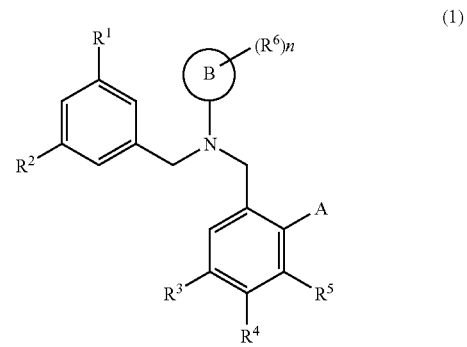

(1)

wherein $R^1$ and $R^2$ are each a $C_{1-6}$ allyl group optionally substituted by halogen atoms and the like; $R^3$, $R^4$ and $R^5$ are each a hydrogen atom, a halogen atom and the like, or $R^3$ and $R^4$ may form, together with carbon atoms bonded thereto, a homocyclic or heterocyclic ring optionally having substituent(s); A is $-N(R^7)(R^8)$ and the like; ring B is an aryl group or a heterocyclic residue; $R^6$ is a hydrogen atom, a halogen atom, a nitro group, a $C_{1-6}$ allyl group and the like; n is an integer of 1 to 3, a prodrug thereof and a pharmaceutically acceptable salt thereof show selective and potent CETP inhibitory activity, and therefore, they can be provided as therapeutic or prophylactic agents for hyperlipidemia or arteriosclerosis and the like.

43 Claims, No Drawings

OTHER PUBLICATIONS

Badimon et al., *Journal of Clinical Investigation*, 85: 1234-1241 (1990).
Connolly et al., *Biochemical and Biophysical Research Communications 223*: 42-47 (1996).
Drayna et al., *Nature*, 327: 632-634 (1987).
Herrera et al., *Nature Medicine*, 5(12): 1383-1389 (1999).
Nichols et al., *Journal of Lipid Research*, 6: 206-210, (1965).
*Therapeutic Bulletin*, 20: 1-3 (May 2003).

* cited by examiner

DIBENZYLAMINE COMPOUNDS AND PHARMACEUTICAL USE THEREOF

CROSS-REFERENCE TO RELATED APPLICATIONS

This patent application is a continuation of copending U.S. patent application Ser. No. 10/503,185, filed Oct. 12, 2004, which is the national phase of International Patent Application No. PCT/JP03/11041, filed Aug. 29, 2003, which claims priority to Japanese Patent Application Nos. 107161/2003, filed Apr. 10, 2003 and 255604/2002, filed Aug. 30, 2002, all of which are incorporated by reference.

TECHNICAL FIELD

The present invention relates to a novel CETP activity inhibitor, particularly a therapeutic agent or a prophylactic agent of arteriosclerosis or hyperlipidemia.

BACKGROUND ART

Regarding the relationship between arteriosclerotic diseases and serum lipoprotein, it has been considered for some time that a certain relationship exists from the results of many epidemiological researches. For example, Badimon et al. (J. Clin. Invest., 85, 1234-1241 (1990)) reported that intravenous injection of fractions containing HDL (high density lipoprotein) and VHDL (very high density lipoprotein) to cholesterol-loaded rabbits resulted in the observation of not only prevention of progression of arteriosclerotic lesion but also regression thereof, and HDL and VHDL are considered to have an anti-arteriosclerotic action in the relationship between arteriosclerotic diseases and serum lipoprotein.

In recent years, the presence of a protein that transfers lipid between blood lipoproteins, or CETP (cholesteryl ester transfer protein), has been clarified. The presence of CETP was first pointed out in 1965 by Nichols & Smith (J. Lipid Res., 6, 206, 1965), and thereafter its cDNA was cloned in 1987 by Drayna et al. The molecular weight thereof is 74,000 Da as glycoprotein and about 58,000 Da when sugar chain is completely cleaved. Its cDNA consists of 1656 residues and encodes 476 amino acids following 17 signal peptides. Since about 44% thereof consists of hydrophobic amino acids, it has extremely high hydrophobicity and is easily inactivated by oxidation. In addition, it has been confirmed that CETP is produced in the organs such as liver, spleen, adrenal gland, adipose tissue, small intestine, kidney, skeletal muscle, heart muscle and the like, and produced in cells of the cell types of human monocyte-derived macrophage, B lymphocyte, fat cell, small intestinal epithelial cell, CaCo2 cell, hepatocyte (exemplified by human liver cancer cell-derived cell line, HepG2 cells) and the like. Besides the above-mentioned tissues, it is present in cerebrospinal fluid and semen, and its presence has been confirmed in culture media of human neuroblastoma and neuroglioma cells, choroid plexus of sheep and the like.

It has been also clarified that CETP is involved in the metabolism of any lipoprotein in living organisms, and has a major role in the reverse cholesterol transfer system. Namely, CETP has drawn attention as a mechanism for preventing accumulation of cholesterol in peripheral cells and preventing arteriosclerosis. In fact, with regard to HDL having an important role in this reverse cholesterol transfer system, a number of epidemiological researches have shown that a decrease in CE (cholesteryl ester) of HDL in blood is one of the risk factors of coronary artery diseases. It has been also clarified that the CETP activity varies depending on the animal species, wherein arteriosclerosis due to cholesterol-loading is hardly induced in animals with lower activity, and in reverse, easily induced in animals with higher activity, and that hyper-HDL-emia and hypo-LDL (low density lipoprotein)-emia are induced in the case of CETP deficiency, thus rendering the development of arteriosclerosis difficult, which in turn led to the recognition of the significance of blood HDL, as well as significance of CETP that mediates transfer of CE in HDL into blood LDL.

Free cholesterol (FC) synthesized in and secreted from the liver is taken up by very low density lipoprotein (VLDL). Then, due to the action of lipoprotein lipase (LPL) and hepatic triglyceride lipase (HTGL), VLDL is metabolized in blood into LDL via intermediate density lipoprotein (IDL). LDL is taken up by peripheral cells via an LDL receptor and FC is supplied to the cells. Conversely from such flow from the liver to the peripheral cells, there exists a flow of cholesterol from peripheral cells toward the liver, which is called a reverse cholesterol transfer system. In other words, FC accumulated in the peripheral tissues is drawn by HDL, further esterified on HDL by the action of LCAT (lecithin-cholesterol acyltransferase) to form CE, and transferred to the hydrophobic core part of HDL, whereby HDL matures into spheric HDL particles. CE in HDL is transferred by CETP present in blood to apoB-containing lipoproteins such as VLDL, IDL, LDL and the like, and in return, TG is transferred to HDL at a molar ratio of 1:1. CE transferred to apoB-containing lipoprotein is taken up by the liver via LDL receptor in the liver, thereby indirectly transferring cholesterol to the liver. Moreover, there is a mechanism in which HDL takes up apoprotein E secreted from macrophage and the like to become apoprotein E-containing HDL rich in CE, and then is directly taken up by the liver via LDL receptor or remnant receptor. There also exists a path in which HDL particles are not taken up by the liver and only CE in HDL is selectively taken up by hepatocytes. Furthermore, another path exists in which HDL particles are taken up by hepatocytes via what is called an HDL receptor in the liver.

Namely, in the state of enhanced CETP activity, since CE transfer from HDL increases, CE in HDL decreases, and CE in VLDL, IDL and LDL increases. When take up of IDL and LDL by the liver increases, down-regulation is imposed on the LDL receptor, and LDL in blood increases. In contrast, in the CETP deficient state, HDL draws cholesterol from peripheral cells with the aid of LCAT, gradually increases its size and acquires apo E. Then, apo E-rich HDL is taken up by the liver via LDL receptor in the liver and catabolized. However, since this mechanism does not function sufficiently in human, large HDL dwells in the blood. Consequently, cholesterol pool in the liver becomes smaller and up-regulation is imposed on the LDL receptor, thereby decreasing LDL. Accordingly, selective inhibition of CETP can lower IDL, VLDL and LDL that promote arteriosclerosis and increase HDL that acts suppressively thereon, and produces expectation for the provision of an unprecedented prophylactic or therapeutic agent for arteriosclerosis or hyperlipidemia.

While many attempts have been made in recent years to develop a drug that inhibits such activity of CETP, a compound having a satisfactory activity has not been developed yet.

Meanwhile, many reports have been found recently on the compounds aiming at inhibiting such activity of CETP. For example, Biochemical and Biophysical Research Communications 223, 42-47 (1996) discloses dithiodipyridine derivatives, substituted dithiodibenzene derivatives and the like as compounds that inactivate CETP by modifying cysteine residue. However, this reference does not contain any description of the compound of the present invention, not to mention a description suggestive thereof.

In addition, WO95/06626 discloses Wiedendiol-A and Wiedendiol-B as CETP activity inhibitors. However, this publication does not contain any description suggesting the compound of the present invention.

Moreover, JP-B-45-11132, JP-B-45-2892, JP-B-45-2891, JP-B-45-2731 and JP-B-45-2730 disclose mercaptoanilides substituted by higher fatty acid such as o-isostearoylaminothiophenol and the like, as a compound having an action to prevent arteriosclerosis. However, these publications only mention the presence of an effect to prevent arteriosclerosis and lack description of Experimental Example that support the effect, much less a description of inhibition of CETP activity. Moreover, no description is found that suggests the compound of the present invention.

JP-T-2001-512416 (WO98/04528) discloses a biaryl compound that inhibits CETP. However, this publication has no description that suggests the compound of the present invention.

WO00/17164, WO00/17166 and WO01/40190 disclose 4-carboxyamino-2-substituted-1,2,3,4-tetrahydroquinoline as a CETP inhibitor. However, these publications contain no description that suggests the compound of the present invention.

On the other hand, various compounds having a structure like the compound of the present invention have been reported. For example, JP-A-2001-106666 and WO01/10825 disclose carbamate derivatives characterized in that phenyl group has an oxime ether group. However, the compounds of these publications are compounds useful as antimicrobial agents for agriculture or gardening, and they lack a disclosure of usefulness as a CETP activity inhibitor, or even a description suggestive thereof.

WO00/69810 discloses compounds such as 3-(4-{[N-[3-(2,6-dichlorophenyl)acryloyl]-N-(4-tert-butylbenzyl)amino]methyl}benzoylamino)propionic acid and the like. However, the compound of this publication is useful as a glucagon antagonist, and this publication lacks a disclosure of usefulness as a CETP activity inhibitor, or even a description suggestive thereof.

WO99/67204 discloses compounds such as 1-[N-(4-chlorobenzyl)-N—(N,N-dimethylcarbamoyl)aminomethyl]-4-guanidinomethylbenzene and the like. However, the compound of this publication is useful as an analgesic, and this publication lacks a disclosure of usefulness as a CETP activity inhibitor, or even a description suggestive thereof.

WO99/44987 and U.S. Pat. No. 6,218,426 disclose compounds such as N-(4-tert-butylbenzyl)-N-[4-(guanidinomethyl)benzyl]benzamide and the like useful as a gonadotropin-releasing hormone antagonist/agonist. However, this publication lacks a disclosure of usefulness as a CETP activity inhibitor, or even a description suggestive thereof.

U.S. Pat. No. 5,834,514 and JP-T-9-512556 (WO95/29672) disclose that halomethylamide compounds such as N-benzyl-N-(2,4-dichlorobenzyl)chloroacetamide and the like are useful as IL-1β protease activity inhibitors. However, these publications lack a disclosure of usefulness as a CETP activity inhibitor, or even a description suggestive thereof.

WO97/24328 discloses 2-amino-heterocyclic compounds such as N,N-bis(2,4-dimethoxybenzyl)-N'-(4-methoxyphenyl)urea and the like. However, the compound of this publication is useful as a leukotriene synthesis inhibitor and this publication lacks a disclosure of usefulness as a CETP activity inhibitor, or even a description suggestive thereof.

WO96/10559 discloses urea derivatives such as 1-benzyl-1-[3-(pyrazol-3-yl)benzyl]-3-(2,4,6-trimethylphenyl)urea and the like. However, the compound of this publication is useful as an acyl-CoA:cholesterol acyltransferase inhibitor and this publication lacks a disclosure of usefulness as a CETP activity inhibitor, or even a description suggestive thereof.

U.S. Pat. No. 4,623,662 discloses that urea compounds such as 1-benzyl-1-(2,4-dichlorobenzyl)-3-(2,4-dimethylphenyl)urea and the like are useful as acyl-CoA:cholesterol acyltransferase inhibitors. However, this publication lacks a disclosure of usefulness as a CETP activity inhibitor, or even a description suggestive thereof.

U.S. Pat. No. 4,473,579 discloses urea compounds such as 1,1-dibenzyl-3-(2,4-dimethylphenyl)-3-phenylurea and the like. However, the compound of this publication is useful as an acyl-CoA:cholesterol acyltransferase inhibitor and this publication lacks a disclosure of usefulness as a CETP activity inhibitor, or even a description suggestive thereof.

U.S. Pat. No. 4,122,255, U.S. Pat. No. 4,064,125, U.S. Pat. No. 4,151,354 and U.S. Pat. No. 4,127,606 disclose compounds such as N-[[2-[3-(dimethylamino)propoxy]phenyl]methyl]-3-phenyl-N-(phenylmethyl)-2-propenamide and the like. However, the compounds of these publications are useful as antiinflammatory agents and they lack a disclosure of usefulness as a CETP activity inhibitor, or even a description suggestive thereof.

WO99/18066 discloses amide carboxylic acid compounds such as ethyl 2-butyl-3-[4-[2-[N-benzyl-(4-pyridin-2-yl)amino]ethoxy]phenyl]propionate and the like having useful lipid-lowering action and the like. However, this publication lacks a disclosure of usefulness as a CETP activity inhibitor, or even a description suggestive thereof. Moreover, this publication lacks a disclosure of a structure such as the compound of the present invention, or even a description suggestive thereof.

In contrast, WO00/18724 discloses a compound having a structure similar to that of the present invention and a CETP inhibitory activity. To be specific, the following formula is disclosed.

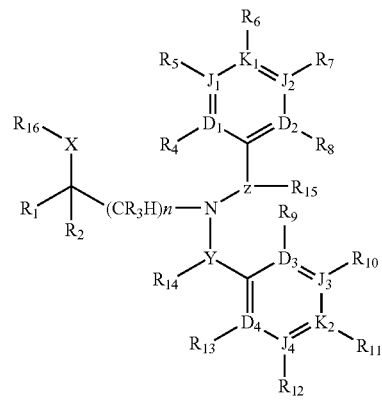

When $R_2$ and $R_3$ form a hetero ring or cycloalkenyl in combination, the compound is structurally similar to the present invention. However, this invention lacks a concrete disclosure (Example) of ring B as shown in the present invention. In addition, this invention is distinct from the present invention in that the invention always has $R_1$ (haloalkyl, haloalkenyl, haloalkoxyalkyl or haloalkenyloxyallyl).

In other words, this invention does not disclose a concrete structure as the compound of the present invention, not to mention a description suggestive thereof.

DISCLOSURE OF THE INVENTION

The present invention aims at providing a novel compound that selectively inhibits the activity of CETP. The present invention also aims at providing a compound useful as a prophylactic or therapeutic agent of arteriosclerosis or hyperlipidemia, which increases HDL cholesterol and simultaneously decreases LDL cholesterol and triglyceride by selectively inhibiting the activity of CETP, and which is free of a CYP inhibitory effect.

The present inventors have conducted intensive studies in an attempt to achieve the above-mentioned objects and found that the compounds shown in the following [1] to [13] have an effect to selectively inhibit the activity of CETP (hereinafter to be referred to as a CETP inhibitory effect), and are useful pharmaceutical agents, particularly, prophylactic or therapeutic agents of arteriosclerosis or hyperlipidemia. Moreover, they have found that a structure such as the formula (1) provides a potent CETP inhibitory effect, which resulted in the completion of the present invention. More particularly, the following [1] to [76] are provided.

[1] A dibenzylamine compound represented by the formula (1)

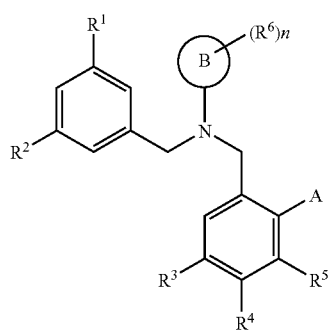

wherein $R^1$ and $R^2$
are the same or different and each is a halogen atom, a nitro group, a cyano group or a $C_{1-6}$ alkyl group optionally substituted by halogen atoms;

$R^3$, $R^4$ and $R^5$
are the same or different and each is a hydrogen atom, a halogen atom, a $C_{1-6}$ alkyl group optionally substituted by halogen atoms, a $C_{1-6}$ allylthio group optionally substituted by halogen atoms or a $C_{1-6}$ alkoxy group optionally substituted by halogen atoms, or $R^3$ and $R^4$ or $R^4$ and $R^5$ may form, together with carbon atoms bonded thereto, a homocyclic ring optionally having substituent(s) or a heterocyclic ring optionally having substituent(s);

A is —N($R^7$)($R^8$) (wherein $R^7$ and $R^8$ are the same or different and each is a hydrogen atom, a $C_{1-6}$ alkyl group (wherein $C_{1-6}$ allyl group is optionally substituted by phenyl group or —($CH_2$)$_m$—COOR$^9$ (wherein $R^9$ is a hydrogen atom or a $C_{1-6}$ allyl group and m is 0 or an integer of 1 to 5)) or a $C_{4-10}$ cycloalkylalkyl group (wherein $C_{4-10}$ cycloalkylalkyl group is optionally substituted by 1 to 3 substituents from halogen atom, nitro group, amino group, hydroxyl group, cyano group, acyl group, $C_{1-6}$ alkoxy group, $C_{1-6}$ alkyl group (wherein $C_{1-6}$ alkyl group is optionally substituted by hydroxyl group, $C_{1-6}$ alkoxy group or phosphono group), —($CH_2$)$_q$—CON($R^{20}$)($R^{21}$) (wherein $R^{20}$ and $R^{21}$ are the same or different and each is hydrogen atom or $C_{1-6}$ allyl group and q is 0 or an integer of 1 to 5) or —($CH_2$)$_r$—COOR$^{10}$ (wherein $R^{10}$ is hydrogen atom or $C_{1-6}$ alkyl group and r is 0 or an integer of 1 to 5))), —C($R^{11}$)($R^{12}$)($R^{13}$) (wherein $R^{11}$, $R^{12}$ and $R^{13}$ are the same or different and each is a hydrogen atom, a $C_{1-6}$ alkyl group (wherein $C_{1-6}$ alkyl group is optionally substituted by phenyl group or —COOR$^9$ (wherein $R^9$ is as defined above)) or a $C_{4-10}$ cycloalkylalkyl group (wherein $C_{4-10}$ cycloalkylalkyl group is optionally substituted by 1 to 3 substituents from halogen atom, nitro group, amino group, hydroxyl group, cyano group, acyl group, $C_{1-6}$ alkoxy group, $C_{1-6}$ allyl group (wherein $C_{1-6}$ alkyl group is optionally substituted by hydroxyl group, $C_{1-6}$ alkoxy group or phosphono group), —($CH_2$)$_q$—CON($R^{20}$)($R^{21}$) (wherein $R^{20}$, $R^{21}$ and q are as defined above) or —($CH_2$)$_r$—COOR$^{10}$ (wherein $R^{10}$ and r are as defined above))) or —O—C($R^{11}$)($R^{12}$)($R^{13}$) (wherein $R^{11}$, $R^{12}$ and $R^{13}$ are as defined above);

ring B is an aryl group or a heterocyclic residue;

$R^6$ is a hydrogen atom, a halogen atom, a nitro group, an amino group, a hydroxyl group, a cyano group, an acyl group, a $C_{1-6}$ alkoxy group, a $C_{2-6}$ alkenyl group or a $C_{1-6}$ alkyl group (wherein $C_{1-6}$ alkyl group is optionally substituted by hydroxyl group or —COOR$^{14}$ (wherein $R^{14}$ is a hydrogen atom or a $C_{1-6}$ alkyl group)); and n is an integer of 1 to 3 or a prodrug thereof or a pharmaceutically acceptable salt thereof.

[2] The dibenzylamine compound of the above-mentioned [1] wherein $R^3$, $R^4$ and $R^5$
are the same or different and each is a hydrogen atom, a halogen atom, a $C_{1-6}$ allyl group optionally substituted by halogen atoms or a $C_{1-6}$ alkoxy group optionally substituted by halogen atoms, or $R^3$ and $R^4$ or $R^4$ and $R^5$ may form, together with carbon atoms bonded thereto, a homocyclic ring optionally having substituent(s) or a heterocyclic ring optionally having substituent(s);

$R^7$ and $R^8$
are the same or different and each is a hydrogen atom, a $C_{1-6}$ allyl group (wherein $C_{1-6}$ alkyl group is optionally substituted by phenyl group or —COOR$^9$ (wherein $R^9$ is a hydrogen atom or a $C_{1-6}$ allyl group)) or a $C_{4-10}$ cycloalkylalkyl group (wherein $C_{4-10}$ cycloalkylalkyl group is optionally substituted by 1 to 3 substituents from halogen atom, nitro group, amino group, hydroxyl group, cyano group, acyl group, $C_{1-6}$ alkoxy group, $C_{1-6}$ alkyl group or —COOR$^{10}$ (wherein $R^{10}$ is a hydrogen atom or a $C_{1-6}$ allyl group));

$R^{11}$, $R^{12}$ and $R^{13}$
are the same or different and each is a hydrogen atom, a $C_{1-6}$ allyl group (wherein $C_{1-6}$ allyl group is optionally substituted by phenyl group or —COOR$^9$ (wherein $R^9$ is as defined above)) or a $C_{4-10}$ cycloalkylalkyl group (wherein $C_{4-10}$ cycloalkylalkyl group is optionally substituted by 1 to 3 substituents from halogen atom, nitro group, amino group, hydroxyl group, cyano group, acyl group, $C_{1-6}$ alkoxy group, $C_{1-6}$ allyl group or —COOR$^{10}$ (wherein R$^{10}$ is as defined above));

R$^6$ is a hydrogen atom, a halogen atom, a nitro group, an amino group, a hydroxyl group, a cyano group, an acyl group, a $C_{1-6}$ alkoxy group or a $C_{1-6}$ alkyl group (wherein $C_{1-6}$ alkyl group is optionally substituted by hydroxyl group or —COOR$^{14}$ (wherein R$^{14}$ is a hydrogen atom or a $C_{1-6}$ alkyl group)), or a prodrug thereof or a pharmaceutically acceptable salt thereof.

[3] The dibenzylamine compound of the above-mentioned [1] or [2], wherein R$^1$ is a $C_{1-6}$ alkyl group substituted by halogen atoms, or a prodrug thereof or a pharmaceutically acceptable salt thereof.

[4] The dibenzylamine compound of the above-mentioned [3], wherein R$^1$ is a trifluoromethyl group, or a prodrug thereof or a pharmaceutically acceptable salt thereof.

[5] The dibenzylamine compound of the above-mentioned [1], [3] or [4], wherein ring B and (R$^6$)$_n$ are each

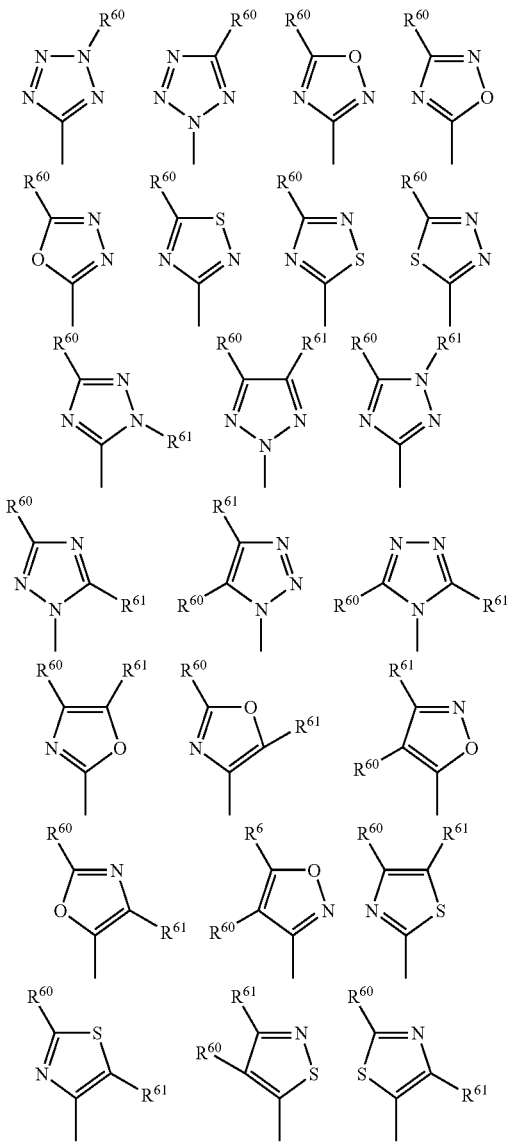

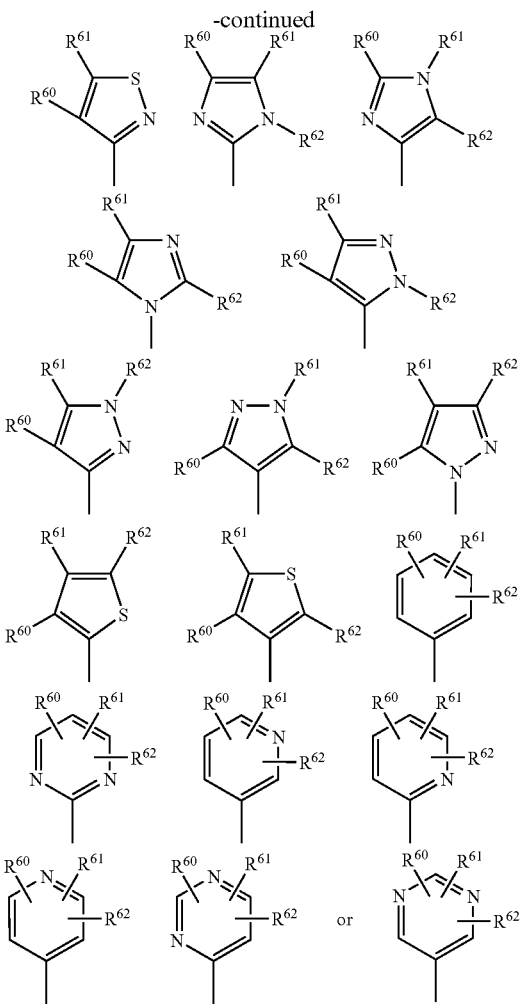

wherein R$^{60}$, R$^{61}$ and R$^{62}$ are the same or different and each is a hydrogen atom, a halogen atom, a nitro group, an amino group, a hydroxyl group, a cyano group, an acyl group, a $C_{1-6}$ alkoxy group, a $C_{2-6}$ alkenyl group or a $C_{1-6}$ allyl group (wherein $C_{1-6}$ alkyl group is optionally substituted by hydroxyl group or —COOR$^{14}$ (wherein R$^{14}$ is as defined above)) or a prodrug thereof or a pharmaceutically acceptable salt thereof.

[6] The dibenzylamine compound of the above-mentioned [5], wherein ring B and (R$^6$)$_n$ are each

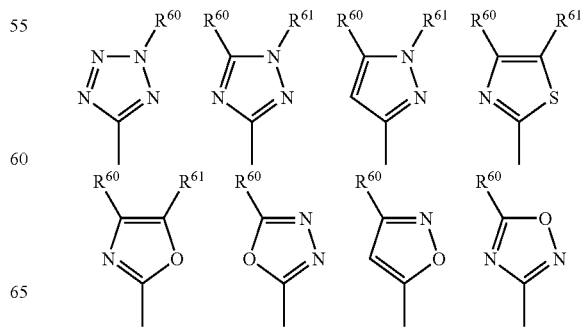

-continued

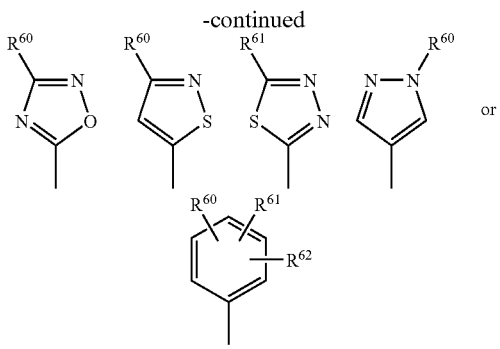

wherein R⁶⁰, R⁶¹ and R⁶² are as defined above or a prodrug thereof or a pharmaceutically acceptable salt thereof.

[7] The dibenzylamine compound of the above-mentioned [6], wherein ring B and $(R^6)_n$ are each

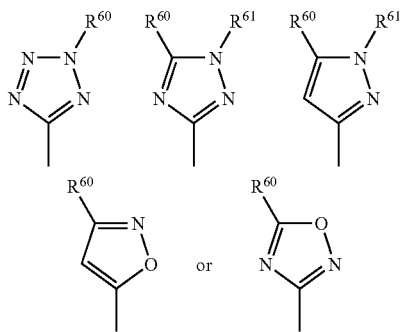

wherein R⁶⁰ and R⁶¹ are as defined above or a prodrug thereof or a pharmaceutically acceptable salt thereof.

[8] The dibenzylamine compound of any of the above-mentioned [1] and [3] to [7], wherein A is —N(R⁷)(R⁸) (wherein R⁷ and R⁸ are as defined in the above-mentioned [1]) or a prodrug thereof or a pharmaceutically acceptable salt thereof.

[9] The dibenzylamine compound of the above-mentioned [8], wherein R⁷ is a $C_{1-6}$ allyl group or a prodrug thereof or a pharmaceutically acceptable salt thereof.

[10] The dibenzylamine compound of the above-mentioned [9], wherein R⁶ is a $C_{1-6}$ allyl group or a prodrug thereof or a pharmaceutically acceptable salt thereof.

[11] The dibenzylamine compound of the above-mentioned [1], which is selected from the group consisting of N-[3-(N'-cyclopentylmethyl-N'-ethylamino)-5,6,7,8-tetrahydronaphthalen-2-ylmethyl]-N-[3,5-bis(trifluoromethyl)benzyl]-(2-methyl-2H-tetrazol-5-yl)amine, 3-{[N-[3-(N'-cyclopentylmethyl-N'-ethylamino)-5,6,7,8-tetrahydronaphthalen-2-ylmethyl]-N-(2-methyl-2H-tetrazol-5-yl)amino]methyl}-5-trifluoromethylbenzonitrile, N-[3,5-bis(trifluoromethyl)benzyl]-N-[6-(N'-cyclopentylmethyl-N'-ethylamino)indan-5-ylmethyl]-(2-methyl-2H-tetrzol-5-yl)amine, N-[3,5-bis(trifluoromethyl)benzyl]-N-[6-(N'-cyclopentylmethyl-N'-ethylamino)indan-5-ylmethyl]-(2-methyl-2H-tetrazol-5-yl)amine hydrochloride, N-[6-(N'-cyclopentylmethyl-N'-ethylamino)indan-5-ylmethyl]-N-(2H-tetrazol-5-yl)-[3,5-bis(trifluoromethyl)benzyl]amine, N-[6-(N'-cyclopentylmethyl-N'-ethylamino)indan-5-ylmethyl]-N-[3,5-bis(trifluoromethyl)benzyl]-(pyrimidin-2-yl)amine hydrochloride, N-[6-(N'-cyclopentylmethyl-N'-ethylamino)indan-5-ylmethyl]-N-[3,5-bis(trifluoromethyl)benzyl]-(5-methyl-1H-pyrazol-3-yl)amine, 5-{N-(6-{[N'-[3,5-bis(trifluoromethyl)benzyl]-N'-(5-methyl-[1,2,4]oxadiazol-3-yl)amino]methyl}indan-5-yl)-N-ethylamino}pentanoic acid hydrochloride, methyl trans-4-{[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]methyl}cyclohexanecarboxylate, 3-{[N-[6-(N'-cyclopentylmethyl-N'-ethylamino)indan-5-ylmethyl]-N-(2-methyl-2H-tetrazol-5-yl)amino]methyl}-5-trifluoromethylbenzonitrile, N-[3,5-bis(trifluoromethyl)benzyl]-N-[6-(N'-cyclopentylmethyl-N'-ethylamino)indan-5-ylmethyl]-(2-ethyl-2H-tetrazol-5-yl)amine, N-[3,5-bis(trifluoromethyl)benzyl]-N-[6-(N'-cyclopentylmethyl-N'-ethylamino)indan-5-ylmethyl]-(1-methyl-1H-[1,2,4]triazol-3-yl)amine, 3-({N-[6-(N'-cyclopentylmethyl-N'-ethylamino)indan-5-ylmethyl]-N-phenylamino}methyl)-5-trifluoromethylbenzonitrile, 3-{[N-[6-(N'-cyclopentylmethyl-N'-ethylamino)indan-5-ylmethyl]-N-(4,5-dimethyl-thiazol-2-yl)amino]methyl}-5-trifluoromethylbenzonitrile, N-[3,5-bis(trifluoromethyl)benzyl]-N-[6-(N'-cyclopentylmethyl-N'-ethylamino)indan-5-ylmethyl]-(thiazol-2-yl)amine hydrochloride, 3-({N-[6-(N'-cyclopentylmethyl-N'-ethylamino)indan-5-ylmethyl]-N-(thiazol-2-yl)amino}methyl)-5-trifluoromethylbenzonitrile hydrochloride, N-[3,5-bis(trifluoromethyl)benzyl]-N-[6-(N'-cyclopentylmethyl-N'-ethylamino)indan-5-ylmethyl]-(oxazol-2-yl)amine hydrochloride, N-[3,5-bis(trifluoromethyl)benzyl]-N-[6-(N'-cyclopentylmethyl-N'-ethylamino)indan-5-ylmethyl]-(5-methylthiazol-2-yl)amine hydrochloride, N-[3,5-bis(trifluoromethyl)benzyl]-N-[6-(N'-cyclopentylmethyl-N'-ethylamino)indan-5-ylmethyl]-(4-methylthiazol-2-yl)amine hydrochloride, N-[3,5-bis(trifluoromethyl)benzyl]-N-[6-(N'-cyclopentylmethyl-N'-ethylamino)indan-5-ylmethyl]-(4,5-dimethylthiazol-2-yl)amine hydrochloride, 3-{[N-[6-(N'-cyclopentylmethyl-N'-ethylamino)indan-5-ylmethyl]-N-(5-methylthiazol-2-yl)amino]methyl}-5-trifluoromethylbenzonitrile hydrochloride, 3-{[N-[6-(N'-cyclopentylmethyl-N'-ethylamino)indan-5-ylmethyl]-N-(4-methylthiazol-2-yl)amino]methyl}-5-trifluoromethylbenzonitrile hydrochloride, N-[3,5-bis(trifluoromethyl)benzyl]-N-[6-(N'-cyclopentylmethyl-N'-ethylamino)indan-5-ylmethyl]-(4-methyloxazol-2-yl)amine hydrochloride, N-[3,5-bis(trifluoromethyl)benzyl]-N-[6-(N'-cyclopentylmethyl-N'-ethylamino)indan-5-ylmethyl]-(3-methylisothiazol-5-yl)amine hydrochloride, N-[3,5-bis(trifluoromethyl)benzyl]-N-[6-(N'-cyclopentylmethyl-N'-ethylamino)indan-5-ylmethyl]-(5-methylisoxazol-3-yl)amine hydrochloride, N-[3,5-bis(trifluoromethyl)benzyl]-N-[6-(N'-cyclopentylmethyl-N'-ethylamino)indan-5-ylmethyl]-(3-methylisoxazol-5-yl)amine hydrochloride, N-[3,5-bis(trifluoromethyl)benzyl]-N-[6-(N'-cyclopentylmethyl-N'-ethylamino)indan-5-ylmethyl]-(1-methyl-1H-pyrazol-3-yl)amine hydrochloride, N-[3,5-bis(trifluoromethyl)benzyl]-N-[6-(N'-cyclopentylmethyl-N'-ethylamino)indan-5-ylmethyl]-(1-methyl-1H-pyrazol-4-yl)amine hydrochloride, N-[3,5-bis(trifluoromethyl)benzyl]-N-[6-(N'-cyclopentylmethyl-N'-ethylamino)indan-5-ylmethyl]-(5-methyl-[1,3,4] thiadiazol-2-yl)amine hydrochloride, N-[3,5-bis(trifluoromethyl)benzyl]-N-[6-(N'-cyclopentylmethyl-N'-ethylamino)indan-5-ylmethyl]-(5-methyl-[1,3,4] oxadiazol-2-yl)amine hydrochloride, N-[3,5-bis(trifluoromethyl)benzyl]-N-[6-(N'-cyclopentylmethyl-N'-ethylamino)indan-5-ylmethyl]-pyridin-3-ylamine hydrochloride, N-[3,5-bis(trifluoromethyl)benzyl]-N-[6-(N'-cyclopentylmethyl-N'-ethylamino)indan-5-ylmethyl]-pyridin-2-ylamine hydrochloride, N-[3,5-bis(trifluoromethyl)benzyl]-N-[2-(N'-cyclopentylmethyl-N'-ethylamino)-5-trifluoromethylbenzyl]-(2-methyl-2H-tetrazol-5-yl)amine hydrochloride, 3-{[N-[2-(N'-cyclopentylmethyl-N'-ethylamino)-5-trifluoromethylbenzyl]-N-(2-methyl-2H-tetrazol-5-yl)amino] methyl}-5-trifluoromethylbenzonitrile hydrochloride, methyl 5-[N-(6-{[N'-[3,5-bis(trifluoromethyl)benzyl]-N'-(2-methyl-2H-tetrazol-5-yl)amino]methyl}indan-5-yl)-N-ethylamino]pentanoate hydrochloride, methyl 5-[N-(6-{[N'-(3-cyano-5-trifluoromethylbenzyl)-N'-(2-methyl-2H-tetrazol-5-yl)amino]methyl}indan-5-ylmethyl)-N-ethylamino]pentanoate hydrochloride, methyl 5-[N-(6-{[N'-[3,5-bis(trifluoromethyl)benzyl]-N'-(1-methyl-1H-pyrazol-3-yl)amino]methyl}indan-5-yl)-N-ethylamino]pentanoate hydrochloride, 5-[N-(6-{[N'-[3,5-bis(trifluoromethyl)benzyl]-N'-(2-methyl-2H-tetrazol-5-yl)amino]methyl}indan-5-yl)-N-ethylamino]pentanoic acid hydrochloride, 5-[N-(6-{[N'-(3-cyano-5-trifluoromethylbenzyl)-N'-(2-methyl-2H-tetrazol-5-yl)amino]methyl} indan-5-yl)-N-ethylamino]pentanoic acid hydrochloride, 5-[N-(6-{[N'-[3,5-bis(trifluoromethyl)benzyl]-N'-(3-methylisoxazol-5-yl)amino]methyl}indan-5-yl)-N-ethylamino]pentanoic acid hydrochloride, 5-[N-(6-{[N'-[3,5-bis(trifluoromethyl)benzyl]-N'-(1-methyl-1H-pyrazol-3-yl)amino]methyl}indan-5-yl)-N-ethylamino]pentanoic acid hydrochloride, methyl trans-4-{[N-(3-{[N'-[3,5-bis(trifluoromethyl)benzyl]-N'-(1-methyl-1H-pyrazol-3-yl)amino]methyl}-5,6,7,8-tetrahydronaphthalen-2-yl)-N-ethylamino] methyl}cyclohexanecarboxylate hydrochloride, methyl trans-4-{[N-(3-{[N'-(3-cyano-5-trifluoromethylbenzyl)-N'-(1-methyl-1H-pyrazol-3-yl)amino]methyl}-5,6,7,8-tetrahydronaphthalen-2-yl)-N-ethylamino] methyl}cyclohexanecarboxylate hydrochloride, trans-4-{[N-(3-[{N'-[3,5-bis(trifluoromethyl)benzyl]-N'-(1-methyl-1H-pyrazol-3-yl)amino]methyl}-5,6,7,8-tetrahydronaphthalen-2-yl)-N-ethylamino] methyl}cyclohexanecarboxylic acid hydrochloride, trans-4-{[N-(3-{[N'-(3-cyano-5-trifluoromethylbenzyl)-N'-(1-methyl-1H-pyrazol-3-yl)amino]methyl}-5,6,7,8-tetrahydronaphthalen-2-yl)-N-ethylamino] methyl}cyclohexanecarboxylic acid hydrochloride, N-[3,5-bis(trifluoromethyl)benzyl]-N-[6-(N'-cyclopentylmethyl-N'-ethylamino)indan-5-ylmethyl]-(5-methyl-[1,2,4] oxadiazol-3-yl)amine hydrochloride, methyl trans-4-{[N-(6-{[N'-[3,5-bis(trifluoromethyl)benzyl]-N'-(1-methyl-1H-pyrazol-3-yl)amino]methyl}indan-5-yl)-N-ethylamino]methyl}cyclohexanecarboxylate hydrochloride, trans-4-{[N-(6-{[N'-[3,5-bis(trifluoromethyl)benzyl]-N'-(1-methyl-1H-pyrazol-3-yl)amino]methyl}indan-5-yl)-N-ethylamino]methyl}cyclohexanecarboxylic acid hydrochloride, methyl trans-4-{[N-(6-{[N'-(3-cyano-5-trifluoromethylbenzyl)-N'-(1-methyl-1H-pyrazol-3-yl)amino]methyl}indan-5-yl)-N-ethylamino]methyl}cyclohexanecarboxylate, trans-4-{[N-(6-{[N'-(3-cyano-5-trifluoromethylbenzyl)-N'-(1-methyl-1H-pyrazol-3-yl)amino]methyl} indan-5-yl)-N-ethylamino]methyl}cyclohexanecarboxylic acid hydrochloride, trans-4-{[N-(6-{[N'-[3,5-bis(trifluoromethyl)benzyl]-N'-(2-methyl-2H-tetrazol-5-yl)amino]methyl}indan-5-yl)-N-ethylamino]methyl}cyclohexanecarboxylic acid hydrochloride, trans-4-{[N-(6-{[N'-(3-cyano-5-trifluoromethylbenzyl)-N'-(2-methyl-2H-tetrazol-5-yl)amino]methyl} indan-5-yl)-N-ethylamino]methyl}cyclohexanecarboxylic acid hydrochloride, trans-4-[{N-(6-{[N'-[3,5-bis(trifluoromethyl)benzyl]-N'-(3-methylisoxazol-5-yl)amino]methyl}indan-5-yl)-N-ethylamino]methyl}cyclohexanecarboxylic acid hydrochloride, trans-4-{[N-(6-{[N'-(3-cyano-5-trifluoromethylbenzyl)-N'-(3-methylisoxazol-5-yl)amino]methyl} indan-5-yl)-N-ethylamino]methyl}cyclohexanecarboxylic acid hydrochloride, methyl 5-[N-(6-{[N'-(3-cyano-5-trifluoromethylbenzyl)-N'-(1-methyl-1H-pyrazol-3-yl)amino]methyl} indan-5-yl)-N-ethylamino]pentanoate hydrochloride, 5-[N-(6-{[N'-(3-cyano-5-trifluoromethylbenzyl)-N'-(3-methyl-isoxazol-5-yl)amino]methyl} indan-5-yl)-N-ethylamino]pentanoic acid hydrochloride, 5-[N-(6-{[N'-(3-cyano-5-trifluoromethylbenzyl)-N'-(1-methyl-1H-pyrazol-3-yl)amino]methyl}indan-5-yl)-N-ethylamino]pentanoic acid hydrochloride, 5-[N-(6-{[N'-[3,5-bis(trifluoromethyl)benzyl]-N'-(1-methyl-1H-[1,2,4]triazol-3-yl)amino]methyl}indan-5-yl)-N-ethylamino]pentanoic acid hydrochloride, trans-4-{[N-(6-{[N'-[3,5-bis(trifluoromethyl)benzyl]-N'-(1-methyl-1H-[1,2,4]triazol-3-yl)amino]methyl}indan-5-yl)-N-ethylamino]methyl}cyclohexanecarboxylic acid hydrochloride, trans-4-{[N-(6-{[N'-(3-cyano-5-trifluoromethylbenzyl)-N'-(1-methyl-1H-[1,2,4]triazol-3-yl)amino]methyl} indan-5-yl)-N-ethylamino]methyl}cyclohexanecarboxylic acid, N-[3,5-bis(trifluoromethyl)benzyl]-N-[6-(N'-cyclopentylmethyl-N'-ethylamino)indan-5-ylmethyl]-(3-methyl-[1,2,4] thiadiazol-5-yl)amine, 5-[N-(6-{[N'-(3-cyano-5-trifluoromethylbenzyl)-N'-(1-methyl-1H-[1,2,4]triazol-3-yl)amino]methyl} indan-5-yl)-N-ethylamino]pentanoic acid hydrochloride, methyl 5-[N-(3-{[N'-[3,5-bis(trifluoromethyl)benzyl]-N'-(1-methyl-1H-pyrazol-3-yl)amino]methyl}-5,6,7,8-tetrahydronaphthalen-2-yl)-N-ethylamino]pentanoate hydrochloride, methyl 5-[N-(3-{[N'-(3-cyano-5-trifluoromethylbenzyl)-N'-(1-methyl-1H-pyrazol-3-yl)amino]methyl}-5,6,7,8-tetrahydronaphthalen-2-yl)-N-ethylamino]pentanoate hydrochloride, 5-[N-(3-{[N'-[3,5-bis(trifluoromethyl)benzyl]-N'-(1-methyl-1H-pyrazol-3-yl)amino]methyl}-5,6,7,8-tetrahydronaphthalen-2-yl)-N-ethylamino]pentanoic acid hydrochloride, 5-[N-(3-{[N'-(3-cyano-5-trifluoromethylbenzyl)-N'-(1-methyl-1H-pyrazol-3-yl)amino]methyl}-5,6,7,8-tetrahydronaphthalen-2-yl)-N-ethylamino]pentanoic acid hydrochloride, trans-4-{[N-(3-{[N'-[3,5-bis(trifluoromethyl)benzyl]-N'-(2-methyl-2H-tetrazol-5-yl)amino]methyl}-5,6,7,8-tetrahydronaphthalen-2-yl)-N-ethylamino] methyl}cyclohexanecarboxylic acid hydrochloride, trans-4-{[N-(3-{[N'-(3-cyano-5-trifluoromethylbenzyl)-N'-(2-methyl-2H-tetrazol-5-yl)amino]methyl}-5,6,7,8-tetrahydronaphthalen-2-yl)-N-ethylamino] methyl}cyclohexanecarboxylic acid hydrochloride, trans-4-{[N-(3-{[N'-[3,5-bis(trifluoromethyl)benzyl]-N'-(1-methyl-1H-[1,2,4]triazol-3-yl)amino]methyl}-5,6,7,8-tetrahydronaphthalen-2-yl)-N-ethylamino] methyl}cyclohexanecarboxylic acid hydrochloride, trans-4-{[N-(3-{[N'-(3-cyano-5-trifluoromethylbenzyl)-N'-(1-methyl-1H-[1,2,4]triazol-3-yl)amino]methyl}-5,6,7,8-tetrahydronaphthalen-2-yl)-N-ethylamino] methyl}cyclohexanecarboxylic acid, trans-4-{[N-(3-{[N'-[3,5-bis(trifluoromethyl)benzyl]-N'-(3-methylisoxazol-5-yl)amino]methyl}-5,6,7,8-tetrahydronaphthalen-2-yl)-N-ethylamino] methyl}cyclohexanecarboxylic acid hydrochloride, trans-4-{[N-(3-{[N'-(3-cyano-5-trifluoromethylbenzyl)-N'-(3-methylisoxazol-5-yl)amino]methyl}-5,6,7,8-tetrahydronaphthalen-2-yl)-N-ethylamino] methyl}cyclohexanecarboxylic acid hydrochloride, 2-(5-{N-[3,5-bis(trifluoromethyl)benzyl]-N-[6-(N'-cyclopentylmethyl-N'-ethylamino)indan-5-ylmethyl] amino}tetrazol-2-yl)ethanol hydrochloride, methyl 5-[N-(3-{[N'-[3,5-bis(trifluoromethyl)benzyl]-N'-(1-methyl-1H-[1,2,4]triazol-3-yl)amino]methyl}-5,6,7,8-tetrahydronaphthalen-2-yl)-N-ethylamino]pentanoate hydrochloride, methyl 5-[N-(3-{[N'-(3-cyano-5-trifluoromethylbenzyl)-N'-(1-methyl-1H-[1,2,4]triazol-3-yl)amino]methyl}-5,6,7,8-tetrahydronaphthalen-2-yl)-N-ethylamino]pentanoate hydrochloride, 5-[N-(3-{[N'-[3,5-bis(trifluoromethyl)benzyl]-N'-(1-methyl-1H-[1,2,4]triazol-3-yl)amino]methyl}-5,6,7,8-tetrahydronaphthalen-2-yl)-N-ethylamino]pentanoic acid hydrochloride, 5-[N-(3-{[N'-(3-cyano-5-trifluoromethylbenzyl)-N'-(1-methyl-1H-[1,2,4]triazol-3-yl)amino]methyl}-5,6,7,8-tetrahydronaphthalen-2-yl)-N-ethylamino]pentanoic acid hydrochloride, 5-[N-(3-{[N'-[3,5-bis(trifluoromethyl)benzyl]-N'-(3-methylisoxazol-5-yl)amino]methyl}-5,6,7,8-tetrahydronaphthalen-2-yl)-N-ethylamino]pentanoic acid hydrochloride, 5-[N-(3-{[N'-(3-cyano-5-trifluoromethylbenzyl)-N'-(3-methylisoxazol-5-yl)amino]methyl}-5,6,7,8-tetrahydronaphthalen-2-yl)-N-ethylamino]pentanoic acid hydrochloride, 5-[N-(3-{[N'-[3,5-bis(trifluoromethyl)benzyl]-N'-(2-methyl-2H-tetrazol-5-yl)amino]methyl}-5,6,7,8-tetrahydronaphthalen-2-yl)-N-ethylamino]pentanoic acid hydrochloride, 5-[N-(3-{[N'-(3-cyano-5-trifluoromethylbenzyl)-N'-(2-methyl-2H-tetrazol-5-yl)amino]methyl}-5,6,7,8-tetrahydronaphthalen-2-yl)-N-ethylamino]pentanoic acid hydrochloride, trans-4-{[N-(6-{[N'-[3,5-bis(trifluoromethyl)benzyl]-N'-(5-methyl-[1,2,4]oxadiazol-3-yl)amino]methyl}indan-5-yl)-N-ethylamino]methyl}cyclohexanecarboxylic acid, 5-[N-(2-[{N'-[3,5-bis(trifluoromethyl)benzyl]-N'-(1-methyl-1H-pyrazol-3-yl)amino]methyl}-4-trifluoromethoxyphenyl)-N-ethylamino]pentanoic acid hydrochloride, 5-[N-(2-{[N'-[3,5-bis(trifluoromethyl)benzyl]-N'-(1-methyl-1H-pyrazol-3-yl)amino]methyl}-4-trifluoromethylphenyl)-N-ethylamino]pentanoic acid hydrochloride, 5-[N-(2-{[N'-(3-cyano-5-trifluoromethylbenzyl)-N'-(1-methyl-1H-pyrazol-3-yl)amino]methyl}-4-trifluoromethylphenyl)-N-ethylamino]pentanoic acid hydrochloride, 5-[N-(2-{[N'-[3,5-bis(trifluoromethyl)benzyl]-N'-(2-methyl-2H-tetrazol-5-yl)amino]methyl}-4-trifluoromethylphenyl)-N-ethylamino]pentanoic acid hydrochloride, 5-[N-(6-{[N'-[3,5-bis(trifluoromethyl)benzyl]-N'-(2-ethyl-2H-tetrazol-5-yl)amino]methyl}indan-5-yl)-N-ethylamino]pentanoic acid hydrochloride, 5-{N-[6-({N'-[3,5-bis(trifluoromethyl)benzyl]-N'-[2-(2-hydroxyethyl)-2H-tetrazol-5-yl]amino}methyl)indan-5-yl]-N-ethylamino}pentanoic acid hydrochloride, 5-[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]pentanoic acid hydrochloride, 5-[N-(6-{[N'-[3,5-bis(trifluoromethyl)benzyl]-N'-(2-methyl-2H-tetrazol-5-yl)amino]methyl}indan-5-yl)-N-ethylamino]-2,2-dimethylpentanoic acid hydrochloride, 6-[N-(6-[({N'-3,5-bis(trifluoromethyl)benzyl]-N'-(2-methyl-2H-tetrazol-5-yl)amino]methylindan-5-yl)-N-ethylamino]hexanoic acid hydrochloride, 5-[N-(6-{[N'-[3,5-bis(trifluoromethyl)benzyl]-N'-(2-methyl-2H-tetrazol-5-yl)amino]methyl}indan-5-yl)-N-ethylamino]-3,3-dimethylpentanoic acid hydrochloride, trans-4-{[N-(6-{[N'-[3,5-bis(trifluoromethyl)benzyl]-N'-(2-ethyl-2H-tetrazol-5-yl)amino]methyl} indan-5-yl)-N-ethylamino]methyl}cyclohexanecarboxylic acid hydrochloride, (1-{2-[N-(6-{[N'-[3,5-bis(trifluoromethyl)benzyl]-N'-(2-methyl-2H-tetrazol-5-yl)amino]methyl} indan-5-yl)-N-ethylamino]ethyl}cyclopentyl)acetic acid hydrochloride, trans-4-({N-[6-({N'-[3,5-bis(trifluoromethyl)benzyl]-N'-[2-(2-hydroxyethyl)-2H-tetrazol-5-yl]amino}methyl)indan-5-yl]-N-ethylamino}methyl)cyclohexanecarboxylic acid, trans-4-{[N-(2-{[N'-[3,5-bis(trifluoromethyl)benzyl]-N'-(2-methyl-2H-tetrazol-5-yl)amino]methyl}-4-trifluoromethylphenyl)-N-ethylamino]methyl}cyclohexanecarboxylic acid hydrochloride, (1-{2-[N-(3-{[N'-[3,5-bis(trifluoromethyl)benzyl]-N'-(2-methyl-2H-tetrazol-5-yl)amino]methyl}-5,6,7,8-tetrahydronaphthalen-2-yl)-N-ethylamino]ethyl}cyclopentyl)acetic acid, trans-4-{[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]methyl}cyclohexanecarboxylic acid hydrochloride, trans-4-[{N-(3-{[N'-[3,5-bis(trifluoromethyl)benzyl]-N'-(2-ethyl-2H-tetrazol-5-yl)amino]methyl}-5,6,7,8-tetrahydronaphthalen-2-yl)-N-ethylamino] methyl}cyclohexanecarboxylic acid hydrochloride, trans-4-({N-[3-({N'-[3,5-bis(trifluoromethyl)benzyl]-N'-[2-(2-hydroxyethyl)-2H-tetrazol-5-yl]amino}methyl)-5,6,7,8-tetrahydronaphthalen-2-yl]-N-ethylamino}methyl)cyclohexanecarboxylic acid hydrochloride, 1-{3-[N-(6-{[N'-[3,5-bis(trifluoromethyl)benzyl]-N'-(2-methyl-2H-tetrazol-5-yl)amino]methyl} indan-5-yl)-N-ethylamino]propyl}cyclohexanecarboxylic acid hydrochloride, 5-[N-(6-{[N'-[3,5-bis(trifluoromethyl)benzyl]-N'-(1-methyl-1H-pyrazol-3-yl)amino]methyl}indan-5-yl)-N-ethylamino]-3,3-dimethylpentanoic acid, 5-[N-(6-{[N'-[3,5-bis(trifluoromethyl)benzyl]-N'-(5-methyl-[1,2,4]oxadiazol-3-yl)amino]methyl}indan-5-yl)-N-ethylamino]-3,3-dimethylpentanoic acid hydrochloride, 5-[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]-3,3-dimethylpentanoic acid hydrochloride, 5-[N-(2-{[N'-[3,5-bis(trifluoromethyl)benzyl]-N'-(2-methyl-2H-tetrazol-5-yl)amino]methyl}-4-trifluoromethylphenyl)-N-ethylamino]-3,3-dimethylpentanoic acid hydrochloride, trans-4-{[N-(2-{[N'-[3,5-bis(trifluoromethyl)benzyl]-N'-(1-methyl-1H-pyrazol-3-yl)amino]methyl}-4-trifluoromethoxyphenyl)-N-ethylamino]methyl}cyclohexanecarboxylic acid hydrochloride, 5-[N-(2-{[N'-[3,5-bis(trifluoromethyl)benzyl]-N'-(1-methyl-1H-pyrazol-3-yl)amino]methyl}-4-trifluoromethoxyphenyl)-N-ethylamino]-3,3-dimethylpentanoic acid hydrochloride, 5-[N-(2-{[N'-[3,5-bis(trifluoromethyl)benzyl]-N'-(5-methyl-[1,2,4]oxadiazol-3-yl)amino]methyl}-4-trifluoromethoxyphenyl)-N-ethylamino]-3,3-dimethylpentanoic acid hydrochloride, trans-4-{[N-(2-{[N'-[3,5-bis(trifluoromethyl)benzyl]-N'-(5-methyl-[1,2,4]oxadiazol-3-yl)amino]methyl}-4-trifluoromethoxyphenyl)-N-ethylamino]methyl}cyclohexanecarboxylic acid hydrochloride, 6-[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]hexanoic acid hydrochloride, trans-(4-{[N-(6-{[N'-[3,5-bis(trifluoromethyl)benzyl]-N'-(2-methyl-2H-tetrazol-5-yl)amino]methyl} indan-5-yl)-N-ethylamino]methyl}cyclohexyl)acetic acid hydrochloride, 6-[N-(6-{[N'-[3,5-bis(trifluoromethyl)benzyl]-N'-(2-methyl-2H-tetrazol-5-yl)amino]methyl} indan-5-yl)-N-ethylamino]-4,4-dimethylhexanoic acid hydrochloride, 6-[N-(6-{[N'-[3,5-bis(trifluoromethyl)benzyl]-N'-(2-methyl-2H-tetrazol-5-yl)amino]methyl}indan-5-yl)-N-ethylamino]-3,3-dimethylhexanoic acid hydrochloride, 5-[N-(6-{[N'-[3,5-bis(trifluoromethyl)benzyl]-N'-(2-methyl-2H-tetrazol-5-yl)amino]methyl}indan-5-yl)-N-ethylamino]-4,4-dimethylpentanoic acid hydrochloride, trans-(4-{[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]methyl}cyclohexyl)acetic acid hydrochloride, 6-[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]-4,4-dimethylhexanoic acid hydrochloride, 6-[N-(2-{[N'-[3,5-bis(trifluoromethyl)benzyl]-N'-(2-methyl-2H-tetrazol-5-yl)amino]methyl}-4-trifluoromethylphenyl)-N-ethylamino]-4,4-dimethylhexanoic acid hydrochloride, trans-(4-{[N-(2-{[N'-[3,5-bis(trifluoromethyl)benzyl]-N'-(2-methyl-2H-tetrazol-5-yl)amino]methyl}-4-trifluoromethylphenyl)-N-ethylamino]methyl}cyclohexyl)acetic acid hydrochloride, trans-(4-{[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]methyl}cyclohexyl)methanol hydrochloride, 6-[N-(6-{[N'-[3,5-bis(trifluoromethyl)benzyl]-N'-(2-methyl-2H-tetrazol-5-yl)amino]methyl}indan-5-yl)-N-ethylamino]-5,5-dimethylhexanoic acid hydrochloride, trans-4-{[N-(2-{[N'-[3,5-bis(trifluoromethyl)benzyl]-N'-(2-methyl-2H-tetrazol-5-yl)amino]methyl}-4-trifluoromethoxyphenyl)-N-propylamino]methyl}cyclohexanecarboxylic acid hydrochloride, trans-4-{[N-(2-{[N'-[3,5-bis(trifluoromethyl)benzyl]-N'-(2-methyl-2H-tetrazol-5-yl)amino]methyl}-4-trifluoromethoxyphenyl)-N-isobutylamino]methyl}cyclohexanecarboxylic acid hydrochloride, trans-4-{[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]methyl}cyclohexanecarboxylic acid amide, trans-4-{[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]methyl}cyclohexanecarboxylic acid methylamide, trans-4-{[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]methyl}cyclohexanecarboxylic acid dimethylamide, trans-4-{[N-(2-{[N'-[3,5-bis(trifluoromethyl)benzyl]-N'-(4-chlorophenyl)amino]methyl}-4-trifluoromethoxyphenyl)-N-ethylamino]methyl}cyclohexanecarboxylic acid hydrochloride, trans-4-{[N-(2-{[N'-[3,5-bis(trifluoromethyl)benzyl]-N'-(p-tolyl)amino]methyl}-4-trifluoromethoxyphenyl)-N-ethylamino]methyl}cyclohexanecarboxylic acid hydrochloride, trans-4-{[N-(2-{[N'-[3,5-bis(trifluoromethyl)benzyl]-N'-(m-tolyl)amino]methyl}-4-trifluoromethoxyphenyl)-N-ethylamino]methyl}cyclohexanecarboxylic acid hydrochloride, trans-4-{[N-(2-{[N'-(3,5-dichlorobenzyl)-N'-(2-methyl-2H-tetrazol-5-yl)amino]methyl}-4-trifluoromethoxyphenyl)-N-ethylamino]methyl}cyclohexanecarboxylic acid hydrochloride, trans-4-{[N-ethyl-N-(2-{[N'-(2-methyl-2H-tetrazol-5-yl)-N'-(3-methyl-5-trifluoromethylbenzyl)amino]methyl}-4-trifluoromethoxyphenyl)amino]methyl}cyclohexanecarboxylic acid hydrochloride, trans-4-{[N-(2-{[N'-(3-chloro-5-trifluoromethylbenzyl)-N'-(2-methyl-2H-tetrazol-5-yl)amino]methyl}-4-trifluoromethoxyphenyl)-N-ethylamino]methyl}cyclohexanecarboxylic acid hydrochloride, trans-4-{[N-ethyl-N-(2-{[N'-(2-methyl-2H-tetrazol-5-yl)-N'-(3-nitro-5-trifluoromethylbenzyl)amino]methyl}-4-trifluoromethoxyphenyl)amino]methyl}cyclohexanecarboxylic acid hydrochloride, trans-(4-{[N-(6-{[N'-[3,5-bis(trifluoromethyl)benzyl]-N'-(2-methyl-2H-tetrazol-5-yl)amino]methyl}-2,2-difluorobenzo[1,3]dioxol-5-yl)-N-ethylamino]methyl}cyclohexyl)methanol hydrochloride, trans-(4-{[N-(6-{[N'-[3,5-bis(trifluoromethyl)benzyl]-N'-(2-methyl-2H-tetrazol-5-yl)amino]methyl}-2,2-difluorobenzo[1,3]dioxol-5-yl)-N-ethylamino]methyl}cyclohexyl)acetic acid hydrochloride, trans-3-(4-{[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]methyl}cyclohexyl)propionic acid hydrochloride, trans-(4-{[N-(7-{[N'-[3,5-bis(trifluoromethyl)benzyl]-N'-(2-methyl-2H-tetrazol-5-yl)amino]methyl}-2,2,3,3-tetrafluoro-2,3-dihydrobenzo[1,4]dioxin-6-yl)-N-ethylamino]methyl}cyclohexyl)methanol hydrochloride, trans-(4-{[N-(7-{[N'-[3,5-bis(trifluoromethyl)benzyl]-N'-(2-methyl-2H-tetrazol-5-yl)amino]methyl}-2,2,3,3-tetrafluoro-2,3-dihydrobenzo[1,4]dioxin-6-yl)-N-ethylamino]methyl}cyclohexyl)acetic acid hydrochloride, trans-2-(4-{[N-(7-[{N'-[3,5-bis(trifluoromethyl)benzyl]-N'-(2-methyl-2H-tetrazol-5-yl)amino]methyl}-2,2,3,3-tetrafluoro-2,3-dihydrobenzo[1,4]dioxin-6-yl)-N-ethylamino]methyl}cyclohexyl)acetamide hydrochloride, trans-N-[3,5-bis(trifluoromethyl)benzyl]-N-{2-[N'-ethyl-N'-(4-(methoxymethyl)cyclohexylmethyl)amino]-5-trifluoromethoxybenzyl}-(2-methyl-2H-tetrazol-5-yl)amine hydrochloride, trans-2-(4-{[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]methyl}cyclohexyl)ethanol hydrochloride, trans-(4-{[N-(2-{[N'-[3,5-bis(trifluoromethyl)benzyl]-N'-(2-methyl-2H-tetrazol-5-yl)amino]methyl}-4-methyl-5-trifluoromethylphenyl)-N-ethylamino]methyl}cyclohexyl)methanol hydrochloride, trans-(4-{[N-(2-{[N'-[3,5-bis(trifluoromethyl)benzyl]-N'-(2-methyl-2H-tetrazol-5-yl)amino]methyl}-5-methyl-4-trifluoromethylphenyl)-N-ethylamino]methyl}cyclohexyl)acetic acid hydrochloride, trans-(4-{[N-(2-{[N'-[3,5-bis(trifluoromethyl)benzyl]-N'-(2-methyl-2H-tetrazol-5-yl)amino]methyl}-4-methyl-5-trifluoromethylphenyl)-N-ethylamino]methyl}cyclohexyl)acetic acid hydrochloride, trans-(4-{[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]methyl}cyclohexylmethyl)phosphonic acid, trans-4-{[N-(2-{[N'-(3-bromo-5-trifluoromethylbenzyl)-N'-(2-methyl-2H-tetrazol-5-yl)amino]methyl}-4-trifluoromethoxyphenyl)-N-ethylamino]methyl}cyclohexanecarboxylic acid hydrochloride, trans-(4-{[N-(2-{[N'-[3,5-bis(trifluoromethyl)benzyl]-N'-(2-methyl-2H-tetrazol-5-yl)amino]methyl}-4-bromophenyl)-N-ethylamino]methyl}cyclohexyl)methanol hydrochloride, trans-(4-{[N-(2-{[N'-[3,5-bis(trifluoromethyl)benzyl]-N'-(2-methyl-2H-tetrazol-5-yl)amino]methyl}-4-bromophenyl)-N-ethylamino]methyl}cyclohexyl)acetic acid hydrochloride, trans-(4-{[N-(2-{[N'-[3,5-bis(trifluoromethyl)benzyl]-N'-(2-methyl-2H-tetrazol-5-yl)amino]methyl}-4-chloro-5-ethylphenyl)-N-ethylamino]methyl}cyclohexyl)methanol hydrochloride, trans-4-{[N-(2-{[N'-[3,5-bis(trifluoromethyl)benzyl]-N'-(4-methoxyphenyl)amino]methyl}-4-trifluoromethoxyphenyl)-N-ethylamino]methyl}cyclohexanecarboxylic acid hydrochloride, trans-(4-{[N-(2-{[N'-[3,5-bis(trifluoromethyl)benzyl]-N'-(2-methyl-2H-tetrazol-5-yl)amino]methyl}-5-methoxy-4-methylphenyl)-N-ethylamino]methyl}cyclohexyl)methanol hydrochloride, trans-(4-{[N-(2-{[N'-[3,5-bis(trifluoromethyl)benzyl]-N'-(2-methyl-2H-tetrazol-5-yl)amino]methyl}-4,5-dimethylphenyl)-N-ethylamino]methyl}cyclohexyl)acetic acid hydrochloride, trans-(4-{[N-(2-{[N'-[3,5-bis(trifluoromethyl)benzyl]-N'-(2-methyl-2H-tetrazol-5-yl)amino]methyl}-4-trifluoromethylthiophenyl)-N-ethylamino]methyl}cyclohexyl)acetic acid hydrochloride, trans-(4-{[N-(2-{[N'-[3,5-bis(trifluoromethyl)benzyl]-N'-(2-methyl-2H-tetrazol-5-yl)amino]methyl}-4-chloro-5-ethylphenyl)-N-ethylamino]methyl}cyclohexyl)acetic acid hydrochloride, trans-(4-{[N-(2-{[N'-[3,5-bis(trifluoromethyl)benzyl]-N'-(2-methyl-2H-tetrazol-5-yl)amino]methyl}-4-trifluoromethylphenyl)-N-propylamino]methyl}cyclohexyl)acetic acid hydrochloride, trans-(4-{[N-(2-{[N'-[3,5-bis(trifluoromethyl)benzyl]-N'-(2-methyl-2H-tetrazol-5-yl)amino]methyl}-5-methoxy-4-methylphenyl)-N-ethylamino]methyl}cyclohexyl)acetic acid hydrochloride, trans-4-({N-[2-{[N'-[3,5-bis(trifluoromethyl)benzyl]-N'-(2-methyl-2H-tetrazol-5-yl)amino]methyl}-4-(2,2,2-trifluoroethyl)phenyl]-N-ethylamino}methyl)cyclohexanecarboxylic acid hydrochloride, trans-(4-{[N-(2-{[N'-[3,5-bis(trifluoromethyl)benzyl]-N'-(2-methyl-2H-tetrazol-5-yl)amino]methyl}-5-methyl-4-trifluoromethylphenyl)-N-propylamino]methyl}cyclohexyl)acetic acid hydrochloride, trans-(4-{[N-(2-{[N'-[3,5-bis(trifluoromethyl)benzyl]-N'-(2-methyl-2H-tetrazol-5-yl)amino]methyl}-4-trifluoromethoxyphenyl)-N-propylamino]methyl}cyclohexyl)acetic acid hydrochloride, trans-4-{[N-(2-{[N'-[3,5-bis(trifluoromethyl)benzyl]-N'-(4-ethylphenyl)amino]methyl}-4-trifluoromethoxyphenyl)-N-ethylamino]methyl}cyclohexanecarboxylic acid hydrochloride, trans-4-{[N-(2-{[N'-(3-cyano-5-trifluoromethylbenzyl)-N'-(2-methyl-2H-tetrazol-5-yl)amino]methyl}-4-trifluoromethoxyphenyl)-N-ethylamino]methyl}cyclohexanecarboxylic acid hydrochloride, trans-4-{[N-(2-{[N'-[3,5-bis(trifluoromethyl)benzyl]-N'-(4-isopropenylphenyl)amino]methyl}-4-trifluoromethoxyphenyl)-N-ethylamino]methyl}cyclohexanecarboxylic acid, trans-(4-{[N-(2-{[N'-[3,5-bis(trifluoromethyl)benzyl]-N'-(p-tolyl)amino]methyl}-4-trifluoromethoxyphenyl)-N-ethylamino]methyl}cyclohexyl)acetic acid dihydrochloride, trans-(4-[{N-(2-{[N'-[3,5-bis(trifluoromethyl)benzyl]-N'-(5-methyl-[1,2,4]oxadiazol-3-yl)amino]methyl}-4-trifluoromethoxyphenyl)-N-ethylamino]methyl}cyclohexyl)acetic acid hydrochloride, trans-(4-{[N-(2-{[N'-[3,5-bis(trifluoromethyl)benzyl]-N'-(5-methyl-[1,2,4]oxadiazol-3-yl)amino]methyl}-5-methyl-4-trifluoromethylphenyl)-N-ethylamino]methyl}cyclohexyl)acetic acid hydrochloride, trans-(4-{[N-(2-{[N'-[3,5-bis(trifluoromethyl)benzyl]-N'-(5-methyl-[1,2,4]oxadiazol-3-yl)amino]methyl}-5-methyl-4-trifluoromethylphenyl)-N-propylamino]methyl}cyclohexyl)acetic acid hydrochloride, trans-(4-{[N-(2-{[N'-[3,5-bis(trifluoromethyl)benzyl]-N'-(2-methyl-2H-tetrazol-5-yl)amino]methyl}-5-methyl-4-trifluoromethylphenyl)-N-propylamino]methyl}cyclohexyl)acetic acid, trans-(4-{[N-(2-{[N'-[3,5-bis(trifluoromethyl)benzyl]-N'-(2-methyl-2H-tetrazol-5-yl)amino]methyl}-4-methyl-5-trifluoromethylphenyl)-N-ethylamino]methyl}cyclohexyl)acetic acid, trans-(4-{[N-(2-{[N'-[3,5-bis(trifluoromethyl)benzyl]-N'-(2-methyl-2H-tetrazol-5-yl)amino]methyl}-5-methyl-4-trifluoromethylphenyl)-N-ethylamino]methyl}cyclohexyl)acetic acid methanesulfonate, ethyl trans-(4-{[N-(2-[{N'-[3,5-bis(trifluoromethyl)benzyl]-N'-(2-methyl-2H-tetrazol-5-yl)amino]methyl}-5-methyl- 4-trifluoromethylphenyl)-N-ethylamino]
methyl}cyclohexyl)acetate and trans-(4-[{N-(2-{[N'-[3,5-bis(trifluoromethyl)benzyl]-N'-
(2-methyl-2H-tetrazol-5-yl)amino]methyl}-5-methyl-4-
trifluoromethylphenyl)-N-ethylamino]
methyl}cyclohexyl)acetic acid or a prodrug thereof or a pharmaceutically acceptable salt thereof.

[12] The dibenzylamine compound of the above-mentioned [1], which is selected from the group consisting of trans-(4-{[N-(2-{[N'-[3,5-bis(trifluoromethyl)benzyl]-N'-
(2-methyl-2H-tetrazol-5-yl)amino]methyl}-4-trifluo-
romethoxyphenyl)-N-ethylamino]methyl}cyclohexyl)
acetic acid hydrochloride, trans-(4-{[N-(2-{[N'-[3,5-bis(trifluoromethyl)benzyl]-N'-
(2-methyl-2H-tetrazol-5-yl)amino]methyl}-4-trifluorom-
ethylphenyl)-N-ethylamino]methyl}cyclohexyl)acetic
acid hydrochloride, trans-(4-{[N-(2-{[N'-[3,5-bis(trifluoromethyl)benzyl]-N'-
(2-methyl-2H-tetrazol-5-yl)amino]methyl}-5-methyl-4-
trifluoromethylphenyl)-N-ethylamino]
methyl}cyclohexyl)acetic acid hydrochloride, trans-(4-{[N-(2-{[N'-[3,5-bis(trifluoromethyl)benzyl]-N'-
(2-methyl-2H-tetrazol-5-yl)amino]methyl}-4-methyl-5-
trifluoromethylphenyl)-N-ethylamino]
methyl}cyclohexyl)acetic acid hydrochloride, trans-(4-{[N-(2-{[N'-[3,5-bis(trifluoromethyl)benzyl]-N'-
(2-methyl-2H-tetrazol-5-yl)amino]methyl}-4-trifluorom-
ethylphenyl)-N-propylamino]methyl}cyclohexyl)acetic
acid hydrochloride, trans-(4-{[N-(2-[{N'-[3,5-bis(trifluoromethyl)benzyl]-N'-
(2-methyl-2H-tetrazol-5-yl)amino]methyl}-5-methyl-4-
trifluoromethylphenyl)-N-propylamino]
methyl}cyclohexyl)acetic acid hydrochloride, trans-(4-{[N-(2-{[N'-[3,5-bis(trifluoromethyl)benzyl]-N'-
(2-methyl-2H-tetrazol-5-yl)amino]methyl}-4-trifluo-
romethoxyphenyl)-N-propylamino]methyl}cyclohexyl)
acetic acid hydrochloride, trans-(4-[{N-(2-{[N'-[3,5-bis(trifluoromethyl)benzyl]-N'-
(2-methyl-2H-tetrazol-5-yl)amino]methyl}-5-methyl-4-
trifluoromethylphenyl)-N-propylamino]
methyl}cyclohexyl)acetic acid, trans-(4-{[N-(2-{[N'-[3,5-bis(trifluoromethyl)benzyl]-N'-
(2-methyl-2H-tetrazol-5-yl)amino]methyl}-4-methyl-5-
trifluoromethylphenyl)-N-ethylamino]
methyl}cyclohexyl)acetic acid and trans-(4-{[N-(2-{[N'-[3,5-bis(trifluoromethyl)benzyl]-N'-
(2-methyl-2H-tetrazol-5-yl)amino]methyl}-5-methyl-4-
trifluoromethylphenyl)-N-ethylamino]
methyl}cyclohexyl)acetic acid methanesulfonate or a prodrug thereof or a pharmaceutically acceptable salt thereof.

[13] The dibenzylamine compound of the above-mentioned [2], which is selected from the group consisting of N-[3-(N'-cyclopentylmethyl-N'-ethylamino)-5,6,7,8-tet-
rahydronaphthalen-2-ylmethyl]-N-[3,5-bis(trifluorom-
ethyl)benzyl]-(2-methyl-2H-tetrazol-5-yl)amine, 3-{[N-[3-(N'-cyclopentylmethyl-N'-ethylamino)-5,6,7,8-tet-
rahydronaphthalen-2-ylmethyl]-N-(2-methyl-2H-tetra-
zol-5-yl)amino]methyl}-5-trifluoromethylbenzonitrile, N-[3,5-bis(trifluoromethyl)benzyl]-N-[6-(N'-cyclopentylm-
ethyl-N'-ethylamino)indan-5-ylmethyl]-(2-methyl-2H-
tetrazol-5-yl)amine, N-[3,5-bis(trifluoromethyl)benzyl]-N-[6-(N'-cyclopentylm-
ethyl-N'-ethylamino)indan-5-ylmethyl]-(2-methyl-2H-
tetrazol-5-yl)amine hydrochloride, N-[6-(N'-cyclopentylmethyl-N'-ethylamino)indan-5-ylm-
ethyl]-N-(2H-tetrazol-5-yl)-[3,5-bis(trifluoromethyl)ben-
zyl]amine, N-[6-(N'-cyclopentylmethyl-N'-ethylamino)indan-5-ylm-
ethyl]-N-[3,5-bis(trifluoromethyl)benzyl]-(pyrimidin-2-
yl)amine hydrochloride, N-[6-(N'-cyclopentylmethyl-N'-ethylamino)indan-5-ylm-
ethyl]-N-[3,5-bis(trifluoromethyl)benzyl]-(5-methyl-1H-
pyrazol-3-yl)amine, 3-{[N-[6-(N'-cyclopentylmethyl-N'-ethylamino)indan-5-yl-
methyl]-N-(2-methyl-2H-tetrazol-5-yl)amino]methyl}-5-
trifluoromethylbenzonitrile, N-[3,5-bis(trifluoromethyl)benzyl]-N-[6-(N'-cyclopentylm-
ethyl-N'-ethylamino)indan-5-ylmethyl]-(2-ethyl-2H-tet-
razol-5-yl)amine, N-[3,5-bis(trifluoromethyl)benzyl]-N-[6-(N'-cyclopentylm-
ethyl-N'-ethylamino)indan-5-ylmethyl]-(1-methyl-1H-[1,
2,4]triazol-3-yl)amine, 3-({N-[6-(N'-cyclopentylmethyl-N'-ethylamino)indan-5-yl-
methyl]-N-phenylamino}methyl)-5-trifluoromethylben-
zonitrile, 3-{[N-[6-(N'-cyclopentylmethyl-N'-ethylamino)indan-5-yl-
methyl]-N-(4,5-dimethyl-thiazol-2-yl)amino]methyl}-5-
trifluoromethylbenzonitrile, N-[3,5-bis(trifluoromethyl)benzyl]-N-[6-(N'-cyclopentylm-
ethyl-N'-ethylamino)indan-5-ylmethyl]-(thiazol-2-yl)
amine hydrochloride, 3-({N-[6-(N'-cyclopentylmethyl-N'-ethylamino)indan-5-yl-
methyl]-N-(thiazol-2-yl)amino}methyl)-5-trifluorometh-
ylbenzonitrile hydrochloride, N-[3,5-bis(trifluoromethyl)benzyl]-N-[6-(N'-cyclopentylm-
ethyl-N'-ethylamino)indan-5-ylmethyl]-(oxazol-2-yl)
amine hydrochloride, N-[3,5-bis(trifluoromethyl)benzyl]-N-[6-(N'-cyclopentylm-
ethyl-N'-ethylamino)indan-5-ylmethyl]-(5-methylthiazol-
2-yl)amine hydrochloride, N-[3,5-bis(trifluoromethyl)benzyl]-N-[6-(N'-cyclopentylm-
ethyl-N'-ethylamino)indan-5-ylmethyl]-(4-methylthiazol-
2-yl)amine hydrochloride, N-[3,5-bis(trifluoromethyl)benzyl]-N-[6-(N'-cyclopentylm-
ethyl-N'-ethylamino)indan-5-ylmethyl]-(4,5-dimethylthi-
azol-2-yl)amine hydrochloride, 3-{[N-[6-(N'-cyclopentylmethyl-N'-ethylamino)indan-5-yl-
methyl]-N-(5-methylthiazol-2-yl)amino]methyl}-5-trif-
luoromethylbenzonitrile hydrochloride, 3-{[N-[6-(N'-cyclopentylmethyl-N'-ethylamino)indan-5-yl-
methyl]-N-(4-methylthiazol-2-yl)amino]methyl}-5-trif-
luoromethylbenzonitrile hydrochloride, N-[3,5-bis(trifluoromethyl)benzyl]-N-[6-(N'-cyclopentylm-
ethyl-N'-ethylamino)indan-5-ylmethyl]-(4-methyloxazol-
2-yl)amine hydrochloride, N-[3,5-bis(trifluoromethyl)benzyl]-N-[6-(N'-cyclopentylm-
ethyl-N'-ethylamino)indan-5-ylmethyl]-(3-methylisothia-
zol-5-yl)amine hydrochloride, N-[3,5-bis(trifluoromethyl)benzyl]-N-[6-(N'-cyclopentylm-
ethyl-N'-ethylamino)indan-5-ylmethyl]-(5-methylisox-
azol-3-yl)amine hydrochloride, N-[3,5-bis(trifluoromethyl)benzyl]-N-[6-(N'-cyclopentylm-
ethyl-N'-ethylamino)indan-5-ylmethyl]-(3-methylisox-
azol-5-yl)amine hydrochloride, N-[3,5-bis(trifluoromethyl)benzyl]-N-[6-(N'-cyclopentylm-
ethyl-N'-ethylamino)indan-5-ylmethyl]-(1-methyl-1H-
pyrazol-3-yl)amine hydrochloride, N-[3,5-bis(trifluoromethyl)benzyl]-N-[6-(N'-cyclopentylmethyl-N'-ethylamino)indan-5-ylmethyl]-(1-methyl-1H-pyrazol-4-yl)amine hydrochloride, N-[3,5-bis(trifluoromethyl)benzyl]-N-[6-(N'-cyclopentylmethyl-N'-ethylamino)indan-5-ylmethyl]-(5-methyl-[1,3,4]thiadiazol-2-yl)amine hydrochloride, N-[3,5-bis(trifluoromethyl)benzyl]-N-[6-(N'-cyclopentylmethyl-N'-ethylamino)indan-5-ylmethyl]-(5-methyl-[1,3,4]oxadiazol-2-yl)amine hydrochloride, N-[3,5-bis(trifluoromethyl)benzyl]-N-[6-(N'-cyclopentylmethyl-N'-ethylamino)indan-5-ylmethyl]-pyridin-3-ylamine hydrochloride, N-[3,5-bis(trifluoromethyl)benzyl]-N-[6-(N'-cyclopentylmethyl-N'-ethylamino)indan-5-ylmethyl]-pyridin-2-ylamine hydrochloride, N-[3,5-bis(trifluoromethyl)benzyl]-N-[2-(N'-cyclopentylmethyl-N'-ethylamino)-5-trifluoromethylbenzyl]-(2-methyl-2H-tetrazol-5-yl)amine hydrochloride and 3-{[N-[2-(N'-cyclopentylmethyl-N'-ethylamino)-5-trifluoromethylbenzyl]-N-(2-methyl-2H-tetrazol-5-yl)amino]methyl}-5-trifluoromethylbenzonitrile hydrochloride or a prodrug thereof or a pharmaceutically acceptable salt thereof.

[14] A pharmaceutical composition comprising the dibenzylamine compound of any of the above-mentioned [1] to [1,3] or a prodrug thereof or a pharmaceutically acceptable salt thereof, and a pharmaceutically acceptable carrier.

[15] A CETP activity inhibitor comprising a dibenzylamine compound of any of the above-mentioned [1] to [13] or a prodrug thereof or a pharmaceutically acceptable salt thereof as an active ingredient.

[16] A therapeutic agent or a prophylactic agent for hyperlipidemia, which comprises a dibenzylamine compound of any of the above-mentioned [1] to [13] or a prodrug thereof or a pharmaceutically acceptable salt thereof as an active ingredient.

[17] A method for treating or preventing hyperlipidemia, which comprises administering a dibenzylamine compound of any of the above-mentioned [1] to [13] or a prodrug thereof or a pharmaceutically acceptable salt thereof to a mammal.

[18] Use of a dibenzylamine compound of any of the above-mentioned [1] to [13] or a prodrug thereof or a pharmaceutically acceptable salt thereof for the production of a therapeutic agent or a prophylactic agent for hyperlipidemia.

[19] A therapeutic agent or a prophylactic agent for arteriosclerosis, which comprises a dibenzylamine compound of any of the above-mentioned [1] to [13] or a prodrug thereof or a pharmaceutically acceptable salt thereof as an active ingredient.

[20] A method for treating or preventing arteriosclerosis, which comprises administering a dibenzylamine compound of any of the above-mentioned [1] to [13] or a prodrug thereof or a pharmaceutically acceptable salt thereof to a mammal.

[21] Use of a dibenzylamine compound of any of the above-mentioned [1] to [13] or a prodrug thereof or a pharmaceutically acceptable salt thereof for the production of a therapeutic agent or a prophylactic agent for arteriosclerosis.

[22] The pharmaceutical composition of the above-mentioned [14], which is used in combination with a different therapeutic agent for hyperlipidemia.

[23] The pharmaceutical composition of the above-mentioned [22], wherein the different therapeutic agent for hyperlipidemia is a statin pharmaceutical agent.

[24] The pharmaceutical composition of the above-mentioned [23], wherein the statin pharmaceutical agent is at least one pharmaceutical agent selected from the group consisting of lovastatin, simvastatin, pravastatin, fluvastatin, atorvastatin and cerivastatin.

[25] The pharmaceutical composition of the above-mentioned [14], which is used in combination with a different therapeutic agent for obesity.

[26] The pharmaceutical composition of the above-mentioned [25], wherein the different therapeutic agent for obesity is mazindol.

[27] The pharmaceutical composition of the above-mentioned [14], which is used in combination with a different therapeutic agent for diabetes.

[28] The pharmaceutical composition of the above-mentioned [27], wherein the different therapeutic agent for diabetes is at least one pharmaceutical agent selected from the group consisting of an insulin preparation, a sulfonylurea, an insulin secretagogue, a sulfonamide, a biguanide, an α glucosidase inhibitor and an insulin sensitizer.

[29] The pharmaceutical composition of the above-mentioned [28], wherein the different therapeutic agent for diabetes is at least one pharmaceutical agent selected from the group consisting of insulin, glibenclamide, tolbutamide, glyclopyramide, acetohexamide, glimepiride, tolazamide, gliclazide, nateglinide, glybuzole, metformin hydrochloride, buformin hydrochloride, voglibose, acarbose and pioglitazone hydrochloride.

[30] The pharmaceutical composition of the above-mentioned [14], which is used in combination with a different therapeutic agent for hypertension.

[31] The pharmaceutical composition of the above-mentioned [30], wherein the different therapeutic agent for hypertension is at least one pharmaceutical agent selected from the group consisting of a loop diuretic, an angiotensin converting enzyme inhibitor, an angiotensin II receptor antagonist, a Ca antagonist, a β blocker, an α,β blocker and an α blocker.

[32] The pharmaceutical composition of the above-mentioned [31], wherein the different therapeutic agent for hypertension is at least one pharmaceutical agent selected from the group consisting of a furosemide sustained-release preparation, captopril, a captopril sustained-release preparation, enalapril maleate, alacepril, delapril hydrochloride, cilazapril, lisinopril, benazepril hydrochloride, imidapril hydrochloride, temocapril hydrochloride, quinapril hydrochloride, trandrapril, perindopril erbumine, losartan potassium, candesartan cilexetil, nicardipine hydrochloride, a nicardipine hydrochloride sustained-release preparation, nilvadipine, nifedipine, a nifedipine sustained-release preparation, benidipine hydrochloride, diltiazem hydrochloride, a diltiazem hydrochloride sustained-release preparation, nisoldipine, nitrendipine, manidipine hydrochloride, barnidipine hydrochloride, efonidipine hydrochloride, amlodipine besylate, felodipine, cilnidipine, aranidipine, propranolol hydrochloride, a propranolol hydrochloride sustained-release preparation, pindolol, a pindolol sustained-release preparation, indenolol hydrochloride, carteolol hydrochloride, a carteolol hydrochloride sustained-release preparation, bunitrolol hydrochloride, a bunitrolol hydrochloride sustained-release preparation, atenolol, acebutolol hydrochloride, metoprolol tartrate, a metoprolol tartrate sustained-release preparation, nipradilol, penbutolol sulfate, tilisolol hydrochloride, carvedilol, bisoprolol fumarate, betaxolol hydrochloride, celiprolol hydrochloride, bopindolol malonate, bevantolol hydrochloride, labetalol hydrochloride, arotinolol hydrochloride, amosulalol hydrochloride, prazosin hydrochloride, terazosin hydrochloride, doxazosin mesylate, bunazosin hydrochloride, a bunazosin hydrochloride sustained-release preparation, urapidil and phentolamine mesylate.

[33] The therapeutic agent or a prophylactic agent of the above-mentioned [16], which aims at the treatment or prophylaxis of hyperlipidemia and which is used in combination with a different therapeutic agent for hyperlipidemia.

[34] The therapeutic agent or a prophylactic agent of the above-mentioned [33], wherein the different therapeutic agent for hyperlipidemia is a statin pharmaceutical agent.

[35] The therapeutic agent or a prophylactic agent of the above-mentioned [34], wherein the statin pharmaceutical agent is at least one pharmaceutical agent selected from the group consisting of lovastatin, simvastatin, pravastatin, fluvastatin, atorvastatin and cerivastatin.

[36] The therapeutic agent or a prophylactic agent of the above-mentioned [16], which aims at the treatment or prophylaxis of hyperlipidemia and which is used in combination with a different therapeutic agent for obesity.

[37] The therapeutic agent or a prophylactic agent of the above-mentioned [36], wherein the different therapeutic agent for obesity is mazindol.

[38] The therapeutic agent or a prophylactic agent of the above-mentioned [16], which aims at the treatment or prophylaxis of hyperlipidemia and which is used in combination with a different therapeutic agent for diabetes.

[39] The therapeutic agent or a prophylactic agent of the above-mentioned [38], wherein the different therapeutic agent for diabetes is at least one pharmaceutical agent selected from the group consisting of an insulin preparation, a sulfonylurea, an insulin secretagogue, a sulfonamide, a biguanide, an $\alpha$ glucosidase inhibitor and an insulin sensitizer.

[40] The therapeutic agent or a prophylactic agent of the above-mentioned [39], wherein the different therapeutic agent for diabetes is at least one pharmaceutical agent selected from the group consisting of insulin, glibenclamide, tolbutamide, glyclopyramide, acetohexamide, glimepiride, tolazamide, gliclazide, nateglinide, glybuzole, metformin hydrochloride, buformin hydrochloride, voglibose, acarbose and pioglitazone hydrochloride.

[41] The therapeutic agent or a prophylactic agent of the above-mentioned [16], which aims at the treatment or prophylaxis of hyperlipidemia and which is used in combination with a different therapeutic agent for hypertension.

[42] The therapeutic agent or a prophylactic agent of the above-mentioned [41], wherein the different therapeutic agent for hypertension is at least one pharmaceutical agent selected from the group consisting of a loop diuretic, an angiotensin converting enzyme inhibitor, an angiotensin II receptor antagonist, a Ca antagonist, a $\beta$ blocker, an $\alpha,\beta$ blocker and an $\alpha$ blocker.

[43] The therapeutic agent or a prophylactic agent of the above-mentioned [42], wherein the different therapeutic agent for hypertension is at least one pharmaceutical agent selected from the group consisting of a furosemide sustained-release preparation, captopril, a captopril sustained-release preparation, enalapril maleate, alacepril, delapril hydrochloride, cilazapril, lisinopril, benazepril hydrochloride, imidapril hydrochloride, temocapril hydrochloride, quinapril hydrochloride, trandrapril, perindopril erbumine, losartan potassium, candesartan cilexetil, nicardipine hydrochloride, a nicardipine hydrochloride sustained-release preparation, nilvadipine, nifedipine, a nifedipine sustained-release preparation, benidipine hydrochloride, diltiazem hydrochloride, a diltiazem hydrochloride sustained-release preparation, nisoldipine, nitrendipine, manidipine hydrochloride, barnidipine hydrochloride, efonidipine hydrochloride, amlodipine besylate, felodipine, cilnidipine, aranidipine, propranolol hydrochloride, a propranolol hydrochloride sustained-release preparation, pindolol, a pindolol sustained-release preparation, indenolol hydrochloride, carteolol hydrochloride, a carteolol hydrochloride sustained-release preparation, bunitrolol hydrochloride, a bunitrolol hydrochloride sustained-release preparation, atenolol, acebutolol hydrochloride, metoprolol tartrate, a metoprolol tartrate sustained-release preparation, nipradilol, penbutolol sulfate, tilisolol hydrochloride, carvedilol, bisoprolol fumarate, betaxolol hydrochloride, celiprolol hydrochloride, bopindolol malonate, bevantolol hydrochloride, labetalol hydrochloride, arotinolol hydrochloride, amosulalol hydrochloride, prazosin hydrochloride, terazosin hydrochloride, doxazosin mesylate, bunazosin hydrochloride, a bunazosin hydrochloride sustained-release preparation, urapidil and phentolamine mesylate.

[44] The method of the above-mentioned [17], which aims at the treatment or prophylaxis of hyperlipidemia and which is used in combination with a different therapeutic agent for hyperlipidemia.

[45] The method of the above-mentioned [44], wherein the different therapeutic agent for hyperlipidemia is a statin pharmaceutical agent.

[46] The method of the above-mentioned [45], wherein the statin pharmaceutical agent is at least one pharmaceutical agent selected from the group consisting of lovastatin, simvastatin, pravastatin, fluvastatin, atorvastatin and cerivastatin.

[47] The method of the above-mentioned [17], which aims at the treatment or prophylaxis of hyperlipidemia and which is used in combination with a different therapeutic agent for obesity.

[48] The method of the above-mentioned [47], wherein the different therapeutic agent for obesity is mazindol.

[49] The method of the above-mentioned [17], which aims at the treatment or prophylaxis of hyperlipidemia and which is used in combination with a different therapeutic agent for diabetes.

[50] The method of the above-mentioned [49], wherein the different therapeutic agent for diabetes is at least one pharmaceutical agent selected from the group consisting of an insulin preparation, a sulfonylurea, an insulin secretagogue, a sulfonamide, a biguanide, an $\alpha$ glucosidase inhibitor and an insulin sensitizer.

[51] The method of the above-mentioned [50], wherein the different therapeutic agent for diabetes is at least one pharmaceutical agent selected from the group consisting of insulin, glibenclamide, tolbutamide, glyclopyramide, acetohexamide, glimepiride, tolazamide, gliclazide, nateglinide, glybuzole, metformin hydrochloride, buformin hydrochloride, voglibose, acarbose and pioglitazone hydrochloride.

[52] The method of the above-mentioned [17], which aims at the treatment or prophylaxis of hyperlipidemia and which is used in combination with a different therapeutic agent for hypertension.

[53] The method of the above-mentioned [52], wherein the different therapeutic agent for hypertension is at least one pharmaceutical agent selected from the group consisting of a loop diuretic, an angiotensin converting enzyme inhibitor, an angiotensin II receptor antagonist, a Ca antagonist, a β blocker, an α,β blocker and an α blocker.

[54] The method of the above-mentioned [53], wherein the different therapeutic agent for hypertension is at least one pharmaceutical agent selected from the group consisting of a furosemide sustained-release preparation, captopril, a captopril sustained-release preparation, enalapril maleate, alacepril, delapril hydrochloride, cilazapril, lisinopril, benazepril hydrochloride, imidapril hydrochloride, temocapril hydrochloride, quinapril hydrochloride, trandrapril, perindopril erbumine, losartan potassium, candesartan cilexetil, nicardipine hydrochloride, a nicardipine hydrochloride sustained-release preparation, nilvadipine, nifedipine, a nifedipine sustained-release preparation, benidipine hydrochloride, diltiazem hydrochloride, a diltiazem hydrochloride sustained-release preparation, nisoldipine, nitrendipine, manidipine hydrochloride, barnidipine hydrochloride, efonidipine hydrochloride, amlodipine besylate, felodipine, cilnidipine, aranidipine, propranolol hydrochloride, a propranolol hydrochloride sustained-release preparation, pindolol, a pindolol sustained-release preparation, indenolol hydrochloride, carteolol hydrochloride, a carteolol hydrochloride sustained-release preparation, bunitrolol hydrochloride, a bunitrolol hydrochloride sustained-release preparation, atenolol, acebutolol hydrochloride, metoprolol tartrate, a metoprolol tartrate sustained-release preparation, nipradilol, penbutolol sulfate, tilisolol hydrochloride, carvedilol, bisoprolol fumarate, betaxolol hydrochloride, celiprolol hydrochloride, bopindolol malonate, bevantolol hydrochloride, labetalol hydrochloride, arotinolol hydrochloride, amosulalol hydrochloride, prazosin hydrochloride, terazosin hydrochloride, doxazosin mesylate, bunazosin hydrochloride, a bunazosin hydrochloride sustained-release preparation, urapidil and phentolamine mesylate.

[55] The therapeutic agent or a prophylactic agent of the above-mentioned [19], which aims at the treatment or prophylaxis of arteriosclerosis and which is used in combination with a different therapeutic agent for hyperlipidemia.

[56] The therapeutic agent or a prophylactic agent of the above-mentioned [55], wherein the different therapeutic agent for hyperlipidemia is a statin pharmaceutical agent.

[57] The therapeutic agent or a prophylactic agent of the above-mentioned [56], wherein the statin pharmaceutical agent is at least one pharmaceutical agent selected from the group consisting of lovastatin, simvastatin, pravastatin, fluvastatin, atorvastatin and cerivastatin.

[58] The therapeutic agent or a prophylactic agent of the above-mentioned [19], which aims at the treatment or prophylaxis of arteriosclerosis and which is used in combination with a different therapeutic agent for obesity.

[59] The therapeutic agent or a prophylactic agent of the above-mentioned [58], wherein the different therapeutic agent for obesity is mazindol.

[60] The therapeutic agent or a prophylactic agent of the above-mentioned [19], which aims at the treatment or prophylaxis of arteriosclerosis and which is used in combination with a different therapeutic agent for diabetes.

[61] The therapeutic agent or a prophylactic agent of the above-mentioned [60], wherein the different therapeutic agent for diabetes is at least one pharmaceutical agent selected from the group consisting of an insulin preparation, a sulfonylurea, an insulin secretagogue, a sulfonamide, a biguanide, an α glucosidase inhibitor and an insulin sensitizer.

[62] The therapeutic agent or a prophylactic agent of the above-mentioned [61], wherein the different therapeutic agent for diabetes is at least one pharmaceutical agent selected from the group consisting of insulin, glibenclamide, tolbutamide, glyclopyramide, acetohexamide, glimepiride, tolazamide, gliclazide, nateglinide, glybuzole, metformin hydrochloride, buformin hydrochloride, voglibose, acarbose and pioglitazone hydrochloride.

[63] The therapeutic agent or a prophylactic agent of the above-mentioned [19], which aims at the treatment or prophylaxis of arteriosclerosis and which is used in combination with a different therapeutic agent for hypertension.

[64] The therapeutic agent or a prophylactic agent of the above-mentioned [63], wherein the different therapeutic agent for hypertension is at least one pharmaceutical agent selected from the group consisting of a loop diuretic, an angiotensin converting enzyme inhibitor, an angiotensin II receptor antagonist, a Ca antagonist, a β blocker, an α,β blocker and an α blocker.

[65] The therapeutic agent or a prophylactic agent of the above-mentioned [64], wherein the different therapeutic agent for hypertension is at least one pharmaceutical agent selected from the group consisting of a furosemide sustained-release preparation, captopril, a captopril sustained-release preparation, enalapril maleate, alacepril, delapril hydrochloride, cilazapril, lisinopril, benazepril hydrochloride, imidapril hydrochloride, temocapril hydrochloride, quinapril hydrochloride, trandrapril, perindopril erbumine, losartan potassium, candesartan cilexetil, nicardipine hydrochloride, a nicardipine hydrochloride sustained-release preparation, nilvadipine, nifedipine, a nifedipine sustained-release preparation, benidipine hydrochloride, diltiazem hydrochloride, a diltiazem hydrochloride sustained-release preparation, nisoldipine, nitrendipine, manidipine hydrochloride, barnidipine hydrochloride, efonidipine hydrochloride, amnlodipine besylate, felodipine, cilnidipine, aranidipine, propranolol hydrochloride, a propranolol hydrochloride sustained-release preparation, pindolol, a pindolol sustained-release preparation, indenolol hydrochloride, carteolol hydrochloride, a carteolol hydrochloride sustained-release preparation, bunitrolol hydrochloride, a bunitrolol hydrochloride sustained-release preparation, atenolol, acebutolol hydrochloride, metoprolol tartrate, a metoprolol tartrate sustained-release preparation, nipradilol, penbutolol sulfate, tilisolol hydrochloride, carvedilol, bisoprolol fumarate, betaxolol hydrochloride, celiprolol hydrochloride, bopindolol malonate, bevantolol hydrochloride, labetalol hydrochloride, arotinolol hydrochloride, amosulalol hydrochloride, prazosin hydrochloride, terazosin hydrochloride, doxazosin mesylate, bunazosin hydrochloride, a bunazosin hydrochloride sustained-release preparation, urapidil and phentolamine mesylate.

[66] The method of the above-mentioned [20], which aims at the treatment or prophylaxis of arteriosclerosis and which is used in combination with a different therapeutic agent for hyperlipidemia.

[67] The method of the above-mentioned [66], wherein the different therapeutic agent for hyperlipidemia is a statin pharmaceutical agent.

[68] The method of the above-mentioned [67], wherein the statin pharmaceutical agent is at least one pharmaceutical agent selected from the group consisting of lovastatin, simvastatin, pravastatin, fluvastatin, atorvastatin and cerivastatin.

[69] The method of the above-mentioned [20], which aims at the treatment or prophylaxis of arteriosclerosis and which is used in combination with a different therapeutic agent for obesity.

[70] The method of the above-mentioned [69], wherein the different therapeutic agent for obesity is mazindol.

[71] The method of the above-mentioned [20], which aims at the treatment or prophylaxis of arteriosclerosis and which is used in combination with a different therapeutic agent for diabetes.

[72] The method of the above-mentioned [71], wherein the different therapeutic agent for diabetes is at least one pharmaceutical agent selected from the group consisting of an insulin preparation, a sulfonylurea, an insulin secretagogue, a sulfonamide, a biguanide, an α glucosidase inhibitor and an insulin sensitizer.

[73] The method of the above-mentioned [72], wherein the different therapeutic agent for diabetes is at least one pharmaceutical agent selected from the group consisting of insulin, glibenclamide, tolbutamide, glyclopyramide, acetohexamide, glimepiride, tolazamide, gliclazide, nateglinide, glybuzole, metformin hydrochloride, buformin hydrochloride, voglibose, acarbose and pioglitazone hydrochloride.

[74] The method of the above-mentioned [20], which aims at the treatment or prophylaxis of arteriosclerosis and which is used in combination with a different therapeutic agent for hypertension.

[75] The method of the above-mentioned [74], wherein the different therapeutic agent for hypertension is at least one pharmaceutical agent selected from the group consisting of a loop diuretic, an angiotensin converting enzyme inhibitor, an angiotensin II receptor antagonist, a Ca antagonist, a β blocker, an α,β blocker and an α blocker.

[76] The method of the above-mentioned [75], wherein the different therapeutic agent for hypertension is at least one pharmaceutical agent selected from the group consisting of a furosemide sustained-release preparation, captopril, a captopril sustained-release preparation, enalapril maleate, alacepril, delapril hydrochloride, cilazapril, lisinopril, benazepril hydrochloride, imidapril hydrochloride, temocapril hydrochloride, quinapril hydrochloride, trandrapril, perindopril erbumine, losartan potassium, candesartan cilexetil, nicardipine hydrochloride, a nicardipine hydrochloride sustained-release preparation, nilvadipine, nifedipine, a nifedipine sustained-release preparation, benidipine hydrochloride, diltiazem hydrochloride, a diltiazem hydrochloride sustained-release preparation, nisoldipine, nitrendipine, manidipine hydrochloride, barnidipine hydrochloride, efonidipine hydrochloride, amlodipine besylate, felodipine, cilnidipine, aranidipine, propranolol hydrochloride, a propranolol hydrochloride sustained-release preparation, pindolol, a pindolol sustained-release preparation, indenolol hydrochloride, carteolol hydrochloride, a carteolol hydrochloride sustained-release preparation, bunitrolol hydrochloride, a bunitrolol hydrochloride sustained-release preparation, atenolol, acebutolol hydrochloride, metoprolol tartrate, a metoprolol tartrate sustained-release preparation, nipradilol, penbutolol sulfate, tilisolol hydrochloride, carvedilol, bisoprolol fumarate, betaxolol hydrochloride, celiprolol hydrochloride, bopindolol malonate, bevantolol hydrochloride, labetalol hydrochloride, arotinolol hydrochloride, amosulalol hydrochloride, prazosin hydrochloride, terazosin hydrochloride, doxazosin mesylate, bunazosin hydrochloride, a bunazosin hydrochloride sustained-release preparation, urapidil and phentolamine mesylate.

DETAILED DESCRIPTION OF THE INVENTION

The definition of each substituent used in the present specification is as follows.

The "halogen atom" is a chlorine atom, a bromine atom, a fluorine atom and the like. For $R^1$, $R^2$, $R^3$, $R^4$, $R^5$, $R^6$, $R^{60}$, $R^{61}$ or $R^{62}$, it is preferably a chlorine atom or a fluorine atom, and a preferable halogen atom as a substituent for the $C_{4-10}$ cycloalkylalkyl group for $R^7$, $R^8$, $R^{11}$, $R^{12}$ or $R^{13}$ is chlorine atom or fluorine atom.

The "$C_{2-6}$ alkenyl group" is a straight chain or optionally branched alkenyl group having 2 to 6 carbon atoms, such as ethenyl group (vinyl group), 1-propenyl group, 2-propenyl group (allyl group), isopropenyl group, 1-butenyl group, 2-butenyl group, 3-butenyl group, 1-methyl-1-propenyl group, 1-methyl-2-propenyl group, 2-methyl-2-propenyl group, 1-ethylvinyl group, 1-pentenyl group, 2-pentenyl group, 3-pentenyl group, 4-pentenyl group, 1,2-dimethyl-1-propenyl group, 1,2-dimethyl-2-propenyl group, 1-ethyl-1-propenyl group, 1-ethyl-2-propenyl group, 1-methyl-1-butenyl group, 1-methyl-2-butenyl group, 2-methyl-1-butenyl group, 1-isopropylvinyl group, 2,4-pentadienyl group, 1-hexenyl group, 2-hexenyl group, 3-hexenyl group, 4-hexenyl group, 5-hexenyl group, 2,4-hexadienyl group, 1-methyl-1-pentenyl group and the like, preferably a straight chain or optionally branched alkenyl group having 2 to 4 carbon atoms. Particularly preferred are ethenyl group, isopropenyl group and 2-methyl-2-propenyl group.

The "$C_{1-6}$ alkyl group" is a straight chain or optionally branched alkyl group having 1 to 6 carbon atoms, such as methyl group, ethyl group, propyl group, isopropyl group, butyl group, isobutyl group, sec-butyl group, tert-butyl group, pentyl group, isopentyl group, neopentyl group, tert-pentyl group, hexyl group and the like, preferably a straight chain or optionally branched alkyl group having 1 to 4 carbon atoms. Particularly preferred are methyl group, ethyl group and isopropyl group. $R^{20}$ and $R^{21}$ are each preferably a methyl group. For $R^6$, $R^{60}$, $R^{61}$ or $R^{62}$, it is preferably a methyl group or an ethyl group, for $R^7$, $R^8$, $R^{11}$, $R^{12}$ or $R^{13}$, it is preferably an ethyl group, a propyl group or a butyl group, and for $R^9$ or $R^{10}$, it is preferably a methyl group or an ethyl group. A preferable $C_{1-6}$ allyl group as a substituent for the $C_{4-10}$ cycloalkylalkyl group for $R^7$, $R^8$, $R^{11}$, $R^{12}$ or $R^{13}$ is a methyl group or an ethyl group. For $R^{14}$, it is preferably a methyl group or an ethyl group.

The "$C_{1-6}$ alkyl group optionally substituted by halogen atoms" is the aforementioned $C_{1-6}$ alkyl group optionally substituted by the aforementioned halogen atoms, such as methyl group, ethyl group, propyl group, isopropyl group, butyl group, isobutyl group, sec-butyl group, tert-butyl group, pentyl group, isopentyl group, neopentyl group, tert-pentyl group, hexyl group, trifluoromethyl group, 1- or 2-chloroethyl group, 1- or 2-bromoethyl group, 1- or 2-fluoroethyl group, 1-, 2- or 3-chloropropyl group, 1-, 2- or 3-bromopropyl group, 1-, 2- or 3-fluoropropyl group, 1-, 2-, 3- or 4-chlorobutyl group, 1-, 2-, 3- or 4-bromobutyl group, 1-, 2-, 3- or 4-fluorobutyl group and the like, preferably methyl group, ethyl group or trifluoromethyl group. For $R^1, R^2, R^3, R^4$ or $R^5$, it is preferably a methyl group, an ethyl group or a trifluoromethyl group.

The "$C_{1-6}$ alkoxy group" means a straight chain or branched chain alkoxy group having 1 to 6 carbon atoms, such as methoxy group, ethoxy group, propoxy group, isopropoxy group, butoxy group, tert-butoxy group, pentyloxy group, tert-pentyloxy group and hexyloxy group. Preferred are methoxy group, ethoxy group, isopropoxy group, butoxy group and tert-butoxy group, which have 1 to 4 carbon atoms. Particularly preferred are methoxy group and ethoxy group. For $R^6, R^{60}, R^{61}$ or $R^{62}$, it is preferably a methoxy group, and a preferable $C_{1-6}$ alkoxy group as a substituent for the $C_{4-10}$ cycloalkylalkyl group for $R^7, R^8, R^{11}, R^{12}$ or $R^{13}$ is a methoxy group or an ethoxy group.

The "$C_{1-6}$ alkoxy group optionally substituted by halogen atoms" is the aforementioned $C_{1-6}$ alkoxy group optionally substituted by the aforementioned halogen atoms, such as methoxy group, ethoxy group, propoxy group, isopropoxy group, butoxy group, tert-butoxy group, pentyloxy group, tert-pentyloxy, hexyloxy group, trifluoromethoxy group, 1- or 2-chloroethoxy group, 1- or 2-bromoethoxy group, 1- or 2-fluoroethoxy group, 1-, 2- or 3-chloropropoxy group, 1-, 2- or 3-bromopropoxy group, 1-, 2- or 3-fluoropropoxy group, 1-, 2-, 3- or 4-chlorobutoxy group, 1-, 2-, 3- or 4-bromobutoxy group, 1-, 2-, 3- or 4-fluorobutoxy group and the like. Preferred are methoxy group, ethoxy group and trifluoromethoxy group. For $R^3, R^4$ or $R^5$, it is preferably a methoxy group, an ethoxy group or a trifluoromethoxy group.

The "$C_{1-6}$ allylthio group optionally substituted by halogen atoms" is one wherein the $C_{1-6}$ allylthio group is optionally substituted by the aforementioned halogen atoms, which is exemplified by methylthio group, ethylthio group, propylthio group, isopropylthio group, butylthio group, tert-butylthio group, pentylthio group, tert-pentylthio group, hexylthio group, trifluoromethylthio group, 1- or 2-chloroethylthio group, 1- or 2-bromoethylthio group, 1- or 2-fluoroethylthio group, 1-, 2- or 3-chloropropylthio group, 1-, 2- or 3-bromopropylthio group, 1-, 2- or 3-fluoropropylthio group, 1-, 2-, 3- or 4-chlorobutylthio group, 1-, 2-, 3- or 4-bromobutylthio group, 1-, 2-, 3- or 4-fluobutylthio group and the like, preferably methylthio group, ethylthio group or trifluoromethylthio group. For $R^3, R^4$ or $R^5$, it is preferably a methylthio group, an ethylthio group or a trifluoromethylthio group.

The "$C_{4-10}$ cycloalkylalkyl group" is a $C_{1-3}$ alkyl group substituted by $C_{3-7}$ cycloalkyl group. Here, the "$C_{3-7}$ cycloalkyl group" means a cycloalkyl group having 3 to 7 carbon atoms, which is exemplified by cyclopropyl group, cyclobutyl group, cyclopentyl group, cyclohexyl group and cycloheptyl group. Preferred is cycloalkyl group having 3 to 6 carbon atoms, which is specifically cyclopropyl group, cyclobutyl group, cyclopentyl group or cyclohexyl group. The "$C_{1-3}$ alkyl group" means a straight chain or optionally branched alkyl group having 1 to 3 carbon atoms, which is exemplified by methyl group, ethyl group, propyl group and isopropyl group. Preferred are methyl group, ethyl group and propyl group.

Concrete examples of the "$C_{4-10}$ cycloalkylalkyl group" include cyclopropylmethyl group, cyclobutylmethyl group, cyclopentylmethyl group, cyclohexylmethyl group, cycloheptylmethyl group, cyclopentylethyl group (1- or 2-(cyclopentyl)ethyl group), cyclohexylethyl group (1- or 2-(cyclohexyl)ethyl group), cyclopentylpropyl group (1-, 2- or 3-(cyclopentyl)propyl group) and cyclohexylpropyl group (1-, 2- or 3-(cyclohexyl)propyl group). Preferred is cycloalkylalkyl group preferably having 3 to 7 carbon atoms, which is specifically cyclopropylmethyl group, cyclobutylmethyl group, cyclopentylmethyl group or cyclohexylmethyl group. A preferable $C_{4-10}$ cycloalkylalkyl group for $R^7, R^8, R^{11}, R^{12}$ or $R^{13}$ is cyclopentylmethyl group, cyclohexylmethyl group or 2-(cyclopentyl)ethyl group.

The "acyl group" includes alkylcarbonyl groups such as acetyl group, propionyl group, butyryl group, pivaloyl group and the like; and arylcarbonyl groups such as benzoyl group, naphthoyl and the like. Preferred is acetyl group. For $R^6, R^{60}, R^{61}$ or $R^{62}$, it is preferably an acetyl group, a preferable acyl group as a substituent for the $C_{4-10}$ cycloalkylalkyl group for $R^7, R^8, R^{11}, R^{12}$ or $R^{13}$ is acetyl group.

The "aryl group" is a phenyl group, a naphthyl group, a biphenyl group and the like, with preference given to a phenyl group.

As the "heterocyclic residue", a 5- to 8-membered aromatic heterocyclic group containing, besides carbon atom, 1 to 4 heteroatoms selected from oxygen atom, sulfur atom, nitrogen atom and the like, a bicyclic or tricyclic heterocyclic group condensed therewith and the like can be mentioned. Examples thereof include pyrrolyl group (1-, 2- or 3-pyrrolyl group), furyl group (2- or 3-furyl group), thienyl group (2- or 3-thienyl group), imidazolyl group (1-, 2-, 4- or 5-imidazolyl group), oxazolyl group (2-, 4- or 5-oxazolyl group), thiazolyl group (2-, 4- or 5-thiazolyl group), pyrazolyl group (1-, 3-, 4- or 5-pyrazolyl group), isoxazolyl group (3-, 4- or 5-isoxazolyl group), isothiazolyl group (3-, 4- or 5-isothiazolyl group), oxadiazolyl group (1,2,4-oxadiazol-3 or 5-yl group, 1,3,4-oxadiazol-2-yl group, 1,2,5-oxadiazol-3-yl group), thiadiazolyl group (1,2,4-thiadiazol-3 or 5-yl group, 1,3,4-thiadiazol-2-yl group, 1,2,5-thiadiazol-3-yl group), triazolyl group (1,2,4-triazol-1,3,4 or 5-yl group, 1,2,3-triazol-1, 2 or 4-yl group), indolyl group (1-, 2-, 3-, 4-, 5-, 6- or 7-indolyl group), benzofuryl group (2-, 3-, 4-, 5-, 6- or 7-benzofuryl group), benzothienyl group (2-, 3-, 4-, 5-, 6- or 7-benzothienyl group), benzimidazolyl group (1-, 2-, 4-, 5-, 6- or 7-benzimidazolyl group), benzoxazolyl group (2-, 4-, 5-, 6- or 7-benzoxazolyl group), benzothiazolyl group (2-, 4-, 5-, 6- or 7-benzothiazolyl group), pyridyl group (2-, 3- or 4-pyridyl group), pyridine-1-oxide group (2-, 3- or 4-pyridine-1-oxide group), pyrimidinyl group (2-, 4- or 5-pyrimidinyl group), tetrazolyl group (1H-tetrazol-1 or 5-yl group, 2H-tetrazol-2 or 5-yl group), quinolyl group (2-, 3-, 4-, 5-, 6-, 7- or 8-quinolyl group), isoquinolyl group (1-, 3-, 4-, 5-, 6-, 7- or 8-isoquinolyl group) and the like.

As the "homocyclic ring", for example, an optionally condensed 3- to 7-membered carbon ring such as $C_{6-10}$ arene ($C_{6-10}$ aryl) (e.g., benzene (phenyl), naphthalene (naphthyl) and the like), $C_{3-7}$ cycloalkane (cycloalkyl) (e.g., cyclopropane (cyclopropyl), cyclobutane (cyclobutyl), cyclopentane (cyclopentyl), cyclohexane (cyclohexyl), cycloheptane (cycloheptyl) etc.), $C_{3-7}$ cycloalkene ($C_{3-7}$ cycloalkenyl group) (e.g., cyclopropene (cyclopronyl), cyclobutene (cyclobutenyl), cyclopentene (cyclopentenyl), cyclohexene (cyclohexenyl), cycloheptene (cycloheptenyl) etc.) and the like, and the like are used. The parenthesis following each name of the homocyclic ring shows a homocyclic group corresponding to the homocyclic ring.

As the substituent that the above-mentioned homocyclic ring may have, for example, (1) a $C_{1-6}$ allyl group optionally substituted by halogens (particularly, $C_{1-6}$ allyl group substituted by halogens is preferable), (2) a $C_{3-10}$ cycloalkyl group, (3) a $C_{2-10}$ alkenyl group, (4) a $C_{2-10}$ alkynyl group, (5) a $C_{6-10}$ aryl group, (6) a $C_{7-20}$ aralkyl group, (7) a nitro group, (8) a hydroxy group, (9) a mercapto group, (10) a oxo group, (11) a thioxo group, (12) a cyano group, (13) a carbamoyl group, (14) a carboxyl group, (15) a $C_{1-6}$ alkoxycarbonyl group (e.g., methoxycarbonyl group, ethoxycarbonyl group etc.), (16) a sulfo, (17) a halogen atom, (18) a $C_{1-6}$ alkoxy group, (19) a $C_{6-10}$ aryloxy group (e.g., phenoxy group etc.), (20) a $C_{1-6}$ acyloxy group (e.g., acetoxy, propionyloxy), (21) a $C_{1-6}$ alkylthio group (e.g., methylthio group, ethylthio group, n-propylthio group, isopropylthio group, n-butylthio group, tert-butylthio group etc.), (22) a $C_{6-10}$ arylthio group (e.g., phenylthio group etc.), (23) a $C_{1-6}$ alkylsulfinyl group (e.g., methylsulfinyl group, ethylsulfinyl group etc.), (24) a $C_{6-10}$ arylsulfinyl group (e.g., phenylsulfinyl group etc.), (25) a $C_{1-6}$ alkylsulfonyl group (e.g., methylsulfonyl group, ethylsulfonyl group etc.), (26) a $C_{6-10}$ arylsulfonyl group (e.g., phenylsulfonyl group etc.), (27) an amino group, (28) a $C_{1-6}$ acylamino group (e.g., acetylamino group, propionylamino group etc.), (29) a mono- or di-$C_{1-4}$ allylamino group (e.g., methylamino group, ethylamino group, n-propylamino group, isopropylamino group, n-butylamino group, dimethylamino group, diethylamino group etc.), (30) a $C_{3-8}$ cycloalkylamino group (e.g., cyclopropylamino group, cyclobutylamino group, cyclopentylamino group, cyclohexylamino group etc.), (31) a $C_{6-10}$ arylamino group (e.g., anilino etc.), (32) a $C_{1-6}$ alkanoyl group (e.g., formyl group, acetyl group, hexanoyl group etc.), (33) $C_{6-10}$ arylcarbonyl group (e.g., benzoyl group etc.), (34) a 5- or 6-membered heterocyclic group containing, besides carbon atom, 1 to 4 heteroatoms selected from oxygen, sulfur, nitrogen and the like (e.g., 2- or 3-thienyl group, 2- or 3-furyl group, 3-, 4- or 5-pyrazolyl group, 2-, 4- or 5-thiazolyl group, 3-, 4- or 5-isothiazolyl group, 2-, 4- or 5-oxazolyl group, 3-, 4- or 5-isoxazolyl group, 2-, 4- or 5-imidazolyl group, 1,2,3- or 1,2,4-triazolyl (1,2,4-triazol-1,3,4 or 5-yl group, 1,2,3-triazol-1, 2 or 4-yl group), 1H or 2H-tetrazolyl (1H-tetrazol-1 or 5-yl group, 2H-tetrazol-2 or 5-yl group), 2-, 3- or 4-pyridyl group, 2-, 4- or 5-pyrimidyl group, 3- or 4-pyridazinyl group, quinolyl group (2-, 3-, 4-, 5-, 6-, 7- or 8-quinolyl group), isoquinolyl group (1-, 3-, 4-, 5-, 6-, 7- or 8-isoquinolyl group), indolyl group (1-, 2-, 3-, 4-, 5-, 6- or 7-indolyl group) etc.) and the like can be mentioned. The number of substitution is 1 to 6, preferably 1 to 3, more preferably 1 or 2.

Preferable examples of the "homocyclic ring optionally having a substituent" formed by $R^3$ and $R^4$ or $R^4$ and $R^5$ together with carbon atoms bonded thereto are $C_{3-7}$ cycloalkane and benzene, and more preferable examples are cyclopentane and cyclohexane.

As the "heterocyclic ring", a 5- to 8-membered heterocyclic group containing, besides carbon atom, 1 to 4 heteroatoms selected from oxygen atom, sulfur atom, nitrogen atom and the like, and a bicyclic or tricyclic heterocyclic group condensed therewith and the like can be mentioned. Specific examples of the heterocyclic ring include (1) a 5-membered heterocyclic ring containing, besides carbon atom, 1 to 4 heteroatoms selected from oxygen atom, sulfur atom, nitrogen atom and the like, such as thiophene (thienyl group), furan (furyl group), pyrrole (pyrrolyl group), pyrroline (pyrrolinyl group), pyrrolidine (pyrrolidinyl group), 1,3-dioxole (1,3-dioxolyl group), oxazole (oxazolyl group), thiazole (thiazolyl group), pyrazole (pyrazolyl group), imidazole (imidazolyl group), imidazoline (imidazolinyl group), isoxazole (isoxazolyl group), isothiazole (isothiazolyl group), furazan (furazanyl group), 1,2,3-thiadiazole (1,2,3-thiadiazolyl group), 1,2,5-thiadiazole (1,2,5-thiadiazolyl group), 1,2, 3-triazole (1,2,3-triazolyl group), 1,2,3-triazolidine (triazolidinyl group) and the like, (2) a 6-membered heterocyclic ring containing, besides carbon atom, 1 to 4 heteroatoms selected from oxygen atom, sulfur atom, nitrogen atom and the like, such as pyridine (pyridyl group), pyrimidine (pyrimidinyl group), thiomorpholine (thiomorpholinyl group), morpholine (morpholinyl group), 1,2,3-triazine, 1,2,4-triazine (triazinyl group), piperidine (piperidinyl group), pyrane (pyranyl group), thiopyrane (thiopyranyl group), 1,4-oxazine (1,4-oxazinyl group), 1,4-dioxane (1,4-dioxanyl group), 1,4-thiazine (1,4-thiazinyl group), 1,3-thiazine (1,3-thiazinyl group), piperazine (piperazinyl group), oxotriazine (oxotriazinyl group), pyridazine (pyridazinyl group), pyrazine (pyrazinyl group) and the like can be mentioned. As the bicyclic or tricyclic condensed heterocyclic ring, a bicyclic or tricyclic condensed heterocyclic ring containing, besides carbon atom, 1 to 4 heteroatoms selected from oxygen atom, sulfur atom, nitrogen atom and the like, such as benzofuran (benzofuryl group), benzothiazole (benzothiazolyl group), benzoxazole (benzoxazolyl group), tetrazolo[1,5-b]pyridazine (tetrazolo[1,5-b]pyridazinyl group), triazolo[4,5-b]pyridazine (triazolo[4,5-b]pyridazinyl group), benzimidazole (benzimidazolyl group), quinoline (quinolyl group), isoquinoline (isoquinolyl group), cinnoline (cinnolinyl group), phthalazine (phthalazinyl group), quinazoline (quinazolinyl group), quinoxaline (quinoxalinyl group), indolizine (indolizinyl group), indole (indolyl group), quinolizine (quinolizinyl group), 1,8-naphthyridine (1,8-naphthyridinyl group), pteridine (pteridinyl group), dibenzofuran (dibenzofuranyl group), carbazole (carbazolyl group), acridine (acrydinyl group), phenanthridine (phenanthridinyl group), chromane (chromanyl group), benzoxazine (benzoxazinyl group), phenazine (phenazinyl group), phenothiazine (phenothiazinyl group), phenoxazine (phenoxazinyl group) and the like can be mentioned. The parenthesis following each name of the heterocyclic ring shows a heterocyclic group corresponding to the heterocyclic ring.

As the substituent that the above-mentioned heterocyclic ring may have, for example, (1) a $C_{1-6}$ allyl group, (2) a $C_{2-6}$ alkenyl group, (3) a $C_{2-6}$ alkynyl group, (4) a $C_{3-6}$ cycloalkyl group, (5) a cycloalkenyl group, (6) a $C_{7-11}$ aralkyl group, (7) a $C_{6-14}$ aryl group, (8) a $C_{1-6}$ alkoxy group, (9) a $C_{6-14}$ aryloxy group (e.g., phenoxy group etc.), (10) a $C_{1-6}$ alkanoyl group (e.g., formyl group, acetyl group, propionyl group, n-butyryl group, iso-butyryl group etc.), (11) a $C_{6-14}$ arylcarbonyl group (e.g., benzoyl group etc.), (12) a $C_{1-6}$ alkanoyloxy group (e.g., formyloxy group, acetyloxy group, propionyloxy group, n-butyryloxy group, iso-butyryloxy group etc.), (13) a $C_{6-14}$ arylcarbonyloxy group (e.g., benzoyloxy group etc.), (14) a carboxyl group, (15) a $C_{1-6}$ alkoxycarbonyl group (e.g., methoxycarbonyl group, ethoxycarbonyl group, n-propoxycarbonyl group, iso-propoxycarbonyl group, n-butoxycarbonyl group, isobutoxycarbonyl group, tert-butoxycarbonyl group etc.), (16) a carbamoyl group, (17) a N-mono-$C_{14}$ alkylcarbamoyl group (e.g., N-methylcarbamoyl group, N-ethylcarbamoyl group, N-propylcarbamoyl group, N-isopropylcarbamoyl group, N-butylcarbamoyl group etc.), (18) an N,N-di-$C_{1-4}$ alkylcarbamoyl group (e.g., N,N-dimethylcarbamoyl group, N,N-diethylcarbamoyl group, N,N-dipropylcarbamoyl group, N,N-dibutylcarbamoyl group etc.), (19) a cyclic aminocarbonyl group (e.g., 1-aziridinylcarbonyl group, 1-azetidinylcarbonyl group, 1-pyrrolizinylcarbonyl group, 1-piperidinylcarbonyl group, N-methylpiperazinylcarbonyl group, morpholinocarbonyl group etc.), (20) a halogen atom, (21) a $C_{1-6}$ alkyl group optionally substituted by halogen atoms (e.g., chloromethyl group, dichloromethyl group, trifluoromethyl group, trifluoroethyl group etc.), (22) an oxo group, (23) an amidino group, (24) an imino group, (25) an amino group, (26) a mono- or di-$C_{1-4}$ alkylamino group (e.g., methylamino group, ethylamino group, propylamino group, isopropylamino group, butylamino group, dimethylamino group, diethylamino group, dipropylamino group, diisopropylamino group, dibutylamino group etc.), (27) a 3- to 6-membered cyclic amino group optionally containing, besides carbon atom and one nitrogen atom, 1 to 3 heteroatoms selected from oxygen atom, sulfur atom, nitrogen atom and the like (e.g., aziridinyl group, azetidinyl group, pyrrolizinyl group, pyrrolinyl group, pyrrolyl group, imidazolyl group, pyrazolyl group, imidazolidinyl group, piperidino group, morpholino group, dihydropyridyl group, pyridyl group, N-methylpiperazinyl group, N-ethylpiperazinyl group etc.), (28) a $C_{1-6}$ alkanoylamino group (e.g., formamide group, acetamide group, trifluoroacetamide group, propionylamide group, butyrylamide group, isobutyrylamide group etc.), (29) a benzamide group, (30) a carbamoylamino group, (31) a N—$C_{1-4}$ alkylcarbamoylamino group (e.g., N-methylcarbamoylamino group, N-ethylcarbamoylamino group, N-propylcarbamoylamino group, N-isopropylcarbamoylamino group, N-butylcarbamoylamino group etc.), (32) a N,N-di-$C_{1-4}$ alkylcarbamoylamino group (e.g., N,N-dimethylcarbamoylamino group, N,N-diethylcarbamoylamino group, N,N-dipropylcarbamoylamino group, N,N-dibutylcarbamoylamino group etc.), (33) a $C_{1-3}$ alkylenedioxy group (e.g., methylenedioxy group, ethylenedioxy group etc.), (34) a —B(OH)$_2$, (35) a hydroxy group, (36) an epoxy group (—O—), (37) a nitro group, (38) a cyano group, (39) a mercapto group, (40) a sulfo group, (41) a sulfino group (42) a phosphono group, (43) a sulfamoyl group, (44) a $C_{1-6}$ alkylsulfamoyl group (e.g., N-methylsulfamoyl group, N-ethylsulfamoyl group, N-propylsulfamoyl group, N-isopropylsulfamoyl group, N-butylsulfamoyl group etc.), (45) a di-$C_{1-6}$ alkylsulfamoyl group (e.g., N,N-dimethylsulfamoyl group, N,N-diethylsulfamoyl group, N,N-dipropylsulfamoyl group, N,N-dibutylsulfamoyl group etc.), (46) a $C_{1-6}$ allylthio group (e.g., methylthio group, ethylthio group, propylthio group, isopropylthio group, n-butylthio group, sec-butylthio group, tert-butylthio group etc.), (47) a phenylthio group, (48) a $C_{1-6}$ alkylsulfinyl group (e.g., methylsulfinyl group, ethylsulfinyl group, propylsulfinyl group, butylsulfinyl group etc.), (49) a phenylsulfinyl group, (50) a $C_{1-6}$ alkylsulfonyl group (e.g., methylsulfonyl group, ethylsulfonyl group, propylsulfonyl group, butylsulfonyl group etc.), (51) a phenylsulfonyl group and the like can be mentioned. The number of substitution is 1 to 6, preferably 1 to 3, more preferably 1 or 2.

Preferable examples of the "heterocyclic ring optionally having a substituent" formed by $R^3$ and $R^4$ or $R^4$ and $R^5$ together with carbon atoms bonded thereto are thiophene, furan, pyrrole, pyrroline, oxazole, thiazole, pyrazole, imidazole, imidazoline, isoxazole, isothiazole, furazan, 1,2,3-thiadiazole, 1,2,5-thiadiazole, 1,2,3-triazole, 1,2,3-triazine, 1,2,4-triazine, 1,2,3-triazolidine, 2,2-difluoro-1,3-dioxole and 2,2,3,3-tetrafluoro-1,4-dioxane.

In the above-mentioned embodiments, the substituent of the "homocyclic ring optionally having substituents" and the substituent of the "heterocyclic ring optionally having substituents" are preferably selected from the group consisting of (1) $C_{1-6}$ alkyl group optionally substituted by halogen atoms, (2) nitro group, (3) hydroxy group, (4) mercapto group, (5) cyano group, (6) carbamoyl group, (7) carboxyl group, (8) $C_{1-6}$ alkoxycarbonyl group, (9) sulfo group, (10) halogen atom, (11) $C_{1-6}$ alkoxy group, (12) $C_{1-6}$ alkylthio group, (13) $C_{1-6}$ alkylsulfinyl group, (14) $C_{1-6}$ alkylsulfonyl group, (15) amino group, (16) mono- or di-$C_{1-4}$ allylamino group, (17) $C_{1-6}$ alkanoyl group and (18) $C_{1-6}$ alkanoyloxy group.

The "pharmaceutically acceptable salt" may be any as long as it forms a nontoxic salt with the aforementioned compound represented by the formula (1). Examples thereof include, but are not limited to, salts with various inorganic acids such as hydrochloride, hydrobromide, hydroiodide, sulfate, nitrate, phosphate, carbonate, hydrogen carbonate, perchlorate and the like; salts with organic acids such as formate, acetate, trifluoroacetate, propionate, oxalate, glycolate, succinate, lactate, maleate, hydroxymaleate, methylmaleate, fumarate, adipate, tartrate, malate, citrate, benzoate, cinnamate, ascorbate, salicylate, 2-acetoxybenzoate, nicotinate, isonicotinate and the like; sulfonates such as methanesulfonate, ethanesulfonate, isethionate, benzenesulfonate, p-toluenesulfonate, naphthalenesulfonate and the like; salts with acidic amino acid such as aspartate, glutamate and the like; alkali metal salts such as sodium salt, potassium salt and the like; alkaline earth metal salts such as magnesium salt, calcium salt and the like; ammonium salt; salts with organic base such as trimethylamine salt, triethylamine salt, pyridine salt, picoline salt, dicyclohexylamine salt, N,N'-dibenzylethylenediamine salt and the like; salts with amino acid such as lysin salt, arginine salt and the like; and the like. In some cases, the salt may be a water-containing product, hydrate or solvate with alcohol and the like.

In addition, the above-mentioned compound represented by the formula (1) may have various isomers. For example, E form and Z form are present as geometric isomers, and when an asymmetric carbon atom exists, enantiomer and diastereomer as stereoisomers based thereon exist, and a tautomer can exist. Accordingly, the present invention encompasses all of these isomers and mixtures thereof.

The compound of the present invention encompasses prodrug compounds and metabolites.

By the "prodrug compound" is meant a derivative of the compound of the present invention, which has a chemically or metabolically decomposable group and which, after administration to the body, restores to the original compound to show its inherent efficacy, including a complex and a salt free of covalent bond.

As the prodrug compound of the compound represented by the formula (1) of the present invention, a compound wherein the carboxyl group of the compound represented by the formula (1) is modified by ethyl group, pivaloyloxymethyl group, 1-(acetyloxy)ethyl group, 1-(ethoxycarbonyloxy) ethyl group, 1-(cyclohexyloxycarbonyloxy)ethyl group, carboxylmethyl group, (5-methyl-2-oxo-1,3-dioxol-4-yl)methyl group, phenyl group, o-tolyl group and the like; a compound wherein the hydroxyl group of the compound represented by the formula (1) is modified by acetyl group, propionyl group, isobutyryl group, pivaloyl group, benzoyl group, 4-methylbenzoyl group, dimethylcarbamoyl group or sulfo group; a compound wherein the amino group of the compound represented by the formula (1) is modified by hexylcarbamoyl group, 3-methylthio-1-(acetylamino)propylcarbonyl group, 1-sulfo-1-(3-ethoxy-4-hydroxyphenyl)methyl group, (5-methyl-2-oxo-1,3-dioxol-4-yl)methyl group and the like, and the like can be mentioned.

BEST MODE FOR EMBODYING THE INVENTION

Now, various substituents and substitution sites are described in more detail in the following.

$R^1$ is preferably a $C_{1-6}$ allyl group optionally substituted by halogen atoms, more preferably a trifluoromethyl group.

$R^2$ is preferably a halogen atom, a $C_{1-6}$ alkyl group optionally substituted by halogen atoms or a cyano group, more preferably a trifluoromethyl group or a cyano group.

$R^3$ and $R^4$ are each preferably a hydrogen atoms, a halogen atom, a $C_{1-6}$ allyl group optionally substituted by halogen atoms, a $C_{1-6}$ alkoxy group optionally substituted by halogen atoms, a $C_{1-6}$ allylthio group optionally substituted by halogen atoms or $R^3$ and $R^4$ form a homocyclic ring together with carbon atoms bonded thereto.

$R^5$ is preferably a hydrogen atom.

$R^6$ is preferably a hydrogen atom or a $C_{1-6}$ alkyl group, more preferably a hydrogen atom, a methyl group or an ethyl group.

n is preferably 0, 1 or 2.

Ring B and $(R^6)_n$ are each preferably

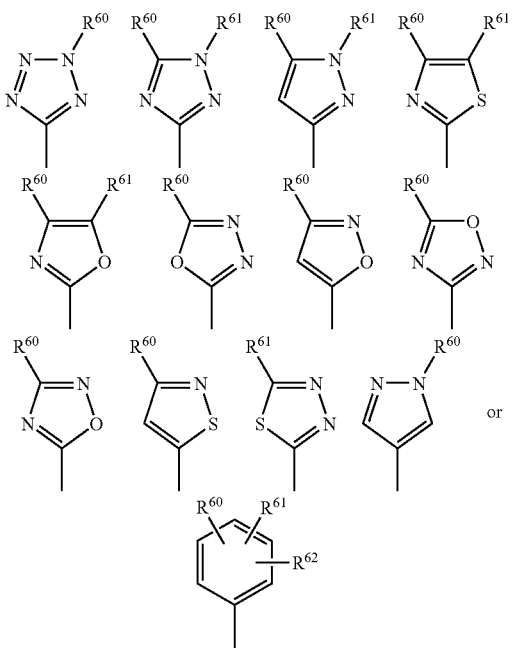

wherein $R^{60}$, $R^{61}$ and $R^{62}$ are as defined above, more preferably

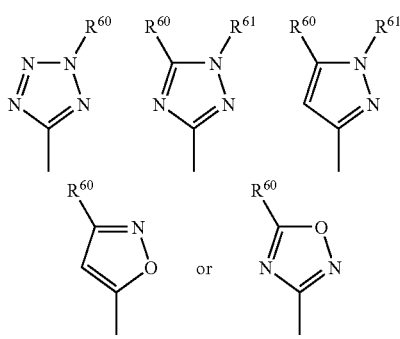

wherein $R^{60}$ and $R^{61}$ are as defined above.

A is preferably —$N(R^7)(R^8)$, more preferably that wherein $R^7$ is a $C_{1-6}$ alkyl group and $R^8$ is a $C_{4-10}$ cycloalkylalkyl group optionally substituted by —$(CH_2)_r$—$COOR^{10}$ (wherein r and $R^{10}$ are as defined above) or a $C_{1-6}$ alkyl group substituted by carboxyl group.

Preferable examples of the compound of the present invention (1) are as follows:

1. N-[3-(N'-cyclopentylmethyl-N'-ethylamino)-5,6,7,8-tetrahydronaphthalen-2-ylmethyl]-N-[3,5-bis(trifluoromethyl)benzyl]-(2-methyl-2H-tetrazol-5-yl)amine,
2. 3-{[N-[3-(N'-cyclopentylmethyl-N'-ethylamino)-5,6,7,8-tetrahydronaphthalen-2-ylmethyl]-N-(2-methyl-2H-tetrazol-5-yl)amino]methyl}-5-trifluoromethylbenzonitrile,
3. N-[3,5-bis(trifluoromethyl)benzyl]-N-[6-(N'-cyclopentylmethyl-N'-ethylamino)indan-5-ylmethyl]-(2-methyl-2H-tetrazol-5-yl)amine,
4. N-[3,5-bis(trifluoromethyl)benzyl]-N-[6-(N'-cyclopentylmethyl-N'-ethylamino)indan-5-ylmethyl]-(2-methyl-2H-tetrazol-5-yl)amine hydrochloride,
5. N-[6-(N'-cyclopentylmethyl-N'-ethylamino)indan-5-ylmethyl]-N-(2H-tetrazol-5-yl)-[3,5-bis(trifluoromethyl)benzyl]amine,
6. N-[6-(N'-cyclopentylmethyl-N'-ethylamino)indan-5-ylmethyl]-N-[3,5-bis(trifluoromethyl)benzyl]-(pyrimidin-2-yl)amine hydrochloride,
7. N-[6-(N'-cyclopentylmethyl-N'-ethylamino)indan-5-ylmethyl]-N-[3,5-bis(trifluoromethyl)benzyl]-(5-methyl-1H-pyrazol-3-yl)amine,
8. 5-{N-(6-{[N'-[3,5-bis(trifluoromethyl)benzyl]-N'-(5-methyl-[1,2,4]oxadiazol-3-yl)amino]methyl} indan-5-yl)-N-ethylamino}pentanoic acid hydrochloride,
9. methyl trans-4-{[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]methyl}cyclohexanecarboxylate,
10. 3-{[N-[6-(N'-cyclopentylmethyl-N'-ethylamino)indan-5-ylmethyl]-N-(2-methyl-2H-tetrazol-5-yl)amino]methyl}-5-trifluoromethylbenzonitrile,
11. N-[3,5-bis(trifluoromethyl)benzyl]-N-[6-(N'-cyclopentylmethyl-N'-ethylamino)indan-5-ylmethyl]-(2-ethyl-2H-tetrazol-5-yl)amine,
12. N-[3,5-bis(trifluoromethyl)benzyl]-N-[6-(N'-cyclopentylmethyl-N'-ethylamino)indan-5-ylmethyl]-(1-methyl-1H-[1,2,4]triazol-3-yl)amine,
13. 3-({N-[6-(N'-cyclopentylmethyl-N'-ethylamino)indan-5-ylmethyl]-N-phenylamino}methyl)-5-trifluoromethylbenzonitrile,
14. 3-{[N-[6-(N'-cyclopentylmethyl-N'-ethylamino)indan-5-ylmethyl]-N-(4,5-dimethyl-thiazol-2-yl)amino]methyl}-5-trifluoromethylbenzonitrile,
15. N-[3,5-bis(trifluoromethyl)benzyl]-N-[6-(N'-cyclopentylmethyl-N'-ethylamino)indan-5-ylmethyl]-(thiazol-2-yl)amine hydrochloride,
16. 3-({N-[6-(N'-cyclopentylmethyl-N'-ethylamino)indan-5-ylmethyl]-N-(thiazol-2-yl)amino}methyl)-5-trifluoromethylbenzonitrile hydrochloride,
17. N-[3,5-bis(trifluoromethyl)benzyl]-N-[6-(N'-cyclopentylmethyl-N'-ethylamino)indan-5-ylmethyl]-(oxazol-2-yl)amine hydrochloride,
18. N-[3,5-bis(trifluoromethyl)benzyl]-N-[6-(N'-cyclopentylmethyl-N'-ethylamino)indan-5-ylmethyl]-(5-methylthiazol-2-yl)amine hydrochloride,
19. N-[3,5-bis(trifluoromethyl)benzyl]-N-[6-(N'-cyclopentylmethyl-N'-ethylamino)indan-5-ylmethyl]-(4-methylthiazol-2-yl)amine hydrochloride,
20. N-[3,5-bis(trifluoromethyl)benzyl]-N-[6-(N'-cyclopentylmethyl-N'-ethylamino)indan-5-ylmethyl]-(4,5-dimethylthiazol-2-yl)amine hydrochloride,
21. 3-{[N-[6-(N'-cyclopentylmethyl-N'-ethylamino)indan-5-ylmethyl]-N-(5-methylthiazol-2-yl)amino]methyl}-5-trifluoromethylbenzonitrile hydrochloride,
22. 3-{[N-[6-(N'-cyclopentylmethyl-N'-ethylamino)indan-5-ylmethyl]-N-(4-methylthiazol-2-yl)amino]methyl}-5-trifluoromethylbenzonitrile hydrochloride, 23. N-[3,5-bis(trifluoromethyl)benzyl]-N-[6-(N'-cyclopentylmethyl-N'-ethylamino)indan-5-ylmethyl]-(4-methyloxazol-2-yl)amine hydrochloride,
24. N-[3,5-bis(trifluoromethyl)benzyl]-N-[6-(N'-cyclopentylmethyl-N'-ethylamino)indan-5-ylmethyl]-(3-methylisothiazol-5-yl)amine hydrochloride,
25. N-[3,5-bis(trifluoromethyl)benzyl]-N-[6-(N'-cyclopentylmethyl-N'-ethylamino)indan-5-ylmethyl]-(5-methylisoxazol-3-yl)amine hydrochloride,
26. N-[3,5-bis(trifluoromethyl)benzyl]-N-[6-(N'-cyclopentylmethyl-N'-ethylamino)indan-5-ylmethyl]-(3-methylisoxazol-5-yl)amine hydrochloride,
27. N-[3,5-bis(trifluoromethyl)benzyl]-N-[6-(N'-cyclopentylmethyl-N'-ethylamino)indan-5-ylmethyl]-(1-methyl-1H-pyrazol-3-yl)amine hydrochloride,
28. N-[3,5-bis(trifluoromethyl)benzyl]-N-[6-(N'-cyclopentylmethyl-N'-ethylamino)indan-5-ylmethyl]-(1-methyl-1H-pyrazol-4-yl)amine hydrochloride,
29. N-[3,5-bis(trifluoromethyl)benzyl]-N-[6-(N'-cyclopentylmethyl-N'-ethylamino)indan-5-ylmethyl]-(5-methyl-[1,3,4]thiadiazol-2-yl)amine hydrochloride,
30. N-[3,5-bis(trifluoromethyl)benzyl]-N-[6-(N'-cyclopentylmethyl-N'-ethylamino)indan-5-ylmethyl]-(5-methyl-[1,3,4]oxadiazol-2-yl)amine hydrochloride,
31. N-[3,5-bis(trifluoromethyl)benzyl]-N-[6-(N'-cyclopentylmethyl-N'-ethylamino)indan-5-ylmethyl]-pyridin-3-ylamine hydrochloride,
32. N-[3,5-bis(trifluoromethyl)benzyl]-N-[6-(N'-cyclopentylmethyl-N'-ethylamino)indan-5-ylmethyl]-pyridin-2-ylamine hydrochloride,
33. N-[3,5-bis(trifluoromethyl)benzyl]-N-[2-(N'-cyclopentylmethyl-N'-ethylamino)-5-trifluoromethylbenzyl]-(2-methyl-2H-tetrazol-5-yl)amine hydrochloride,
34. 3-{[N-[2-(N'-cyclopentylmethyl-N'-ethylamino)-5-trifluoromethylbenzyl]-N-(2-methyl-2H-tetrazol-5-yl)amino]methyl}-5-trifluoromethylbenzonitrile hydrochloride,
35. methyl 5-[N-(6-{[N'-[3,5-bis(trifluoromethyl)benzyl]-N'-(2-methyl-2H-tetrazol-5-yl)amino]methyl}indan-5-yl)-N-ethylamino]pentanoate hydrochloride,
36. methyl 5-[N-(6-{[N'-(3-cyano-5-trifluoromethylbenzyl)-N'-(2-methyl-2H-tetrazol-5-yl)amino]methyl}indan-5-ylmethyl)-N-ethylamino]pentanoate hydrochloride,
37. methyl 5-[N-(6-{[N'-[3,5-bis(trifluoromethyl)benzyl]-N'-(1-methyl-1H-pyrazol-3-yl)amino]methyl} indan-5-yl)-N-ethylamino]pentanoate hydrochloride,
38. 5-[N-(6-{[N'-[3,5-bis(trifluoromethyl)benzyl]-N'-(2-methyl-2H-tetrazol-5-yl)amino]methyl}indan-5-yl)-N-ethylamino]pentanoic acid hydrochloride,
39. 5-[N-(6-{[N'-(3-cyano-5-trifluoromethylbenzyl)-N'-(2-methyl-2H-tetrazol-5-yl)amino]methyl}indan-5-yl)-N-ethylamino]pentanoic acid hydrochloride,
40. 5-[N-(6-{[N'-[3,5-bis(trifluoromethyl)benzyl]-N'-(3-methylisoxazol-5-yl)amino]methyl}indan-5-yl)-N-ethylamino]pentanoic acid hydrochloride,
41. 5-[N-(6-{[N'-[3,5-bis(trifluoromethyl)benzyl]-N'-(1-methyl-1H-pyrazol-3-yl)amino]methyl} indan-5-yl)-N-ethylamino]pentanoic acid hydrochloride,
42. methyl trans-4-{[N-(3-{[N'-[3,5-bis(trifluoromethyl)benzyl]-N'-(1-methyl-1H-pyrazol-3-yl)amino]methyl}-5,6,7,8-tetrahydronaphthalen-2-yl)-N-ethylamino]methyl}cyclohexanecarboxylate hydrochloride,
43. methyl trans-4-{[N-(3-{[N'-(3-cyano-5-trifluoromethylbenzyl)-N'-(1-methyl-1H-pyrazol-3-yl)amino]methyl}-5,6,7,8-tetrahydronaphthalen-2-yl)-N-ethylamino]methyl}cyclohexanecarboxylate hydrochloride,
44. trans-4-{[N-(3-{[N'-[3,5-bis(trifluoromethyl)benzyl]-N'-(1-methyl-1H-pyrazol-3-yl)amino]methyl}-5,6,7,8-tetrahydronaphthalen-2-yl)-N-ethylamino]methyl}cyclohexanecarboxylic acid hydrochloride,
45. trans-4-{[N-(3-{[N'-(3-cyano-5-trifluoromethylbenzyl)-N'-(1-methyl-1H-pyrazol-3-yl)amino]methyl}-5,6,7,8-tetrahydronaphthalen-2-yl)-N-ethylamino]methyl}cyclohexanecarboxylic acid hydrochloride,
46. N-[3,5-bis(trifluoromethyl)benzyl]-N-[6-(N'-cyclopentylmethyl-N'-ethylamino)indan-5-ylmethyl]-(5-methyl-[1,2,4]oxadiazol-3-yl)amine hydrochloride,
47. methyl trans-4-{[N-(6-{[N'-[3,5-bis(trifluoromethyl)benzyl]-N'-(1-methyl-1H-pyrazol-3-yl)amino]methyl}indan-5-yl)-N-ethylamino]methyl}cyclohexanecarboxylate hydrochloride,
48. trans-4-{[N-(6-{[N'-[3,5-bis(trifluoromethyl)benzyl]-N'-(1-methyl-1H-pyrazol-3-yl)amino]methyl} indan-5-yl)-N-ethylamino]methyl}cyclohexanecarboxylic acid hydrochloride,
49. methyl trans-4-{[N-(6-{[N'-(3-cyano-5-trifluoromethylbenzyl)-N'-(1-methyl-1H-pyrazol-3-yl)amino]methyl} indan-5-yl)-N-ethylamino]methyl}cyclohexanecarboxylate,
50. trans-4-{[N-(6-{[N'-(3-cyano-5-trifluoromethylbenzyl)-N'-(1-methyl-1H-pyrazol-3-yl)amino]methyl}indan-5-yl)-N-ethylamino]methyl}cyclohexanecarboxylic acid hydrochloride,
51. trans-4-{[N-(6-{[N'-[3,5-bis(trifluoromethyl)benzyl]-N'-(2-methyl-2H-tetrazol-5-yl)amino]methyl}indan-5-yl)-N-ethylamino]methyl}cyclohexanecarboxylic acid hydrochloride,
52. trans-4-{[N-(6-{[N'-(3-cyano-5-trifluoromethylbenzyl)-N'-(2-methyl-2H-tetrazol-5-yl)amino]methyl}indan-5-yl)-N-ethylamino]methyl}cyclohexanecarboxylic acid hydrochloride,
53. trans-4-{[N-(6-{[N'-[3,5-bis(trifluoromethyl)benzyl]-N'-(3-methylisoxazol-5-yl)amino]methyl}indan-5-yl)-N-ethylamino]methyl}cyclohexanecarboxylic acid hydrochloride,
54. trans-4-{[N-(6-{[N'-(3-cyano-5-trifluoromethylbenzyl)-N'-(3-methylisoxazol-5-yl)amino]methyl}indan-5-yl)-N-ethylamino]methyl}cyclohexanecarboxylic acid hydrochloride,
55. methyl 5-[N-(6-{[N'-(3-cyano-5-trifluoromethylbenzyl)-N'-(1-methyl-1H-pyrazol-3-yl)amino]methyl}indan-5-yl)-N-ethylamino]pentanoate hydrochloride,
56. 5-[N-(6-{[N'-(3-cyano-5-trifluoromethylbenzyl)-N'-(3-methyl-isoxazol-5-yl)amino]methyl}indan-5-yl)-N-ethylamino]pentanoic acid hydrochloride,
57. 5-[N-(6-{[N'-(3-cyano-5-trifluoromethylbenzyl)-N'-(1-methyl-1H-pyrazol-3-yl)amino]methyl} indan-5-yl)-N-ethylamino]pentanoic acid hydrochloride,
58. 5-[N-(6-{[N'-[3,5-bis(trifluoromethyl)benzyl]-N'-(1-methyl-1H-[1,2,4]triazol-3-yl)amino]methyl}indan-5-yl)-N-ethylamino]pentanoic acid hydrochloride,
59. trans-4-{[N-(6-{[N'-[3,5-bis(trifluoromethyl)benzyl]-N'-(1-methyl-1H-[1,2,4]triazol-3-yl)amino]methyl} indan-5-yl)-N-ethylamino]methyl}cyclohexanecarboxylic acid hydrochloride,
60. trans-4-{[N-(6-{[N'-(3-cyano-5-trifluoromethylbenzyl)-N'-(1-methyl-1H-[1,2,4]triazol-3-yl)amino]methyl}indan-5-yl)-N-ethylamino]methyl}cyclohexanecarboxylic acid,
61. N-[3,5-bis(trifluoromethyl)benzyl]-N-[6-(N'-cyclopentylmethyl-N'-ethylamino)indan-5-ylmethyl]-(3-methyl-[1,2,4]thiadiazol-5-yl)amine, 62. 5-[N-(6-{[N'-(3-cyano-5-trifluoromethylbenzyl)-N'-(1-methyl-1H-[1,2,4]triazol-3-yl)amino]methyl}indan-5-yl)-N-ethylamino]pentanoic acid hydrochloride,
63. methyl 5-[N-(3-{[N'-[3,5-bis(trifluoromethyl)benzyl]-N'-(1-methyl-1H-pyrazol-3-yl)amino]methyl}-5,6,7,8-tetrahydronaphthalen-2-yl)-N-ethylamino]pentanoate hydrochloride,
64. methyl 5-[N-(3-{[N'-(3-cyano-5-trifluoromethylbenzyl)-N'-(1-methyl-1H-pyrazol-3-yl)amino]methyl}-5,6,7,8-tetrahydronaphthalen-2-yl)-N-ethylamino]pentanoate hydrochloride,
65. 5-[N-(3-{[N'-[3,5-bis(trifluoromethyl)benzyl]-N'-(1-methyl-1H-pyrazol-3-yl)amino]methyl}-5,6,7,8-tetrahydronaphthalen-2-yl)-N-ethylamino]pentanoic acid hydrochloride,
66. 5-[N-(3-{[N'-(3-cyano-5-trifluoromethylbenzyl)-N'-(1-methyl-1H-pyrazol-3-yl)amino]methyl}-5,6,7,8-tetrahydronaphthalen-2-yl)-N-ethylamino]pentanoic acid hydrochloride,
67. trans-4-{[N-(3-{[N'-[3,5-bis(trifluoromethyl)benzyl]-N'-(2-methyl-2H-tetrazol-5-yl)amino]methyl}-5,6,7,8-tetrahydronaphthalen-2-yl)-N-ethylamino]methyl}cyclohexanecarboxylic acid hydrochloride,
68. trans-4-{[N-(3-{[N'-(3-cyano-5-trifluoromethylbenzyl)-N'-(2-methyl-2H-tetrazol-5-yl)amino]methyl}-5,6,7,8-tetrahydronaphthalen-2-yl)-N-ethylamino]methyl}cyclohexanecarboxylic acid hydrochloride,
69. trans-4-{[N-(3-{[N'-[3,5-bis(trifluoromethyl)benzyl]-N'-(1-methyl-1H-[1,2,4]triazol-3-yl)amino]methyl}-5,6,7,8-tetrahydronaphthalen-2-yl)-N-ethylamino]methyl}cyclohexanecarboxylic acid hydrochloride,
70. trans-4-{[N-(3-{[N'-(3-cyano-5-trifluoromethylbenzyl)-N'-(1-methyl-1H-[1,2,4]triazol-3-yl)amino]methyl}-5,6,7,8-tetrahydronaphthalen-2-yl)-N-ethylamino]methyl}cyclohexanecarboxylic acid,
71. trans-4-{[N-(3-{[N'-[3,5-bis(trifluoromethyl)benzyl]-N'-(3-methylisoxazol-5-yl)amino]methyl}-5,6,7,8-tetrahydronaphthalen-2-yl)-N-ethylamino]methyl}cyclohexanecarboxylic acid hydrochloride,
72. trans-4-{[N-(3-{[N'-(3-cyano-5-trifluoromethylbenzyl)-N'-(3-methylisoxazol-5-yl)amino]methyl}-5,6,7,8-tetrahydronaphthalen-2-yl)-N-ethylamino]methyl}cyclohexanecarboxylic acid hydrochloride,
73. 2-(5-{N-[3,5-bis(trifluoromethyl)benzyl]-N-[6-(N'-cyclopentylmethyl-N'-ethylamino)indan-5-ylmethyl]amino}tetrazol-2-yl)ethanol hydrochloride,
74. methyl 5-[N-(3-{[N'-[3,5-bis(trifluoromethyl)benzyl]-N'-(1-methyl-1H-[1,2,4]triazol-3-yl)amino]methyl}-5,6,7,8-tetrahydronaphthalen-2-yl)-N-ethylamino]pentanoate hydrochloride,
75. methyl 5-[N-(3-{[N'-(3-cyano-5-trifluoromethylbenzyl)-N'-(1-methyl-1H-[1,2,4]triazol-3-yl)amino]methyl}-5,6,7,8-tetrahydronaphthalen-2-yl)-N-ethylamino]pentanoate hydrochloride,
76. 5-[N-(3-{[N'-[3,5-bis(trifluoromethyl)benzyl]-N'-(1-methyl-1H-[1,2,4]triazol-3-yl)amino]methyl}-5,6,7,8-tetrahydronaphthalen-2-yl)-N-ethylamino]pentanoic acid hydrochloride,
77. 5-[N-(3-{[N'-(3-cyano-5-trifluoromethylbenzyl)-N'-(1-methyl-1H-[1,2,4]triazol-3-yl)amino]methyl}-5,6,7,8-tetrahydronaphthalen-2-yl)-N-ethylamino]pentanoic acid hydrochloride,
78. 5-[N-(3-{[N'-[3,5-bis(trifluoromethyl)benzyl]-N'-(3-methylisoxazol-5-yl)amino]methyl}-5,6,7,8-tetrahydronaphthalen-2-yl)-N-ethylamino]pentanoic acid hydrochloride,
79. 5-[N-(3-{[N'-(3-cyano-5-trifluoromethylbenzyl)-N'-(3-methylisoxazol-5-yl)amino]methyl}-5,6,7,8-tetrahydronaphthalen-2-yl)-N-ethylamino]pentanoic acid hydrochloride,
80. 5-[N-(3-{[N'-[3,5-bis(trifluoromethyl)benzyl]-N'-(2-methyl-2H-tetrazol-5-yl)amino]methyl}-5,6,7,8-tetrahydronaphthalen-2-yl)-N-ethylamino]pentanoic acid hydrochloride,
81. 5-[N-(3-{[N'-(3-cyano-5-trifluoromethylbenzyl)-N'-(2-methyl-2H-tetrazol-5-yl)amino]methyl}-5,6,7,8-tetrahydronaphthalen-2-yl)-N-ethylamino]pentanoic acid hydrochloride,
82. trans-4-{[N-(6-{[N'-[3,5-bis(trifluoromethyl)benzyl]-N'-(5-methyl-[1,2,4]oxadiazol-3-yl)amino]methyl}indan-5-yl)-N-ethylamino]methyl}cyclohexanecarboxylic acid,
83. 5-[N-(2-{[N'-[3,5-bis(trifluoromethyl)benzyl]-N'-(1-methyl-1H-pyrazol-3-yl)amino]methyl}-4-trifluoromethoxyphenyl)-N-ethylamino]pentanoic acid hydrochloride,
84. 5-[N-(2-{[N'-[3,5-bis(trifluoromethyl)benzyl]-N'-(1-methyl-1H-pyrazol-3-yl)amino]methyl}-4-trifluoromethylphenyl)-N-ethylamino]pentanoic acid hydrochloride,
85. 5-[N-(2-{[N'-(3-cyano-5-trifluoromethylbenzyl)-N'-(1-methyl-1H-pyrazol-3-yl)amino]methyl}-4-trifluoromethylphenyl)-N-ethylamino]pentanoic acid hydrochloride,
86. 5-[N-(2-{[N'-[3,5-bis(trifluoromethyl)benzyl]-N'-(2-methyl-2H-tetrazol-5-yl)amino]methyl}-4-trifluoromethylphenyl)-N-ethylamino]pentanoic acid hydrochloride,
87. 5-[N-(6-{[N'-[3,5-bis(trifluoromethyl)benzyl]-N'-(2-ethyl-2H-tetrazol-5-yl)amino]methyl} indan-5-yl)-N-ethylamino]pentanoic acid hydrochloride,
88. 5-{N-[6-({N'-[3,5-bis(trifluoromethyl)benzyl]-N'-[2-(2-hydroxyethyl)-2H-tetrazol-5-yl]amino}methyl)indan-5-yl]-N-ethylamino}pentanoic acid hydrochloride,
89. 5-[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]pentanoic acid hydrochloride,
90. 5-[N-(6-{[N'-[3,5-bis(trifluoromethyl)benzyl]-N'-(2-methyl-2H-tetrazol-5-yl)amino]methyl}indan-5-yl)-N-ethylamino]-2,2-dimethylpentanoic acid hydrochloride,
91. 6-[N-(6-{[N'-[3,5-bis(trifluoromethyl)benzyl]-N'-(2-methyl-2H-tetrazol-5-yl)amino]methyl}indan-5-yl)-N-ethylamino]hexanoic acid hydrochloride,
92. 5-[N-(6-{[N'-[3,5-bis(trifluoromethyl)benzyl]-N'-(2-methyl-2H-tetrazol-5-yl)amino]methyl}indan-5-yl)-N-ethylamino]-3,3-dimethylpentanoic acid hydrochloride,
93. trans-4-{[N-(6-{[N'-[3,5-bis(trifluoromethyl)benzyl]-N'-(2-ethyl-2H-tetrazol-5-yl)amino]methyl} indan-5-yl)-N-ethylamino]methyl}cyclohexanecarboxylic acid hydrochloride,
94. (1-{2-[N-(6-{[N'-[3,5-bis(trifluoromethyl)benzyl]-N'-(2-methyl-2H-tetrazol-5-yl)amino]methyl}indan-5-yl)-N-ethylamino]ethyl}cyclopentyl)acetic acid hydrochloride,
95. trans-4-({N-[6-({N'-[3,5-bis(trifluoromethyl)benzyl]-N'-[2-(2-hydroxyethyl)-2H-tetrazol-5-yl]amino}methyl)indan-5-yl]-N-ethylamino}methyl)cyclohexanecarboxylic acid,
96. trans-4-{[N-(2-{[N'-[3,5-bis(trifluoromethyl)benzyl]-N'-(2-methyl-2H-tetrazol-5-yl)amino]methyl}-4-trifluoromethylphenyl)-N-ethylamino]methyl}cyclohexanecarboxylic acid hydrochloride,
97. (1-{2-[N-(3-{[N'-[3,5-bis(trifluoromethyl)benzyl]-N'-(2-methyl-2H-tetrazol-5-yl)amino]methyl}-5,6,7,8-tetrahydronaphthalen-2-yl)-N-ethylamino]ethyl}cyclopentyl)acetic acid,
98. trans-4-[{N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]
methyl}cyclohexanecarboxylic acid hydrochloride,
99. trans-4-{[N-(3-{[N'-[3,5-bis(trifluoromethyl)benzyl]-N'-(2-ethyl-2H-tetrazol-5-yl)amino]methyl}-5,6,7,8-tetrahydronaphthalen-2-yl)-N-ethylamino]
methyl}cyclohexanecarboxylic acid hydrochloride,
100. trans-4-({N-[3-({N'-[3,5-bis(trifluoromethyl)benzyl]-N'-[2-(2-hydroxyethyl)-2H-tetrazol-5-yl]amino}methyl)-5,6,7,8-tetrahydronaphthalen-2-yl]-N-ethylamino}methyl)cyclohexanecarboxylic acid hydrochloride,
101. 1-{3-[N-(6-{[N'-[3,5-bis(trifluoromethyl)benzyl]-N'-(2-methyl-2H-tetrazol-5-yl)amino]methyl} indan-5-yl)-N-ethylamino]propyl}cyclohexanecarboxylic acid hydrochloride,
102. 5-[N-(6-{[N'-[3,5-bis(trifluoromethyl)benzyl]-N'-(1-methyl-1H-pyrazol-3-yl)amino]methyl}indan-5-yl)-N-ethylamino]-3,3-dimethylpentanoic acid,
103. 5-[N-(6-{[N'-[3,5-bis(trifluoromethyl)benzyl]-N'-(5-methyl-[1,2,4]oxadiazol-3-yl)amino]methyl}indan-5-yl)-N-ethylamino]-3,3-dimethylpentanoic acid hydrochloride,
104. 5-[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]-3,3-dimethylpentanoic acid hydrochloride,
105. 5-[N-(2-{[N'-[3,5-bis(trifluoromethyl)benzyl]-N'-(2-methyl-2H-tetrazol-5-yl)amino]methyl}-4-trifluoromethylphenyl)-N-ethylamino]-3,3-dimethylpentanoic acid hydrochloride,
106. trans-4-{[N-(2-{[N'-[3,5-bis(trifluoromethyl)benzyl]-N'-(1-methyl-1H-pyrazol-3-yl)amino]methyl}-4-trifluoromethoxyphenyl)-N-ethylamino]
methyl}cyclohexanecarboxylic acid hydrochloride,
107. 5-[N-(2-{[N'-[3,5-bis(trifluoromethyl)benzyl]-N'-(1-methyl-1H-pyrazol-3-yl)amino]methyl}-4-trifluoromethoxyphenyl)-N-ethylamino]-3,3-dimethylpentanoic acid hydrochloride,
108. 5-[N-(2-{[N'-[3,5-bis(trifluoromethyl)benzyl]-N'-(5-methyl-[1,2,4]oxadiazol-3-yl)amino]methyl}-4-trifluoromethoxyphenyl)-N-ethylamino]-3,3-dimethylpentanoic acid hydrochloride,
109. trans-4-{[N-(2-{[N'-[3,5-bis(trifluoromethyl)benzyl]-N'-(5-methyl-[1,2,4]oxadiazol-3-yl)amino]methyl}-4-trifluoromethoxyphenyl)-N-ethylamino]
methyl}cyclohexanecarboxylic acid hydrochloride,
110. 6-[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]hexanoic acid hydrochloride,
111. trans-(4-{[N-(6-{[N'-[3,5-bis(trifluoromethyl)benzyl]-N'-(2-methyl-2H-tetrazol-5-yl)amino]methyl}indan-5-yl)-N-ethylamino]methyl}cyclohexyl)acetic acid hydrochloride,
112. 6-[N-(6-{[N'-[3,5-bis(trifluoromethyl)benzyl]-N'-(2-methyl-2H-tetrazol-5-yl)amino]methyl}indan-5-yl)-N-ethylamino]-4,4-dimethylhexanoic acid hydrochloride,
113. 6-[N-(6-{[N'-[3,5-bis(trifluoromethyl)benzyl]-N'-(2-methyl-2H-tetrazol-5-yl)amino]methyl}indan-5-yl)-N-ethylamino]-3,3-dimethylhexanoic acid hydrochloride,
114. 5-[N-(6-{[N'-[3,5-bis(trifluoromethyl)benzyl]-N'-(2-methyl-2H-tetrazol-5-yl)amino]methyl}indan-5-yl)-N-ethylamino]-4,4-dimethylpentanoic acid hydrochloride,
115. trans-(4-{[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]methyl}cyclohexyl)acetic acid hydrochloride,
116. 6-[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]-4,4-dimethylhexanoic acid hydrochloride,
117. 6-[N-(2-{[N'-[3,5-bis(trifluoromethyl)benzyl]-N'-(2-methyl-2H-tetrazol-5-yl)amino]methyl}-4-trifluoromethylphenyl)-N-ethylamino]-4,4-dimethylhexanoic acid hydrochloride,
118. trans-(4-{[N-(2-{[N'-[3,5-bis(trifluoromethyl)benzyl]-N'-(2-methyl-2H-tetrazol-5-yl)amino]methyl}-4-trifluoromethylphenyl)-N-ethylamino]methyl}cyclohexyl)acetic acid hydrochloride,
119. trans-(4-{[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]methyl}cyclohexyl) methanol hydrochloride,
120. 6-[N-(6-{[N'-[3,5-bis(trifluoromethyl)benzyl]-N'-(2-methyl-2H-tetrazol-5-yl)amino]methyl}indan-5-yl)-N-ethylamino]-5,5-dimethylhexanoic acid hydrochloride,
121. trans-4-{[N-(2-{[N'-[3,5-bis(trifluoromethyl)benzyl]-N'-(2-methyl-2H-tetrazol-5-yl)amino]methyl}-4-trifluoromethoxyphenyl)-N-propylamino]
methyl}cyclohexanecarboxylic acid hydrochloride,
122. trans-4-{[N-(2-{[N'-[3,5-bis(trifluoromethyl)benzyl]-N'-(2-methyl-2H-tetrazol-5-yl)amino]methyl}-4-trifluoromethoxyphenyl)-N-isobutylamino]
methyl}cyclohexanecarboxylic acid hydrochloride,
123. trans-4-{[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]
methyl}cyclohexanecarboxylic acid amide,
124. trans-4-{[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]
methyl}cyclohexanecarboxylic acid methylamide,
125. trans-4-{[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]
methyl}cyclohexanecarboxylic acid dimethylamide,
126. trans-4-{[N-(2-{[N'-[3,5-bis(trifluoromethyl)benzyl]-N'-(4-chlorophenyl)amino]methyl}-4-trifluoromethoxyphenyl)-N-ethylamino]methyl}cyclohexanecarboxylic acid hydrochloride,
127. trans-4-{[N-(2-{[N'-[3,5-bis(trifluoromethyl)benzyl]-N'-(p-tolyl)amino]methyl}-4-trifluoromethoxyphenyl)-N-ethylamino]methyl}cyclohexanecarboxylic acid hydrochloride,
128. trans-4-{[N-(2-{[N'-[3,5-bis(trifluoromethyl)benzyl]-N'-(m-tolyl)amino]methyl}-4-trifluoromethoxyphenyl)-N-ethylamino]methyl}cyclohexanecarboxylic acid hydrochloride,
129. trans-4-{[N-(2-{[N'-(3,5-dichlorobenzyl)-N'-(2-methyl-2H-tetrazol-5-yl)amino]methyl}-4-trifluoromethoxyphenyl)-N-ethylamino]methyl}cyclohexanecarboxylic acid hydrochloride,
130. trans-4-{[N-ethyl-N-(2-{[N'-(2-methyl-2H-tetrazol-5-yl)-N'-(3-methyl-5-trifluoromethylbenzyl)amino]methyl}-4-trifluoromethoxyphenyl)amino]
methyl}cyclohexanecarboxylic acid hydrochloride,
131. trans-4-{[N-(2-{[N'-(3-chloro-5-trifluoromethylbenzyl)-N'-(2-methyl-2H-tetrazol-5-yl)amino]methyl}-4-trifluoromethoxyphenyl)-N-ethylamino]
methyl}cyclohexanecarboxylic acid hydrochloride,
132. trans-4-{[N-ethyl-N-(2-{[N'-(2-methyl-2H-tetrazol-5-yl)-N'-(3-nitro-5-trifluoromethylbenzyl)amino]methyl}-4-trifluoromethoxyphenyl)amino]
methyl}cyclohexanecarboxylic acid hydrochloride, 133. trans-(4-{[N-(6-{[N'-[3,5-bis(trifluoromethyl)benzyl]-N'-(2-methyl-2H-tetrazol-5-yl)amino]methyl}-2,2-difluorobenzo[1,3]dioxol-5-yl)-N-ethylamino]methyl}cyclohexyl)methanol hydrochloride, 134. trans-(4-{[N-(6-{[N'-[3,5-bis(trifluoromethyl)benzyl]-N'-(2-methyl-2H-tetrazol-5-yl)amino]methyl}-2,2-difluorobenzo[1,3]dioxol-5-yl)-N-ethylamino]methyl}cyclohexyl)acetic acid hydrochloride, 135. trans-3-(4-{[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]methyl}cyclohexyl)propionic acid hydrochloride, 136. trans-(4-{[N-(7-{[N'-[3,5-bis(trifluoromethyl)benzyl]-N'-(2-methyl-2H-tetrazol-5-yl)amino]methyl}-2,2,3,3-tetrafluoro-2,3-dihydrobenzo[1,4]dioxin-6-yl)-N-ethylamino]methyl}cyclohexyl)methanol hydrochloride, 137. trans-(4-{[N-(7-{[N'-[3,5-bis(trifluoromethyl)benzyl]-N'-(2-methyl-2H-tetrazol-5-yl)amino]methyl}-2,2,3,3-tetrafluoro-2,3-dihydrobenzo[1,4]dioxin-6-yl)-N-ethylamino]methyl}cyclohexyl)acetic acid hydrochloride, 138. trans-2-(4-{[N-(7-{[N'-[3,5-bis(trifluoromethyl)benzyl]-N'-(2-methyl-2H-tetrazol-5-yl)amino]methyl}-2,2,3,3-tetrafluoro-2,3-dihydrobenzo[1,4]dioxin-6-yl)-N-ethylamino]methyl}cyclohexyl)acetamide hydrochloride, 139. trans-N-[3,5-bis(trifluoromethyl)benzyl]-N-{2-[N'-ethyl-N'-(4-(methoxymethyl)cyclohexylmethyl)amino]-5-trifluoromethoxybenzyl}-(2-methyl-2H-tetrazol-5-yl)amine hydrochloride, 140. trans-2-(4-{[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]methyl}cyclohexyl)ethanol hydrochloride, 141. trans-(4-{[N-(2-{[N'-[3,5-bis(trifluoromethyl)benzyl]-N'-(2-methyl-2H-tetrazol-5-yl)amino]methyl}-4-methyl-5-trifluoromethylphenyl)-N-ethylamino]methyl}cyclohexyl)methanol hydrochloride, 142. trans-(4-{[N-(2-{[N'-[3,5-bis(trifluoromethyl)benzyl]-N'-(2-methyl-2H-tetrazol-5-yl)amino]methyl}-5-methyl-4-trifluoromethylphenyl)-N-ethylamino]methyl}cyclohexyl)acetic acid hydrochloride, 143. trans-(4-{[N-(2-{[N'-[3,5-bis(trifluoromethyl)benzyl]-N'-(2-methyl-2H-tetrazol-5-yl)amino]methyl}-4-methyl-5-trifluoromethylphenyl)-N-ethylamino]methyl}cyclohexyl)acetic acid hydrochloride, 144. trans-(4-{[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]methyl}cyclohexylmethyl)phosphonic acid, 145. trans-4-{[N-(2-{[N'-(3-bromo-5-trifluoromethylbenzyl)-N'-(2-methyl-2H-tetrazol-5-yl)amino]methyl}-4-trifluoromethoxyphenyl)-N-ethylamino]methyl}cyclohexanecarboxylic acid hydrochloride, 146. trans-(4-{[N-(2-{[N'-[3,5-bis(trifluoromethyl)benzyl]-N'-(2-methyl-2H-tetrazol-5-yl)amino]methyl}-4-bromophenyl)-N-ethylamino]methyl}cyclohexyl)methanol hydrochloride, 147. trans-(4-{[N-(2-{[N'-[3,5-bis(trifluoromethyl)benzyl]-N'-(2-methyl-2H-tetrazol-5-yl)amino]methyl}-4-bromophenyl)-N-ethylamino]methyl}cyclohexyl)acetic acid hydrochloride, 148. trans-(4-{[N-(2-{[N'-[3,5-bis(trifluoromethyl)benzyl]-N'-(2-methyl-2H-tetrazol-5-yl)amino]methyl}-4-chloro-5-ethylphenyl)-N-ethylamino]methyl}cyclohexyl)methanol hydrochloride, 149. trans-4-{[N-(2-{[N'-[3,5-bis(trifluoromethyl)benzyl]-N'-(4-methoxyphenyl)amino]methyl}-4-trifluoromethoxyphenyl)-N-ethylamino]methyl}cyclohexanecarboxylic acid hydrochloride, 150. trans-(4-{[N-(2-{[N'-[3,5-bis(trifluoromethyl)benzyl]-N'-(2-methyl-2H-tetrazol-5-yl)amino]methyl}-5-methoxy-4-methylphenyl)-N-ethylamino]methyl}cyclohexyl]methanol hydrochloride, 151. trans-(4-{[N-(2-{[N'-[3,5-bis(trifluoromethyl)benzyl]-N'-(2-methyl-2H-tetrazol-5-yl)amino]methyl}-4,5-dimethylphenyl)-N-ethylamino]methyl}cyclohexyl)acetic acid hydrochloride, 152. trans-(4-{[N-(2-{[N'-[3,5-bis(trifluoromethyl)benzyl]-N'-(2-methyl-2H-tetrazol-5-yl)amino]methyl}-4-trifluoromethylthiophenyl)-N-ethylamino]methyl}cyclohexyl)acetic acid hydrochloride, 153. trans-(4-{[N-(2-{[N'-[3,5-bis(trifluoromethyl)benzyl]-N'-(2-methyl-2H-tetrazol-5-yl)amino]methyl}-4-chloro-5-ethylphenyl)-N-ethylamino]methyl}cyclohexyl)acetic acid hydrochloride, 154. trans-(4-{[N-(2-{[N'-[3,5-bis(trifluoromethyl)benzyl]-N'-(2-methyl-2H-tetrazol-5-yl)amino]methyl}-4-trifluoromethylphenyl)-N-propylamino]methyl}cyclohexyl)acetic acid hydrochloride, 155. trans-(4-{[N-(2-{[N'-[3,5-bis(trifluoromethyl)benzyl]-N'-(2-methyl-2H-tetrazol-5-yl)amino]methyl}-5-methoxy-4-methylphenyl)-N-ethylamino]methyl}cyclohexyl)acetic acid hydrochloride, 156. trans-4-({N-[2-{[N'-[3,5-bis(trifluoromethyl)benzyl]-N'-(2-methyl-2H-tetrazol-5-yl)amino]methyl}-4-(2,2,2-trifluoroethyl)phenyl]-N-ethylamino}methyl)cyclohexanecarboxylic acid hydrochloride, 157. trans-(4-{[N-(2-{[N'-[3,5-bis(trifluoromethyl)benzyl]-N'-(2-methyl-2H-tetrazol-5-yl)amino]methyl}-5-methyl-4-trifluoromethylphenyl)-N-propylamino]methyl}cyclohexyl)acetic acid hydrochloride, 158. trans-(4-{[N-(2-{[N'-[3,5-bis(trifluoromethyl)benzyl]-N'-(2-methyl-2H-tetrazol-5-yl)amino]methyl}-4-trifluoromethoxyphenyl)-N-propylamino]methyl}cyclohexyl)acetic acid hydrochloride, 159. trans-4-{[N-(2-{[N'-[3,5-bis(trifluoromethyl)benzyl]-N'-(4-ethylphenyl)amino]methyl}-4-trifluoromethoxyphenyl)-N-ethylamino]methyl}cyclohexanecarboxylic acid hydrochloride, 160. trans-4-{[N-(2-{[N'-(3-cyano-5-trifluoromethylbenzyl)-N'-(2-methyl-2H-tetrazol-5-yl)amino]methyl}-4-trifluoromethoxyphenyl)-N-ethylamino]methyl}cyclohexanecarboxylic acid hydrochloride, 161. trans-4-{[N-(2-[{N'-[3,5-bis(trifluoromethyl)benzyl]-N'-(4-isopropenylphenyl)amino]methyl}-4-trifluoromethoxyphenyl)-N-ethylamino]methyl}cyclohexanecarboxylic acid, 162. trans-(4-{[N-(2-{[N'-[3,5-bis(trifluoromethyl)benzyl]-N'-(p-tolyl)amino]methyl}-4-trifluoromethoxyphenyl)-N-ethylamino]methyl}cyclohexyl)acetic acid dihydrochloride, 163. trans-(4-{[N-(2-{[N'-[3,5-bis(trifluoromethyl)benzyl]-N'-(5-methyl-[1,2,4]oxadiazol-3-yl)amino]methyl}-4-trifluoromethoxyphenyl)-N-ethylamino]methyl}cyclohexyl)acetic acid hydrochloride, 164. trans-(4-{[N-(2-{[N'-[3,5-bis(trifluoromethyl)benzyl]-N'-(5-methyl-[1,2,4]oxadiazol-3-yl)amino]methyl}-5-methyl-4-trifluoromethylphenyl)-N-ethylamino]methyl}cyclohexyl)acetic acid hydrochloride, 165. trans-(4-{[N-(2-{[N'-[3,5-bis(trifluoromethyl)benzyl]-N'-(5-methyl-[1,2,4]oxadiazol-3-yl)amino]methyl}-5-methyl-4-trifluoromethylphenyl)-N-propylamino]methyl}cyclohexyl)acetic acid hydrochloride, 166. trans-(4-{[N-(2-{[N'-[3,5-bis(trifluoromethyl)benzyl]-N'-(2-methyl-2H-tetrazol-5-yl)amino]methyl}-5-methyl-4-trifluoromethylphenyl)-N-propylamino]methyl}cyclohexyl)acetic acid, 167. trans-(4-{[N-(2-{[N'-[3,5-bis(trifluoromethyl)benzyl]-N'-(2-methyl-2H-tetrazol-5-yl)amino]methyl}-4-methyl-5-trifluoromethylphenyl)-N-ethylamino]methyl}cyclohexyl)acetic acid, 168. trans-(4-{[N-(2-{[N'-[3,5-bis(trifluoromethyl)benzyl]-N'-(2-methyl-2H-tetrazol-5-yl)amino]methyl}-5-methyl-4-trifluoromethylphenyl)-N-ethylamino]methyl}cyclohexyl)acetic acid methanesulfonate, 169. ethyl trans-(4-{[N-(2-{[N'-[3,5-bis(trifluoromethyl)benzyl]-N'-(2-methyl-2H-tetrazol-5-yl)amino]methyl}-5-methyl-4-trifluoromethylphenyl)-N-ethylamino]methyl}cyclohexyl)acetate, 170. trans-(4-{[N-(2-{[N'-[3,5-bis(trifluoromethyl)benzyl]-N'-(2-methyl-2H-tetrazol-5-yl)amino]methyl}-4-trifluoromethylphenyl)-N-ethylamino]methyl}cyclohexyl)acetic acid, 171. trans-(4-{[N-(2-{[N'-(3-methyl-5-trifluoromethylbenzyl)-N'-(2-methyl-2H-tetrazol-5-yl)amino]methyl}-5-methyl-4-trifluoromethylphenyl)-N-ethylamino]methyl}cyclohexyl)acetic acid, 172. trans-(4-{[N-(2-{[N'-(3-methyl-5-trifluoromethylbenzyl)-N'-(5-methyl-[1,2,4]oxadiazol-3-yl)amino]methyl}-5-methyl-4-trifluoromethylphenyl)-N-ethylamino]methyl}cyclohexyl)acetic acid, 173. ethyl cis-(4-{[N-(2-{[N'-[3,5-bis(trifluoromethyl)benzyl]-N'-(2-methyl-2H-tetrazol-5-yl)amino]methyl}-5-methyl-4-trifluoromethylphenyl)-N-ethylamino]methyl}cyclohexyl)acetate, 174. {4-[2-(2-{[N-[3,5-bis(trifluoromethyl)benzyl]-N-(2-methyl-2H-tetrazol-5-yl)amino]methyl}-5-methyl-4-trifluoromethylphenyl)butyl]cyclohexyl}acetic acid and 175. 5-[2-({N-[3,5-bis(trifluoromethyl)benzyl]-N-[2-methyl-2H-tetrazol-5-yl]amino}methyl)-5-methyl-4-trifluoromethylphenoxy]heptanoic acid.

Of the compounds recited above, the compound shown below are particularly preferable.

115. trans-(4-{[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]methyl}cyclohexyl)acetic acid hydrochloride, 118. trans-(4-{[N-(2-{[N'-[3,5-bis(trifluoromethyl)benzyl]-N'-(2-methyl-2H-tetrazol-5-yl)amino]methyl}-4-trifluoromethylphenyl)-N-ethylamino]methyl}cyclohexyl)acetic acid hydrochloride, 142. trans-(4-{[N-(2-{[N'-[3,5-bis(trifluoromethyl)benzyl]-N'-(2-methyl-2H-tetrazol-5-yl)amino]methyl}-5-methyl-4-trifluoromethylphenyl)-N-ethylamino]methyl}cyclohexyl)acetic acid hydrochloride, 143. trans-(4-{[N-(2-{[N'-[3,5-bis(trifluoromethyl)benzyl]-N'-(2-methyl-2H-tetrazol-5-yl)amino]methyl}-4-methyl-5-trifluoromethylphenyl)-N-ethylamino]methyl}cyclohexyl)acetic acid hydrochloride, 154. trans-(4-{[N-(2-[{N'-[3,5-bis(trifluoromethyl)benzyl]-N'-(2-methyl-2H-tetrazol-5-yl)amino]methyl}-4-trifluoromethylphenyl)-N-propylamino]methyl}cyclohexyl)acetic acid hydrochloride, 157. trans-(4-{[N-(2-{[N'-[3,5-bis(trifluoromethyl)benzyl]-N'-(2-methyl-2H-tetrazol-5-yl)amino]methyl}-5-methyl-4-trifluoromethylphenyl)-N-propylamino]methyl}cyclohexyl)acetic acid hydrochloride, 158. trans-(4-{[N-(2-{[N'-[3,5-bis(trifluoromethyl)benzyl]-N'-(2-methyl-2H-tetrazol-5-yl)amino]methyl}-4-trifluoromethoxyphenyl)-N-propylamino]methyl}cyclohexyl)acetic acid hydrochloride, 166. trans-(4-{[N-(2-{[N'-[3,5-bis(trifluoromethyl)benzyl]-N'-(2-methyl-2H-tetrazol-5-yl)amino]methyl}-5-methyl-4-trifluoromethylphenyl)-N-propylamino]methyl}cyclohexyl)acetic acid, 167. trans-(4-{[N-(2-{[N'-[3,5-bis(trifluoromethyl)benzyl]-N'-(2-methyl-2H-tetrazol-5-yl)amino]methyl}-4-methyl-5-trifluoromethylphenyl)-N-ethylamino]methyl}cyclohexyl)acetic acid and 168. trans-(4-{[N-(2-{[N'-[3,5-bis(trifluoromethyl)benzyl]-N'-(2-methyl-2H-tetrazol-5-yl)amino]methyl}-5-methyl-4-trifluoromethylphenyl)-N-ethylamino]methyl}cyclohexyl)acetic acid methanesulfonate.

The compound of the present invention, a prodrug thereof and a pharmaceutically acceptable salt thereof have superior CETP inhibitory activity in mammals (e.g., human, monkey, bovine, horse, dog, cat, rabbit, rat, mouse and the like), and can be used as CETP activity inhibitors. In addition, utilizing the superior CETP inhibitory activity of the compound of the present invention, a prodrug thereof and a pharmaceutically acceptable salt thereof, they are useful as pharmaceutical agents effective for the prophylaxis or treatment of the diseases in which CETP is involved (e.g., hyperlipidemia, arteriosclerosis, atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorder, angina, ischemia, heart ischemia, thrombosis, cardiac infarction, reperfusion injury, angioplasty restenosis, hypertension, diabetic vascular complications, obesity or endotoxemia etc.), particularly as prophylactic or therapeutic agents for hyperlipidemia or arteriosclerotic diseases.

When the compound represented by the formula (1) of the present invention, a prodrug thereof or a pharmaceutically acceptable salt thereof is used as a pharmaceutical preparation, it is generally admixed with a pharmacologically acceptable carrier, excipient, diluent, filler, disintegrant, stabilizer, preservative, buffer, emulsifier, aromatic, coloring agent, sweetening agent, thickening agent, corrigent, dissolution aids, and other additives, which are known per se, specifically water, vegetable oil, alcohol such as ethanol and benzyl alcohol, polyethylene glycol, glycerol triacetate gelatin, carbohydrates such as lactose, starch and the like, magnesium stearate, talc, lanolin, petrolatum and the like, and can be administered orally or parenterally in the form of tablet, pill, powder, granule, suppository, injection, eye drop, liquid, capsule, troche, aerosol, elixir, suspension, emulsion, syrup and the like.

While the dose of the pharmaceutical agent of the present invention varies depending on the kind and severity of the disease, the compound to be administered and administration route, age, sex and body weight of patients and the like, it is generally about 1-1000 mg, particularly about 50 mg-800 mg in the amount of the compound represented by the formula (1) of the present invention, a prodrug thereof or a pharmaceutically acceptable salt thereof per day for an adult by oral administration.

The pharmaceutical agent of the present invention may be administered alone or concurrently with a different prophylactic or therapeutic agent for hyperlipidemia and/or a prophylactic or therapeutic agent for arteriosclerotic diseases, or may be used concurrently with a different pharmaceutical agent (e.g., therapeutic agent for obesity, therapeutic agent for diabetes, therapeutic agent for hypertension, therapeutic agent for arteriosclerosis, therapeutic agent for coronary artery disease etc.). Particularly, concurrent use with a different therapeutic agent for hyperlipidemia (statin pharmaceutical agent) is expected to provide an extremely superior synergistic effect of particularly remarkable suppression of blood cholesterol.

As used herein, by "concurrent use" means a combined use of the compound of the present invention, a prodrug thereof or a pharmaceutically acceptable salt thereof with a different pharmaceutical agent, such as a therapeutic agent for hyperlipidemia, wherein the mode of use thereof is not particularly limited. For example, it includes both the administration of a pharmaceutical composition containing the compound of the present invention, a prodrug thereof or a pharmaceutically acceptable salt thereof and a different pharmaceutical agent, and the simultaneous or staggered administration of respective preparations produced separately without mixing.

While the dose of the different pharmaceutical agent to be used concurrently varies depending on the kind and severity of the disease, administration route, age, sex and body weight of patients and the like, it is generally about 1-1000 mg, particularly about 50 mg-800 mg thereof per day for an adult by oral administration.

As a therapeutic agent for hyperlipidemia to be used concurrently with the pharmaceutical agent of the present invention, statin pharmaceutical agents such as lovastatin, simvastatin, pravastatin, fluvastatin, atorvastatin, cerivastatin and the like can be mentioned.

As a therapeutic agent for obesity to be used concurrently with the pharmaceutical agent of the present invention, mazindol and the like can be mentioned.

As a therapeutic agent for diabetes to be used concurrently with the pharmaceutical agent of the present invention, insulin preparations, sulfonylureas (e.g., glibenclamide, tolbutamide, glyclopyramide, acetohexamide, glimepiride, tolazamide, gliclazide etc.), insulin secretagogues (e.g., nateglinide etc.), sulfonamides (e.g., glybuzole etc.), biguanides (e.g., metformin hydrochloride, buformin hydrochloride etc.), α glucosidase inhibitors (e.g., voglibose, acarbose etc.), insulin sensitizers (e.g., pioglitazone hydrochloride etc.) and the like can be mentioned.

As a therapeutic agent for hypertension to be used concurrently with the pharmaceutical agent of the present invention, loop diuretics (e.g., furosemide sustained-release preparation etc.), angiotensin converting enzyme inhibitors (e.g., captopril, captopril sustained-release preparation, enalapril maleate, alacepril, delapril hydrochloride, cilazapril, lisinopril, benazepril hydrochloride, imidapril hydrochloride, temocapril hydrochloride, quinapril hydrochloride, trandrapril, perindopril erbumine etc.), angiotensin II receptor antagonists (e.g., losartan potassium, candesartan cilexetil etc.), Ca antagonists (e.g., nicardipine hydrochloride, nicardipine hydrochloride sustained-release preparation, nilvadipine, nifedipine, nifedipine sustained-release preparation, benidipine hydrochloride, diltiazem hydrochloride, diltiazem hydrochloride sustained-release preparation, nisoldipine, nitrendipine, manidipine hydrochloride, barnidipine hydrochloride, efonidipine hydrochloride, amlodipine besylate, felodipine, cilnidipine, aranidipine etc.), β blockers (e.g., propranolol hydrochloride, propranolol hydrochloride sustained-release preparation, pindolol, pindolol sustained-release preparation, indenolol hydrochloride, carteolol hydrochloride, carteolol hydrochloride sustained-release preparation, bunitrolol hydrochloride, bunitrolol hydrochloride sustained-release preparation, atenolol, acebutolol hydrochloride, metoprolol tartrate, metoprolol tartrate sustained-release preparation, nipradilol, penbutolol sulfate, tilisolol hydrochloride, carvedilol, bisoprolol fumarate, betaxolol hydrochloride, celiprolol hydrochloride, bopindolol malonate, bevantolol hydrochloride etc.), α,β blockers (e.g., labetalol hydrochloride, arotinolol hydrochloride, amosulalol hydrochloride etc.), α blockers (e.g., prazosin hydrochloride, terazosin hydrochloride, doxazosin mesylate, bunazosin hydrochloride, bunazosin hydrochloride sustained-release preparation, urapidil, phentolamine mesylate etc.) and the like can be mentioned.

Moreover, the pharmaceutical agent of the present invention can be administered not only to humans but also to other mammals (e.g., monkey, bovine, horse, dog, cat, rabbit, rat, mouse and the like).

Now, one embodiment of the production method of the dibenzylamino compound represented by compound (I) is explained, but the production method of the present invention is not limited to this example.

When the reaction to be mentioned below is carried out, functional groups at positions other than the reaction site may be protected beforehand as necessary and may be deprotected at a suitable stage.

Moreover, the reaction in each step may be carried out according to a conventional method, wherein isolation and purification are performed by appropriately selecting or combining conventional methods, such as crystallization, recrystallization, column chromatography, preparative HPLC and the like.

Conventional Production Method

The production method of the compound represented by the formula (1) is exemplarily shown in the following.

Production Method 1
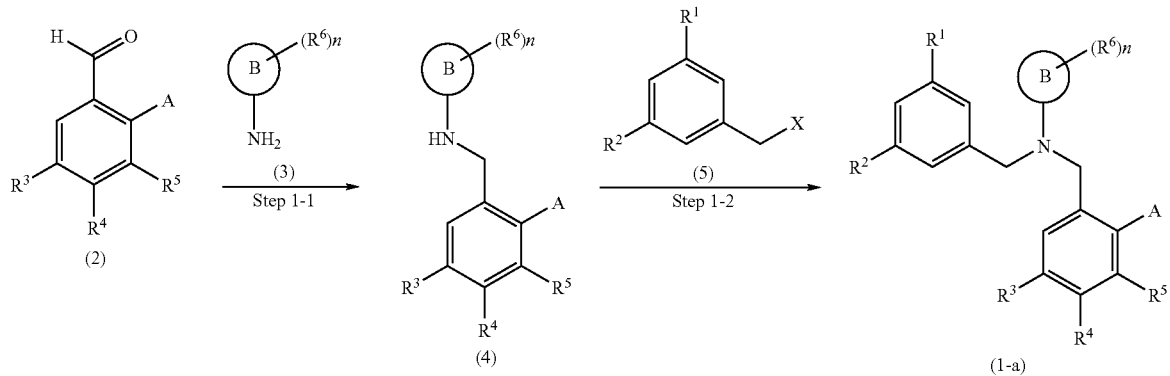
Production Method 2
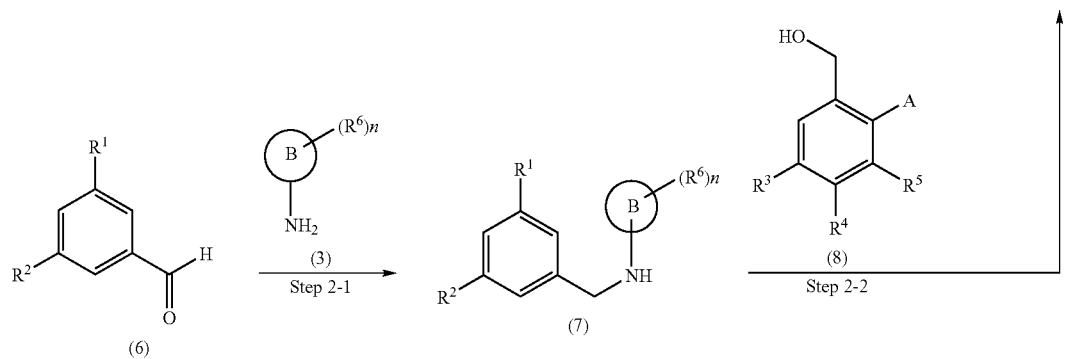
Production Method 3
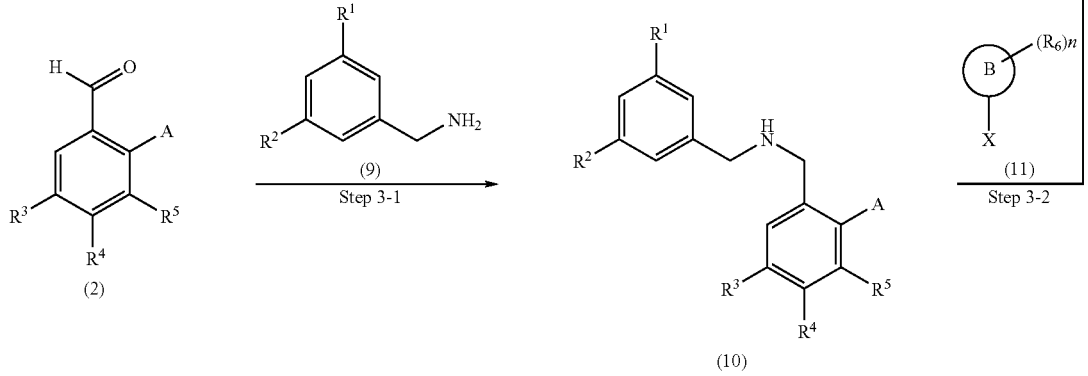
Production Method 3'
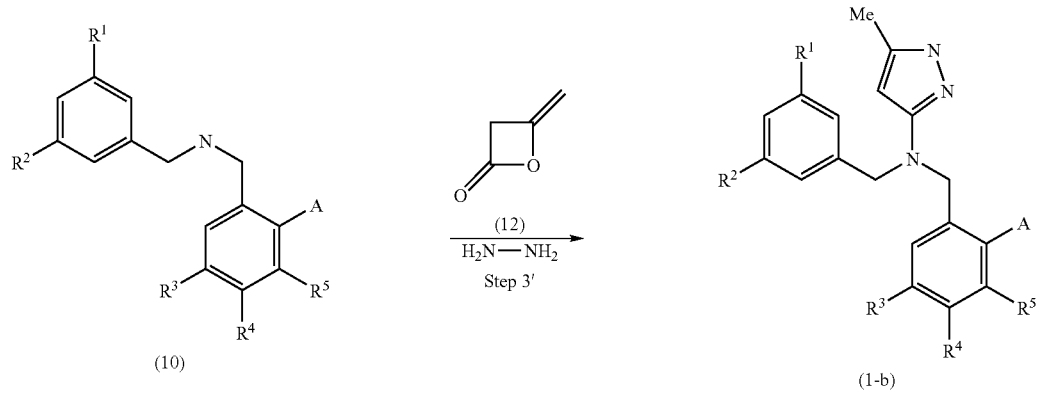

-continued
Production Method 3″

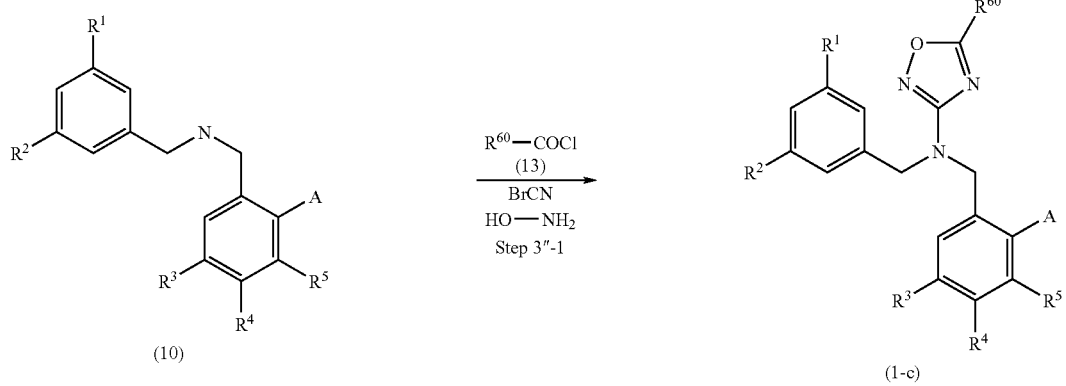

wherein $R^1$, $R^2$, $R^3$, $R^4$, $R^5$, $R^6$, A, ring B and n are as defined above, X is a halogen atom and Ph is a phenyl group.

Production Method 1

Step 1-1

This step is directed to a general reductive amination. The compound represented by the formula (2) is reacted with a compound represented by the formula (3) in the presence of a reducing agent in a solvent to give a compound represented by the formula (4).

As the solvent to be used for the reaction, for example, ether solvents such as diethyl ether, tetrahydrofuran (THF), dioxane, 1,2-dimethoxyethane, diglyme and the like; hydrocarbon solvents such as benzene, toluene, hexane, xylene and the like; halogenated solvents such as dichloromethane, chloroform, carbon tetrachloride, 1,2-dichloroethane and the like; alcohol solvents such as methanol, ethanol, isopropyl alcohol, tert-butanol and the like; ester solvents such as ethyl acetate, methyl acetate, butyl acetate and the like; polar solvents such as acetic acid, N,N-dimethylformamide and the like; and the like can be mentioned, which can be used alone or in combination. Preferable solvents in this reaction are chloroform and dichloromethane.

As the reducing agent, sodium triacetoxyborohydride, sodium cyanoborohydride, sodium borohydride and the like can be mentioned. A preferable reducing agent in this reaction is sodium triacetoxyborohydride.

Step 1-2

This step is directed to a general alkylation. A compound represented by the formula (4) is reacted with a compound represented by the formula (5) in a solvent in the presence of a base to give one of the object compounds, which is represented by the formula (1-a).

As the solvent to be used for the reaction, for example, ether solvents such as diethyl ether, tetrahydrofuran (THF), dioxane, 1,2-dimethoxyethane, diglyme and the like; hydrocarbon solvents such as benzene, toluene, hexane, xylene and the like; alcohol solvents such as methanol, ethanol, isopropyl alcohol, tert-butanol and the like; ester solvents such as ethyl acetate, methyl acetate, butyl acetate and the like; polar solvents such as acetone, N,N-dimethylformamide, dimethyl sulfoxide and the like; and the like can be mentioned, which can be used alone or in combination. A preferable solvent in this reaction is N,N-dimethylformamide.

As the base, for example, alkali metal hydrides (e.g., sodium hydride, potassium hydride etc.); alkali metal alkoxides (e.g., sodium ethoxide, sodium methoxide, potassium tert-butoxide etc.); alkyllithiums (e.g., n-butyllithium, sec-butyllithium etc.); alkali metal amides (e.g., lithium diisopropylamide, sodium amide, lithium bistrimethylsilylamide etc.); alkali metal carbonates (e.g., sodium carbonate, potassium carbonate, sodium hydrogen carbonate, potassium hydrogen carbonate etc.); alkali metal hydroxides (e.g., lithium hydroxide, sodium hydroxide, potassium hydroxide etc.); alkali metal phosphates (e.g., sodium phosphate, potassium phosphate etc.); and organic bases (e.g., triethylamine, pyridine, N-methylmorpholine etc.) can be mentioned, with preference given to sodium hydride and potassium tert-butoxide.

The obtained object compound may be subjected to a salt-forming reaction to give a desired salt.

Production Method 2

Step 2-1

This step is directed to a general reductive amination. A compound represented by the formula (6) is reacted with a compound represented by the formula (3) in a solvent in the presence of a reducing agent to give a compound represented by the formula (7).

As the solvent, for example, ether solvents such as diethyl ether, tetrahydrofuran, dioxane, 1,2-dimethoxyethane, diglyme and the like; hydrocarbon solvents such as benzene, toluene, hexane, xylene and the like; halogenated solvents such as dichloromethane, chloroform, carbon tetrachloride, 1,2-dichloroethane and the like; alcohol solvents such as methanol, ethanol, isopropyl alcohol, tert-butanol and the like; ester solvents such as ethyl acetate, methyl acetate, butyl acetate and the like; polar solvents such as N,N-dimethylformamide and the like; and the like can be mentioned, which can be used alone or in combination. Preferable solvents in this reaction are dichloromethane and toluene.

As the reducing agent, sodium triacetoxyborohydride, sodium cyanoborohydride, sodium borohydride, lithium hydride, aluminum hydride and the like can be mentioned. A preferable reducing agent in this reaction is sodium borohydride.

As a different method, the formula (6) is reacted with the formula (3) to once give a Schiff base, which is followed by a reduction. For a reaction to form a Schiff base, azeotropic dehydration may be conducted in a solvent such as benzene, toluene, ethanol and the like without catalyst or in the presence of an acid catalyst such as hydrochloric acid, acetic acid and the like, or a method using a dehydrating agent such as molecular sieves and the like in an aprotic solvent such as methylene chloride, toluene and the like may be employed.

Step 2-2

A compound represented by the formula (8), which is obtained by treating the formula (2) by a general reduction, is reacted with thionyl chloride in a solvent such as toluene, tetrahydrofuran, chloroform and the like to give a compound wherein hydroxyl group of the formula (8) is chlorinated. Next, a similar reaction as in Step 1-2 using the obtained compound and a compound represented by the formula (7) gives one of the object compounds, which is represented by the formula (1-a).

Production Method 3

Step 3-1

This step is directed to a general reductive amination. A compound represented by the formula (2) is reacted with a compound represented by the formula (9) in a solvent in the presence of a reducing agent to give a compound represented by the formula (10).

As the solvent, for example, ether solvents such as diethyl ether, tetrahydrofuran, dioxane, 1,2-dimethoxyethane, diglyme and the like; hydrocarbon solvents such as benzene, toluene, hexane, xylene and the like; halogenated solvents such as dichloromethane, chloroform, carbon tetrachloride, 1,2-dichloroethane and the like; alcohol solvents such as methanol, ethanol, isopropyl alcohol, tert-butanol and the like; ester solvents such as ethyl acetate, methyl acetate, butyl acetate and the like; polar solvents such as N,N-dimethylformamide and the like; and the like can be mentioned, which can be used alone or in combination. A preferable solvent in this reaction is dichloromethane.

As the reducing agent, sodium triacetoxyborohydride, sodium cyanoborohydride, sodium borohydride and the like can be mentioned. A preferable reducing agent in this reaction is sodium triacetoxyborohydride.

Step 3-2

This step is directed to a general nucleophilic substitution reaction. In a similar manner as in Step 1-2, a compound represented by the formula (10) is reacted with a compound represented by the formula (11) to give one of the object compounds, which is represented by the formula (1-a).

Besides such method comprising directly reacting a compound having ring B, which is represented by the formula (11), there is a method comprising forming ring B on the nitrogen atom of compound (10) by a known method. As an example of this method, the following production method 3' and production method 3" are shown.

Production Method 3'

When

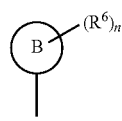

is

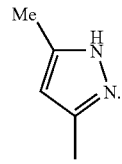

Step 3'-1

A compound represented by the formula (10) is reacted with compound (12) in a solvent. The obtained residue is reacted with hydrazine hydrate in a solvent in the presence of an acid to give a compound represented by the formula (1-b), which is one of the object compounds.

As the solvent to be used for the first reaction, for example, ether solvents such as diethyl ether, tetrahydrofuran, dioxane, 1,2-dimethoxyethane, diglyme and the like; hydrocarbon solvents such as benzene, toluene, hexane, xylene and the like; halogenated solvents such as dichloromethane, chloroform, carbon tetrachloride, 1,2-dichloroethane and the like; ester solvents such as ethyl acetate, methyl acetate, butyl acetate and the like; polar solvents such as N,N-dimethylformamide and the like; and the like can be mentioned, which can be used alone or in combination. A preferable solvent in this reaction is dichloromethane.

As the solvent to be used for the next reaction, for example, ether solvents such as diethyl ether, tetrahydrofuran, dioxane, 1,2-dimethoxyethane, diglyme and the like; hydrocarbon solvents such as benzene, toluene, hexane, xylene and the like; halogenated solvents such as dichloromethane, chloroform, carbon tetrachloride, 1,2-dichloroethane and the like; alcohol solvents such as methanol, ethanol, isopropyl alcohol, tert-butanol and the like; ester solvents such as ethyl acetate, methyl acetate, butyl acetate and the like; polar solvents such as N,N-dimethylformamide, dimethyl sulfoxide and the like; and the like can be mentioned, which can be used alone or in combination. A preferable solvent in this reaction is 1,2-dimethoxyethane.

As the acid to be used for the reaction, for example, inorganic acids such as hydrochloric acid, sulfuric acid, nitric acid and the like; organic acids such as trifluoroacetic acid, trichloroacetic acid, acetic acid, methanesulfonic acid, p-toluenesulfonic acid and the like; and a mixture thereof can be mentioned, with preference given to methanesulfonic acid.

Production Method 3"

When

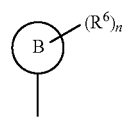

is

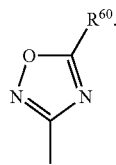

Step 3"-1

A compound represented by the formula (10) is reacted with cyanogen bromide in a solvent in the presence of a base, and the obtained residue is reacted with hydroxylamine in a solvent. The obtained residue is reacted with an acylating agent, such as acid chloride represented by the formula (13) and the like, in a solvent to give a compound represented by the formula (1-c), which is one of the object compounds.

As the solvent to be used for the first reaction, for example, alcohol solvents such as methanol, ethanol, isopropyl alcohol, tert-butanol and the like; ether solvents such as diethyl ether, tetrahydrofuran, dioxane, 1,2-dimethoxyethane, diglyme and the like; hydrocarbon solvents such as benzene, toluene, hexane, xylene and the like; halogenated solvents such as dichloromethane, chloroform, carbon tetrachloride, 1,2-dichloroethane and the like; ester solvents such as ethyl acetate, methyl acetate, butyl acetate and the like; polar solvents such as N,N-dimethylformamide and the like; and the like can be mentioned, which can be used alone or in combination. A preferable solvent in this reaction is methanol.

As the base to be used for the first reaction, for example, alkali metal carbonates (e.g., sodium carbonate, potassium carbonate, sodium hydrogen carbonate, potassium hydrogen carbonate etc.); alkali metal phosphates (e.g., sodium phosphate, potassium phosphate etc.); and organic bases (e.g., triethylamine, pyridine, N-methylmorpholine etc.) can be mentioned, with preference given to sodium hydrogen carbonate.

As the solvent to be used for the next reaction, for example, ether solvents such as diethyl ether, tetrahydrofuran, dioxane, 1,2-dimethoxyethane, diglyme and the like; hydrocarbon solvents such as benzene, toluene, hexane, xylene and the like; halogenated solvents such as dichloromethane, chloroform, carbon tetrachloride, 1,2-dichloroethane and the like; alcohol solvents such as methanol, ethanol, isopropyl alcohol, tert-butanol and the like; polar solvents such as N,N-dimethylformamide, dimethyl sulfoxide and the like; and the like can be mentioned, which can be used alone or in combination. A preferable solvent in this reaction is dioxane.

As the solvent to be used for the final reaction, for example, ether solvents such as diethyl ether, tetrahydrofuran, dioxane, 1,2-dimethoxyethane, diglyme and the like; hydrocarbon solvents such as benzene, toluene, hexane, xylene and the like; halogenated solvents such as dichloromethane, chloroform, carbon tetrachloride, 1,2-dichloroethane and the like; ester solvents such as ethyl acetate, methyl acetate, butyl acetate and the like; polar solvents such as N,N-dimethylformamide, dimethyl sulfoxide and the like; and the like can be mentioned, which can be used alone or in combination. A preferable solvent in this reaction is pyridine.

In addition, A, B and $R^1$ to $R^6$ may be further subjected to conversion of a functional group according to a known method, after synthesis of compound (I) in the above-mentioned production method.

As a functional group conversion reaction, for example, when the terminal of substituent A is an ester, the obtained compound (1-a) is subjected to a conventional ester hydrolysis, whereby a compound having a carboxyl group as the terminal of substituent A can be easily obtained. As the solvent to be used for this ester hydrolysis reaction, for example, ether solvents such as diethyl ether, tetrahydrofuran, dioxane, 1,2-dimethoxyethane, diglyme and the like; alcohol solvents such as methanol, ethanol, isopropyl alcohol, tert-butanol and the like, and water can be mentioned, which may be used alone or in combination. Similarly, as the base to be used for this ester hydrolysis reaction, metal hydroxides such as sodium hydroxide, potassium hydroxide, lithium hydroxide and the like, and the like can be mentioned.

In addition, a method exists which comprises, after deprotection of protected hydroxyl group at the terminal of substituent A, conversion to cyano group, carboxyl group and the like.

A compound represented by the formula (2), which is a starting material of the above-mentioned production method, can be produced according to a conventionally known method. In the following, some examples thereof are explained.

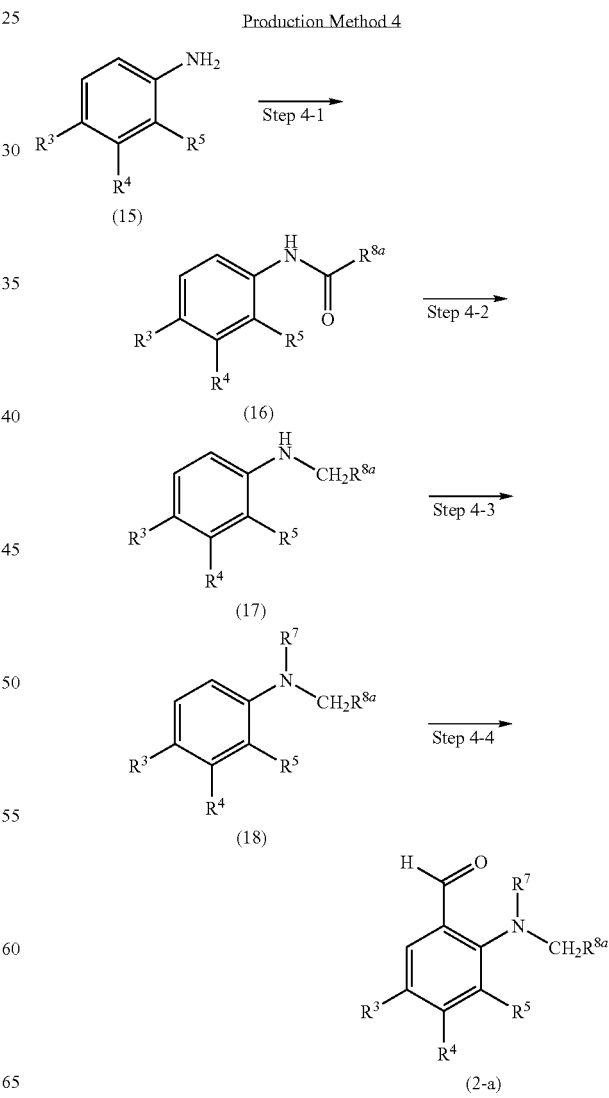

wherein $R^3$, $R^4$, $R^5$ and $R^7$ are as defined above, and —$CH_2R^{8a}$ is a group corresponding to the aforementioned $R^8$.

Aniline represented by the formula (15) is reacted with an acid halide and the like in the presence or absence of a base under cooling to heating in an organic solvent, water, or without solvent, whereby a compound represented by the formula (16) can be synthesized (Step 4-1). The compound represented by the formula (16) is reacted with a reducing agent such as lithium aluminum hydride, Red-Al, sodium borohydride and the like under cooling to heating in an organic solvent, whereby a compound represented by the formula (17) can be synthesized (Step 4-2). The compound represented by the formula (17) is reacted with allyl halide and the like in the presence or absence of a base under cooling to heating in an organic solvent or water, or without solvent, whereby a compound represented by the formula (18) can be synthesized (Step 4-3). The compound represented by the formula (18) is reacted using a Vilsmeier reagent prepared from phosphorus oxychloride and N,N-dimethylformamide and the like under cooling to heating in an organic solvent or without solvent, whereby a compound represented by the formula (2-a), which is one of the desired starting materials, can be synthesized (Step 4-4).

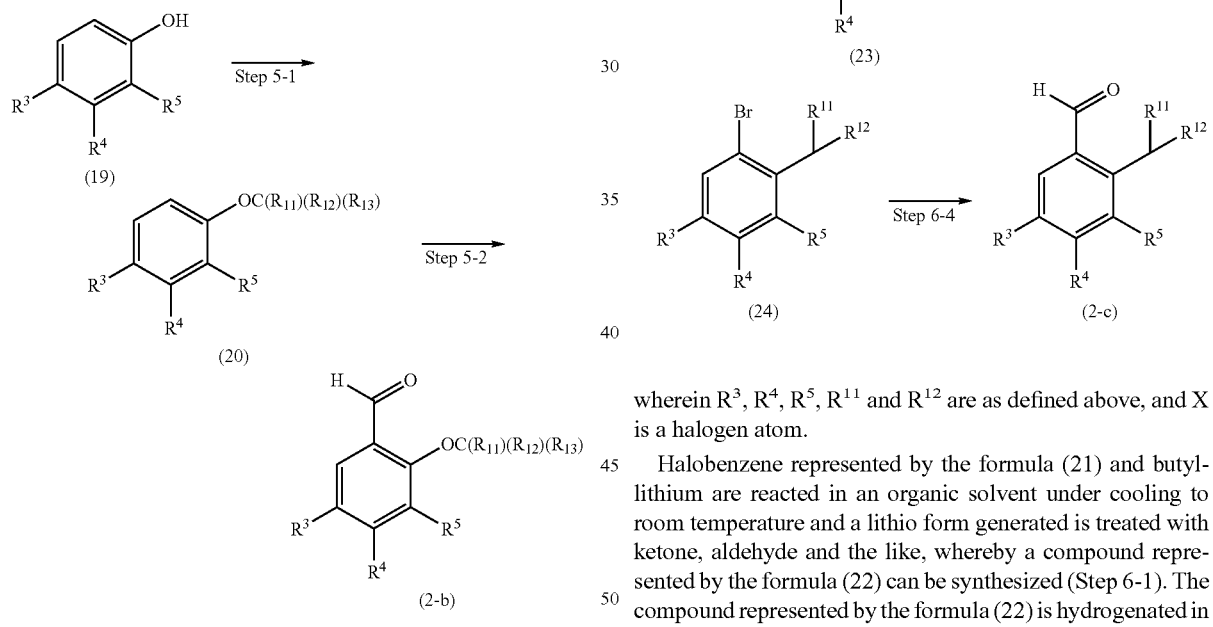

wherein $R^3$, $R^4$, $R^5$, $R^{11}$, $R^{12}$ and $R^{13}$ are as defined above.

Phenol represented by the formula (19) is reacted with alcohol represented by the formula; $(R^{11})(R^{12})(R^{13})COH$ (wherein $R^{11}$, $R^{12}$ and $R^{13}$ are as defined above) in the presence of triphenylphosphine using a condensing agent such as diethyl azodicarboxylate and the like under cooling to heating in an organic solvent or water, or without solvent, whereby a compound represented by the formula (20) can be synthesized (Step 5-1). The compound represented by the formula (20) is reacted using a Vilsmeier reagent prepared from phosphorus oxychloride and N,N-dimethylformamide and the like under cooling to heating in an organic solvent or without solvent, whereby a compound represented by the formula (2-b), which is one of the desired starting materials, can be synthesized (Step 5-2).

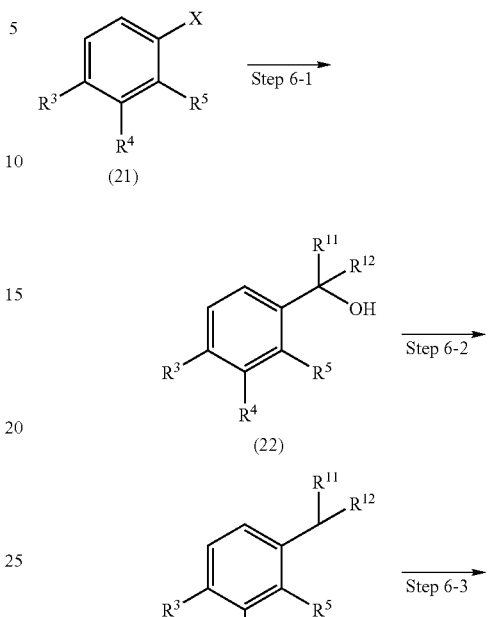

wherein $R^3$, $R^4$, $R^5$, $R^{11}$ and $R^{12}$ are as defined above, and X is a halogen atom.

Halobenzene represented by the formula (21) and butyllithium are reacted in an organic solvent under cooling to room temperature and a lithio form generated is treated with ketone, aldehyde and the like, whereby a compound represented by the formula (22) can be synthesized (Step 6-1). The compound represented by the formula (22) is hydrogenated in the presence of a catalyst such as palladium hydroxide and the like at room temperature or under heating in an organic solvent or water, whereby a compound represented by the formula (23) can be synthesized (Step 6-2). The compound represented by the formula (23) is reacted using a brominating agent such as bromosuccinimide and the like under cooling to heating in an organic solvent or without solvent, whereby a compound represented by the formula (24) can be synthesized (Step 6-3). The compound represented by the formula (24) and butyllithium are reacted in an organic solvent under cooling to room temperature and a lithio form generated is treated with N,N-dimethylformamide and the like, whereby a compound represented by the formula (2-c), which is one of the desired starting materials, can be synthesized (Step 6-4).

Production Method 7

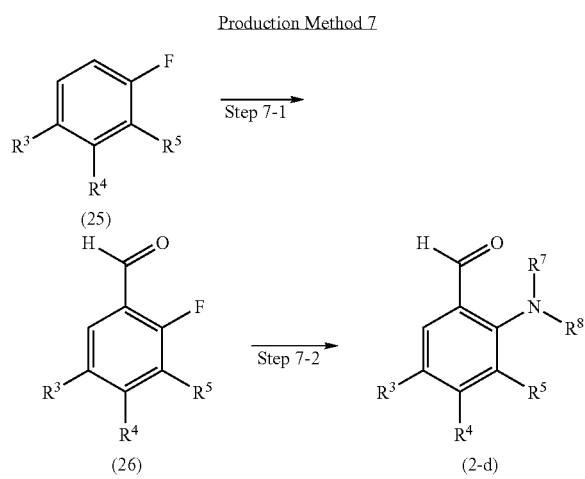

wherein $R^3$, $R^4$, $R^5$, $R^7$ and $R^8$ are as defined above.

A fluorobenzene compound represented by the formula (25) and LDA, butyllithium and the like are reacted in an organic solvent under cooling to room temperature and a lithio form generated is treated with N,N-dimethylformamide and the like, whereby a compound represented by the formula (26) can be synthesized (Step 7-1). The compound represented by the formula (26) is reacted with an amine represented by the formula; $(R_7)(R_8)NH$ in the presence of a base such as potassium carbonate and the like under cooling to heating in an organic solvent or without solvent, whereby a compound represented by the formula (2-d), which is one of the desired starting materials, can be synthesized (Step 7-2).

The present invention is explained in more detail in the following by referring to Examples, which are not to be construed as limitative.

EXAMPLES

Example 1

N-[3-(N'-cyclopentylmethyl-N'-ethylamino)-5,6,7,8-tetrahydronaphthalen-2-ylmethyl]-N-[3,5-bis(trifluoromethyl)benzyl]-(2-methyl-2H-tetrazol-5-yl)amine a) N-[3-(N'-cyclopentylmethyl-N'-ethylamino)-5,6,7,8-tetrahydronaphthalen-2-ylmethyl]-(2-methyl-2H-tetrazol-5-yl)amine To a solution (10 ml) of 3-(N-cyclopentylmethyl-N-ethylamino)-5,6,7,8-tetrahydronaphthalene-2-carbaldehyde (333 mg) and 5-amino-2-methyltetrazole (231 mg) in chloroform was added sodium triacetoxyborohydride (745 mg) with stirring at room temperature, and acetic acid (13 μl) was added successively. The reaction solution was stirred overnight and sodium borohydride (50 mg) and methanol (3 ml) were added. The mixture was further stirred for 2 hr. The reaction solution was washed successively with saturated aqueous sodium hydrogen carbonate, water and saturated brine, and the organic layer was dried over sodium sulfate. Sodium sulfate was filtered off and the filtrate was concentrated. The obtained residue was purified by column chromatography (n-hexane:ethyl acetate=6:1→3:1) to give the title compound (254 mg, 59%).

$^1$HNMR (CDCl$_3$, 400 MHz) δ: 1.01 (t, J=7.1 Hz, 3H), 1.10-1.30 (m, 2H), 1.30-1.62 (m, 4H), 1.67-1.82 (m, 6H), 1.93-2.10 (m, 1H), 2.63-2.77 (m, 4H), 2.81 (d, J=7.1 Hz, 2H), 2.94 (q, J=7.1 Hz, 2H), 4.14 (s, 3H), 4.51 (d, J=5.8 Hz, 2H), 5.35-5.50 (brs, 1H), 6.87 (s, 1H), 7.03 (s, 1H).

b) N-[3-(N'-cyclopentylmethyl-N'-ethylamino)-5,6,7,8-tetrahydronaphthalen-2-ylmethyl]-N-[3,5-bis(trifluoromethyl)benzyl]-(2-methyl-2H-tetrazol-5-yl)amine To a solution (2 ml) of N-[3-(N'-cyclopentylmethyl-N'-ethylamino)-5,6,7,8-tetrahydronaphthalen-2-ylmethyl]-(2-methyl-2H-tetrazol-5-yl)amine (121 mg) obtained in Example 1 a) in N,N-dimethylformamide (DMF) was added sodium hydride (16 mg) with stirring at room temperature. The reaction solution was stirred for 1 hr and 3,5-bis(trifluoromethyl)benzyl bromide (73 μl) was added. The mixture was further stirred overnight. Water was added to the reaction solution and the mixture was extracted with ethyl acetate. The extract was washed successively with water and saturated brine and the organic layer was dried over sodium sulfate. Sodium sulfate was filtered off and the filtrate was concentrated. The obtained residue was purified by column chromatography (n-hexane:ethyl acetate=10:1) to give the title compound (102 mg, 52%) (see Table 1).

Example 2

3-{[N-[3-(N'-cyclopentylmethyl-N'-ethylamino)-5,6,7,8-tetrahydronaphthalen-2-ylmethyl]-N-(2-methyl-2H-tetrazol-5-yl)amino]methyl}-5-trifluoromethylbenzonitrile a) 3-bromomethyl-5-trifluoromethylbenzonitrile To a solution (10 ml) of 3-hydroxymethyl-5-trifluoromethylbenzonitrile (1.00 g) and carbon tetrabromide (1.81 g) in dichloromethane was added triphenylphosphine (1.37 g) with stirring under ice-cooling, and the mixture was continuously stirred for 30 min. The reaction solution was concentrated and the obtained residue was purified by column chromatography (n-hexane:ethyl acetate=9:1) to give the title compound (1.11 g, 84%).

$^1$HNMR (CDCl$_3$, 400 MHz) δ: 4.50 (s, 2H), 7.85 (s, 1H), 7.87 (s, 2H).

b) 3-{[N-[3-(N'-cyclopentylmethyl-N'-ethylamino)-5,6,7,8-tetrahydronaphthalen-2-ylmethyl]-N-(2-methyl-2H-tetrazol-5-yl)amino]methyl}-5-trifluoromethylbenzonitrile To a solution (2 ml) of N-[3-(N'-cyclopentylmethyl-N'-ethylamino)-5,6,7,8-tetrahydronaphthalen-2-ylmethyl]-(2-methyl-2H-tetrazol-5-yl)amine (132 mg) obtained in Example 1 a) in DMF was added sodium hydride (17 mg) with stirring at room temperature. The reaction solution was stirred for 1 hr and 3-bromomethyl-5-trifluoromethylbenzonitrile (114 mg) obtained in Example 2b) was added. The mixture was further stirred overnight.

Water was added to the reaction solution and the mixture was extracted with ethyl acetate. The extract was washed successively with water and saturated brine and the organic layer was dried over sodium sulfate. Sodium sulfate was filtered off and the filtrate was concentrated. The obtained residue was purified by column chromatography (n-hexane:ethyl acetate=6:1) to give the title compound (86 mg, 44%) (see Table 1).

Example 3

N-[3,5-bis(trifluoromethyl)benzyl]-N-[6-(N'-cyclopentylmethyl-N'-ethylamino)indan-5-ylmethyl]-(2-methyl-2H-tetrazol-5-yl)amine In a similar manner as in Example 1, the title compound was obtained (see Table 1).

Example 4

N-[3,5-bis(trifluoromethyl)benzyl]-N-[6-(N'-cyclopentylmethyl-N'-ethylamino)indan-5-ylmethyl]-(2-methyl-2H-tetrazol-5-yl)amine hydrochloride To a solution (12 ml) of N-[3,5-bis(trifluoromethyl)benzyl]-N-[6-(N'-cyclopentylmethyl-N'-ethylamino)indan-5-ylmethyl]-(2-methyl-2H-tetrazol-5-yl)amine (550 mg) obtained in Example 3 in n-hexane was added dropwise 1N hydrochloric acid-diethyl ether (0.76 ml) with stirring at room temperature. The precipitated solid was collected by filtration and dried to give the title compound (332 mg) (see Table 1).

Example 5

N-[6-(N'-cyclopentylmethyl-N'-ethylamino)indan-5-ylmethyl]-N-(2H-tetrazol-5-yl)-[3,5-bis(trifluoromethyl)benzyl]amine To a solution (1 ml) of a compound obtained in a similar manner as in Example 1, N-[6-(N'-cyclopentylmethyl-N'-ethylamino)indan-5-ylmethyl]-N-[3,5-bis(trifluoromethyl)benzyl]-(2-triphenylmethyl-2H-tetrazol-5-yl)amine (75 mg), in ethyl acetate was added dropwise 4N hydrochloric acid-ethyl acetate (3 ml) with stirring at room temperature. The mixture was stirred at room temperature for 1.5 hr and 1N aqueous sodium hydroxide, then aqueous citric acid solution were added. The mixture was extracted with ethyl acetate and the extract was washed successively with water and saturated brine. The organic layer was dried over sodium sulfate. Sodium sulfate was filtered off and the filtrate was concentrated. The obtained residue was purified using a preparative TLC plate (n-hexane:ethyl acetate=2:1) to give the title compound (24 mg, 46%) (see Table 1).

Example 6

N-[6-(N'-cyclopentylmethyl-N'-ethylamino)indan-5-ylmethyl]-N-[3,5-bis(trifluoromethyl)benzyl]-(pyrimidin-2-yl)amine hydrochloride a) N-cyclopentylmethyl-N-{6-[[3,5-bis(trifluoromethyl)benzylamino]methyl]indan-5-yl}-ethylamine To a solution (20 ml) of 6-(N-cyclopentylmethyl-N-ethylamino)indane-5-carbaldehyde (1.09 g) and 3,5-bis(trifluoromethyl)benzylamine (1.26 g) in dichloromethane was added sodium triacetoxyborohydride (1.70 g) with stirring at room temperature. The reaction solution was stirred overnight. The reaction solution was washed successively with saturated aqueous sodium hydrogen carbonate, water and saturated brine, and the organic layer was dried over sodium sulfate. Sodium sulfate was filtered off and the filtrate was concentrated. The obtained residue was purified by column chromatography (n-hexane:ethyl acetate=6:1) to give the title compound (1.65 g, 83%).

$^1$HNMR (CDCl$_3$, 300 MHz) δ: 0.95 (t, J=7.1 Hz, 3H), 1.04-1.22 (m, 2H), 1.35-1.78 (m, 6H), 1.90-2.17 (m, 3H), 2.78 (d, J=7.4 Hz, 2H), 2.75-2.95 (m, 6H), 3.84 (s, 2H), 3.88 (s, 2H), 7.07 (s, 1H), 7.12 (s, 1H), 7.75 (s, 1H), 7.83 (s, 2H).

b) N-[6-(N'-cyclopentylmethyl-N'-ethylamino)indan-5-ylmethyl]-N-[3,5-bis(trifluoromethyl)benzyl]-(pyrimidin-2-yl)amine To a solution (3 ml) of N-cyclopentylmethyl-N-{6-[[3,5-bis(trifluoromethyl)benzylamino]methyl]indan-5-yl}-ethylamine (150 mg) obtained in Example 6 a) and 2-chloropyrimidine (69 mg) in toluene was added triethylamine (0.17 ml) with stirring at room temperature. The reaction solution was refluxed with stirring overnight and concentrated. The obtained residue was purified using a preparative TLC plate (n-hexane:ethyl acetate=6:1) to give the title compound (68 mg, 39%).

$^1$HNMR (CDCl$_3$, 400 MHz) δ: 0.92 (t, J=7.1 Hz, 3H), 0.97-1.12 (m, 2H), 1.30-1.60 (m, 6H), 1.83-2.08 (m, 3H), 2.80-2.93 (m, 8H), 4.86 (s, 2H), 5.06 (s, 2H), 6.59 (t, J=4.7 Hz, 1H), 6.91 (s, 1H), 7.04 (s, 1H), 7.66 (s, 2H), 7.71 (s, 1H), 8.36 (d, J=4.7 Hz, 2H).

c) N-[6-(N'-cyclopentylmethyl-N'-ethylamino)indan-5-ylmethyl]-N-[3,5-bis(trifluoromethyl)benzyl]-(pyrimidin-2-yl)amine hydrochloride In a similar manner as in Example 4, the title compound (50 mg) was obtained from N-[6-(N'-cyclopentylmethyl-N'-ethylamino)indan-5-ylmethyl]-N-[3,5-bis(trifluoromethyl)benzyl]-(pyrimidin-2-yl)amine (68 mg) obtained in Example 6b) (see Table 2).

Example 7

N-[6-(N'-cyclopentylmethyl-N'-ethylamino)indan-5-ylmethyl]-N-[3,5-bis(trifluoromethyl)benzyl]-(5-methyl-1H-pyrazol-3-yl)amine To a solution (20 ml) of N-cyclopentylmethyl-N-{6-[[3,5-bis(trifluoromethyl)benzylamino]methyl]indan-5-yl}-ethylamine (500 mg) obtained in Example 6 a) in dichloromethane was added diketene (85 μl) with stirring under ice-cooling. The reaction solution was stirred for 2 hr. The reaction solution was concentrated and a part (250 mg) of the obtained residue was dissolved in dimethoxyethane (0.7 ml) and methanesulfonic acid (0.56 ml) and then hydrazine hydrate (0.21 ml) were added dropwise with stirring under ice-cooling. The reaction solution was stirred at room temperature for 5 days and saturated aqueous sodium hydrogen carbonate was added. The mixture was extracted with ethyl acetate and washed successively with water and saturated brine. The organic layer was dried over sodium sulfate. Sodium sulfate was filtered off and the filtrate was concentrated. The obtained residue was purified using a preparative thin layer chromatography (TLC) plate (n-hexane:ethyl acetate=4:1) to give the title compound (58 mg) (see Table 2).

Example 8

5-{N-(6-{[N'-[3,5-bis(trifluoromethyl)benzyl]-N'-(5-methyl-[1,2,4]oxadiazol-3-yl)amino]methyl} indan-5-yl)-N-ethylamino}pentanoic acid hydrochloride a) methyl 5-[N-(6-{[N'-[3,5-bis(trifluoromethyl)benzyl]-N'-(5-methyl-[1,2,4]oxadiazol-3-yl)amino]methyl} indan-5-yl)-N-ethylamino]pentanoate To a suspension (10 ml) of methyl 5-(N-{6-[N'-(3,5-bis(trifluoromethyl)benzylamino)methyl]indan-5-yl}-N-ethylamino)pentanoate (500 mg) obtained in a similar manner as in Example 6 a) and sodium hydrogen carbonate (160 mg) in methanol was added cyanogen bromide (165 mg) with stirring at room temperature and the stirring was continued for 2 hr.

The reaction solution was diluted with ethyl acetate and washed successively with water and saturated brine. The organic layer was dried over sodium sulfate. Sodium sulfate was filtered off and the filtrated was concentrated. The obtained residue was dissolved in 1,4-dioxane (5 ml). Thereto was added aqueous hydroxylamine solution (50%, 0.14 ml) and the mixture was stirred at room temperature for 5 hr. The reaction solution was concentrated and the obtained residue was dissolved in pyridine (10 ml). Acetyl chloride (0.1 ml) was added with stirring under ice-cooling. The stirring was continued at room temperature for 30 min, and at 130° C. for 3 hr. The reaction solution was concentrated and the obtained residue was purified by column chromatography (n-hexane: ethyl acetate=4:1) to give the title compound (178 mg, 31%).

$^1$HNMR (CDCl$_3$, 300 MHz) δ: 0.88 (t, J=7.0 Hz, 3H), 1.25-1.60 (m, 4H), 1.95-2.10 (m, 2H), 2.20 (t, J=7.3 Hz, 2H), 2.49 (s, 3H), 2.70-2.90 (m, 8H), 4.56 (s, 2H), 4.72 (s, 2H), 6.99 (s, 1H), 7.02 (s, 1H), 7.65 (s, 2H), 7.72 (s, 1H).

b) 5-{N-(6-{[N'-[3,5-bis(trifluoromethyl)benzyl]-N'-(5-methyl-[1,2,4]oxadiazol-3-yl)amino]methyl}indan-5-yl)-N-ethylamino}pentanoic acid hydrochloride To a solution (5 ml) of methyl 5-[N-(6-{[N'-[3,5-bis(trifluoromethyl)benzyl]-N'-(5-methyl-[1,2,4]oxadiazol-3-yl)amino]methyl}indan-5-yl)-N-ethylamino]pentanoate (178 mg) obtained in Example 8 a) in tetrahydrofuran-methanol (THF-MeOH 4:1) was added aqueous sodium hydroxide solution (4N, 2 ml) with stirring at room temperature. The reaction solution was stirred overnight and water was added. The mixture was extracted with ethyl acetate and the extract was washed successively with water and saturated brine. The organic layer was dried over sodium sulfate and sodium sulfate was filtered off. The filtrate was concentrated and the obtained residue was purified by column chromatography (n-hexane:ethyl acetate=2:1). To a solution (7 ml) of the obtained compound in n-hexane was added dropwise 1N hydrochloric acid-diethyl ether (0.3 ml) with stirring at room temperature. The precipitated solid was collected by filtration and dried to give the title compound (158 mg, 86%) (see Table 2).

Example 9 methyl trans-4-{[N-(2-[{N'-[3,5-bis(trifluoromethyl)benzyl]-N'-(2-methyl-2H-tetrazol-5-yl)amino]methyl}-4-trifluoromethoxyphenyl)-N-ethylamino]methyl}cyclohexanecarboxylate a) 5-{[3,5-bis(trifluoromethyl)benzyl]amino}-2-methyl-2H-tetrazole A solution (70 ml) of 3,5-bis(trifluoromethyl)benzaldehyde (6.71 g) and 5-amino-2-methyltetrazole (3.30 g) in toluene was heated under reflux for 4 hr. The reaction solution was concentrated and the obtained residue was dissolved in ethanol (70 ml), and sodium borohydride (2.10 g) was added with stirring at room temperature. The reaction solution was stirred at room temperature for 30 min, and saturated aqueous ammonium chloride was added. The mixture was extracted with ethyl acetate. The extract was washed successively with water and saturated brine. The organic layer was dried over sodium sulfate and sodium sulfate was filtered off. The filtrate was concentrated and the obtained residue was recrystallized from isopropanol-water (3:7, 50 ml) to give the title compound.

$^1$HNMR (CDCl$_3$, 300 MHz) δ: 4.16 (s, 3H), 4.66 (d, J=6.3 Hz2H), 4.92 (brs, 1H), 7.79 (s, 1H), 7.83 (s, 2H).

b) methyl trans-4-{[N-(2-{[N'-[3,5-bis(trifluoromethyl)benzyl]-N'-(2-methyl-2H-tetrazol-5-yl)amino]methyl}-4-trifluoromethoxyphenyl)-N-ethylamino]methyl}cyclohexanecarboxylate To a solution (5 ml) of methyl trans-4-{[N-ethyl-N-(2-hydroxymethyl-4-trifluoromethoxyphenyl)amino]methyl}cyclohexylcarboxylate (330 mg) in chloroform was added thionyl chloride (0.074 ml) with stirring under ice-cooling, and the stirring was continued for 10 min. The reaction solution was treated with aqueous sodium hydrogen carbonate, extracted with ethyl acetate and washed successively with water and saturated brine. The organic layer was dried over sodium sulfate and sodium sulfate was filtered off. The filtrate was concentrated and the obtained residue was dissolved in DMF (3 ml). This solution was added dropwise to a solution (3 ml) of 5-[[3,5-bis(trifluoromethyl)benzyl]amino]-2-methyl-2H-tetrazole (331 mg) obtained in Example 9 a) and sodium hydride (51 mg) in DMF with stirring at room temperature. The stirring was continued for 15 min and saturated aqueous ammonium chloride was added. The mixture was extracted with ethyl acetate. The extract was washed successively with water and saturated brine. The organic layer was dried over sodium sulfate and sodium sulfate was filtered off. The filtrate was concentrated and the obtained residue was purified by column chromatography (n-hexane:ethyl acetate=4:1) to give the title compound (366 mg, 62%) (see Table 2).

Example 169 ethyl trans-(4-{[N-(2-{[N'-[3,5-bis(trifluoromethyl)benzyl]-N'-(2-methyl-2H-tetrazol-5-yl)amino]methyl}-5-methyl-4-trifluoromethylphenyl)-N-ethylamino]methyl}cyclohexyl)acetate a) 2-fluoro-4-methyl-5-trifluoromethylbenzaldehyde To a suspension (200 ml) of 5-fluoro-2-iodotoluene (110.6 g) and copper iodide (76.2 g) in N-methylmorpholine was added dropwise methyl fluorosulfonyl(difluoro)acetate (150 g) with stirring at 120° C. over 2 hr. The stirring was continued at the same temperature for 3.5 hr and the reaction solution was distilled under atmospheric pressure to give a yellow liquid. This was diluted with hexane (300 ml) and washed with saturated brine. The organic layer was dried over sodium sulfate and sodium sulfate was filtered off. The obtained hexane solution was added dropwise over 1.5 hr to a mixture of tetrahydrofuran (300 ml) and 1.0 M solution (600 ml) of s-butyllithium in hexane, which had been cooled to −78° C. and stirred. The stirring was continued for 1 hr and N,N-dimethylformamide (57 ml) was added dropwise. After completion of the dropwise addition, 2N aqueous hydrochloric acid (600 ml) was added and the mixture was allowed to warm to room temperature. This was extracted with hexane and washed with water and saturated brine. The organic layer was dried over sodium sulfate and sodium sulfate was filtered off. The filtrate was concentrated to give the title compound (61.54 g, 52%).

$^1$HNMR (CDCl$_3$, 300 MHz) δ: 2.56 (s, 3H), 7.14 (d, J=10.7 Hz, 1H), 8.15 (d, J=6.8 Hz, 1H), 10.32 (s, 1H).

b) ethyl trans-8 {4-[(N-ethylamino)methyl]cyclohexyl}acetate b-1) trans-4-(ethoxycarbonylmethyl)cyclohexanecarboxylic acid To a solution (600 ml) of ethyl 4-oxocyclohexanecarboxylate (150 g) in ethanol was added sodium hydroxide (38.8 g) with stirring at room temperature. The reaction solution was stirred for 1 hr and ethyl diethylphosphonoacetate (192 ml) was added. To this reaction solution was added dropwise 21% sodium ethoxide/ethanol solution (363 ml) with stirring under ice-cooling over 1 hr. The stirring was continued for 1 hr and acetic acid (126 ml) was added. Then ammonium formate (111 g) and palladium carbon (5%, 15 g) were added and the mixture was stirred at 60° C. for 6 hr with heating. The reaction solution was allowed to return to room temperature and insoluble materials were filtered off through celite. The filtrate was concentrated and the obtained residue was diluted with ethyl acetate. The mixture was washed successively with 2N aqueous hydrochloric acid, water and saturated brine. The organic layer was dried over sodium sulfate and sodium sulfate was filtered off. The filtrate was concentrated to give a crudely purified product (180.4 g) of the title compound.

b-2) ethyl trans-[4-(N-ethylcarbamoyl)cyclohexyl]acetate

To a solution (200 ml) of the crudely purified product (180.4 g) of trans-4-(ethoxycarbonylmethyl)cyclohexanecarboxylic acid obtained in b-1) in tetrahydrofuran was added thionyl chloride (74 ml) with stirring at room temperature. The reaction solution was stirred for 3 hr and concentrated to give an acid chloride. A solution (80 ml) of the above-mentioned acid chloride in tetrahydrofuran was added dropwise to tetrahydrofuran (250 ml) and 70% aqueous ethylamine (250 ml) with stirring under ice-cooling. This reaction solution was stirred for 30 min and water (800 ml) was added. The mixture was extracted with ethyl acetate and the extract was washed successively with water and saturated brine. The organic layer was dried over sodium sulfate and sodium sulfate was filtered off. The filtrate was concentrated and the obtained residue was recrystallized from hexane-ethyl acetate to give the title compound (78.9 g, yield from ethyl 4-oxocyclohexanecarboxylate 37%).

$^1$HNMR (CDCl$_3$, 300 MHz) δ: 0.90-1.10 (m, 2H), 1.13 (t, J=7.3 Hz, 3), 1.25 (t, J=7.1 Hz, 3H), 1.40-1.60 (m, 2H), 1.72-1.95 (m, 5H), 1.99 (m, 1H), 2.19 (d, J=6.8 Hz, 2H), 3.28 (m, 2H), 4.13 (q, J=7.1 Hz, 2H), 5.39 (brs, 1H).

b-3) ethyl trans-8 {4-[(N-ethylamino)methyl]cyclohexyl}acetate

To a suspension (800 ml) of ethyl trans-[4-(N-ethylcarbamoyl)cyclohexyl]acetate (100 g) and sodium borohydride (75.2 g) in tetrahydrofuran was added dropwise acetic acid (114 ml) over 1 hr with stirring under reflux, and the reaction solution was further stirred for 2 hr. The reaction solution was quenched by dropwise addition of water (200 ml) with stirring under ice-cooling. 1.5N Aqueous sodium hydroxide (1000 ml) was added. The mixture was extracted with ethyl acetate and the extract was washed successively with water and saturated brine. The organic layer was dried over sodium sulfate and sodium sulfate was filtered off. The filtrate was concentrated and the obtained residue was dissolved in ethanol (500 ml). 4N Hydrochloric acid-ethyl acetate (125 ml) was added dropwise with stirring at room temperature, and the stirring was continued for 20 hr. The reaction mixture was diluted with ethyl acetate and washed successively with 2N aqueous sodium hydroxide, water and saturated brine. The organic layer was dried over sodium sulfate and sodium sulfate was filtered off. The filtrate was concentrated to give the title compound (81.9 g, 87%).

$^1$HNMR (CDCl$_3$, 300 MHz) δ: 0.82-1.08 (m, 4H), 1.10 (t, J=7.1 Hz, 3H), 1.25 (t, J=7.1 Hz, 3H), 1.37 (m, 1H), 1.66-1.88 (m, 5H), 1.99 (m, 1H), 2.18 (d, J=6.8 Hz, 2H), 2.44 (d, J=6.6 Hz, 2H), 2.62 (q, J=7.1 Hz, 2H), 4.12 (q, J=7.1 Hz, 2H).

c) ethyl trans-(4-{[N-(2-{[N'-[3,5-bis(trifluoromethyl)benzyl]-N'-(2-methyl-2H-tetrazol-5-yl)amino]methyl}-5-methyl-4-trifluoromethylphenyl)-N-ethylamino]methyl}cyclohexyl)acetate c-1) ethyl trans-(4-{[N-ethyl-N-(2-hydroxymethyl-5-methyl-4-trifluoromethylphenyl)amino]methyl}cyclohexyl)acetate p-toluenesulfonate A solution (470 ml) of 2-fluoro-4-methyl-5-trifluoromethylbenzaldehyde (47.03 g), ethyl trans-{4-[(N-ethylamino)methyl]cyclohexyl}acetate (57.05 g) and potassium carbonate (94.5 g) in toluene was heated under reflux for 48 hr. The reaction solution was allowed to return to room temperature and washed successively with water, aqueous potassium hydrogen sulfate and saturated brine. The organic layer was dried over magnesium sulfate and magnesium sulfate was filtered off. Ethanol (100 ml) was added to the obtained solution and sodium borohydride (4.31 g) was added with stirring at room temperature. The reaction solution was stirred for 1 hr and aqueous ammonium chloride (200 ml) was added to allow for partitioning. The organic layer was washed successively with water and saturated brine, and dried over sodium sulfate. Sodium sulfate was filtered off and the filtrate was concentrated. The obtained residue was dissolved in diethyl ether (1060 ml), and p-toluenesulfonic acid hydrate (43.4 g) was added with stirring at room temperature. The stirring was continued for 2 hr. The precipitated crystals were collected by filtration and dried to give the title compound (120 g, 32%).

$^1$HNMR (CDCl$_3$, 300 MHz) δ: 0.70-1.14 (m, 4H), 1.21 (t, J=7.1 Hz, 3H), 1.23 (t, J=7.1 Hz, 3H), 1.42 (m, 1H), 1.50-1.78 (m, 4H), 1.93 (m, 1H), 2.09 (d, J=6.7 Hz, 2H), 2.36 (s, 3H), 2.54 (s, 3H), 3.10-4.15 (m, 4H), 4.09 (q, J=7.1 Hz, 2H), 4.85-5.25 (m, 2H), 7.07 (d, J=8.0 Hz, 2H), 7.33 (s, 1H), 7.54 (s, 1H), 7.77 (d, J=8.0 Hz, 2H), 11.57 (brs, 1H).

c-2) ethyl trans-(4-{[N-(2-{[N'-[3,5-bis(trifluoromethyl)benzyl]-N'-(2-methyl-2H-tetrazol-5-yl)amino]methyl}5-methyl-4-trifluoromethylphenyl)-N-ethylamino]methyl}cyclohexyl)acetate A solution of ethyl trans-(4-{[N-ethyl-N-(2-hydroxymethyl-5-methyl-4-trifluoromethylphenyl)amino]methyl}cyclohexyl)acetate p-toluenesulfonate (120 g) and sodium hydrogen carbonate (32.3 g) in toluene-water (480-480 ml) was stirred at room temperature for 30 min and partitioned. The organic layer was washed successively with water and saturated brine and dried over magnesium sulfate. Magnesium sulfate was filtered off and the resulting solution was added dropwise to a solution (360 ml) of thionyl chloride (17.65 ml) in toluene with stirring under ice-cooling. The stirring was continued at room temperature for 30 min and pyridine (33 ml) was added to the reaction solution. The mixture was washed successively with water and saturated brine. The organic layer was dried over sodium sulfate and sodium sulfate was filtered off. The filtrate was concentrated and potassium t-butoxide (27.5 g) was added to a solution (900 ml) of the obtained residue and 5-{[3,5-bis(trifluoromethyl)benzyl]amino}-2-methyl-2H-tetrazole (69.7 g) obtained in Example 9 a) in N,N-dimethylformamide with stirring at room temperature. The stirring was continued for 2 hr and saturated aqueous ammonium chloride was added. The mixture was extracted with ethyl acetate and the extract was washed successively with water and saturated brine. The organic layer was dried over sodium sulfate and sodium sulfate was filtered off. The filtrate was concentrated and the obtained residue was purified by column chromatography (n-hexane:ethyl acetate=4:1) to give the title compound (118 g, 80%) (see Table 34).

Example 170 trans-(4-{[N-(2-{[N'-[3,5-bis(trifluoromethyl)benzyl]-N'-(2-methyl-2H-tetrazol-5-yl)amino]methyl}-5-methyl-4-trifluoromethylphenyl)-N-ethylamino]methyl}cyclohexyl)acetic acid To a solution (326 ml) of ethyl trans-(4-{[N-(2-{[N'-[3,5-bis(trifluoromethyl)benzyl]-N'-(2-methyl-2H-tetrazol-5-yl)amino]methyl}-5-methyl-4-trifluoromethylphenyl)-N-ethylamino]methyl}cyclohexyl)acetate (118 g) in ethanol was added 4N aqueous sodium hydroxide solution (163 ml) with stirring at room temperature. The reaction solution was stirred at 60° C. for 2 hr and aqueous citric acid was added with stirring under ice-cooling for neutralization. The mixture was extracted with ethyl acetate and the extract was washed successively with water and saturated brine. The organic layer was dried over sodium sulfate and sodium sulfate was filtered off. The filtrate was concentrated. The obtained residue was purified by column chromatography (n-hexane:ethyl acetate=2:1) to give the title compound (104 g, 92%) (see Table 34).

Example 142 trans-(4-{[N-(2-{[N'-[3,5-bis(trifluoromethyl)benzyl]-N'-(2-methyl-2H-tetrazol-5-yl)amino]methyl}-5-methyl-4-trifluoromethylphenyl)-N-ethylamino]methyl}cyclohexyl)acetic acid hydrochloride To a solution (1.5 ml) of trans-(4-{[N-(2-{[N'-[3,5-bis(trifluoromethyl)benzyl]-N'-(2-methyl-2H-tetrazol-5-yl)amino]methyl}-5-methyl-4-trifluoromethylphenyl)-N-ethylamino]methyl}cyclohexyl)acetic acid (130 mg) in ether was added 1N hydrochloric acid-ether (0.20 ml) with stirring at room temperature. The precipitated solid was collected by filtration and dried to give the title compound (128 mg, 94%) (see Table 29).

Example 168 trans-(4-{[N-(2-{[N'-[3,5-bis(trifluoromethyl)benzyl]-N'-(2-methyl-2H-tetrazol-5-yl)amino]methyl}-5-methyl-4-trifluoromethylphenyl)-N-ethylamino]methyl}cyclohexyl)acetic acid methanesulfonate To a solution (580 ml) of trans-(4-{[N-(2-{[N'-[3,5-bis(trifluoromethyl)benzyl]-N'-(2-methyl-2H-tetrazol-5-yl)amino]methyl}-5-methyl-4-trifluoromethylphenyl)-N-ethylamino]methyl}cyclohexyl)acetic acid (96.3 g) in ethyl acetate was added methanesulfonic acid (13.56 ml) with stirring at room temperature. The stirring was continued for 15 hr and the precipitated solid was collected by filtration and dried to give an ethyl acetate solvate of methanesulfonate. This was suspended in heptane-ethyl acetate (3:1, 990 ml) and the suspension was stirred with heating at 80° C. for 20 hr, allowed to return to room temperature, filtered and dried to give the title compound (91.0 g, 83%) (see Table 34).

In a similar manner as in Examples 1-9, 142, 168, 169 and 170, the compounds of Examples 10-141 and 143-167 were obtained. These are shown in Tables 1-34 together with Examples 1-9, 142, 168, 169 and 170.

TABLE 1

| Example | Structural Formula | NMR (δ value, 300 MHz) |
|---|---|---|
| 1 | 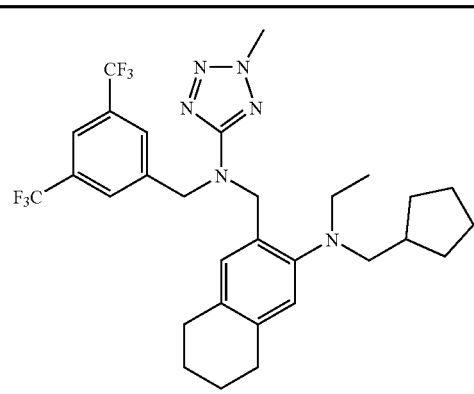
m.p. 98-100 | CDCl3:<br>0.90 (t, J = 7.0 Hz, 3H), 0.98-1.10 (m, 2H), 1.32-1.60 (m, 6H), 1.67-1.82 (m, 4H), 1.90 (m, 1H), 2.53-2.63 (m, 2H), 2.64-2.77 (m, 2H), 2.74 (d, J = 7.5 Hz, 2H), 2.81 (q, J = 7.0 Hz, 2H), 4.17 (s, 3H), 4.67 (s, 2H), 4.82 (s, 2H), 6.79 (s, 1H), 6.82 (s, 1H), 7.65 (s, 2H), 7.72 (s, 1H) |

TABLE 1-continued
| Example | Structural Formula | NMR (δ value, 300 MHz) |
|---|---|---|
| 2 | 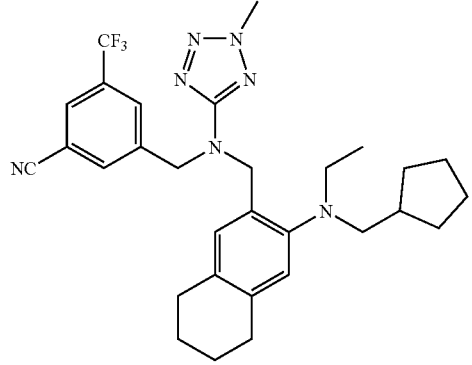 m.p. 116-119 | CDCl3: 0.91 (t, J = 7.0 Hz, 3H), 0.98-1.14 (m, 2H), 1.33-1.62 (m, 6H), 1.68-1.82 (m, 4H), 1.92 (m, 1H), 2.51-2.62 (m, 2H), 2.65-2.77 (m, 2H), 2.76 (d, J = 7.5 Hz, 2H), 2.83 (q, J = 7.0 Hz, 2H), 4.18 (s, 3H), 4.63 (s, 2H), 4.81 (s, 2H), 6.78 (s, 1H), 6.83 (s, 1H), 7.64 (s, 1H), 7.66 (s, 1H), 7.74 (s, 1H) |
| 3 | 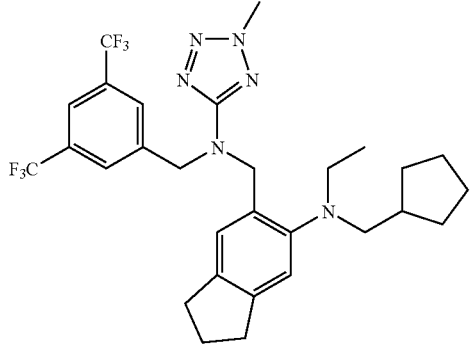 | DMSO-d6: 0.81 (t, J = 6.9 Hz, 3H), 0.90-1.10 (m, 2H), 1.20-1.53 (m, 6H), 1.80 (m, 1H), 1.96 (m, 2H), 2.60-2.90 (m, 8H), 4.17 (s, 3H), 4.75 (s, 2H), 4.76 (s, 2H), 6.91 (s, 1H), 7.07 (s, 1H), 7.83 (s, 2H), 7.97 (s, 1H) |
| 4 | 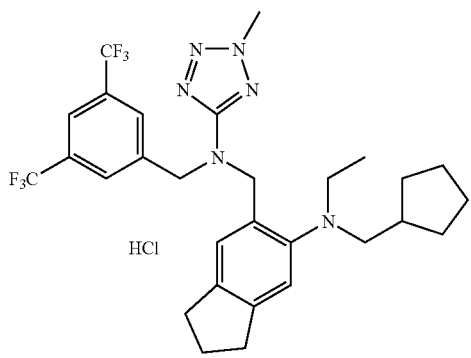 HCl | DMSO-d6: 0.70-1.10 (m, 4.5H), 1.15-1.70 (m, 6.5H), 1.70-2.14 (m, 3H), 2.58-3.00 (m, 6H), 3.35-4.00 (m, 2H), 4.16 (s, 3H), 4.76 (brs, 2H), 4.75-5.10 (m, 2H), 6.91 (brs, 0.5H), 7.07 (brs, 1H), 7.62-8.10 (m, 3.5H) |
| 5 | 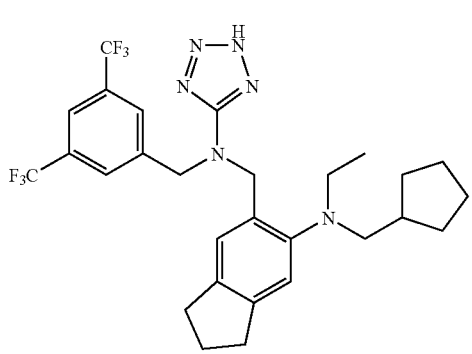 | CDCl3: 1.06 (t, J = 7.2 Hz, 3H), 1.00-1.25 (m, 2H), 1.32-1.69 (m, 4H), 1.71-1.90 (m, 2H), 2.06 (m, 2H), 2.19 (m, 1H), 2.76 (t, J = 7.3 Hz, 2H), 2.88 (t, J = 7.4 Hz, 2H), 2.98 (d, J = 6.8 Hz, 2H), 3.26 (q, J = 7.2 Hz, 2H), 4.38 (s, 2H), 5.04 (s, 2H), 6.85 (s, 1H), 7.10 (s, 1H), 7.74 (s, 2H), 7.81 (s, 1H) |

TABLE 2
| Example | Structural Formula | NMR (δ value, 300 MHz) |
|---|---|---|
| 6 | 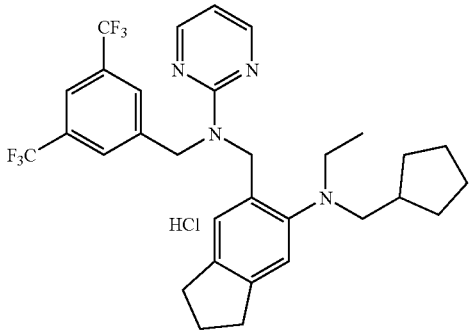<br>m.p. 83-85 | DMSO-d6:<br>0.83 (t, J = 6.9 Hz, 3H), 0.92-1.23 (m, 2H), 1.23-1.60 (m, 6H),<br>1.86 (m, 1H), 2.01 (m, 2H),<br>2.76 (t, J = 7.3 Hz, 2H), 2.87 (t, J = 7.4 Hz, 2H), 3.00-3.80 (m, 4H), 5.01 (s, 2H),<br>5.08 (s, 2H), 6.83 (t, J = 4.7 Hz, 1H)<br>7.09 (s, 1H), 7.52 (brs, 1H), 7.83 (s, 2H),<br>7.96 (s, 1H), 8.50 (d, J = 4.7 Hz, 2H) |
| 7 | 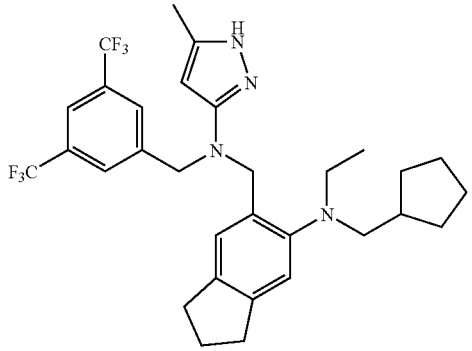 | CDCl3:<br>0.90 (t, J = 7.1 Hz, 3H), 1.00-1.15 (m, 2H), 1.30-1.60 (m, 6H), 1.88 (m, 1H), 2.04 (m, 2H), 2.22 (s, 1H), 2.70-2.91 (m, 8H), 4.55 (s, 2H), 4.59 (s, 2H), 5.37 (s, 1H), 7.03 (s, 1H), 7. 12 (s, 1H), 7.71 (s, 3H) |
| 8 | 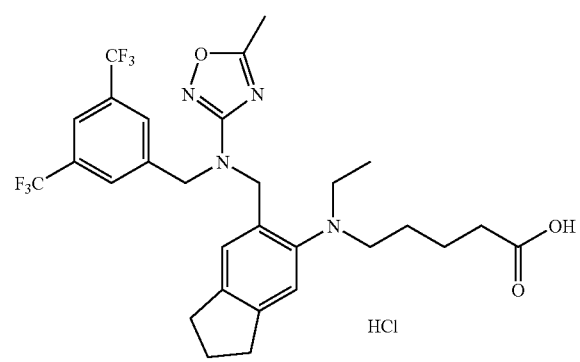 | DMSO-d6:<br>0.65-1.05 (m, 5H), 1.05-1.70 (m, 4H),<br>1.83-2.20 (m, 4H), 2.60-3.00 (m, 4H),<br>2.46 (s, 3H), 3.00-4.20 (m, 4H),<br>4.50-5.10 (m, 4H), 6.80-8.10 (m, 5H) |
| 9 | 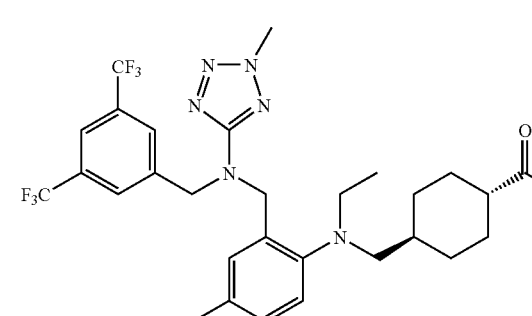 | CDCl3:<br>0.70-0.85 (m, 2H), 0.89 (t, J = 7.2 Hz, 3H), 1.10-1.50 (m, 3H), 1.67-1.90 (m, 4H), 2.15 (m, 1H), 2.69 (d, J = 7.2 Hz, 2H), 2.83 (q, J = 7.2 Hz, 2H), 3.64 (s, 3H), 4.20 (s, 3H), 4.68 (s, 2H), 4.83 (s, 2H), 6.96 (s, 1H), 7.06 (d, J = 8.8 Hz, 1H), 7.13 (d, J = 8.8 Hz, 1H), 7.65 (s, 2H), 7.75 (s, 1H) |

TABLE 2-continued

| Example | Structural Formula | NMR (δ value, 300 MHz) |
| --- | --- | --- |
| 10 | 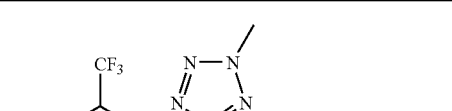 | CDCl3:<br>0.91 (t, J = 6.9 Hz, 3H), 0.95-1.18 (m, 2H),<br>1.30-1.60 (m, 6H), 1.92 (m, 1H),<br>2.04 (m, 2H), 2.70-2.92 (m, 8H),<br>4.19 (s, 3H), 4.64 (s, 2H), 4.85 (s, 2H),<br>6.96 (s, 1H), 7.04 (s, 1H),<br>7.66 (s, 2H), 7.75 (s, 1H) |

TABLE 3

| Example | Structural Formula | NMR (δ value, 300 MHz) |
| --- | --- | --- |
| 11 | 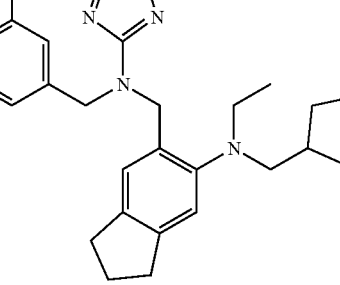 | CDCl3:<br>0.90 (t, J = 6.9 Hz, 3H), 0.95-1.15 (m, 2H),<br>1.30-1.62 (m, 6H), 1.59 (t, J = 7.2 Hz,<br>3H), 1.91 (m, 1H), 2.03 (m, 2H), 2.75 (d,<br>J = 7.5 Hz, 2H), 2.70-2.93 (m, 6H),<br>4.48 (q, J = 7.2 Hz, 2H), 4.66 (s, 2H),<br>4.86 (s, 2H), 6.99 (s, 1H), 7.04 (s, 1H),<br>7.66 (s, 2H), 7.71 (s, 1H) |
| 12 | 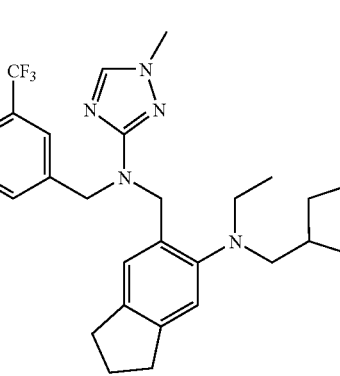 | CDCl3:<br>0.88 (t, J = 7.0 Hz, 3H), 0.95-1.10 (m, 2H),<br>1.30-1.56 (m, 6H), 1.90 (m, 1H),<br>2.02 (m, 2H), 2.68-2.88 (m, 8H),<br>3.76 (s, 3H), 4.63 (s, 2H), 4.81 (s, 2H),<br>7.00 (s, 1H), 7.04 (s, 1H),<br>7.67 (s, 2H), 7.69 (s, 1H) |
| 13 | 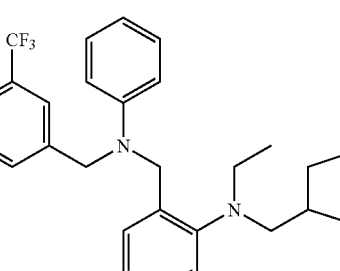 | CDCl3:<br>0.75-0.95 (m, 1H), 0.95 (t, J = 7.0 Hz, 3H),<br>1.00-1.20 (m, 2H), 1.30-1.60 (m, 5H),<br>1.80-2.10 (m, 3H), 2.70-2.93 (m, 8H),<br>4.65 (s, 2H), 4.70 (s, 2H), 6.67 (d, J = 8.2<br>Hz, 2H), 6.76 (t, J = 7.2 Hz, 1H),<br>7.04 (s, 1H), 7.09 (s, 1H), 7.20 (dd, J =<br>7.2, 8.2 Hz, 2H), 7.72 (s, 2H), 7.79 (s, 1H) |

TABLE 3-continued

| Example | Structural Formula | NMR (δ value, 300 MHz) |
|---|---|---|
| 14 | | DMSO-d6:<br>0.84 (t, J = 6.9 Hz, 3H), 0.92-1.12 (m, 2H), 1.25-1.58 (m, 6H), 1.83 (m, 1H), 1.97 (m, 2H), 2.04 (s, 3H), 2.13 (s, 3H), 2.62-2.90 (m, 8H), 4.64 (s, 2H), 4.76 (s, 2H), 6.91 (s, 1H), 7.09 (s, 1H), 7.91 (s, 1H), 7.93 (s, 1H), 8.31 (s, 1H) |
| 15 | | DMSO-d6:<br>0.79 (t, J = 6.9 Hz, 3H), 1.02-1.12 (m, 2H), 1.27-1.62 (m, 6H), 1.86-2.05 (m, 3H), 2.75 (t, J =7.3 Hz, 2H), 2.87 (t, J = 7.3 Hz, 2H), 3.00-3.70 (m, 4H), 4.92 (s, 2H), 5.02 (s, 2H), 6.90 (d, J = 3.5 Hz, 1H), 7.17 (s, 1H), 7.34 (s, 1H) 7.50 (brs, 1H), 7.83 (s, 1H), 8.00 (s, 1H) |

TABLE 4

| Example | Structural Formula | NMR (δ value, 300 MHz) |
|---|---|---|
| 16 | | DMSO-d6:<br>0.80 (t, J = 6.9 Hz, 3H), 1.00-1.25 (m, 2H), 1.27-1.63 (m, 6H), 1.80-2.10 (m, 3H), 2.78 (t, J = 7.3 Hz, 2H), 2.88 (t, J = 7.3 Hz, 2H), 3.00-3.70 (m, 4H), 4.92 (brs, 2H), 4.96 (s, 2H), 6.91 (d, J = 3.7 Hz, 1H), 7.20 (brs, 1H), 7.35 (d, J = 3.7 Hz, 1H), 7.54 (brs, 1H), 7.83 (s, 1H), 8.00 (s, 1H) 8.28 (s, 1H) |
| 17 | | DMSO-d6:<br>0.81 (t, J = 7.0 Hz, 3H), 0.95-1.18 (m, 2H), 1.20-1.60 (m, 6H), 1.75-2.10 (m, 3H), 2.75 (t, J = 7.4 Hz, 2H), 2.84 (t, J = 7.4 Hz, 2H), 2.90-3.35 (m, 4H), 4.79 (s, 2H), 4.87 (s, 2H), 7.04 (s, 1H), 7.09 (s, 1H), 7.36 (brs, 1H), 7.65 (s, 1H), 7.86 (s, 2H) 7.99 (s, 1H) |

TABLE 4-continued

| Example | Structural Formula | NMR (δ value, 300 MHz) |
|---|---|---|
| 18 | 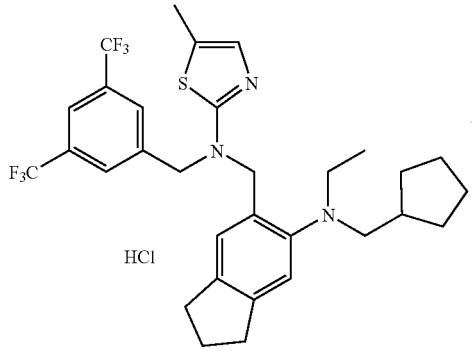 | DMSO-d6:<br>0.78 (t, J = 6.9 Hz, 3H), 1.00-1.25 (m, 2H), 1.25-1.70 (m, 6H), 1.85-2.10 (m, 3H), 2.25 (s, 3H), 2.75 (t, J = 7.3 Hz, 2H), 2.88 (t, J = 7.3 Hz, 2H), 3.16-3.62 (m, 4H), 4.89 (s, 2H), 4.99 (s, 2H), 7.07 (s, 1H), 7.19 (s, 1H), 7.53 (brs, 1H), 7.82 (s, 2H), 8.02 (s, 1H) |
| 19 | 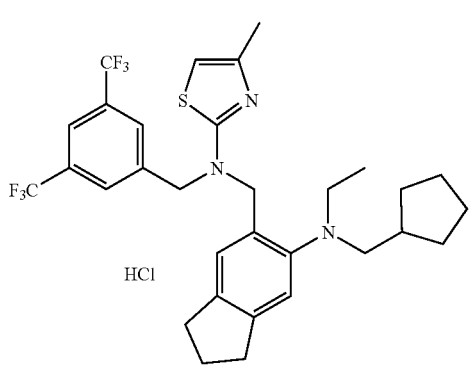 | DMSO-d6:<br>0.80 (t, J = 6.9 Hz, 3H), 0.95-1.20 (m, 2H), 1.20-1.60 (m, 6H), 1.85 (m, 1H), 2.02 (m, 2H), 2.24 (s, 3H), 2.77 (t, J = 7.5 Hz, 2H), 2.88 (t, J = 7.5 Hz, 2H), 3.10-3.60 (m, 4H), 4.92 (s, 2H), 4.99 (s, 2H), 6.50 (s, 1H), 7.17 (s, 1H), 7.57 (brs, 1H), 7.88 (s, 2H), 8.02 (s, 1H) |
| 20 | 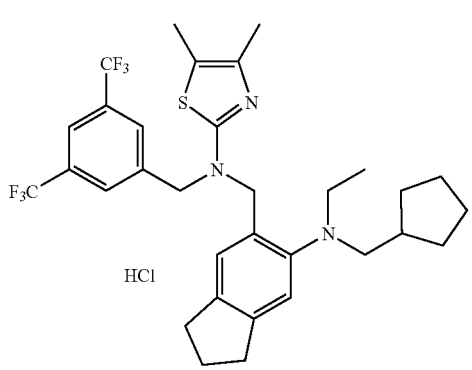 | DMSO-d6:<br>0.79 (t, J = 7.2 Hz, 3H), 0.97-1.20 (m, 2H), 1.20-1.60 (m, 6H), 1.85 (m, 1H), 2.02 (m, 2H), 2.17 (s, 6H), 2.77 (t, J = 7.5 Hz, 2H), 2.87 (t, J = 7.5 Hz, 2H), 3.05-3.60 (m, 4H), 4.90 (s, 2H), 4.98 (s, 2H), 7.15 (s, 1H), 7.54 (brs, 1H), 7.89 (s, 2H), 8.03 (s, 1H) |

TABLE 5

| Example | Structural Formula | NMR (δ value, 300 MHz) |
|---|---|---|
| 21 | 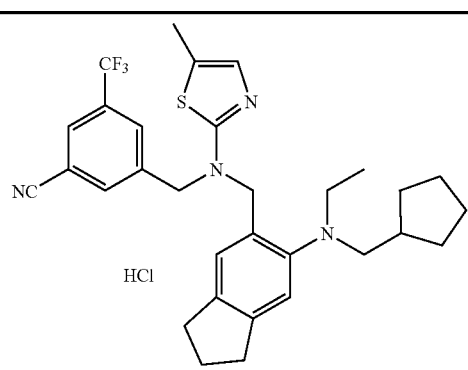 | DMSO-d6:<br>0.80 (t, J = 6.9 Hz, 3H), 1.00-1.25 (m, 2H), 1.30-1.65 (m, 6H), 1.82-2.10 (m, 3H), 2.25 (s, 3H), 2.78 (t, J = 7.5 Hz, 2H), 2.88 (t, J = 7.5 Hz, 2H), 3.10-3.60 (m, 4H), 4.88 (s, 2H), 4.92 (s, 2H), 7.06 (s, 1H), 7.20 (s, 1H), 7.52 (brs, 1H), 7.83 (s, 1H), 7.99 (s, 1H), 8.27 (s, 1H) |

TABLE 5-continued
| Example | Structural Formula | NMR (δ value, 300 MHz) |
|---|---|---|
| 22 | 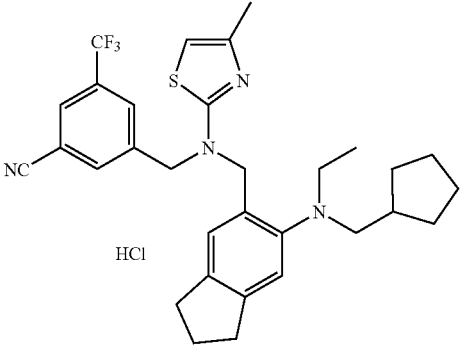 | DMSO-d6:<br>0.82 (t, J = 6.9 Hz, 3H), 0.97-1.20 (m, 2H),<br>1.25-1.60 (m, 6H), 1.84 (m, 1H),<br>2.03 (m, 2H), 2.38 (s, 3H), 2.80 (t,<br>J = 7.5 Hz, 2H), 2.88 (t, J = 7.5 Hz, 2H),<br>3.00-3.60 (m, 4H), 4.91 (s, 4H),<br>6.50 (s, 1H), 7.17 (s, 1H), 7.53 (brs, 1H),<br>7.88 (s, 1H), 8.02 (s, 1H), 8.28 (s, 1H) |
| 23 | 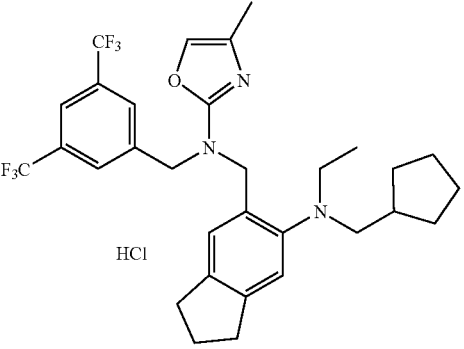 | DMSO-d6:<br>0.80 (t, J = 6.9 Hz, 3H), 0.95-1.15 (m, 2H),<br>1.20-1.60 (m, 6H), 1.85 (m, 1H),<br>2.00 (m, 2H), 2.03 (s, 3H), 2.76 (t,<br>J = 7.3 Hz, 2H), 2.84 (t, J = 7.4 Hz, 2H),<br>2.90-4.00 (m, 4H), 4.76 (s, 2H), 4.84<br>(s, 2H), 7.10 (s, 1H), 7.39 (m, 2H),<br>7.86 (s, 2H), 8.00 (s, 1H) |
| 24 | 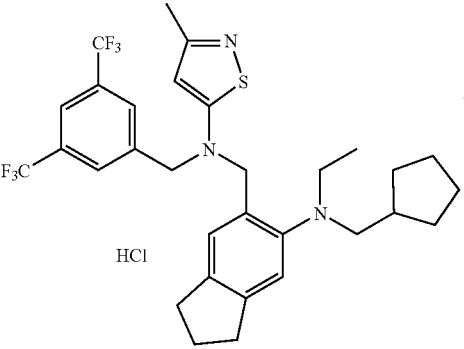 | DMSO-d6:<br>0.70-1.15 (m, 5H), 1.20-1.63 (m, 6H),<br>1.73-2.12 (m, 3H), 2.18 (s, 3H),<br>2.56-3.00 (m, 6H), 3.25-4.00 (m, 2H),<br>4.50-5.00 (m, 4H), 6.20 (s, 1H),<br>6.97 (brs, 1H), 7.11 (brs, 1H),<br>7.60-8.10 (m, 3H) |
| 25 | 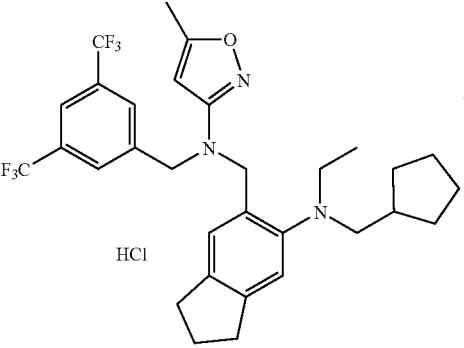 | DMSO-d6:<br>0.70-1.15 (m, 5H), 1.20-1.70 (m, 6H),<br>1.71-2.13 (m, 3H), 2.27 (s, 3H),<br>2.55-3.00 (m, 6H), 3.20-4.00 (m, 2H),<br>4.40-5.00 (m, 4H), 6.02 (brs, 1H),<br>6.83-7.35 (m, 2H), 7.85 (s, 2H),<br>7.98 (s, 1H) |

TABLE 6
| Example | Structural Formula | NMR (δ value, 300 MHz) |
|---|---|---|
| 26 | 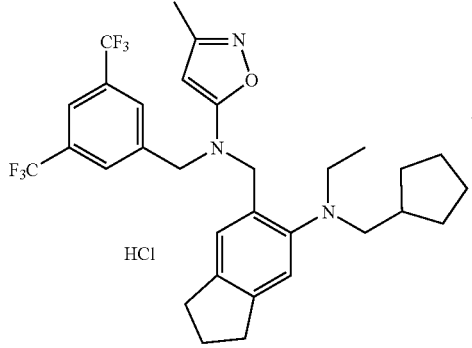 | CDCl3:<br>0.70-1.07 (m, 4.5H), 1.18-1.80 (m, 6.5H), 1.82-2.10 (m, 3H), 2.17 (s, 3H), 2.80-3.00 (m, 4H), 3.00-3.35 (m, 2H), 3.45-4.05 (m, 2H), 4.79 (s, 1H), 4.65-5.70 (m, 4H), 7.03 (s, 1H), 7.32 (brs, 1H), 7.65 (s, 2H), 7.70 (s, 1H) |
| 27 | 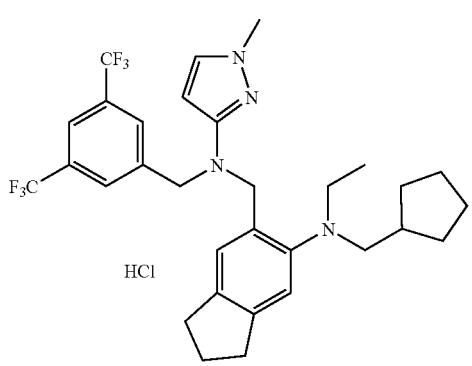 | CDCl3:<br>1.05 (m, 3H), 1.20-1.80 (m, 8H), 2.00 (m, 1H), 2.13 (m, 2H), 2.80-3.30 (m, 4H), 3.10-4.00 (m, 4H), 3.93 (s, 3H), 4.90 (s, 2H), 5.24 (brs, 2H), 5.46 (d, J = 3.3 Hz, 1H), 7.10 (brs, 1H), 7.23 (d, J = 3.3 Hz, 1H), 7.34 (s, 1H), 7.70 (s, 1H), 7.74 (s, 2H) |
| 28 | 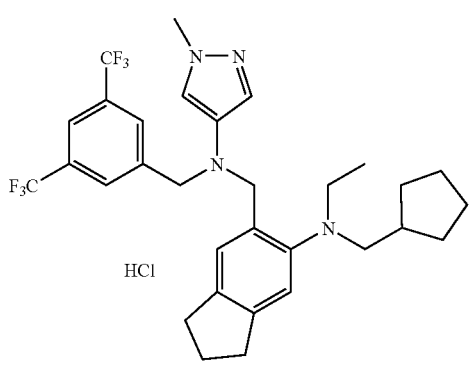 | DMSO-d6:<br>0.93 (m, 3H), 1.10-1.60 (m, 8H), 1.84 (m, 1H), 2.04 (m, 2H), 2.60-3.00 (m, 4H), 3.56 (m, 2H), 3.67 (s, 3H), 4.49 (m, 2H), 4.52 (s, 2H), 5.15 (m, 2H), 7.06 (s, 1H), 7.21 (s, 1H), 7.30 (brs, 1H), 7.71 (brs, 1H), 7.96 (s, 3H) |
| 29 | 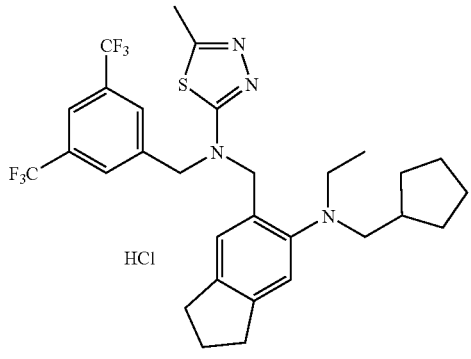 | DMSO-d6:<br>0.85 (t, J = 6.9 Hz, 3H), 1.02-1.20 (m, 2H), 1.30-1.62 (m, 6H), 1.84-2.06 (m, 3H), 2.50 (s, 3H), 2.74 (t, J = 7.3 Hz, 2H), 2.86 (t, J = 7.3 Hz, 2H), 2.91-3.35 (m, 4H), 4.82 (s, 2H), 4.99 (s, 2H), 7.07 (s, 1H), 7.38 (brs, 2H), 7.89 (s, 2H), 8.01 (s, 1H) |

TABLE 6-continued

| Example | Structural Formula | NMR (δ value, 300 MHz) |
|---|---|---|
| 30 | 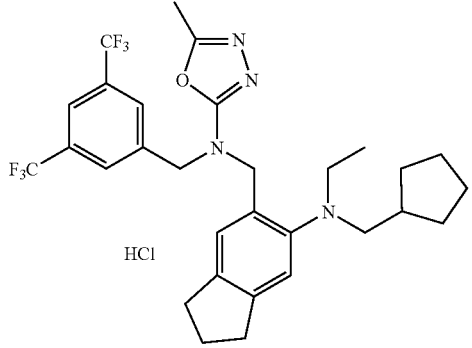 | DMSO-d6:<br>0.85 (t, J = 6.9 Hz, 3H), 0.90-1.15 (m, 2H),<br>1.24-1.56 (m, 6H), 1.82 (m, 1H),<br>2.00 (m, 2H), 2.33 (s, 3H), 2.77 (t,<br>J = 7.5 Hz, 2H), 2.84 (t, J = 7.5 Hz, 2H),<br>2.92-3.25 (m, 4H), 4.77 (s, 2H), 4.82<br>(s, 2H), 7.08 (s, 1H), 7.36 (brs, 1H),<br>7.92 (s, 2H), 8.01 (s, 1H) |

TABLE 7

| Example | Structural Formula | NMR (δ value, 300 MHz) |
|---|---|---|
| 31 | 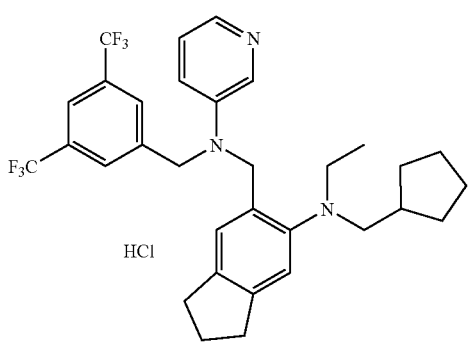 | CDCl3:<br>1.05 (m, 3H), 1.30-1.80 (m, 8H),<br>1.87-2.22 (m, 3H), 2.75-3.00 (m, 4H),<br>2.50-4.00 (m, 4H), 4.93 (s, 2H),<br>4.50-6.00 (m, 2H), 6.93 (brs, 1H),<br>7.15 (s, 1H), 7.45 (m, 1H), 7.60 (m, 1H),<br>7.67 (s, 2H), 7.82 (s, 1H),<br>8.03-8.15 (m, 2H) |
| 32 | 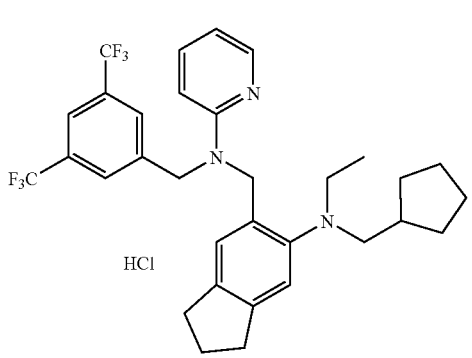 | CDCl3:<br>1.08 (t, J = 6.9 Hz, 3H), 1.00-1.80 (m, 8H),<br>1.96-2.20 (m, 3H), 2.87 (t, J = 7.5 Hz, 2H),<br>2.94 (t, J = 7.5 Hz, 2H), 3.20-3.90 (m, 4H),<br>5.37 (s, 2H), 5.70 (brs, 2H), 6.69 (m, 1H),<br>6.96 (m, 1H), 7.14 (s, 2H), 7.73 (s, 2H),<br>7.75 (s, 1H), 7.77 (m, 1H), 8.34 (m, 1H) |
| 33 | 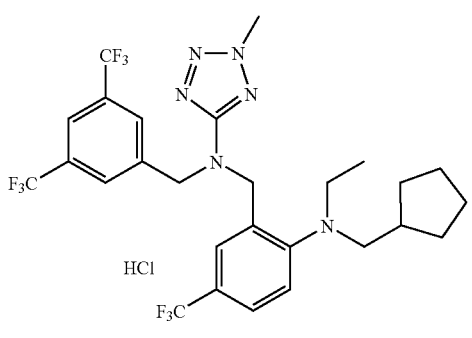 | CDCl3:<br>0.95-1.23 (m, 5H), 1.30-1.70 (m, 6H),<br>2.02 (m, 1H), 3.05-3.40 (m, 4H),<br>4.20 (s, 3H), 4.80 (s, 2H), 5.12 (s, 2H),<br>7.30 (m, 1H), 7.45 (s, 1H), 7.56 (m, 1H),<br>7.70 (s, 1H), 7.76 (s, 2H) |

TABLE 7-continued

| Example | Structural Formula | NMR (δ value, 300 MHz) |
|---|---|---|
| 34 | 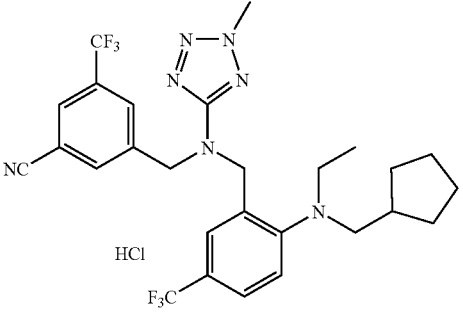 | CDCl3:<br>0.90-1.25 (m, 5H), 1.30-1.75 (m, 6H),<br>2.00 (m, 1H), 3.05-3.45 (m, 4H),<br>4.19 (s, 3H), 4.86 (s, 2H), 5.13 (s, 2H),<br>7.30 (m, 1H), 7.47 (s, 1H), 7.56 (m, 1H),<br>7.71 (s, 2H), 7.73 (s, 1H) |
| 35 | 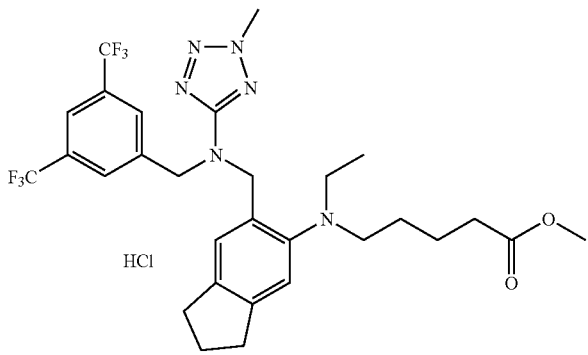 | CDCl3:<br>0.92-1.25 (m, 4H), 1.40-2.00 (m, 3H),<br>2.00-2.40 (m, 4H), 2.82 (t, J = 7.4 Hz, 2H),<br>2.93 (t, J = 7.2 Hz, 2H), 3.05-4.00 (m, 4H),<br>3.60 (s, 3H), 4.17 (s, 3H), 5.01 (brs, 2H),<br>5.39 (brs, 2H), 7.06 (brs, 1H),<br>7.25 (brs, 1H), 8.02 (s, 3H) |

TABLE 8

| Example | Structural Formula | NMR (δ value, 300 MHz) |
|---|---|---|
| 36 | 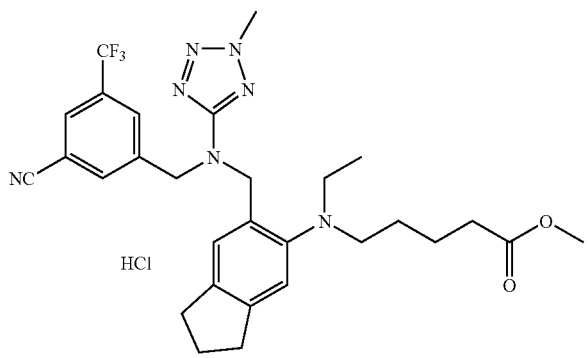 | CDCl3:<br>0.88 (m, 3H), 1.25 (m, 1H), 1.42-1.78 (m, 2H),<br>1.88 (m, 1H), 2.12 (m, 2H), 2.25 (m, 2H),<br>2.84 (t, J = 7.5 Hz, 2H), 2.94 (t, J = 7.4 Hz, 2H), 3.28 (m, 2H), 3.61 (s, 3H),<br>3.80 (m, 2H), 4.17 (s, 3H), 4.96 (s, 2H),<br>5.41 (brs, 2H), 7.06 (brs, 1H),<br>7.24 (brs, 1H), 7.71 (s, 2H), 7.77 (s, 1H) |
| 37 | 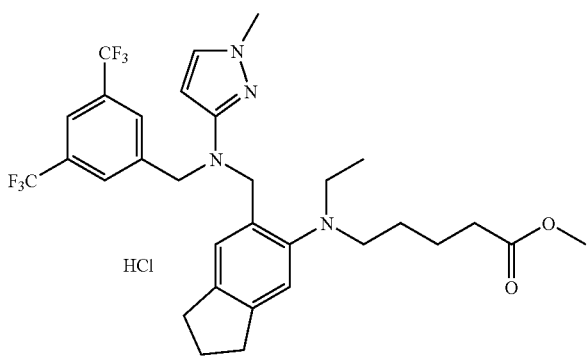 | CDCl3:<br>1.08 (m, 3H), 1.34-1.80 (m, 4H),<br>2.12 (m, 2H), 2.23 (m, 2H), 2.86 (t, J = 7.2 Hz, 2H), 2.94 (t, J = 7.1 Hz, 2H),<br>3.10-4.00 (m, 4H), 3.60 (s, 3H),<br>3.86 (s, 3H), 4.79 (brs, 2H), 5.09 (brs, 2H), 5.46 (s, 1H), 7.22 (s, 1H),<br>7.24 (brs, 1H), 7.30 (s, 1H), 7.70 (s, 1H),<br>7.73 (s, 2H) |

TABLE 8-continued

| Example | Structural Formula | NMR (δ value, 300 MHz) |
|---|---|---|
| 38 | 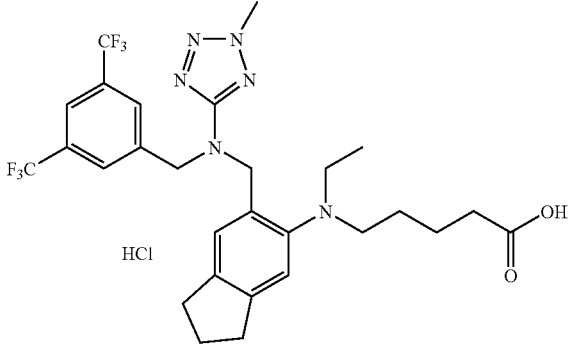 | CDCl3:<br>1.07 (m, 3H), 1.27 (m, 1H), 1.42-1.70 (m, 2H), 1.82 (m, 1H), 2.10 (m, 2H), 2.28 (t, J = 7.3 Hz, 2H), 2.81 (t, J = 7.3 Hz, 2H), 2.93 (t, J = 7.4 Hz, 2H), 3.10-3.45 (m, 2H), 3.50-4.00 (m, 2H), 4.17 (s, 3H), 4.99 (s, 2H), 5.33 (brs, 2H), 7.06 (brs, 1H), 7.21 (s, 1H), 7.70 (s, 3H) |
| 39 | 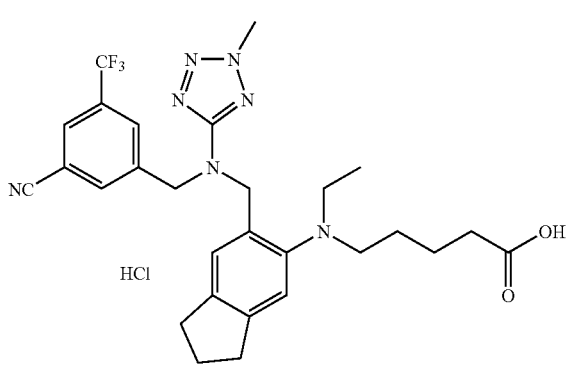 | CDCl3:<br>1.13 (m, 3H), 1.30 (m, 1H), 1.45-2.20 (m, 3H), 2.12 (m, 2H), 2.31 (t, J = 7.3 Hz, 2H), 2.84 (t, J = 7.4 Hz, 2H), 2.95 (t, J = 7.3 Hz, 2H), 3.10-4.00 (m, 4H), 4.17 (s, 3H), 4.94 (s, 2H), 5.35 (brs, 2H), 7.08 (brs, 1H), 7.21 (s, 1H), 7.73 (s, 2H), 7.79 (s, 1H) |
| 40 | 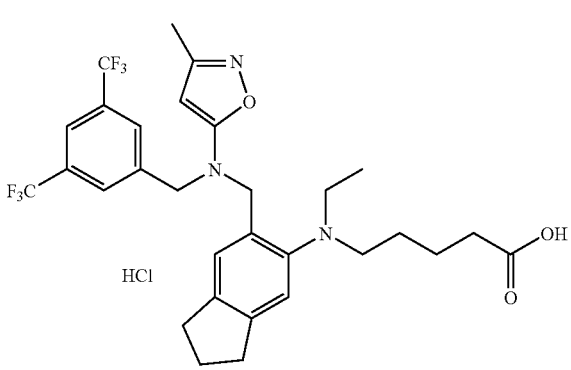 | CDCl3:<br>1.04 (brt, J = 6.6 Hz, 3H), 1.23 (m, 1H), 1.41-1.66 (m, 2H), 1.79 (m, 1H), 2.13 (m, 2H), 2.17 (s, 3H), 2.24 (t, J = 7.2 Hz, 2H), 2.87 (t, J = 7.3 Hz, 2H), 2.94 (t, J = 7.4 Hz, 2H), 3.00-4.00 (m, 4H), 4.82 (s, 1H), 4.84 (s, 2H), 5.22 (s, 2H), 7.07 (s, 1H), 7.26 (s, 1H), 7.67 (s, 2H), 7.70 (s, 1H) |

TABLE 9

| Example | Structural Formula | NMR (δ value, 300 MHz) |
|---|---|---|
| 41 | 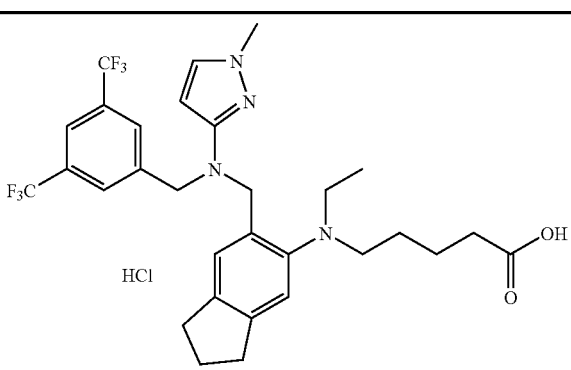 | CDCl3:<br>1.04 (brt, J = 6.6 Hz, 3H), 1.18-1.73 (m, 4H), 2.12 (m, 2H), 2.42 (m, 2H), 2.85 (t, J = 7.5 Hz, 2H), 2.98 (t, J = 7.0 Hz, 2H), 3.10-4.00 (m, 4H), 3.89 (s, 3H), 4.62 (s, 2H), 4.76 (s, 2H), 5.47 (d, J = 2.2 Hz, 1H), 7.07 (s, 1H), 7.30 (d, J = 2.2 Hz, 1H), 7.45 (brs, 1H), 7.66 (s, 2H), 7.74 (s, 1H) |

TABLE 9-continued

| Example | Structural Formula | NMR (δ value, 300 MHz) |
| --- | --- | --- |
| 42 | | DMSO-d6:<br>0.80 (t, J = 6.9 Hz, 3H), 0.80-0.97 (m, 2H),<br>1.02-1.20 (m, 2H), 1.34 (m, 1H),<br>1.58-1.80 (m, 8H), 2.13 (m, 1H), 2.56 (m, 2H), 2.71 (m, 2H), 2.90-3.70 (m, 4H),<br>3.55 (s, 3H), 3.73 (s, 3H), 4.58 (s, 2H),<br>4.69 (s, 2H), 5.63 (s, 1H), 6.97 (s, 1H),<br>7.30 (brs, 1H), 7.53 (s, 1H), 7.78 (s, 2H),<br>7.93 (s, 1H) |
| 43 | | DMSO-d6:<br>0.82 (t, J = 6.9 Hz, 3H), 0.80-1.00 (m, 2H),<br>1.04-1.22 (m, 2H), 1.36 (m, 1H),<br>1.60-1.84 (m, 8H), 2.16 (m, 1H), 2.58 (m, 2H), 2.72 (m, 2H), 2.90-3.70 (m, 4H),<br>3.56 (s, 3H), 3.73 (s, 3H), 4.58 (s, 2H),<br>4.62 (s, 2H), 5.61 (s, 1H), 6.99 (s, 1H),<br>7.30 (brs, 1H), 7.53 (s, 1H), 7.76 (s, 1H),<br>7.87 (s, 1H), 8.19 (s, 1H) |
| 44 | | DMSO-d6:<br>0.79 (t, J = 6.9 Hz, 3H), 0.80-1.01 (m, 2H),<br>1.03-1.21 (m, 2H), 1.37 (m, 1H),<br>1.60-1.84 (m, 8H), 2.04 (m, 1H), 2.55 (m, 2H), 2.71 (m, 2H), 3.00-3.60 (m, 4H),<br>3.74 (s, 3H), 4.59 (s, 2H),<br>4.70 (s, 2H), 5.63 (s, 1H), 6.97 (s, 1H),<br>7.32 (brs, 1H), 7.54 (s, 1H), 7.78 (s, 2H),<br>7.93 (s, 1H) |
| 45 | | DMSO-d6:<br>0.80 (t, J = 6.9 Hz, 3H), 0.80-1.01 (m, 2H),<br>1.04-1.21 (m, 2H), 1.37 (m, 1H),<br>1.60-1.85 (m, 8H), 2.05 (m, 1H), 2.58 (m, 2H), 2.72 (m, 2H), 3.00-3.60 (m, 4H),<br>3.74 (s, 3H), 4.59 (s, 2H),<br>4.63 (s, 2H), 5.62 (s, 1H), 7.00 (s, 1H),<br>7.33 (brs, 1H), 7.55 (s, 1H), 7.75 (s, 1H),<br>7.87 (s, 1H), 8.19 (s, 1H) |

TABLE 10

| Example | Structural Formula | NMR (δ value, 300 MHz) |
|---|---|---|
| 46 | 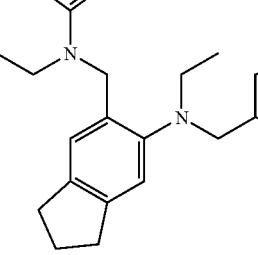 | CDCl3:<br>0.70-2.20 (m, 14H), 2.49 (brs, 3H),<br>2.60-4.20 (m, 8H), 4.40-6.00 (m, 4H),<br>6.70-7.50 (m, 2H), 7.68 (s, 3H) |
| 47 | 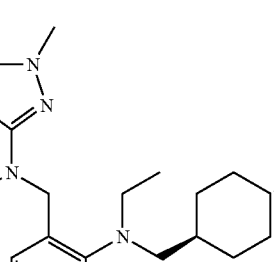 | DMSO-d6:<br>0.80 (t, J = 7.3 Hz, 3H), 0.70-1.00 (m, 2H),<br>1.00-1.20 (m, 2H), 1.34 (m, 1H),<br>1.60-1.80 (m, 4H), 1.99 (m, 2H),<br>2.12 (m, 1H), 2.73 (t, J = 7.4 Hz, 2H),<br>2.84 (t, J = 7.3 Hz, 2H), 2.90-3.70 (m, 4H),<br>3.54 (s, 3H), 3.69 (s, 3H), 4.58 (s, 2H),<br>4.66 (s, 2H), 5.58 (s, 1H), 7.12 (s, 1H),<br>7.36 (brs, 1H), 7.49 (s, 1H), 7.80 (s, 2H),<br>7.92 (s, 1H) |
| 48 | 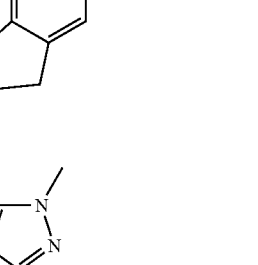 | DMSO-d6:<br>0.70-1.00 (m, 5H), 1.00-1.20 (m, 2H),<br>1.34 (m, 1H), 1.60-1.80 (m, 4H),<br>1.90-2.10 (m, 3H), 2.73 (t, J = 7.3 Hz, 2H),<br>2.85 (t, J = 7.4 Hz, 2H), 2.90-4.20 (m, 4H),<br>3.70 (s, 3H), 4.59 (s, 2H),<br>4.67 (s, 2H), 5.59 (s, 1H), 7.12 (s, 1H),<br>7.40 (brs, 1H), 7.50 (s, 1H), 7.80 (s, 2H),<br>7.92 (s, 1H) |
| 49 | 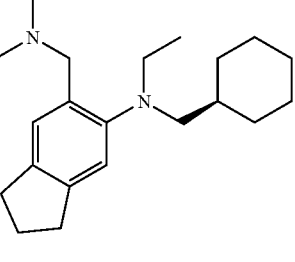 | CDCl3:<br>0.63-0.93 (m, 2H), 0.89 (t, J = 7.0 Hz, 3H),<br>1.12-1.42 (m, 3H),<br>1.70-1.93 (m, 4H), 2.04 (m, 2H),<br>2.14 (m, 1H), 2.68 (d, J = 7.3 Hz, 2H),<br>2.70-2.92 (m, 6H), 3.64 (s, 3H),<br>3.73 (s, 3H), 4.52 (s, 2H),<br>4.54 (s, 2H), 5.43 (s, 1H), 7.01 (s, 1H),<br>7.12 (s, 1H), 7.13 (s, 1H), 7.72 (s, 2H),<br>7.75 (s, 1H) |

TABLE 10-continued
| Example | Structural Formula | NMR (δ value, 300 MHz) |
|---|---|---|
| 50 | 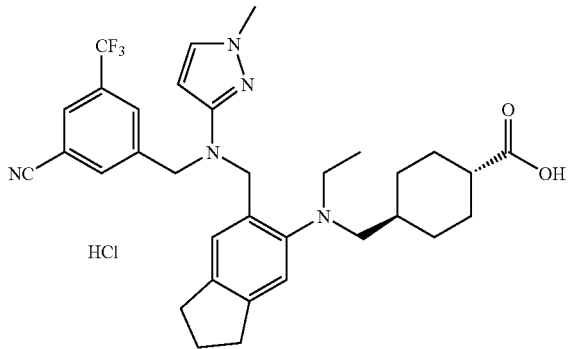 | DMSO-d6:<br>0.80 (t, J = 6.9 Hz, 3H), 0.80-1.00 (m, 2H),<br>1.00-1.22 (m, 2H), 1.37 (m, 1H),<br>1.57-1.84 (m, 4H), 1.92-2.12 (m, 3H),<br>2.77 (t, J = 8.0 Hz, 2H), 2.87 (t, J = 7.3 Hz, 2H), 3.00-3.55 (m, 4H),<br>3.72 (s, 3H), 4.63 (s, 4H), 5.60 (s, 1H),<br>7.16 (s, 1H), 7.49 (brs, 1H), 7.52 (s, 1H),<br>7.77 (s, 1H), 7.89 (s, 1H), 8.19 (s, 1H) |
TABLE 11
| Example | Structural Formula | NMR (δ value, 300 MHz) |
|---|---|---|
| 51 | 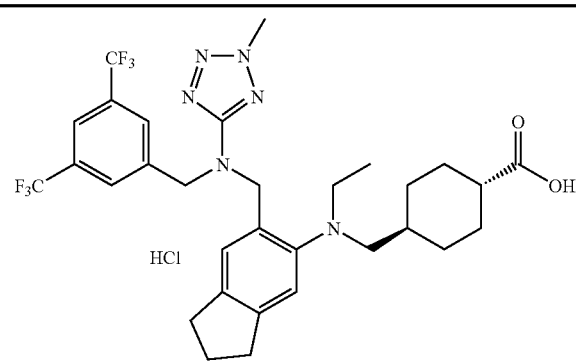 | DMSO-d6:<br>0.55-2.20 (m, 15H), 2.40-3.80 (m, 8H),<br>4.16 (s, 3H), 4.50-5.20 (m, 4H),<br>6.91, 7.07, 7.60-8.12 (m, 5H) |
| 52 | 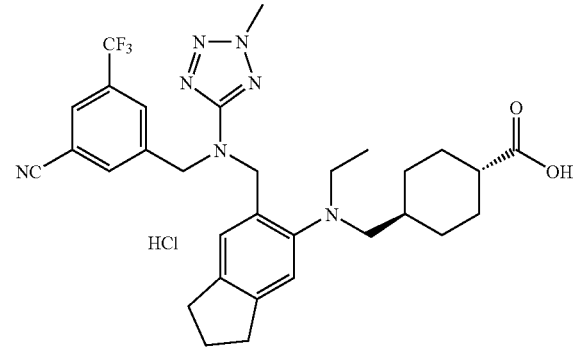 | DMSO-d6:<br>0.60-2.20 (m, 15H), 2.40-3.80 (m, 8H),<br>4.15 (s, 3H), 4.00-5.20 (m, 4H),<br>6.70-7.30, 7.60-8.40 (m, 5H) |
| 53 | 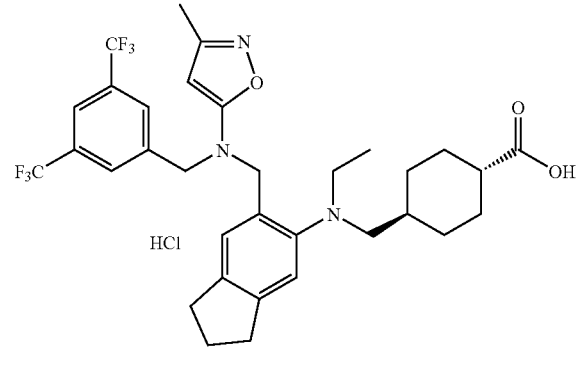 | DMSO-d6:<br>0.60-1.40 (m, 8H), 1.60-1.85 (m, 4H),<br>1.85-2.15 (m, 3H), 2.05 (s, 3H),<br>2.50-3.00 (m, 8H), 4.62 (s, 2H),<br>4.68 (s, 2H), 5.11 (s, 1H), 6.93 (s, 1H),<br>7.08 (s, 1H), 7.83 (s, 2H), 7.99 (s, 1H) |

TABLE 11-continued

| Example | Structural Formula | NMR (δ value, 300 MHz) |
|---|---|---|
| 54 | 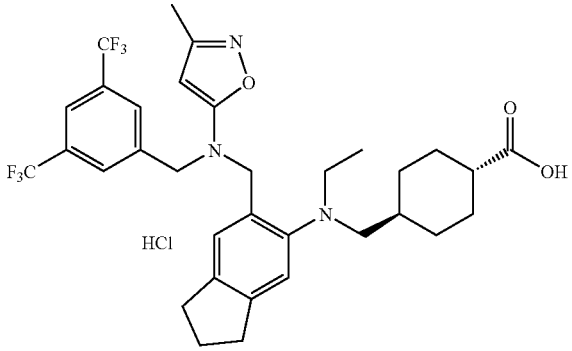 | DMSO-d6:<br>0.60-1.22 (m, 7H), 1.30 (m, 1H),<br>1.60-1.84 (m, 4H), 1.87-2.15 (m, 3H),<br>2.05 (s, 3H), 2.40-3.00 (m, 8H),<br>4.62 (s, 4H), 5.10 (s, 1H), 6.93 (s, 1H),<br>7.08 (s, 1H), 7.84 (s, 1H), 7.93 (s, 1H),<br>8.24 (s, 1H) |
| 55 | 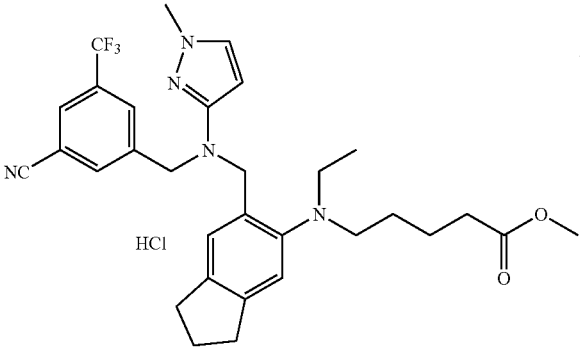 | CDCl3:<br>1.11 (brt, J = 6.9 Hz, 3H), 1.30-1.90 (m, 4H), 2.13 (m, 2H), 2.25 (m, 2H), 2.83-3.00 (m, 4H), 3.20-3.80 (m, 4H), 3.60 (s, 3H), 3.81 (s, 3H), 4.77 (s, 2H), 5.08 (brs, 2H), 5.44 (s, 1H), 7.16 (brs, 1H), 7.17 (s, 1H), 7.33 (s, 1H), 7.73 (s, 1H), 7.77 (s, 1H), 7.81 (s, 1H) |

TABLE 12

| Example | Structural Formula | NMR (δ value, 300 MHz) |
|---|---|---|
| 56 | 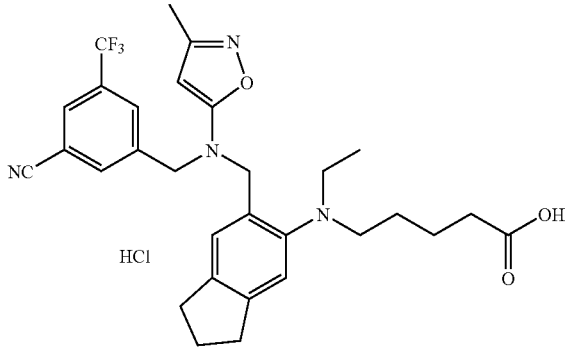 | CDCl3:<br>1.05 (m, 3H), 1.05-1.40 (m, 2H),<br>1.42-1.96 (m, 2H), 2.16 (s, 3H),<br>2.16 (m, 2H), 2.27 (m, 2H), 2.70-3.05 (m, 4H), 3.00-4.00 (m, 4H),<br>4.79 (s, 3H), 5.22 (s, 2H),<br>7.08 (s, 1H), 7.26 (s, 1H), 7.70 (s, 1H),<br>7.76 (s, 2H) |
| 57 | 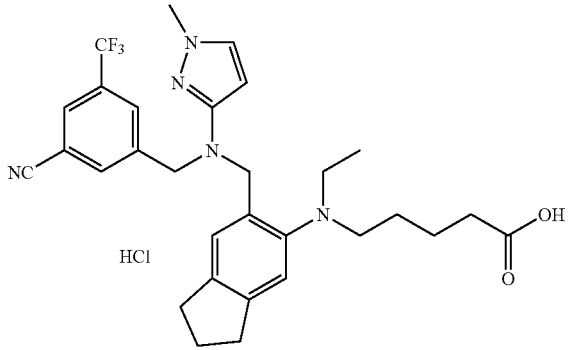 | CDCl3:<br>1.08 (brt, J = 6.9 Hz, 3H), 1.25-1.70 (m, 4H), 2.14 (m, 2H), 2.38 (m, 2H), 2.89 (t, J = 7.3 Hz, 2H), 2.98 (t, J = 7.0 Hz, 2H), 3.30-4.00 (m, 4H), 3.90 (s, 3H),<br>4.71 (s, 2H), 4.92 (s, 2H),<br>5.49 (s, 1H), 7.15 (s, 1H), 7.36 (s, 2H),<br>7.73 (s, 1H), 7.77 (s, 1H), 7.81 (s, 1H) |

TABLE 12-continued

| Example | Structural Formula | NMR (δ value, 300 MHz) |
|---|---|---|
| 58 | | CDCl3:<br>0.97 (m, 3H), 1.27-1.80 (m, 4H),<br>2.13 (m, 2H), 2.20-2.75 (m, 2H), 2.82 (t,<br>J = 7.3 Hz, 2H), 2.97 (t, J = 7.3 Hz, 2H),<br>3.10-4.00 (m, 4H), 3.86 (s, 3H),<br>4.80 (s, 4H), 6.90 (s, 1H), 7.30 (s, 1H),<br>7.67 (s, 2H), 7.73 (s, 1H), 8.88 (s, 1H) |
| 59 | | DMSO-d6:<br>0.80 (t, J = 7.0 Hz, 3H), 0.70-1.00 (m,<br>2H), 1.00-1.23 (m, 2H), 1.40 (m, 1H),<br>1.58-1.82 (m, 4H), 1.92-2.12 (m, 3H),<br>2.74 (t, J = 7.0 Hz, 2H), 2.86 (t, J = 7.3 Hz,<br>2H), 3.14 (m, 2H), 3.31 (m, 2H), 3.71 (s,<br>3H), 4.75 (s, 2H), 4.80 (s, 2H),<br>7.09 (s, 1H), 7.46 (s, 1H), 7.82 (s, 2H),<br>7.93 (s, 1H), 8.26 (s, 1H) |
| 60 | | CDCl3:<br>0.63-0.90 (m, 2H), 0.87 (t, J = 7.0 Hz, 3H),<br>1.15-1.55 (m, 3H), 1.70-1.95 (m, 4H),<br>2.03 (m, 2H), 2.16 (m, 1H),<br>2.66 (d, J = 7.0 Hz, 2H), 2.67-2.92 (m, 6H),<br>3.77)s, 3H), 4.56 (s, 2H), 4.79 (s, 2H),<br>7.00 (s, 2H), 7.67 (s, 2H), 7.72 (s, 1H),<br>7.75 (s, 1H) |

TABLE 13

| Example | Structural Formula | NMR (δ value, 300 MHz) |
|---|---|---|
| 61 | 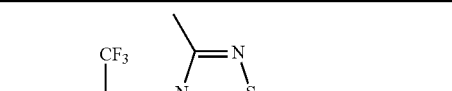 | CDCl3:<br>0.90 (m, 3H), 0.90-1.20 (m, 2H),<br>1.32-1.70 (m, 6H), 1.90 (m, 1H),<br>2.06 (t, J = 7.2 Hz, 2H), 2.46 (s, 3H),<br>2.65-3.00 (m, 8H), 4.68 (s, 2H),<br>4.80 (s, 2H), 6.94 (s, 1H), 7.06 (s, 1H),<br>7.67 (s, 2H), 7.76 (s, 1H) |

TABLE 13-continued

| Example | Structural Formula | NMR (δ value, 300 MHz) |
|---|---|---|
| 62 | 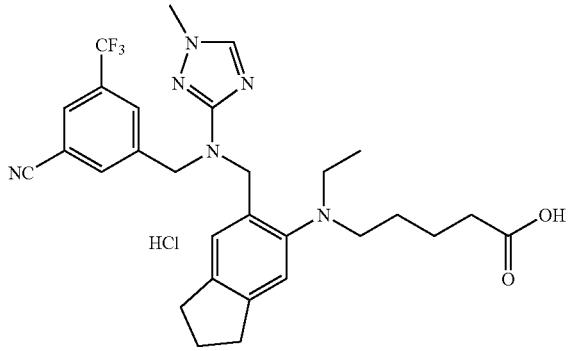 | CDCl3:<br>1.02 (m, 3H), 1.30-1.74 (m, 4H),<br>2.15 (m, 2H), 2.26-2.68 (m, 2H), 2.88 (t,<br>J = 7.4 Hz, 2H), 2.98 (t, J = 7.7 Hz, 2H),<br>3.20-4.40 (m, 4H), 3.86 (s, 3H),<br>4.79 (s, 2H), 4.95 (s, 2H), 7.02 (s, 1H),<br>7.31 (s, 1H), 7.72 (s, 1H), 7.78 (s, 1H),<br>7.80 (s, 1H), 8.90 (s, 1H) |
| 63 | 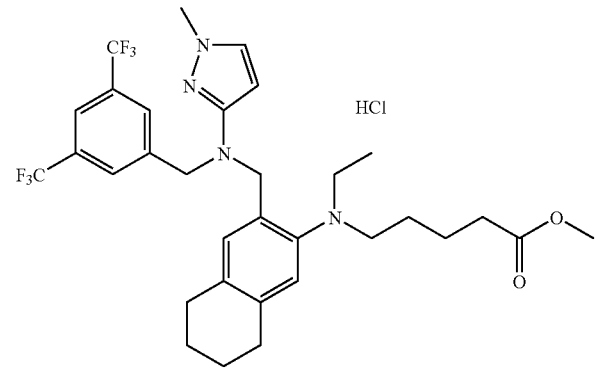 | CDCl3:<br>1.12 (t, J = 6.6 Hz, 3H), 1.30-2.00 (m, 8H),<br>2.25 (m, 2H), 2.67 (m, 2H), 2.76 (m, 2H),<br>3.20-3.80 (m, 4H), 3.60 (s, 3H),<br>3.95 (s, 3H), 4.86 (s, 2H), 5.33 (brs,<br>2H), 5.51 (d, J = 2.3 Hz, 1H), 6.98 (brs,<br>1H), 7.11 (s, 1H), 7.23 (d, J = 2.3 Hz, 1H),<br>7.72 (s, 3H) |
| 64 | 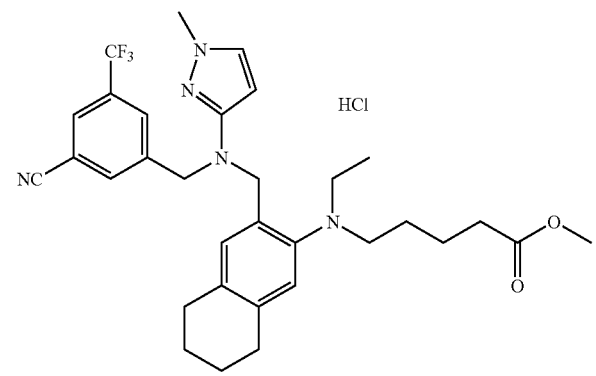 | CDCl3:<br>1.15 (t, J = 6.9 Hz, 3H), 1.30-2.00 (m, 8H),<br>2.27 (m, 2H), 2.69 (m, 2H), 2.77 (m, 2H),<br>3.20-3.80 (m, 4H), 3.61 (s, 3H),<br>3.93 (s, 3H), 4.86 (s, 2H), 5.22 (brs,<br>2H), 5.52 (d, J = 2.5 Hz, 1H), 6.99 (brs,<br>1H), 7.08 (s, 1H), 7.24 (d, J = 2.5 Hz, 1H),<br>7.74 (s, 1H), 7.76 (s, 1H), 7.82 (s, 1H) |
| 65 | 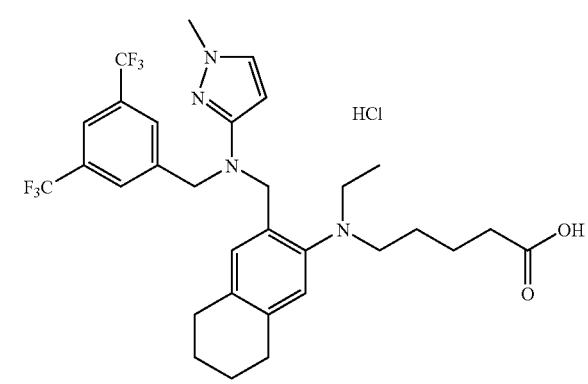 | CDCl3:<br>1.04 (m, 3H), 1.30-1.88 (m, 8H),<br>2.42 (m, 2H), 2.65 (m, 2H), 2.80 (m, 2H),<br>3.30-4.00 (m, 4H),<br>3.96 (s, 3H), 4.70 (s, 2H), 4.85 (s, 2H),<br>5.52 (s, 1H), 6.89 (s, 1H), 7.26 (s, 1H),<br>7.41 (s, 1H), 7.67 (s, 2H), 7.75 (s, 1H) |

TABLE 14

| Example | Structural Formula | NMR (δ value, 300 MHz) |
| --- | --- | --- |
| 66 | | CDCl3:<br>1.08 (m, 3H), 1.30-1.88 (m, 8H),<br>2.38 (m, 2H), 2.69 (m, 2H), 2.81 (m, 2H),<br>3.30-4.00 (m, 4H),<br>3.94 (s, 3H), 4.74 (s, 2H), 4.90 (s, 2H),<br>5.52 (s, 1H), 6.94 (s, 1H), 7.26 (s, 1H),<br>7.44 (s, 1H), 7.73 (s, 1H), 7.78 (s, 1H),<br>7.79 (s, 1H) |
| 67 | | DMSO-d6:<br>0.60-0.90 (m, 2H), 0.80 (m, 3H),<br>1.00-1.20 (m, 2H), 1.26 (m, 1H),<br>1.55-1.80 (m, 8H), 1.99 (m, 1H)<br>2.40-3.80 (m, 8H), 4.16 (s, 3H),<br>4.74 (s, 4H), 6.73 (s, 1H), 6.85 (s, 1H),<br>7.80 (s, 2H), 7.95 (s, 1H) |
| 68 | | DMSO-d6:<br>0.60-0.90 (m, 2H), 0.82 (t, J = 6.9 Hz, 3H),<br>1.00-1.40 (m, 3H),<br>1.58-1.85 (m, 8H), 2.02 (m, 1H),<br>2.40-3.80 (m, 8H), 4.16 (s, 3H),<br>4.68 (s, 2H), 4.73 (s, 2H), 6.72 (s, 1H),<br>6.84 (s, 1H), 7.80 (s, 1H), 7.84 (s, 1H)<br>8.19 (s, 1H) |
| 69 | | DMSO-d6:<br>0.80 (m, 3H), 0.80-1.00 (m, 2H),<br>1.01-1.23 (m, 2H), 1.42 (m, 1H),<br>1.57-1.804 (m, 8H), 2.04 (m, 1H),<br>2.54 (m, 2H), 2.71 (m, 2H), 3.23 (m, 2H),<br>3.43 (m, 2H), 3.71 (s, 3H), 4.73 (s, 2H),<br>4.82 (s, 2H), 6.93 (s, 1H), 7.36 (s, 1H),<br>7.81 (s, 2H), 7.93 (s, 1H), 8.30 (s, 1H) |

TABLE 14-continued

| Example | Structural Formula | NMR (δ value, 300 MHz) |
|---|---|---|
| 70 | | CDCl3:<br>0.65-1.00 (m, 2H), 0.87 (t, J = 7.0 Hz, 3H),<br>1.15-1.50 (m, 3H),<br>1.65-2.00 (m, 8H), 2.17 (m, 1H),<br>2.58 (m, 2H), 2.66 (d, J = 7.3 Hz, 2H),<br>2.69 (m, 2H), 2.80 (q, J = 7.0 Hz, 2H),<br>3.77 (s, 3H), 4.56 (s, 2H), 4.73 (s, 2H),<br>6.79 (s, 1H), 6.82 (s, 1H), 7.66 (s, 2H),<br>7.72 (s, 1H), 7.74 (s, 1H) |

TABLE 15

| Example | Structural Formula | NMR (δ value, 300 MHz) |
|---|---|---|
| 71 | | DMSO-d6:<br>0.65-0.90 (m, 2H), 0.81 (t, J = 7.0 Hz, 3H),<br>1.00-1.25 (m, 2H), 1.25 (m, 1H),<br>1.58-1.80 (m, 8H), 2.00 (m, 1H),<br>2.05 (s, 3H), 2.40-2.80 (m, 8H),<br>4.59 (s, 2H), 4.68 (s, 2H), 5.11 (s, 1H),<br>6.75 (s, 1H), 6.86 (s, 1H), 7.82 (s, 2H),<br>7.99 (s, 1H) |
| 72 | | DMSO-d6:<br>0.65-0.90 (m, 2H), 0.82 (brt, J = 6.9 Hz,<br>3H), 1.00-1.30 (m, 2H), 1.30 (m, 1H),<br>1.60-1.82 (m, 8H), 2.04 (m, 1H),<br>2.05 (s, 3H), 2.40-2.80 (m, 8H),<br>4.59 (s, 2H), 4.61 (s, 2H), 5.09 (s, 1H),<br>6.73 (s, 1H), 6.85 (s, 1H), 7.82 (s, 1H),<br>7.90 (s, 1H), 8.23 (s, 1H) |
| 73 | | DMSO-d6:<br>0.70-1.70 (m, 11H), 1.70-2.11 (m, 3H),<br>2.60-3.00 (m, 6H), 3.30-4.60 (m, 6H),<br>4.71, 4.77, 4.88, 4.97 (s, 4H),<br>6.93, 7.06, 7.11, 7.74 (s, 2H),<br>7.83, 7.97, 8.00, 8.03 (s, 3H) |

TABLE 15-continued
| Example | Structural Formula | NMR (δ value, 300 MHz) |
|---|---|---|
| 74 | 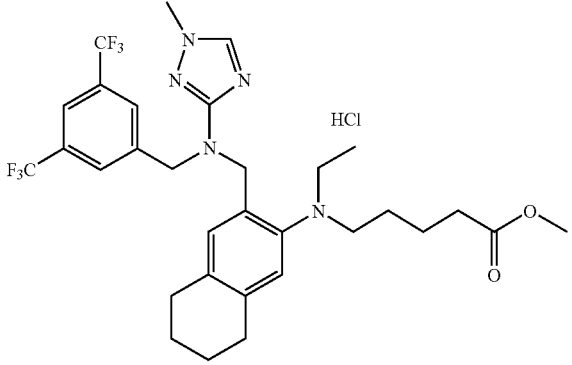 | CDCl3:<br>1.03 (m, 3H), 1.20-1.86 (m, 8H),<br>2.23 (m, 2H), 2.62 (m, 2H), 2.77 (m, 2H),<br>3.10-4.00 (m, 4H), 3.59 (s, 3H),<br>3.80 (s, 3H), 4.88 (s, 2H), 5.02 (brs, 2H),<br>6.96 (s, 1H), 7.01 (brs, 1H), 7.69 (s, 3H),<br>8.39 (brs, 1H) |
| 75 | 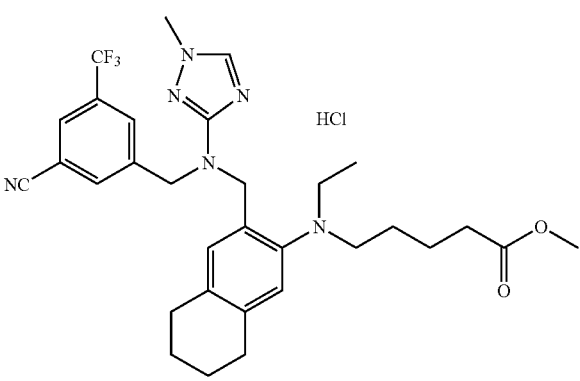 | CDCl3:<br>1.10 (m, 3H), 1.20-1.86 (m, 8H),<br>2.26 (m, 2H), 2.65 (m, 2H), 2.78 (m, 2H),<br>3.10-4.00 (m, 4H), 3.61 (s, 3H),<br>3.80 (s, 3H), 4.87 (s, 2H), 5.16 (brs, 2H),<br>7.02 (brs, 1H), 7.02 (s, 1H), 7.72 (s, 2H),<br>7.79 (s, 1H), 8.28 (brs, 1H) |
TABLE 16
| Example | Structural Formula | NMR (δ value, 300 MHz) |
|---|---|---|
| 76 | 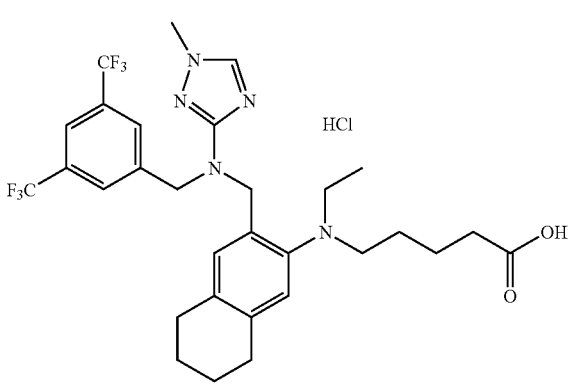 | CDCl3:<br>0.97 (m, 3H), 1.30-1.90 (m, 8H),<br>2.25-2.95 (m, 2H), 2.60 (m, 2H),<br>2.80 (m, 2H), 3.20-4.50 (m, 4H),<br>3.86 (s, 3H), 4.77 (s, 2H), 4.78 (s, 2H),<br>6.68 (s, 1H), 7.13 (s, 1H), 7.66 (s, 2H),<br>7.75 (s, 1H), 8.90 (brs, 1H) |

TABLE 16-continued
| Example | Structural Formula | NMR (δ value, 300 MHz) |
|---|---|---|
| 77 | 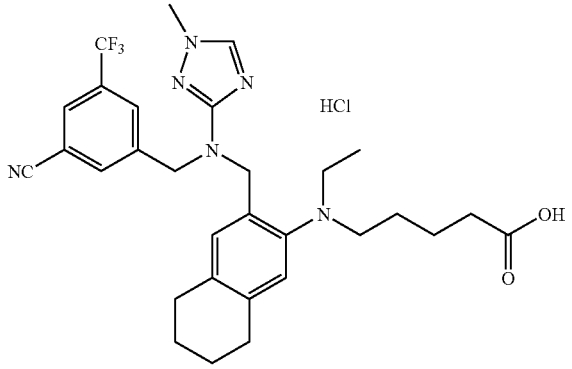 | CDCl3:<br>1.03 (m, 3H), 1.30-1.90 (m, 8H),<br>2.20-2.70 (m, 2H), 2.66 (m, 2H),<br>2.81 (m, 2H), 3.20-4.40 (m, 4H),<br>3.88 (s, 3H), 4.78 (s, 2H), 4.93 (s, 2H),<br>6.81 (s, 1H), 7.12 (s, 1H), 7.71 (s, 1H),<br>7.79 (s, 2H), 9.01 (brs, 1H) |
| 78 | 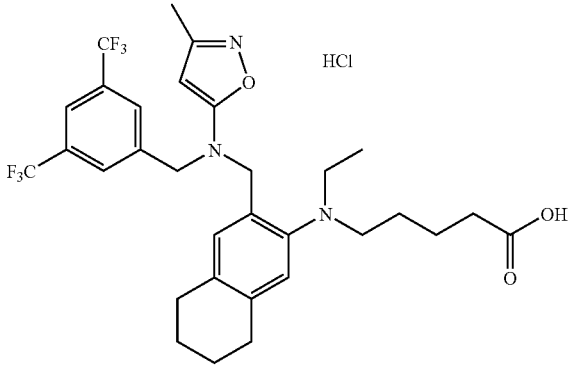 | CDCl3:<br>1.05 (m, 3H), 1.12-1.90 (m, 8H), 2.16 (s, 3H), 2.25 (m, 2H), 2.67 (m, 2H), 2.76 (m, 2H), 3.25 (m, 2H), 3.45-4.00 (m, 2H),<br>4.82 (s, 3H), 5.17 (brs, 2H),<br>6.91 (brs, 1H), 7.07 (s, 1H), 7.67 (s, 2H),<br>7.72 (s, 1H) |
| 79 | 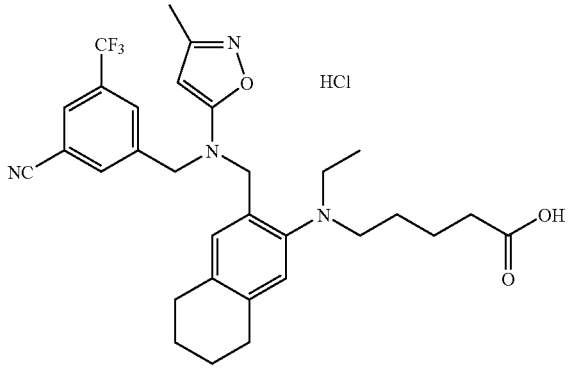 | CDCl3:<br>1.10 (m, 3H), 1.13-1.90 (m, 8H), 2.16 (s, 3H), 2.28 (m, 2H), 2.69 (m, 2H),<br>2.77 (m, 2H), 3.00-4.00 (m, 4H),<br>4.78 (s, 2H), 4.82 (s, 1H), 5.16 (brs, 2H),<br>6.93 (brs, 1H), 7.05 (s, 1H), 7.70 (s, 1H),<br>7.77 (s, 2H) |
| 80 | 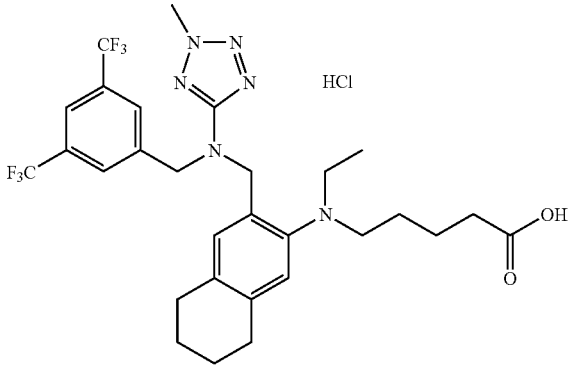 | CDCl3:<br>1.09 (m, 3H), 1.27 (m, 1H),<br>1.40-1.95 (m, 7H), 2.28 (t, J = 7.3 Hz, 2H),<br>2.60 (m, 2H), 2.76 (m, 2H), 3.30 (m, 2H),<br>3.50-3.90 (m, 2H), 4.17 (s, 3H),<br>4.98 (brs, 2H), 5.28 (brs, 2H),<br>6.91 (brs, 1H), 7.02 (s, 1H), 7.71 (s, 3H) |

TABLE 17
| Example | Structural Formula | NMR (δ value, 300 MHz) |
|---|---|---|
| 81 | 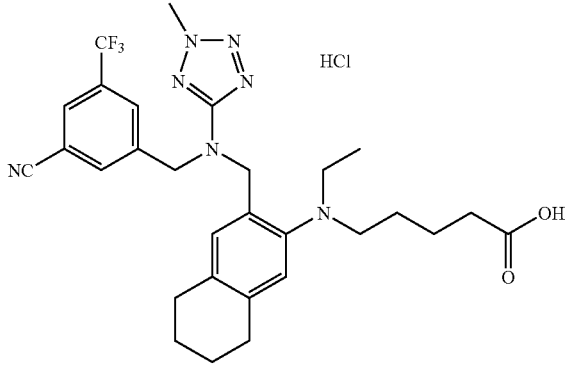 | CDCl3:<br>1.00-1.43 (m, 4H),<br>1.43-1.96 (m, 7H), 2.30 (t, J = 7.3 Hz, 2H),<br>2.63 (m, 2H), 2.77 (m, 2H), 3.32 (m, 2H),<br>3.55-3.95 (m, 2H), 4.17 (s, 3H),<br>4.93 (s, 2H), 5.29 (brs, 2H),<br>6.94 (brs, 1H), 7.02 (s, 1H), 7.74 (s, 2H),<br>7.80 (s, 1H) |
| 82 | 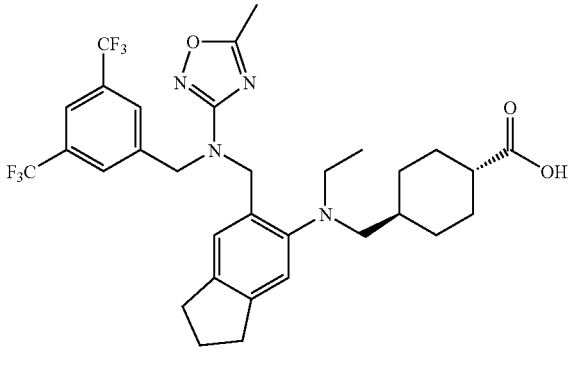 | CDCl3:<br>0.62-0.92 (m, 2H), 0.86 (t, J = 7.0 Hz, 3H),<br>1.20-1.94 (m, 7H), 2.07 (m, 2H),<br>2.17 (m, 1H), 2.49 (s, 3H),<br>2.64 (d, J = 7.0 Hz, 2H), 2.70-2.90 (m, 6H),<br>4.58 (s, 2H), 4.77 (s, 2H),<br>6.98 (s, 1H), 7.02 (s, 1H), 7.62 (s, 2H),<br>7.73 (s, 1H) |
| 83 | 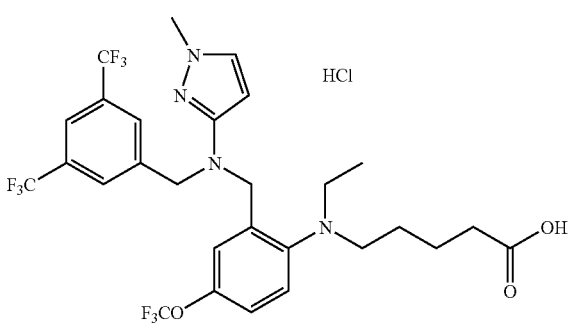 | CDCl3:<br>1.08 (m, 3H), 1.40-1.80 (m, 4H),<br>2.32 (m, 2H), 3.30-4.00 (m, 4H),<br>3.90 (s, 3H), 4.78 (s, 2H), 5.12 (brs, 2H),<br>5.54 (s, 1H), 7.16 (s, 1H), 7.33 (m, 1H),<br>7.35 (s, 1H), 7.63 (m, 1H), 7.73 (s, 3H) |
| 84 | 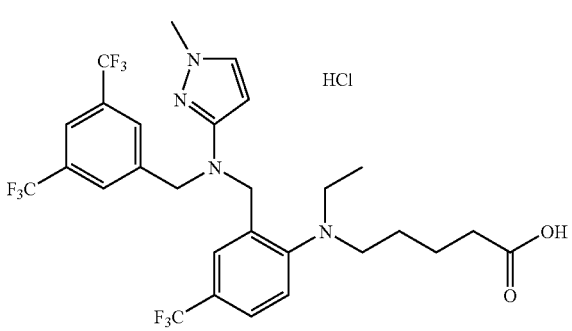 | CDCl3:<br>1.01 (m, 3H), 1.33-1.70 (m, 4H),<br>2.31 (t, J = 7.0 Hz, 2H), 2.70-4.00 (m, 4H),<br>3.87 (s, 3H), 4.68 (s, 2H), 4.84 (s, 2H),<br>5.53 (s, 1H), 7.26 (s, 1H), 7.46 (m, 1H),<br>7.54 (s, 1H), 7.60 (m, 1H), 7.70 (s, 2H),<br>7.74 (s, 1H) |

TABLE 17-continued
| Example | Structural Formula | NMR (δ value, 300 MHz) |
|---------|-------------------|------------------------|
| 85 | 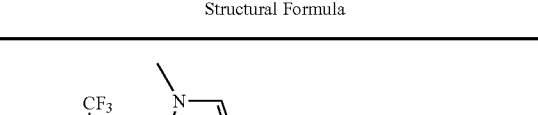 | CDCl3:<br>1.05 (m, 3H), 1.36-1.70 (m, 4H),<br>2.31 (t, J = 7.0 Hz, 2H), 2.60-4.00 (m, 4H),<br>3.84 (s, 3H), 4.68 (s, 2H), 4.82 (s, 2H),<br>5.49 (d, J = 2.3 Hz, 1H), 7.23 (d, J = 2.3 Hz, 1H), 7.39 (m, 1H), 7.56 (s, 1H), 7.58 (m, 1H), 7.73 (s, 1H), 7.78 (s, 2H) |
TABLE 18
| Example | Structural Formula | NMR (δ value, 300 MHz) |
|---------|-------------------|------------------------|
| 86 | 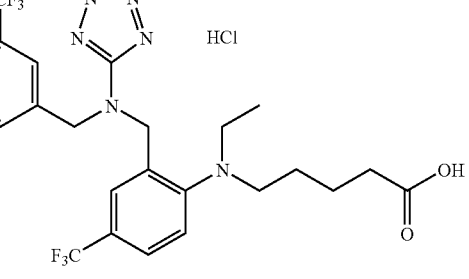 | CDCl3:<br>1.08 (m, 3H), 1.40-1.70 (m, 4H),<br>2.29 (m, 2H), 3.10-3.80 (m, 4H),<br>4.18 (s, 3H), 4.90 (s, 2H), 5.19 (s, 2H),<br>7.34 (m, 1H), 7.49 (s, 1H), 7.60 (m, 1H),<br>7.74 (s, 3H) |
| 87 | 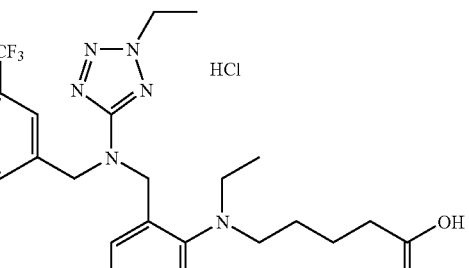 | DMSO-d6:<br>0.80-1.70 (m, 7H), 1.42 (t, J = 7.3 Hz, 3H),<br>1.80-2.24 (m, 4H), 2.60-3.05, 3.30-4.20 (m, 8H), 4.48 (q, J = 7.3 Hz, 2H),<br>4.55-5.10 (m, 4H), 6.85-7.20, 7.60-8.13 (m, 5H) |
| 88 | 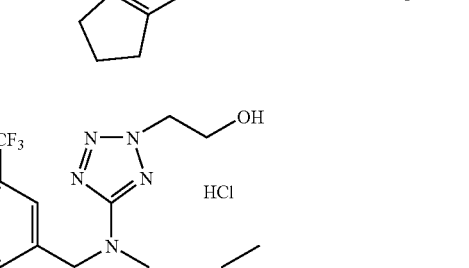 | DMSO-d6:<br>0.70-1.70 (m, 7H), 1.84-2.22 (m, 4H),<br>2.60-3.00, 3.30-4.40 (m, 8H),<br>4.48 (t, J = 5.4 Hz, 2H), 4.60-5.10 (m, 4H),<br>6.86-8.13 (m, 5H) |

TABLE 18-continued
| Example | Structural Formula | NMR (δ value, 300 MHz) |
|---|---|---|
| 89 | 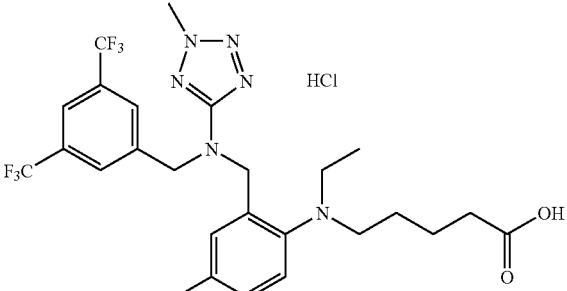 | DMSO-d6:<br>0.85 (brt, J = 6.6 Hz, 3H), 1.18-1.50 (m, 4H), 2.10 (t, J = 7.0 Hz, 2H), 2.65-3.10 (m, 4H), 4.14 (s, 3H), 4.60-4.98 (m, 4H), 6.90 (s, 1H), 7.05-7.45 (m, 2H), 7.86 (s, 2H), 7.94 (s, 1H) |
| 90 | 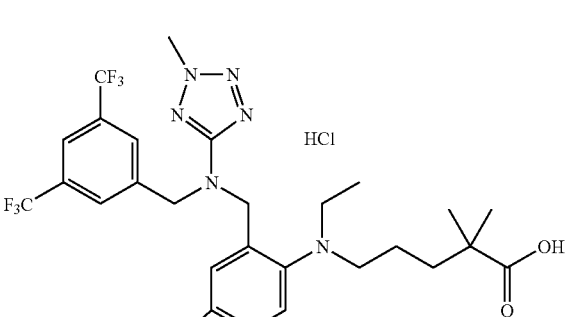 | CDCl3:<br>1.05 (s, 9H), 1.15-1.60 (m, 3H), 1.86 (m, 1H), 2.10 (m, 2H), 2.81 (t, J = 7.5 Hz, 2H), 2.92 (t, J = 7.5 Hz, 2H), 3.28 (m, 2H), 3.30-4.00 (m, 2H), 4.17 (s, 3H), 5.00 (s, 2H), 5.37 (s, 2H), 7.07 (s, 1H), 7.19 (s, 1H), 7.70 (s, 3H) |
TABLE 19
| Example | Structural Formula | NMR (δ value, 300 MHz) |
|---|---|---|
| 91 | 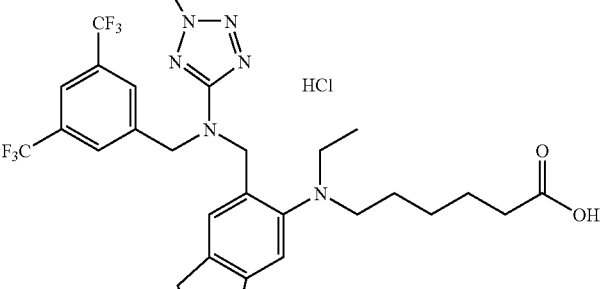 | CDCl3:<br>1.06 (m, 3H), 1.00-1.70 (m, 5H), 1.86 (m, 1H), 2.11 (m, 2H), 2.26 (t, J = 6.9 Hz, 2H), 2.81 (t, J = 7.2 Hz, 2H), 2.92 (t, J = 7.5 Hz, 2H), 3.00-3.40 (m, 2H), 3.50-3.90 (m, 2H), 4.17 (s, 3H), 4.98, 5.03 (brs, 2H), 5.37 (brs, 2H), 7.03 (brs, 1H), 7.22 (s, 1H), 7.67 (s, 1H), 7.69 (s, 2H) |
| 92 | 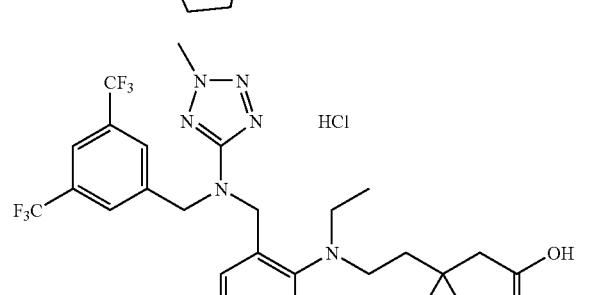 | CDCl3:<br>0.96 (brs, 6H), 1.10 (m, 3H), 1.28 (m, 1H), 1.86 (m, 1H), 2.10 (m, 2H), 2.18 (s, 2H), 2.81 (t, J = 7.4 Hz, 2H), 2.93 (t, J = 7.4 Hz, 2H), 3.38 (m, 2H), 3.78 (m, 2H), 4.16 (s, 3H), 4.99 (s, 2H), 5.35 (s, 2H), 7.10 (s, 1H), 7.21 (s, 1H), 7.69 (s, 3H) |

TABLE 19-continued

| Example | Structural Formula | NMR (δ value, 300 MHz) |
|---|---|---|
| 93 | 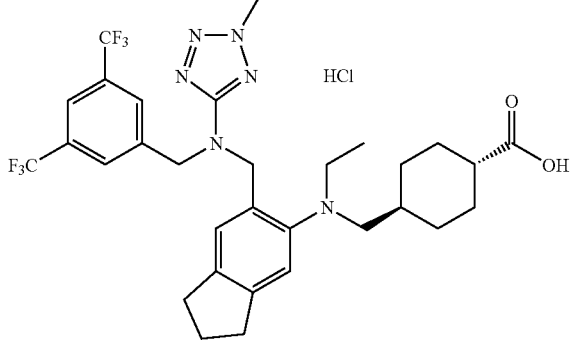 | DMSO-d6:<br>0.56-1.45 (m, 8H), 1.44 (t, J = 7.2 Hz, 3H),<br>1.52-2.10 (m, 7H), 2.50-3.80 (m, 8H),<br>4.49 (q, J = 7.2 Hz, 2H), 4.71 (s, 2H),<br>4.79 (s, 2H), 6.92 (s, 1H), 7.08 (s, 1H),<br>7.80 (s, 2H), 7.95 (s, 1H) |
| 94 | 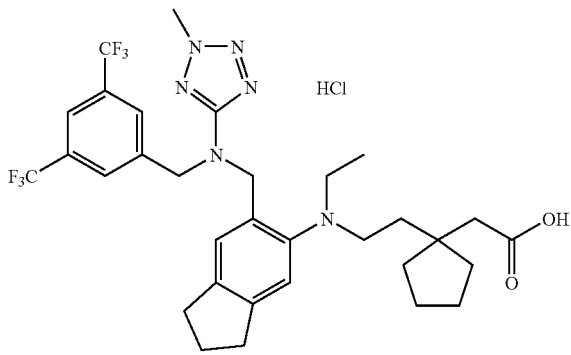 | CDCl3:<br>1.00-2.00 (m, 12H), 2.10 (m, 1H),<br>2.00-2.70 (m, 3H), 2.80 (t, J = 7.0 Hz, 2H),<br>2.93 (t, J = 7.7 Hz, 2H), 3.10-4.00 (m, 4H),<br>4.16 (s, 3H), 5.00 (s, 2H), 5.34 (brs, 2H),<br>7.13 (s, 1H), 7.22 (brs, 1H), 7.67 (s, 3H) |
| 95 | 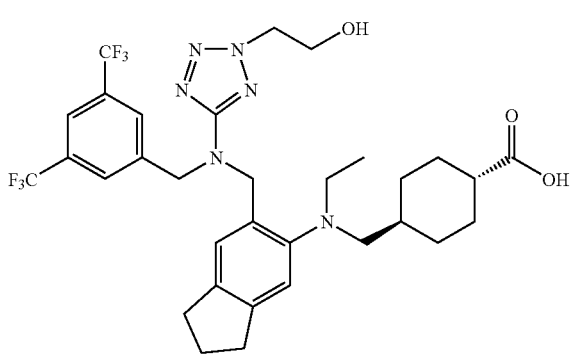 | CDCl3:<br>0.67-0.90 (m, 2H), 0.88 (t, J = 7.0 Hz, 3H),<br>1.15-1.96 (m, 7H), 2.04 (m, 2H), 2.20 (m, 1H), 2.66 (d, J = 6.8 Hz, 2H), 2.70-2.92 (m, 6H), 4.12 (m, 2H), 4.59 (m, 2H),<br>4.69 (s, 2H), 4.86 (s, 2H), 6.96 (s, 1H),<br>7.04 (s, 1H), 7.64 (s, 2H), 7.73 (s, 1H) |

TABLE 20

| Example | Structural Formula | NMR (δ value, 300 MHz) |
|---|---|---|
| 96 | 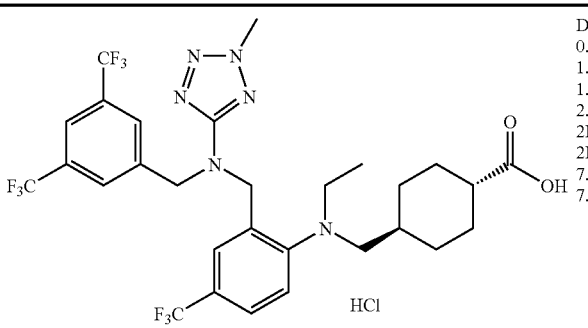 | DMSO-d6:<br>0.68-0.95 (m, 2H), 0.90 (t, J = 6.9 Hz, 3H),<br>1.00-1.24 (m, 2H), 1.32 (m, 1H),<br>1.63-1.85 (m, 4H), 2.02 (m, 1H),<br>2.80 (d, J = 6.9 Hz, 2H), 2.89 (q, J = 6.9 Hz, 2H), 4.17 (s, 3H), 4.80 (s, 2H), 4.82 (s, 2H), 7.22 (s, 1H), 7.31 (d, J = 8.0 Hz, 1H),<br>7.45 (d, J = 8.0 Hz, 1H), 7.83 (s, 2H),<br>7.95 (s, 1H) |

TABLE 20-continued

| Example | Structural Formula | NMR (δ value, 300 MHz) |
|---|---|---|
| 97 | | CDCl3:<br>0.91 (t, J = 7.0 Hz, 3H), 1.30-1.46 (m, 2H),<br>1.46-1.65 (m, 10H), 1.68-1.85 (m, 4H),<br>2.23 (s, 2H), 2.59 (m, 2H), 2.71 (m, 2H),<br>2.80-2.98 (m, 4H), 4.18 (s, 3H),<br>4.66 (s, 2H), 4.76 (s, 2H), 6.81 (s, 1H),<br>6.83 (s, 1H), 7.67 (s, 2H), 7.73 (s, 1H) |
| 98 | | DMSO-d6:<br>0.66-0.90 (m, 2H), 0.85 (t, J = 7.0 Hz, 3H),<br>1.00-1.40 (m, 3H),<br>1.60-1.80 (m, 4H), 2.01 (m, 1H),<br>2.69 (m, 2H), 2.81 (m, 2H), 4.16 (s, 3H),<br>4.80 (s, 2H), 4.84 (s, 2H), 6.90 (s, 1H),<br>7.17 (m, 1H), 7.29 (m, 1H), 7.88 (s, 2H),<br>7.96 (s, 1H) |
| 99 | | DMSO-d6:<br>0.55-2.15 (m, 17H), 1.44 (m, 3H),<br>2.40-2.90 (m, 6H), 3.36, 3.58 (m, 2H),<br>4.49 (q, J = 7.3 Hz, 2H), 4.74 (s, 2H),<br>4.93, 4.95 (s, 2H),<br>6.74, 6.85, 6.90, 7.55 (s, 2H),<br>7.79 (s, 1H), 7.95 (s, 2H) |
| 100 | | DMSO-d6:<br>0.55-2.15 (m, 17H), 2.40-2.90 (m, 6H),<br>3.34, 3.57 (m, 2H), 3.83 (m, 2H),<br>4.49 (m, 2H), 4.72, 4.73 (s, 2H),<br>4.91, 4.98 (s, 2H),<br>6.75, 6.83, 6.92, 7.55 (s, 2H),<br>7.80 (s, 1H), 7.95 (s, 2H) |

TABLE 21
| Example | Structural Formula | NMR (δ value, 300 MHz) |
|---|---|---|
| 101 | 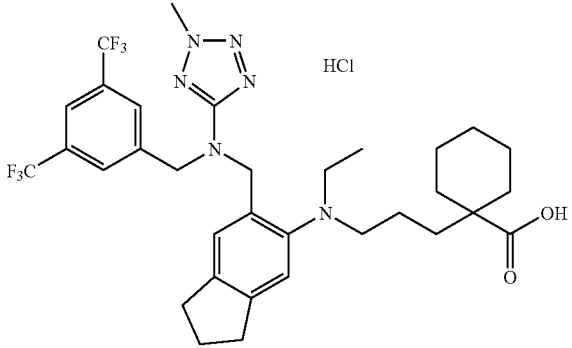 | CDCl3:<br>0.90-1.65 (m, 14H), 1.70-2.00 (m, 3H), 2.10 (m, 2H), 2.81 (t, J = 7.3 Hz, 2H), 2.93 (t, J = 7.4 H, 2H), 3.00-4.00 (m, 4H), 4.18 (s, 3H), 4.98 (brs, 2H), 5.37 (brs, 2H), 7.09 (brs, 1H), 7.18 (s, 1H), 7.68 (s, 1H), 7.70 (s, 2H) |
| 102 | 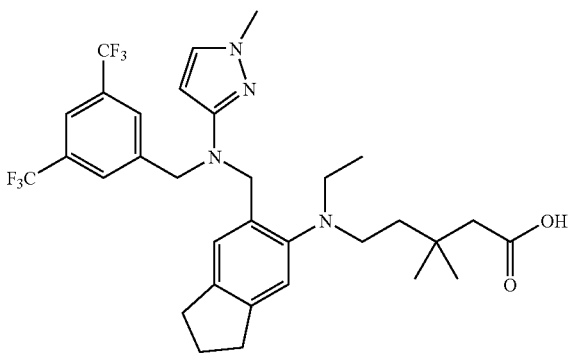 | CDCl3:<br>0.88 (t, J = 6.9 Hz, 3H), 1.00 (s, 6H), 1.52 (m, 2H), 2.04 (m, 2H), 2.13 (s, 2H), 2.73-2.97 (m, 8H), 3.77 (s, 3H), 4.52 (s, 2H), 4.57 (s, 2H), 5.44 (s, 1H), 7.01 (s, 1H), 7.08 (s, 1H), 7.11 (s, 1H), 7.71 (s, 3) |
| 103 | 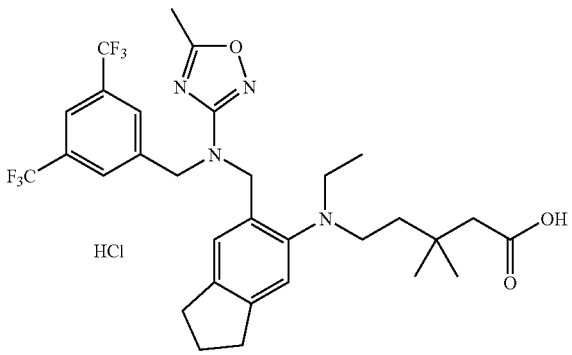 | CDCl3:<br>0.98 (s, 6H), 1.08 (m, 3H), 1.31 (m, 1H), 1.83 (m, 1H), 2.10 (m, 2H), 2.17 (s, 2H), 2.50 (s, 3H), 2.82 (m, 2H), 2.93 (m, 2H), 3.05-4.10 (m, 4H), 4.94 (s, 2H), 5.30 (s, 2H), 7.07 (s, 1H), 7.18 (brs, 1H), 7.66 (s, 3H) |
| 104 | 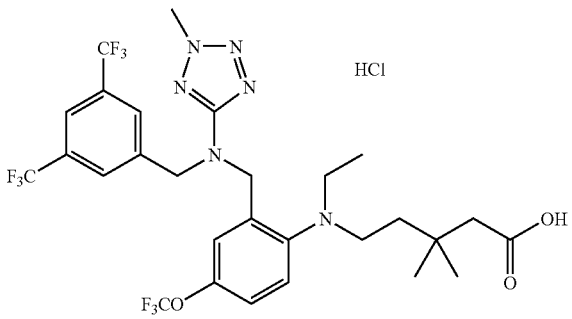 | DMSO-d6:<br>0.88 (s, 6H), 0.88 (m, 3H), 1.32 (m, 2H), 2.04 (s, 2H), 2.60-3.70 (m, 4H), 4.16 (s, 3H), 4.84 (brs, 2H), 4.86 (s, 2H), 6.97 (s, 1H), 7.07-7.60 (m, 2H), 7.87 (S, 2H), 7.97 (s, 1H) |

TABLE 21-continued

| Example | Structural Formula | NMR (δ value, 300 MHz) |
|---|---|---|
| 105 | 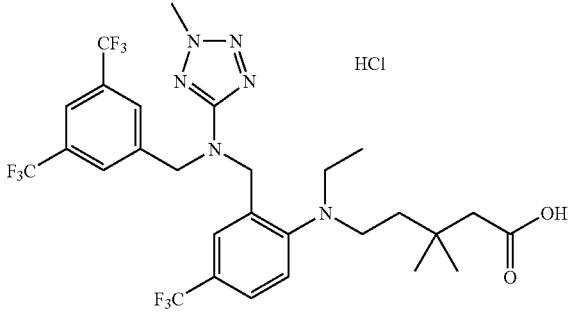 | DMSO-d6:<br>0.89 (s, 6H), 0.89 (m, 3H), 1.35 (m, 1H),<br>2.05 (s, 2H), 2.82-3.20 (m, 4H),<br>4.17 (s, 3H), 4.77 (s, 2H), 4.82 (s, 2H),<br>7.28 (s, 1H), 7.29 (m, 1H), 7.50 (d,<br>J = 8.4 Hz, 1H), 7.81 (s, 2H), 7.94 (s, 1H) |

TABLE 22

| Example | Structural Formula | NMR (δ value, 300 MHz) |
|---|---|---|
| 106 | 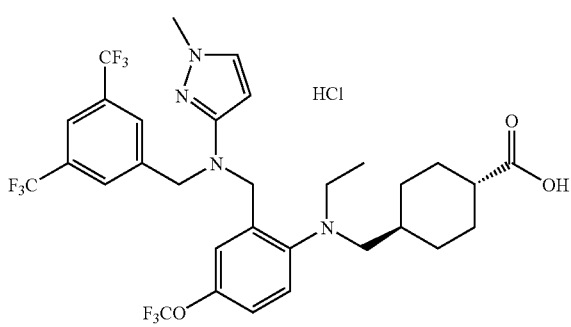 | CDCl3:<br>0.75-1.10 (m, 5H), 1.10-1.55 (m, 3H),<br>1.60-2.00 (m, 4H), 2.18 (m, 1H),<br>2.80-3.60 (m, 4H), 3.84 (s, 3H),<br>4.73 (s, 2H), 4.77 (s, 2H), 5.42 (s, 1H),<br>7.06-7.30 (m, 3H), 7.19 (d, J = 2.1 Hz, 1H),<br>7.73 (s, 2H), 7.74 (s, 1H) |
| 107 | 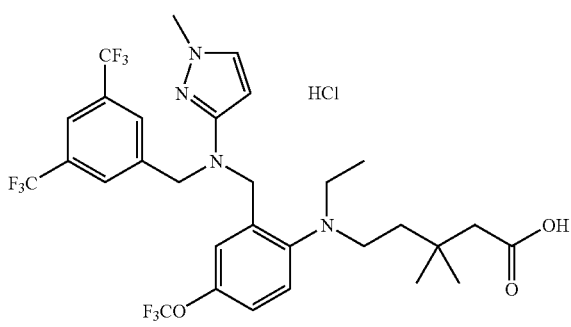 | DMSO-d6:<br>0.86 (s, 6H), 0.91 (t, J = 6.9 Hz, 3H),<br>1.33 (m, 2H), 2.04 (s, 2H), 3.20-3.55 (m,<br>4H), 3.71 (s, 3H), 4.70 (s, 2H), 4.74 (s,<br>2H), 5.61 (d, J = 2.1 Hz, 1H), 7.24 (s, 1H),<br>7.39 (d, J = 8.1 Hz, 1H), 7.53 (d, J = 2.4 Hz,<br>1H), 7.72 (m, 1H), 7.83 (s, 2H),<br>7.92 (s, 1H) |
| 108 | 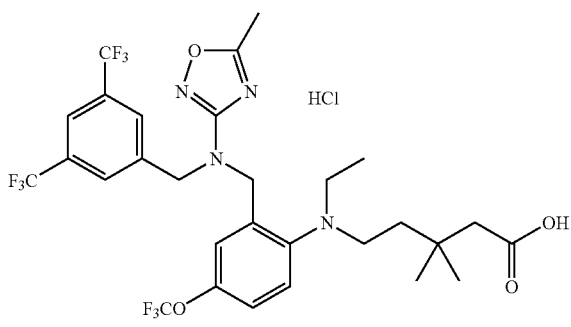 | CDCl3:<br>1.00 (s, 6H), 1.15 (m, 3H), 1.20-2.00 (m,<br>2H), 2.19 (s, 2H), 2.48 (s, 3H),<br>3.00-4.00 (m, 4H), 4.94 (s, 2H),<br>5.32 (s, 2H), 7.10 (s, 1H), 7.20-7.60 (m,<br>2H), 7.74 (s, 1H), 7.77 (s, 2H) |

TABLE 22-continued
| Example | Structural Formula | NMR (δ value, 300 MHz) |
|---|---|---|
| 109 | 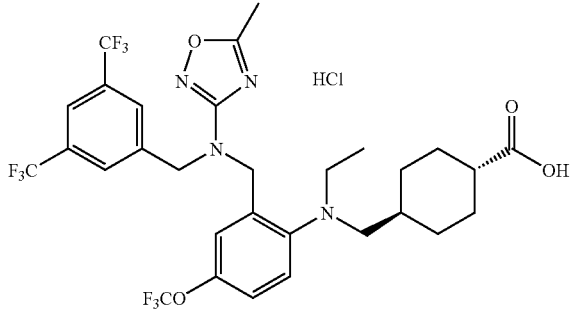 | DMSO-d6:<br>0.62-0.90 (m, 2H), 0.84 (t, J = 6.9 Hz, 3H),<br>1.00-1.25 (m, 2H), 1.28 (m, 1H),<br>1.60-1.83 (m, 4H), 2.00 (m, 1H),<br>2.50 (s, 3H), 2.67 (d, J = 6.6 Hz, 2H),<br>2.80 (q, J = 6.9 Hz, 2H), 4.73 (s, 2H),<br>4.74 (s, 2H), 6.90 (s, 1H), 7.18 (d,<br>J = 8.7 Hz, 1H), 7.29 (d, J = 8.7 Hz, 1H),<br>7.86 (s, 2H), 7.97 (s, 1H) |
| 110 | 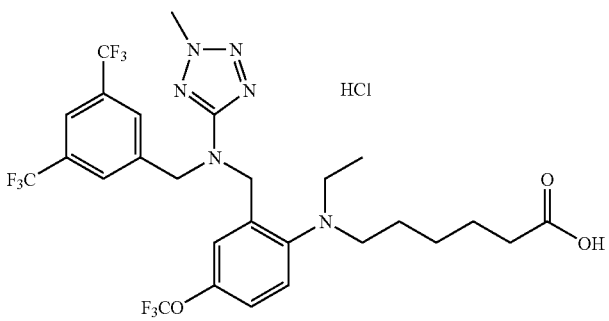 | DMSO-d6:<br>0.85 (m, 6H), 1.06-1.35 (m, 4H),<br>1.40 (m, 2H), 2.09 (t, J = 7.2 Hz, 2H),<br>2.60-3.60 (m, 4H), 4.16 (s, 3H),<br>4.78 (s, 2H), 4.84 (s, 2H), 6.93 (s, 1H),<br>7.08-7.40 (m, 2H) 7.87 (s, 2H),<br>7.95 (s, 1H) |
TABLE 23
| Example | Structural Formula | NMR (δ value, 300 MHz) |
|---|---|---|
| 111 | 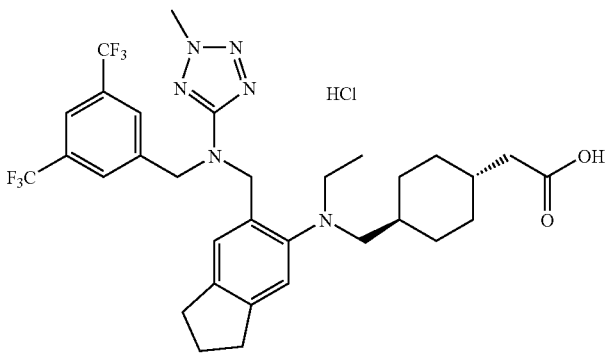 | DMSO-d6:<br>0.57-2.14 (m, 15H), 1.97 (d, J = 6.6 Hz,<br>2H), 2.40-3.80 (m, 8H), 4.16 (s, 3H),<br>4.60-5.20 (m, 4H),<br>6.91, 7.07, 7.60-8.10 (m, 5H) |
| 112 | 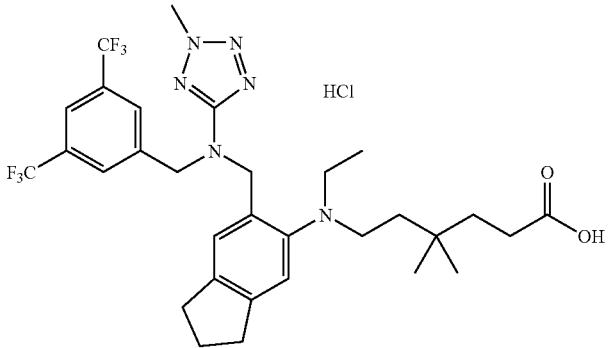 | DMSO-d6:<br>0.60-1.65 (m, 13H), 1.80-2.16 (m, 4H),<br>2.60-4.30 (m, 8H), 4.15 (s, 3H),<br>4.60-5.10 (m, 4H),<br>6.86-7.10, 7.64-8.10 (m, 5H) |

TABLE 23-continued

| Example | Structural Formula | NMR (δ value, 300 MHz) |
| --- | --- | --- |
| 113 | 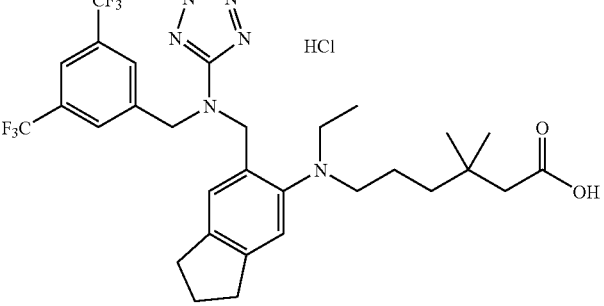 | DMSO-d6:<br>0.79 (s, 6H), 0.96 (m, 3H), 0.83-1.74 (m, 4H), 1.82-2.16 (m, 4H),<br>2.60-3.00 (m, 6H), 3.40-3.78 (m, 2H),<br>4.14 (s, 3H), 4.60-5.10 (m, 4H),<br>6.90-7.20, 7.60-8.07 (m, 5H) |
| 114 | | CDCl3:<br>0.69 (brs, 6H), 0.95 (m, 3H), 1.44 (m, 2H),<br>2.07 (brs, 2H), 2.18 (m, 2H),<br>2.50-3.40 (m, 8H), 4.19 (s, 3H),<br>4.81 (s, 2H), 4.97 (brs, 2H), 6.98 (s, 1H),<br>7.10 (s, 1H), 7.71 (s, 1H), 7.73 (s, 2H) |
| 115 | 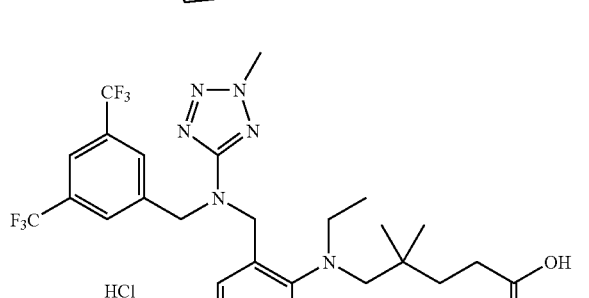 | DMSO-d6:<br>0.63-0.85 (m, 4H), 0.83 (t, J = 6.9 Hz, 3H),<br>1.22 (m, 1H), 1.47 (m, 1H),<br>1.45-1.73 (m, 4H), 1.98 (d, J =6.7 Hz, 2H), 2.67 (d, J = 6.5 Hz, 2H), 2.79 (q, J = 6.9 Hz, 2H), 4.15 (s, 3H), 4.77 (s, 2H),<br>4.81 (s, 2H), 6.87 (s, 1H), 7.15 (d, J = 8.7 Hz, 1H), 7.26 (d, J = 8.7 Hz, 1H),<br>7.84 (s, 2H), 7.95 (s, 1H) |

TABLE 24

| Example | Structural Formula | NMR (δ value, 300 MHz) |
| --- | --- | --- |
| 116 | 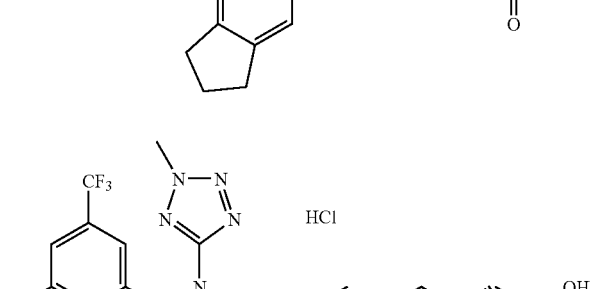 | CDCl3:<br>0.85 (s, 6H), 1.11 (m, 3H), 1.27 (m, 2H),<br>1.55 (m, 2H), 2.27 (m, 2H),<br>3.10-3.90 (m, 4H), 4.18 (s, 3H),<br>4.97 (s, 2H), 5.33 (s, 2H), 7.12 (s, 1H),<br>7.10-7.40 (m, 2H), 7.74 (s, 1H),<br>7.78 (s, 2H) |

TABLE 24-continued
| Example | Structural Formula | NMR (δ value, 300 MHz) |
|---|---|---|
| 117 | 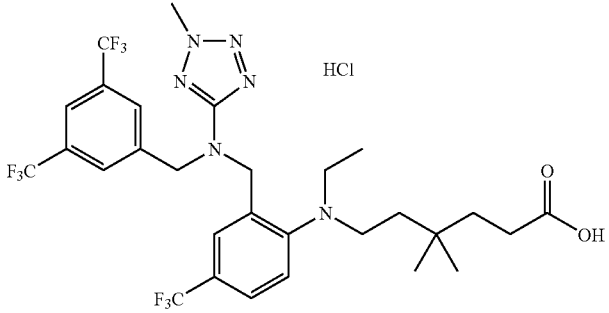 | CDCl3:<br>0.88 (s, 6H), 1.12 (m, 3H), 1.27 (m, 2H), 1.57 (m, 2H), 2.29 (m, 2H),<br>3.00-4.00 (m, 4H), 4.19 (s, 3H),<br>4.99 (s, 2H), 5.36 (s, 2H), 7.26 (m, 1H), 7.52 (s, 1H), 7.70 (m, 1H), 7.74 (s, 1H), 7.77 (s, 2H) |
| 118 | 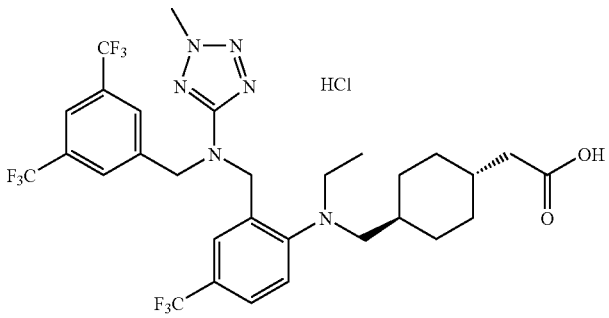 | DMSO-d6:<br>0.63-0.85 (m, 4H), 0.87 (t, J = 6.9 Hz, 3H), 1.24 (m, 1H), 1.47 (m, 1H),<br>1.40-1.73 (m, 4H), 1.97 (d, J = 6.9 Hz, 2H), 2.76 (d, J = 6.7 Hz, 2H), 2.86 (q, J = 6.9 Hz, 2H), 4.14 (s, 3H), 4.77 (s, 2H), 4.78 (s, 2H), 7.18 (s, 1H), 7.29 (d, J = 8.2 Hz, 1H), 7.45 (d, J = 8.2 Hz, 1H), 7.78 (s, 2H), 7.92 (s, 1H) |
| 119 | 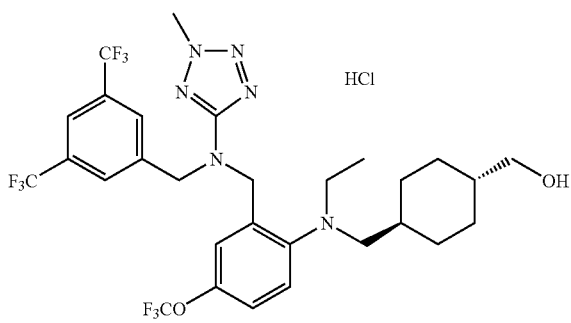 | CDCl3:<br>0.70-2.00 (m, 13H) 3.00-3.85 (m, 4H), 3.36 (d, J = 6.1 Hz, 2H), 4.17 (s, 3H), 4.98 (s, 2H), 5.37 (brs, 2H),<br>7.05-7.45 (m, 2H), 7.14 (s, 1H), 7.74 (s, 1H), 7.76 (s, 2H) |
| 120 | 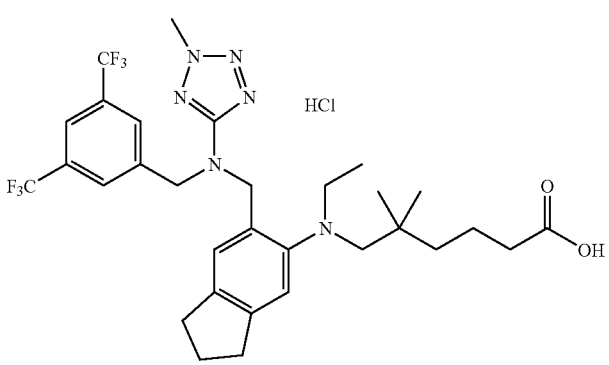 | CDCl3:<br>0.82 (brs, 6H), 0.94 (m, 3H), 0.80-1.75 (m, 4H), 2.09 (m, 2H), 2.21 (m, 2H), 2.81 (m, 2H), 2.90 (m, 2H), 2.88-3.80 (m, 4H), 4.19 (s, 3H), 4.60-5.90 (m, 4H), 7.14 (brs, 2H), 7.70 (s, 3H) |

TABLE 25

| Example | Structural Formula | NMR (δ value, 300 MHz) |
| --- | --- | --- |
| 121 | | DMSO-d6:<br>0.65-0.85 (m, 2H), 0.71 (t, J = 7.2 Hz, 3H),<br>1.04-1.18 (m, 2H), 1.18-1.37 (m, 3H),<br>1.60-1.78 (m, 4H), 1.99 (m, 1H),<br>2.60-2.80 (m, 4H), 4.14 (s, 3H),<br>4.77 (s, 2H), 4.82 (s, 2H), 6.87 (s, 1H),<br>7.15 (d, J = 8.9 Hz, 1H), 7.29 (d, J = 8.9 Hz,<br>1H), 7.86 (s, 2H), 7.96 (s, 1H) |
| 122 | | DMSO-d6:<br>0.65-0.85 (m, 2H), 0.74 (t, J = 6.5 Hz, 3H),<br>1.05-1.20 (m, 2H), 1.58 (m, 1H), 1.60 (m,<br>1H), 1.62-1.80 (m, 4H), 1.98 (m, 1H),<br>2.57 (d, J = 7.1 Hz, 2H), 2.59 (d, J = 7.9 Hz,<br>2H), 4.14 (s, 3H), 4.77 (s, 2H), 4.85 (s,<br>2H), 6.86 (s, 1H), 7.16 (d, J = 8.8 Hz, 1H),<br>7.34 (d, J = 8.8 Hz,1H), 7.89 (s, 2H),<br>7.98 (s, 1H) |
| 123 | | CDCl3:<br>0.70-0.90 (m, 2H), 0.89 (t, J = 7.0 Hz, 3H),<br>1.27-1.52 (m, 3H), 1.71-1.86 (m, 4H),<br>2.02 (m, 1H), 2.69 (d, J = 7.0 Hz, 2H),<br>2.84 (q, J = 7.0 Hz, 2H), 4.20 (s, 3H),<br>4.69 (s, 2H), 4.83 (s, 2H), 5.19 (s, 1H),<br>5.33 (s, 1H), 6.96 (s, 1H), 7.06 (d,<br>J = 8.8 Hz, 1H), 7.13 (d, J = 8.8 Hz, 1H),<br>7.66 (s, 2H), 7.76 (s, 1H) |
| 124 | | CDCl3:<br>0.67-0.90 (m, 2H), 0.89 (t, J = 7.0 Hz, 3H),<br>1.22-1.50 (m, 3H), 1.72-1.82 (m, 4H),<br>1.92 (m, 1H), 2.68 (d, J = 7.0 Hz, 2H),<br>2.79 (d, J = 4.7 Hz, 3H), 2.83 (q, J = 7.0 Hz,<br>2H), 4.20 (s, 3H), 4.68 (s, 2H),<br>4.82 (s, 2H), 5.34 (m, 1H), 6.96 (s, 1H),<br>7.06 (d, J = 8.6 Hz, 1H), 7.12 (d, J = 8.6 Hz,<br>1H), 7.65 (s, 2H), 7.75 (s, 1H) |

TABLE 25-continued

| Example | Structural Formula | NMR (δ value, 300 MHz) |
|---|---|---|
| 125 | 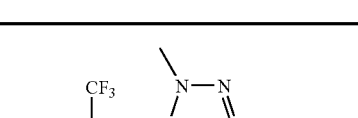 | CDCl3:<br>0.70-0.85 (m, 2H), 0.88 (t, J = 7.0 Hz, 3H),<br>1.30-1.70 (m, 5H), 1.70-1.82 (m, 2H),<br>2.38 (m, 1H), 2.67 (d, J = 7.0 Hz, 2H),<br>2.85 (q, J = 7.0 Hz, 2H), 2.92 (s, 3H),<br>3.00 (s, 3H), 4.20 (s, 3H), 4.67 (s, 2H),<br>4.82 (s, 2H), 6.96 (s, 1H), 7.07 (d,<br>J = 8.8 Hz, 1H), 7.13 (d, J = 8.8 Hz, 1H),<br>7.66 (s, 2H), 7.74 (s, 1H) |

TABLE 26

| Example | Structural Formula | NMR (δ value, 300 MHz, DMSO-d6) |
|---|---|---|
| 126 | | 0.70-1.00 (m, 2H), 0.91 (t, J = 6.9 Hz, 3H),<br>1.05-1.30 (m, 2H), 1.36 (m, 1H),<br>1.65-1.90 (m, 4H), 2.04 (m, 1H), 2.76 (d,<br>J = 6.6 Hz, 2H), 2.88 (q, J = 6.9 Hz, 2H),<br>4.72 (s, 2H), 4.91 (s, 2H), 6.64 (d,<br>J = 9.0 Hz, 2H), 6.94 (s, 1H), 7.13 (d,<br>J = 9.0 Hz, 2H), 7.13 (d, J = 9.0 Hz, 1H),<br>7.32 (d, J = 9.0 Hz, 1H), 7.89 (s, 2H),<br>7.99 (s, 1H) |
| 127 | | 0.75-0.95 (m, 2H), 0.90 (t, J = 7.0 Hz,<br>3H), 1.06-1.25 (m, 2H), 1.34 (m, 1H),<br>1.70-1.83 (m, 4H), 2.02 (m, 1H), 2.12 (s,<br>3H), 2.74 (d, J = 7.0 Hz, 2H), 2.89 (q,<br>J = 7.0 Hz, 2H), 4.65 (s, 2H), 4.84 (s,<br>2H), 6.52 (d, J = 8.6 Hz, 2H), 6.90 (d,<br>J = 8.6 Hz, 2H), 6.96 (s, 1H), 7.16 (d,<br>J = 8.8 Hz, 1H), 7.29 (d, J = 8.8 Hz,<br>1H), 7.88 (s, 2H), 7.96 (s, 1H) |
| 128 | | 0.75-0.95 (m, 2H), 0.90 (t, J = 6.9 Hz, 3H),<br>1.06-1.25 (m, 2H), 1.33 (m, 1H),<br>1.66-1.82 (m, 4H), 2.01 (m, 1H), 2.12 (s,<br>3H), 2.74 (d, J = 5.3 Hz, 2H), 2.86 (q,<br>J = 6.9 Hz, 2H), 4.67 (s, 2H), 4.86 (s, 2H),<br>6.41 (m, 1H), 6.46 (s, 1H), 6.47 (m, 1H),<br>6.95 (s, 1H), 6.97 (m, 1H), 7.17 (d,<br>J = 8.3 Hz, 1H), 7.30 (d, J = 8.3 Hz, 1H),<br>7.88 (s, 2H), 7.96 (s, 1H) |

TABLE 26-continued

| Example | Structural Formula | NMR (δ value, 300 MHz, DMSO-d6) |
|---|---|---|
| 129 | 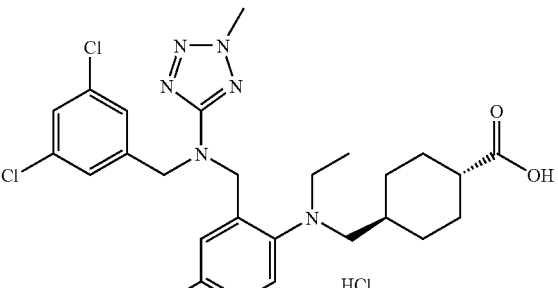 | 0.68-0.90 (m, 2H), 0.86 (t, J = 6.9 Hz, 3H), 1.07-1.23 (m, 2H), 1.31 (m, 1H), 1.62-1.85 (m, 4H), 2.03 (m, 1H), 2.69 (d, J = 5.1 Hz, 2H), 2.82 (q, J = 6.9 Hz, 2H), 4.14 (s, 3H), 4.61 (s, 2H), 4.72 (s, 2H), 6.90 (s, 1H), 7.17 (d, J = 8.3 Hz, 1H), 7.22 (s, 2H), 7.28 (d, J = 8.3 Hz, 1H), 7.46 (s, 1H) |
| 130 |  | 0.62-0.85 (m, 2H), 0.83 (t, J = 6.7 Hz, 3H), 1.03-1.19 (m, 2H), 1.27 (m, 1H), 1.60-1.78 (m, 4H), 2.00 (m, 1H), 2.30 (s, 3H), 2.66 (d, J = 6.1 Hz, 2H), 2.78 (q, J = 6.7 Hz, 2H), 4.14 (s, 3H), 4.66 (s, 2H), 4.71 (s, 2H), 6.89 (s, 1H), 7.16 (d, J = 8.1 Hz, 1H), 7.27 (d, J = 8.1 Hz, 1H), 7.29 (s, 1H), 7.31 (s, 1H), 7.39 (s, 1H) |

TABLE 27

| Example | Structural Formula | NMR (δ value, 300 MHz, DMSO-d6) |
|---|---|---|
| 131 | 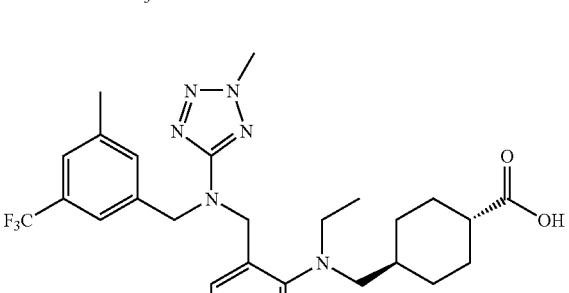 | 0.67-0.85 (m, 2H), 0.85 (t, J = 6.9 Hz, 3H), 1.05-1.22 (m, 2H), 1.30 (m, 1H), 1.60-1.80 (m, 4H), 2.01 (m, 1H), 2.68 (m, 2H), 2.81 (q, J = 6.9 Hz, 2H), 4.14 (s, 3H), 4.71 (s, 2H), 4.74 (s, 2H), 6.89 (s, 1H), 7.18 (d, J = 8.4 Hz, 1H), 7.28 (d, J = 8.4 Hz, 1H), 7.50 (s, 1H), 7.56 (s, 1H), 7.70 (s, 1H) |
| 132 |  | 0.67-0.85 (m, 2H), 0.85 (t, J = 6.9 Hz, 3H), 1.02-1.20 (m, 2H), 1.29 (m, 1H), 1.62-1.80 (m, 4H), 2.00 (m, 1H), 2.79 (d, J = 6.3 Hz, 2H), 2.81 (q, J = 6.9 Hz, 2H), 4.14 (s, 3H), 4.79 (s, 2H), 4.85 (s, 2H), 6.90 (s, 1H), 7.16 (d, J = 8.8 Hz, 1H), 7.27 (d, J = 8.8 Hz, 1H), 8.02 (s, 1H), 8.33 (s, 1H), 8.35 (s, 1H) |

TABLE 27-continued
| Example | Structural Formula | NMR (δ value, 300 MHz, DMSO-d6) |
| --- | --- | --- |
| 133 | 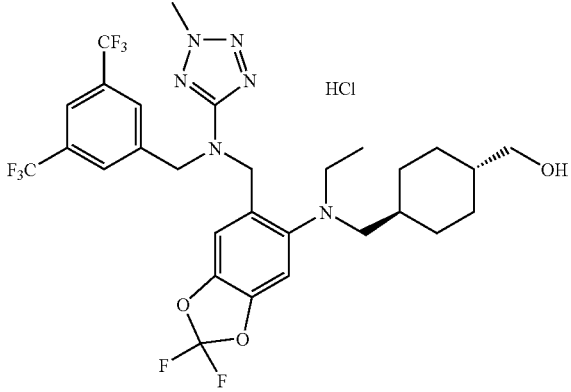 | 0.55-0.80 (m, 4H), 0.80 (t, J = 6.9 Hz, 3H), 1.02-1.32 (m, 2H), 1.47-1.78 (m, 4H), 2.61 (d, J = 6.6 Hz, 2H), 2.75 (q, J = 6.9 Hz, 2H), 3.11 (d, J = 6.3 Hz, 2H), 4.17 (s, 3H), 4.78 (s, 2H), 4.81 (s, 2H), 7.01 (s, 1H), 7.35 (s, 1H), 7.81 (s, 2H), 7.95 (s, 1H) |
| 134 | 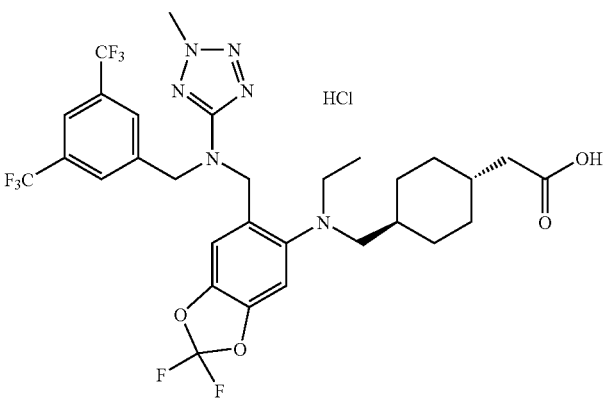 | 0.60-0.80 (m, 4H), 0.78 (t, J = 6.9 Hz, 3H), 1.15 (m, 1H), 1.45 (m, 1H), 1.45-1.68 (m, 4H), 1.97 (d, J = 6.8 Hz, 2H), 2.58 (d, J = 6.5 Hz, 2H), 2.72 (q, J = 6.9 Hz, 2H), 4.15 (s, 3H), 4.75 (s, 2H), 4.79 (s, 2H), 7.00 (s, 1H), 7.34 (s, 1H), 7.79 (s, 2H), 7.93 (s, 1H) |
| 135 | 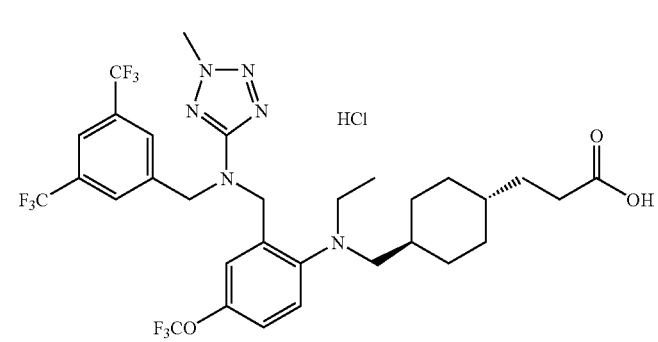 | 0.56-0.75 (m, 4H), 0.84 (t, J = 6.9 Hz, 3H), 1.02 (m, 1H), 1.22 (m, 1H), 1.30 (m, 2H), 1.45-1.70 (m, 4H), 2.12 (d, J = 7.6 Hz, 2H), 2.65 (m, 2H), 2.79 (m, 2H), 4.15 (s, 3H), 4.77 (s, 2H), 4.80 (s, 2H), 6.89 (s, 1H), 7.15 (d, J = 8.1 Hz, 1H), 7.26 (d, J = 8.1 Hz, 1H), 7.84 (s, 2H), 7.96 (s, 1H) |

TABLE 28
| Example | Structural Formula | NMR (δ value, 300 MHz) |
| --- | --- | --- |
| 136 | 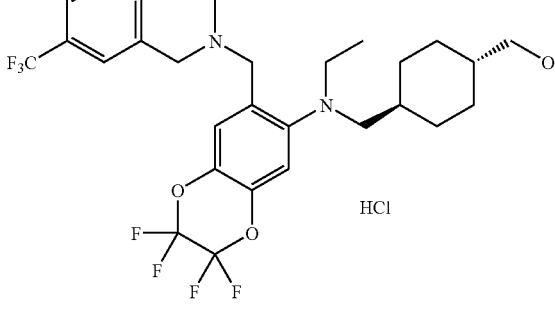 | CDCl3:<br>0.70-0.92 (m, 2H), 1.06 (m, 3H),<br>0.94-1.17 (m, 2H), 1.36 (m, 1H), 1.47 (m, 1H), 1.61-1.82 (m, 4H), 3.19 (m, 2H),<br>3.37 (m, 2H), 3.38 (d, J = 6.0 Hz, 2H),<br>4.19 (s, 3H), 4.94 (s, 2H), 5.22 (brs, 2H),<br>7.06 (brs, 1H), 7.08 (s, 1H), 7.73 (s, 3H) |
| 137 | 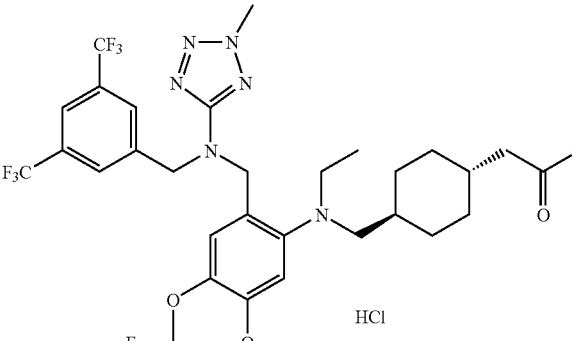 | CDCl3:<br>0.70-1.18 (m, 4H), 1.03 (m, 3H),<br>1.45 (m, 1H), 1.55-1.82 (m, 5H), 2.16 (d, J = 6.7 Hz, 2H), 3.07 (m, 2H), 3.24 (m, 2H),<br>4.19 (s, 3H), 4.89 (s, 2H), 5.11 (s, 2H),<br>7.02 (brs, 1H), 7.03 (s, 1H), 7.72 (s, 2H),<br>7.75 (s, 1H) |
| 138 | 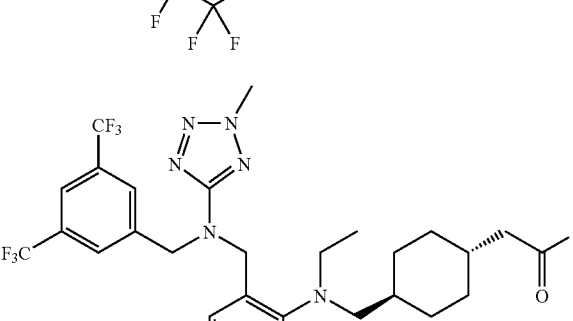 | CDCl3:<br>0.70-1.20 (m, 4H), 1.00 (m, 3H),<br>1.30-2.40 (m, 8H), 2.97 (m, 2H), 3.14 (m, 2H), 4.20 (s, 3H), 4.85 (s, 2H), 5.04 (s, 2H), 5.39 (s, 2H), 6.98 (brs, 1H),<br>6.99 (s, 1H), 7.70 (s, 2H), 7.75 (s, 1H) |
| 139 | 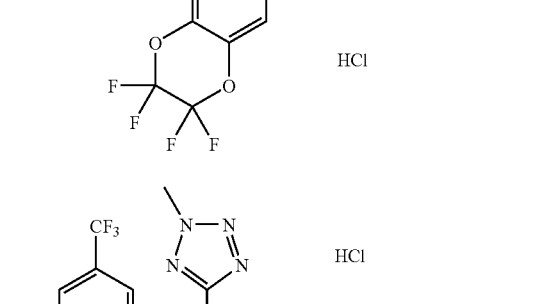 | CDCl3:<br>0.70-1.10 (m, 4H), 1.00 (m, 3H),<br>1.33-1.82 (m, 6H), 2.75-3.40 (m, 4H),<br>3.10 (d, J = 6.0 Hz, 2H), 3.28 (s, 3H),<br>4.18 (s, 3H), 4.82 (s, 2H), 5.08 (brs, 2H), 7.04 (s, 1H), 7.06-7.30 (m, 2H),<br>7.70 (s, 2H), 7.74 (s, 1H) |

TABLE 28-continued

| Example | Structural Formula | NMR (δ value, 300 MHz) |
|---|---|---|
| 140 | 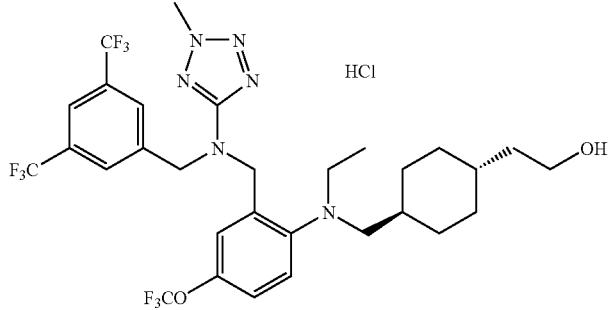 | DMSO-d6:<br>0.55-0.85 (m, 4H), 0.85 (t, J = 6.9 Hz, 3H),<br>1.05-1.35 (m, 4H), 1.40-1.80 (m, 4H),<br>2.68 (d, J = 6.6 Hz, 2H), 2.81 (q, J = 6.9 Hz, 2H), 3.36 (d, J = 6.9 Hz, 2H), 4.17 (s, 3H),<br>4.79 (s, 2H), 4.81 (s, 2H), 6.89 (s, 1H),<br>7.16 (d, J = 8.7 Hz, 1H), 7.28 (d, J = 8.7 Hz, 1H), 7.86 (s, 2H), 7.97 (s, 1H) |

TABLE 29

| Example | Structural Formula | NMR (δ value, 300 MHz) |
|---|---|---|
| 141 | 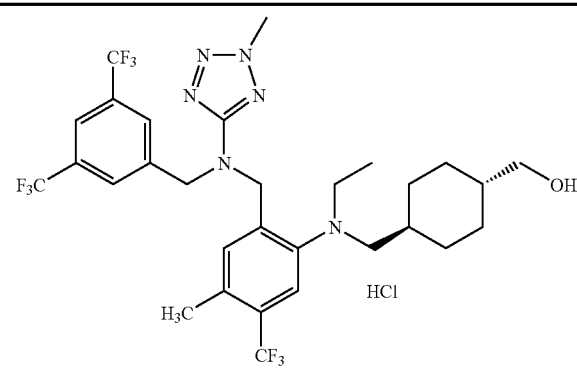 | CDCl3:<br>0.65-0.95 (m, 2H), 0.95-1.25 (m, 2H),<br>1.06 (m, 3H), 1.25-1.95 (m, 6H),<br>2.38 (s, 3H), 3.05-3.70 (m, 4H),<br>3.35 (m, 2H), 4.19 (s, 3H), 4.96 (s, 2H),<br>5.34 (brs, 2H), 7.26 (s, 1H),<br>7.36 (brs, 1H), 7.74 (s, 3H) |
| 142 | 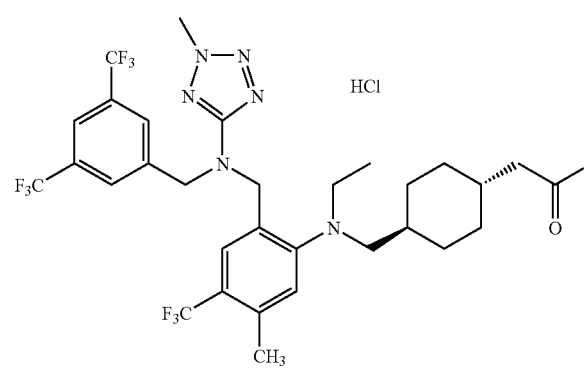 | DMSO-d6:<br>0.63-0.90 (m, 4H), 0.89 (t, J = 6.9 Hz, 3H),<br>1.29 (m, 1H), 1.50 (m, 1H), 1.45-1.80 (m, 4H), 2.00 (d, J = 6.6 Hz, 2H), 2.33 (s, 3H),<br>2.77 (d, J = 6.6 Hz, 2H), 2.88 (q, J = 6.9 Hz, 2H), 4.17 (s, 3H), 4.77 (s, 4H),<br>7.14 (s, 1H), 7.16 (s, 1H), 7.78 (s, 2H),<br>7.93 (s, 1H) |
| 143 | 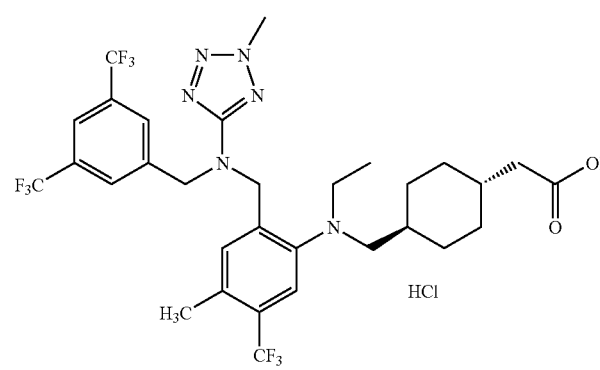 | CDCl3:<br>0.70-0.95 (m, 2H), 0.95-1.32 (m, 2H),<br>1.07 (m, 3H), 1.35-1.95 (m, 6H),<br>2.12 (d, J = 6.7 Hz, 2H), 2.38 (s, 3H),<br>3.34 (m, 2H), 3.50 (m, 2H), 4.18 (s, 3H),<br>4.99 (s, 2H), 5.36 (s, 2H), 7.22 (s, 1H),<br>7.38 (brs, 1H), 7.73 (s, 1H), 7.76 (s, 2H) |

TABLE 29-continued

| Example | Structural Formula | NMR (δ value, 300 MHz) |
|---------|-------------------|------------------------|
| 144 | | CDCl3:<br>0.68-0.95 (m, 4H), 0.87 (t, J = 6.9 Hz, 3H),<br>1.27 (m, 1H), 1.50-1.85 (m, 7H),<br>2.67 (d, J = 6.5 Hz, 2H), 2.81 (q, J = 6.9 Hz, 2H), 4.17 (s, 3H), 4.67 (s, 2H),<br>4.81 (s, 2H), 6.92 (s, 1H), 7.03 (d, J = 8.4 Hz, 1H), 7.10 (d, J = 8.4 Hz, 1H),<br>7.62 (s, 2H), 7.73 (s, 1H) |
| 145 | | DMSO-d6:<br>0.66-0.85 (m, 2H), 0.83 (t, J = 6.9 Hz, 3H),<br>1.04-1.22 (m, 2H), 1.29 (m, 1H),<br>1.60-1.82 (m, 4H), 2.00 (m, 1H),<br>2.66 (d, J = 6.7 Hz, 2H), 2.79 (q, J = 6.9 Hz, 2H), 4.13 (s, 3H), 4.69 (s, 2H),<br>4.72 (s, 2H), 6.87 (s, 1H), 7.15 (d, J = 8.3 Hz, 1H), 7.26 (d, J = 8.3 Hz, 1H),<br>7.52 (s, 1H), 7.68 (s, 1H), 7.80 (s, 1H) |

TABLE 30

| Example | Structural Formula | NMR (δ value, 300 MHz) |
|---------|-------------------|------------------------|
| 146 | | DMSO-d6:<br>0.57-0.80 (m, 4H), 0.84 (t, J = 7.2 Hz, 3H),<br>1.05-1.35 (m, 2H), 1.47-1.75 (m, 4H),<br>2.67 (d, J = 6.6 Hz, 2H), 2.79 (q, J = 7.2 Hz, 2H), 3.11 (d, J = 6.0 Hz, 2H), 4.17 (s, 3H),<br>4.76 (s, 2H), 4.82 (s, 2H), 7.11 (s, 1H),<br>7.12 (d, J = 8.4 Hz, 1H), 7.35 (d, J = 8.4 Hz, 1H), 7.86 (s, 2H), 7.99 (s, 1H) |
| 147 | | DMSO-d6:<br>0.60-0.90 (m, 4H), 0.84 (t, J = 6.9 Hz, 3H),<br>1.23 (m, 1H), 1.40-1.75 (m, 5H),<br>1.99 (d, J = 6.9 Hz, 2H), 2.66 (d, J = 6.6 Hz, 2H), 2.78 (q, J = 6.9 Hz, 2H), 4.17 (s, 3H),<br>4.76 (s, 2H), 4.82 (s, 2H), 7.11 (s, 1H),<br>7.13 (d, J = 8.4 Hz, 1H), 7.36 (d, J = 8.4 Hz, 1H), 7.86 (s, 2H), 7.98 (s, 1H) |

TABLE 30-continued

| Example | Structural Formula | NMR (δ value, 300 MHz) |
|---|---|---|
| 148 | 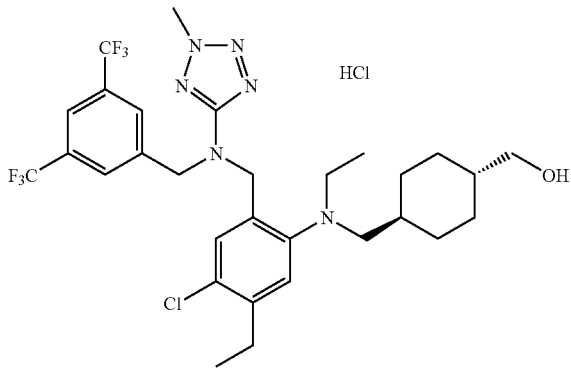 | DMSO-d6:<br>0.55-0.75 (m, 4H), 0.81 (t, J = 6.7 Hz, 3H),<br>1.09 (t, J = 7.5 Hz, 3H), 1.15 (m, 1H),<br>1.22 (m, 1H), 1.50-1.69 (m, 4H),<br>2.53-2.68 (m, 4H), 2.76 (q, J = 6.7 Hz, 2H),<br>3.08 (d, J = 6.1 Hz, 2H), 4.14 (s, 3H),<br>4.70 (s, 2H), 4.77 (s, 2H), 6.92 (s, 1H),<br>7.08 (s, 1H), 7.80 (s, 2H), 7.94 (s, 1H) |
| 149 | 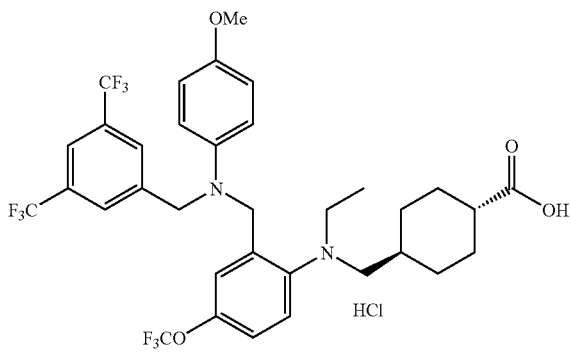 | DMSO-d6:<br>0.72-1.00 (m, 2H), 0.91 (t, J = 6.9 Hz, 3H),<br>1.02-1.35 (m, 2H), 1.33 (m, 1H),<br>1.69-1.87 (m, 4H), 2.03 (m, 1H),<br>2.76 (d, J = 6.6 Hz, 2H), 2.86 (q, J = 6.9 Hz, 2H), 3.62 (s, 3H), 4.61 (s, 2H), 4.82 (s, 2H), 6.60 (d, J = 9.0 Hz, 2H), 6.73 (d, J = 9.0 Hz, 2H), 7.06 (s, 1H), 7.18 (d, J = 8.4 Hz, 1H), 7.31 (d, J = 8.4 Hz, 1H), 7.91 (s, 2H), 7.97 (s, 1H) |
| 150 | 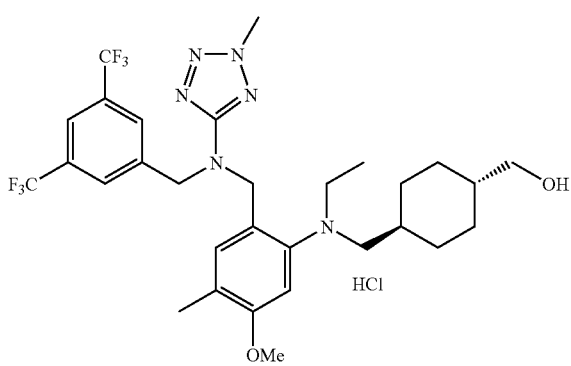 | CDCl3:<br>0.60-1.80 (m, 13H), 2.12 (s, 3H),<br>2.60-4.00 (m, 4H), 3.05 (m, 2H),<br>3.84 (S, 3H), 4.16 (s, 3H), 4.17 (s, 2H),<br>4.87 (brs, 2H), 6.56 (brs, 1H),<br>7.10 (brs, 1H), 7.67 (s, 3H) |

TABLE 31

| Example | Structural Formula | NMR (δ value, 300 MHz) |
|---|---|---|
| 151 | 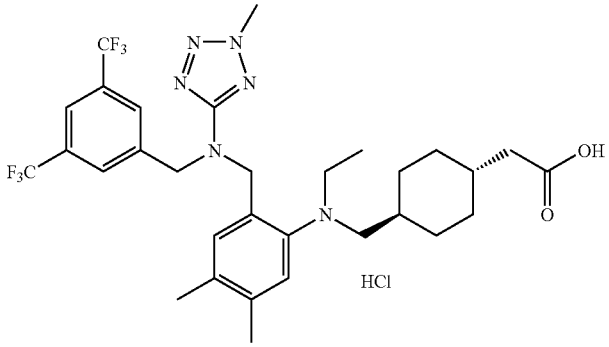 | CDCl3:<br>0.65-1.85 (m, 10H), 1.03 (m, 3H),<br>2.09 (m, 2H), 2.15 (s, 3H), 2.27 (s, 3H),<br>3.00-4.00 (m, 4H), 4.15 (s, 3H),<br>4.93 (s, 2H), 5.34 (s, 2H), 6.90 (s, 1H),<br>7.10 (s, 1H), 7.69 (s, 3H) |

TABLE 31-continued

| Example | Structural Formula | NMR (δ value, 300 MHz) |
|---|---|---|
| 152 | | DMSO-d6:<br>0.60-0.90 (m, 4H), 0.89 (t, J = 6.9 Hz, 3H), 1.27 (m, 1H), 1.35-1.75 (m, 5H), 1.99 (d, J = 6.6 Hz, 2H), 2.77 (d, J = 6.9 Hz, 2H), 2.88 (q, J = 6.9 Hz, 2H), 4.16 (s, 3H), 4.77 (s, 2H), 4.80 (s, 2H), 7.26 (d, J = 7.8 Hz, 1H), 7.28 (s, 1H), 7.49 (d, J = 7.8 Hz, 1H), 7.85 (s, 2H), 7.97 (s, 1H) |
| 153 | | DMSO-d6:<br>0.61-0.80 (m, 4H), 0.81 (t, J = 6.3 Hz, 3H), 1.09 (t, J = 7.4 Hz, 3H), 1.22 (m, 1H), 1.45 (m, 1H), 1.45-1.67 (m, 4H), 1.96 (d, J = 6.7 Hz, 2H), 2.52-2.67 (m, 4H), 2.76 (q, J = 6.3 Hz, 2H), 4.14 (s, 3H), 4.70 (s, 2H), 4.77 (s, 2H), 6.93 (s, 1H), 7.08 (s, 1H), 7.80 (s, 2H), 7.93 (s, 1H) |
| 154 | | DMSO-d6:<br>0.66-0.83 (m, 4H), 0.71 (t, J = 7.4 Hz, 3H), 1.20-1.38 (m, 3H), 1.47 (m, 1H), 1.45-1.70 (m, 4H), 1.97 (d, J = 6.7 Hz, 2H), 2.70-2.83 (m, 4H), 4.14 (s, 3H), 4.76 (s, 2H), 4.79 (s, 2H), 7.19 (s, 1H), 7.30 (d, J = 8.3 Hz, 1H), 7.45 (d, J = 8.3 Hz, 1H), 7.79 (s, 2H), 7.93 (s, 1H) |
| 155 | | CDCl3:<br>0.66-1.87 (m, 10H), 1.04 (m, 3H), 2.11 (s, 3H), 2.15 (m, 2H), 3.00-3.80 (m, 4H), 3.85 (s, 3H), 4.16 (s, 3H), 4.93 (s, 2H), 5.30 (s, 2H), 6.55 (s, 1H), 7.11 (s, 1H), 7.66 (s, 3H) |

TABLE 32

| Example | Structural Formula | NMR (δ value, 300 MHz) |
|---|---|---|
| 156 | 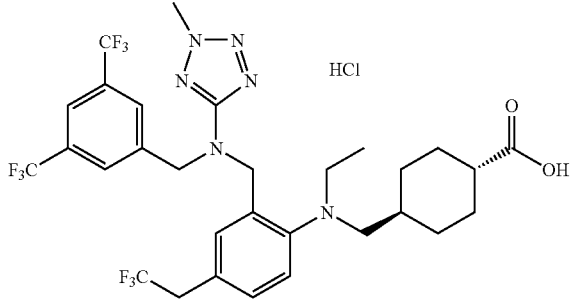 | DMSO-d6:<br>0.60-0.85 (m, 2H), 0.83 (m, 3H),<br>1.00-1.18 (m, 2H), 1.28 (m, 1H),<br>1.58-1.80 (m, 4H), 1.99 (m, 1H),<br>2.65 (m, 2H), 2.79 (m, 2H), 3.47 (m, 2H),<br>4.16 (s, 3H), 4.76 (s, 2H), 4.78 (s, 2H),<br>7.08 (s, 1H), 7.19 (s, 2H), 7.85 (s, 2H),<br>7.97 (s, 1H) |
| 157 | 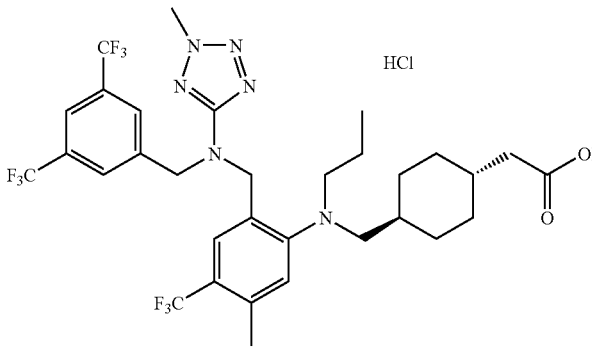 | DMSO-d6:<br>0.65-0.83 (m, 4H), 0.70 (t, J = 7.4 Hz, 3H),<br>1.22-1.38 (m, 3H), 1.41-1.73 (m, 5H),<br>1.97 (d, J = 6.9 Hz, 2H), 2.30 (s, 3H),<br>2.68-2.83 (m, 4H), 4.14 (s, 3H),<br>4.73 (s, 2H), 4.75 (s, 2H), 7.12 (s, 2H),<br>7.75 (s, 2H), 7.91 (s, 1H) |
| 158 | 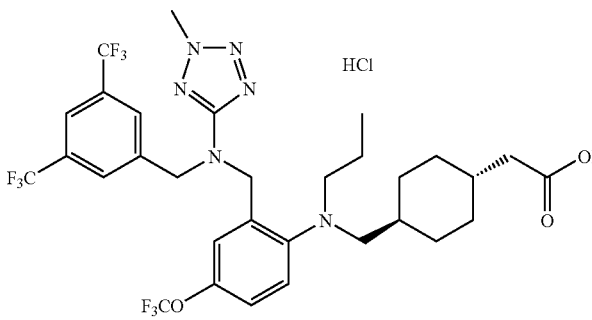 | DMSO-d6:<br>0.60-0.85 (m, 4H), 0.73 (t, J = 7.1 Hz, 3H),<br>1.15-1.38 (m, 3H), 1.40-1.73 (m, 5H),<br>1.99 (d, J = 6.7 Hz, 2H),<br>2.57-2.80 (m, 4H), 4.16 (s, 3H),<br>4.79 (s, 2H), 4.83 (s, 2H), 6.90 (s, 1H),<br>7.16 (d, J = 8.1 Hz, 1H), 7.32 (d, J = 8.1 Hz, 1H), 7.87 (s, 2H), 7.98 (s, H) |
| 159 | 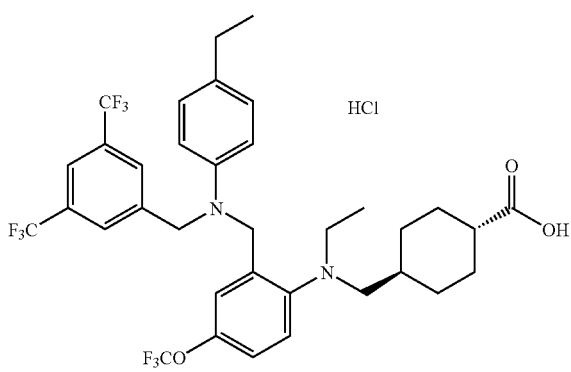 | DMSO-d6:<br>0.70-0.98 (m, 2H), 0.91 (t, J = 6.9 Hz, 3H),<br>1.09 (t, J = 7.5 Hz, 3H), 1.00-1.25 (m, 2H),<br>1.34 (m, 1H), 1.66-1.88 (m, 4H),<br>2.04 (m, 1H), 2.44 (q, J = 7.5 Hz, 2H),<br>2.76 (d, J = 6.1 Hz, 2H), 2.88 (q, J = 6.9 Hz, 2H), 4.67 (s, 2H), 4.86 (s, 2H),<br>6.56 (d, J = 8.7 Hz, 2H), 6.95 (d, J = 8.7 Hz, 2H), 6.99 (s, 1H), 7.18 (d, J = 8.4 Hz, 1H),<br>7.31 (d, J = 8.4 Hz, 1H), 7.91 (s, 2H),<br>7.97 (s, 1H) |

TABLE 32-continued

| Example | Structural Formula | NMR (δ value, 300 MHz) |
|---|---|---|
| 160 | | DMSO-d6:<br>0.67-0.90 (m, 2H), 0.86 (t, J = 6.9 Hz, 3H),<br>1.05-1.30 (m, 2H), 1.30 (m, 1H),<br>1.64-1.85 (m, 4H), 2.03 (m, 1H),<br>2.70 (d, J = 6.6 Hz, 2H), 2.83 (q, J = 6.9 Hz, 2H), 4.15 (s, 3H), 4.77 (s, 4H),<br>6.92 (s, 1H), 7.18 (d, J = 8.4 Hz, 1H),<br>7.29 (d, J = 8.4 Hz, 1H), 7.88 (s, 1H),<br>7.98 (s, 1H), 8.23 (s, 1H) |

TABLE 33

| Example | Structural Formula | NMR (δ value, 300 MHz) |
|---|---|---|
| 161 | | CDCl3:<br>0.70-1.00 (m, 2H), 0.95 (t, J = 7.2 Hz, 3H),<br>1.10-1.50 (m, 3H), 1.70-2.00 (m, 4H),<br>2.10 (s, 3H), 2.19 (m, 1H), 2.74 (d, J = 6.9 Hz, 2H), 2.86 (q, J = 7.2 Hz, 2H),<br>4.68 (s, 2H), 4.70 (s, 2H), 4.93 (s, 1H),<br>5.25 (s, 1H), 6.60 (d, J = 8.7 Hz, 2H),<br>7.06 (s, 1H), 7.08 (d, J = 8.7 Hz, 1H),<br>7.18 (d, J = 8.7 Hz, 1H), 7.34 (d, J = 8.7 Hz, 2H), 7.70 (s, 2H), 7.79 (s, 1H) |
| 162 | | DMSO-d6:<br>0.70-0.95 (m, 4H), 0.91 (t, J = 6.9 Hz, 3H),<br>1.27 (m, 1H), 1.42-1.80 (m, 5H),<br>2.02 (d, J = 6.9 Hz, 2H), 2.14 (s, 3H),<br>2.76 (d, J = 6.1 Hz, 2H), 2.87 (q, J = 6.9 Hz, 2H), 4.66 (s, 2H), 4.86 (s, 2H), 6.54 (d, J = 8.7 Hz, 2H), 6.92 (d, J = 8.7 Hz, 2H),<br>6.98 (s, 1H), 7.17 (d, J = 8.1 Hz, 1H),<br>7.31 (d, J = 8.1 Hz, 1H), 7.89 (s, 2H),<br>7.97 (s, 1H) |
| 163 | | DMSO-d6:<br>0.62-0.84 (m, 4H), 0.83 (t, J = 6.9 Hz, 3H),<br>1.22 (m, 1H), 1.39-1.73 (m, 5H),<br>1.99 (d, J = 6.7 Hz, 2H), 2.47 (s, 3H),<br>2.67 (d, J = 6.1 Hz, 2H), 2.79 (q, J = 6.9 Hz, 2H), 4.73 (s, 4H), 6.90 (s, 1H), 7.17 (d, J = 8.4 Hz, 1H), 7.29 (d, J = 8.4 Hz, 1H),<br>7.85 (s, 2H), 7.98 (s, 1H) |

TABLE 33-continued

| Example | Structural Formula | NMR (δ value, 300 MHz) |
|---|---|---|
| 164 | | DMSO-d6:<br>0.65-0.90 (m, 4H), 0.88 (t, J = 6.9 Hz, 3H),<br>1.29 (m, 1H), 1.42-1.78 (m, 5H),<br>2.00 (d, J = 6.7 Hz, 2H), 2.34 (s, 3H),<br>2.50 (s, 3H), 2.76 (d, J = 6.9 Hz, 2H),<br>2.85 (q, J = 6.9 Hz, 2H), 4.68 (s, 4H),<br>7.12 (s, 1H), 7.14 (s, 1H), 7.75 (s, 2H),<br>7.94 (s, 1H) |
| 165 | | DMSO-d6:<br>0.65-0.83 (m, 4H), 0.70 (t, J = 7.5 Hz, 3H),<br>1.22-1.37 (m, 3H), 1.40-1.70 (m, 5H),<br>1.97 (d, J = 6.7 Hz, 2H), 2.31 (s, 3H),<br>2.46 (s, 3H), 2.67-2.80 (m, 4H),<br>4.66 (s, 4H), 7.11 (s, 2H), 7.73 (s, 2H),<br>7.92 (s, 1H) |

TABLE 34

| Example | Structural Formula | NMR (δ value, 300 MHz) |
|---|---|---|
| 166 | | CDCl3:<br>0.76 (t, J = 7.4 Hz, 3H), 0.77-0.90 (m, 4H),<br>1.30-1.42 (m, 4H), 1.42-1.75 (m, 5H),<br>2.17 (d, J = 6.4 Hz, 2H), 2.38 (s, 3H),<br>2.74 (d, J = 7.0 Hz, 2H), 2.77 (m, 2H),<br>4.19 (s, 3H), 4.62 (s, 2H), 4.79 (s, 2H),<br>6.92 (s, 1H), 7.25 (s, 1H), 7.57 (s, 2H),<br>7.70 (s, 1H) |
| 167 | | CDCl3:<br>0.65-1.00 (m, 4H), 0.88 (t, J = 7.0 Hz, 3H),<br>1.31 (m, 1H), 1.57-1.77 (m, 5H),<br>2.17 (d, J = 6.7 Hz, 2H), 2.30 (s, 3H),<br>2.68 (d, J = 7.0 Hz, 2H), 2.83 (q, J = 7.0 Hz, 2H), 4.20 (s, 3H), 4.68 (s, 2H),<br>4.85 (s, 2H), 6.98 (s, 1H), 7.33 (s, 1H),<br>7.63 (s, 2H), 7.74 (s, 1H) |

TABLE 34-continued

| Example | Structural Formula | NMR (δ value, 300 MHz) |
| --- | --- | --- |
| 168 | | CDCl3:<br>0.75-1.30 (m, 4H), 1.05 (m, 3H),<br>1.32-1.85 (m, 6H), 2.13 (d, J = 6.5 Hz, 2H),<br>2.50 (s, 3H), 2.80 (s, 3H),<br>3.00-4.00 (m, 4H), 4.18 (s, 3H),<br>4.92 (s, 2H), 4.97 (s, 2H), 7.20 (s, 1H),<br>7.38 (s, 1H), 7.77 (s, 3H) |
| 179 | | CDCl3:<br>0.70-1.00 (m, 4H), 0.92 (t, J = 7.0 Hz, 3H),<br>1.24 (t, J = 7.1 Hz, 3H), 1.36 (m, 1H),<br>1.45-1.85 (m, 5H), 2.12 (d, J = 6.6 Hz, 2H),<br>2.39 (s, 3H), 2.75 (d, J = 7.0 Hz, 2H),<br>2.88 (q, J = 7.0 Hz, 2H), 4.11 (q, J = 7.1 Hz, 2H), 4.20 (s, 3H), 4.63 (s, 2H),<br>4.80 (s, 2H), 6.93 (s, 1H), 7.26 (s, 1H),<br>7.59 (s, 2H), 7.72 (s, 1H) |
| 170 | | CDCl3:<br>0.68-1.05 (m, 4H), 0.92 (t, J = 7.0 Hz, 3H),<br>1.36 (m, 1H), 1.57-1.81 (m, 5H),<br>2.18 (d, J = 6.6 Hz, 2H), 2.40 (s, 3H),<br>2.76 (d, J = 7.0 Hz, 2H), 2.88 (q, J = 7.0 Hz, 2H), 4.20 (s, 3H), 4.63 (s, 2H),<br>4.80 (s, 2H), 6.93 (s, 1H), 7.27 (s, 1H),<br>7.59 (s, 2H), 7.72 (s, 1H) |

The compounds shown in Table 35 can be produced in a similar manner.

TABLE 35

| Structural Formula | Compound Name |
| --- | --- |
| | trans-(4-{[N-(2-{[N'-(3-methyl-5-trifluoromethylbenzyl)-N'-(2-methyl-2H-tetrazol-5-yl)amino]methyl}-5-methyl-4-trifluoromethylphenyl)-N-ethylamino]methyl}cyclohexyl)acetic acid |

TABLE 35-continued

| Structural Formula | Compound Name |
|---|---|
| 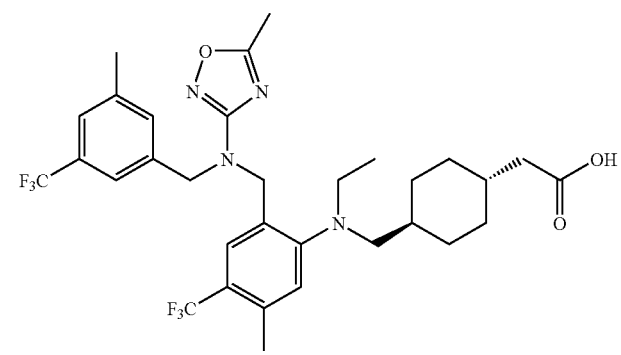 | trans-(4-{[N-(2-{[N'-(3-methyl-5-trifluoromethylbenzyl)-N'-(5-methyl-[1,2,4]oxadiazol-3-yl)amino]methyl}-5-methyl-4-trifluoromethylphenyl)-N-ethylamino]methyl}cyclohexyl)acetic acid |
| 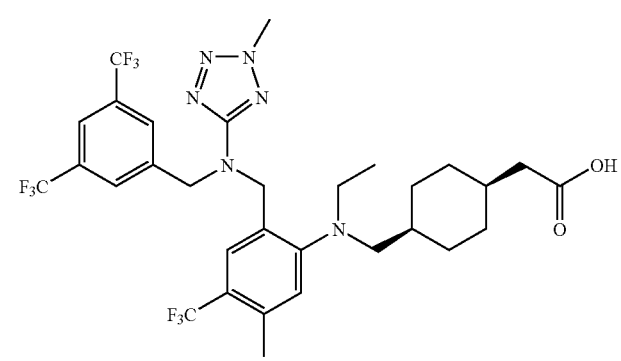 | ethyl cis-(4-{[N-(2-{[N'-[3,5-bis(trifluoromethyl)benzyl]-N'-(2-methyl-2H-tetrazol-5-yl)amino]methyl}-5-methyl-4-trifluoromethylphenyl)-N-ethylamino]methyl}cyclohexyl)acetate |
| 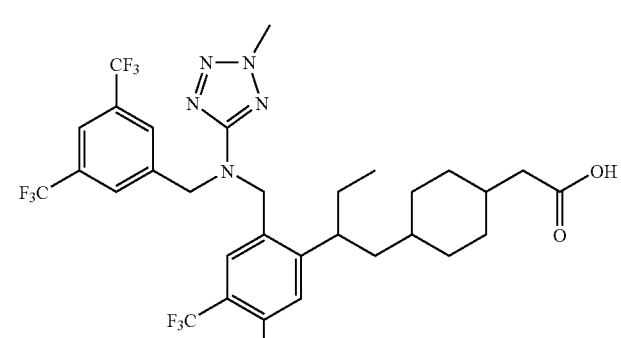 | {4-[2-(2-{[N-[3,5-bis(trifluoromethyl)benzyl]-N-(2-methyl-2H-tetrazol-5-yl)amino]methyl}-5-methyl-4-trifluoromethylphenyl)butyl]-cyclohexyl}acetic acid |
| 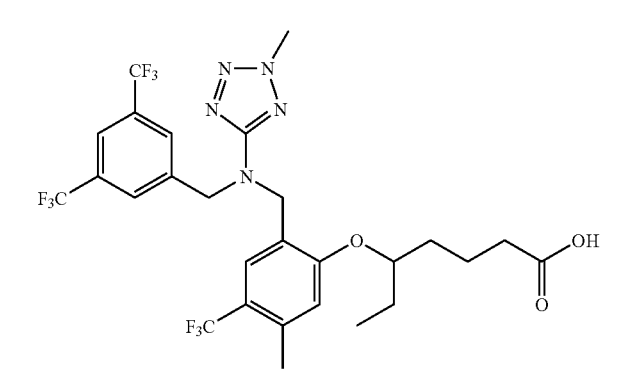 | 5-[2-({N-[3,5-bis(trifluoromethyl)benzyl]-N-[2-methyl-2H-tetrazol-5-yl]amino}methyl)-5-methyl-4-trifluoromethylphenoxy]heptanoic acid |

Experimental Examples

The following tests were performed for the CETP activity inhibitory effect of the compound of the present invention.

Preparation of Donor Lipoprotein

Potassium bromide (KBr) was added to plasma (40 mL) of healthy subject and the mixture was adjusted to have a specific density d=1.125 g/mL. The mixture was subjected to density gradient centrifugation (227,000×g, 4° C., 17 hr) and a fraction showing a specific density of d>1.125 g/mL (HDL$_3$ fraction) was harvested. The obtained fraction was dialyzed against PBS solution [10 mmol/L Na$_2$HPO$_4$; 10 mmol/L NaH$_2$PO$_4$; 0.15 mol/L NaCl; 1 mol/L EDTA (pH 7.4)]. Then, tritium-labeled cholesterol (37 MBq) was dissolved in 95% ethanol, gradually added to the above-mentioned HDL$_3$ fraction with stirring and incubated at 37° C. for 18 hr. [By this operation, tritium-labeled cholesterol was esterified by the action of lecithin acyl transferase (LCAT) present on the HDL$_3$ surface and taken up into HDL$_3$ as tritium-labeled cholesteryl ester ([$^3$H]CE)]. After incubation, KBr was added, the mixture was adjusted to have a specific density d=1.21 g/mL, subjected to density gradient centrifugation (227,000×g, 4° C., 17 hr) and a fraction of specific density d>1.21 g/mL was harvested. The obtained fraction was dialyzed against the aforementioned PBS solution to give HDL$_3$ incorporating [$^3$H]CE ([$^3$H]CE-HDL$_3$, specific density: 1.125<d<1.21, specific activity: 10,000 dpm/μL), which was used as a donor lipoprotein.

Experimental Example 1

Inhibitory Effect In Vitro on CETP Activity in Total Plasma

The donor lipoprotein obtained above was added to plasma of healthy subject to prepare a [$^3$H]CE-HDL$_3$-containing plasma (1,000 dpm/μL). The compound was dissolved in dimethyl formamide. A solution of the compound or a solvent alone (2 μL) and the [$^3$H]CE-HDL$_3$-containing plasma (100 μL) were added into a microtube, and this was incubated at 37° C. or 4° C. for 4 hr. After ice-cooling, TBS solution [100 μL, 20 mmol/L Tris; 0.15 mol/L NaCl (pH 7.4)] containing 1 mol/L magnesium chloride and 2% dextran sulfate was added to each microtube and the mixture was thoroughly stirred. After keeping at 4° C. for 30 min, the mixture was centrifuged (10,000×g, 4° C., 10 min), and the radioactivity in the obtained supernatant (HDL fraction) was measured with a scintillation counter. The difference in the measurement values obtained by incubation of solvent alone at 4° C. and 37° C. was taken as CETP activity, and the proportion of decrease in the difference in the measurement values of specimen was taken as percent inhibition of CETP activity. The concentration of the compound necessary for inhibiting the CETP activity by 50% was calculated as an IC$_{50}$ value. The results are shown in the following.

TABLE 36

| Example No. | IC$_{50}$ (μM) | Example No. | IC$_{50}$ (μM) |
|---|---|---|---|
| 1 | 0.23 | 2 | 0.08 |
| 3 | 0.24 | 4 | 0.18 |
| 7 | 0.27 | 8 | 0.63 |
| 10 | 0.23 | 11 | 0.63 |
| 12 | 0.25 | 13 | 0.58 |
| 26 | 0.47 | 27 | 0.58 |
| 28 | 0.44 | 33 | 0.56 |

TABLE 36-continued

| Example No. | IC$_{50}$ (μM) | Example No. | IC$_{50}$ (μM) |
|---|---|---|---|
| 34 | 0.22 | 35 | 0.35 |
| 36 | 0.34 | 37 | 0.80 |
| 38 | 0.47 | 39 | 0.88 |
| 40 | 0.39 | 41 | 0.51 |
| 42 | 0.70 | 43 | 0.55 |
| 44 | 0.36 | 45 | 0.49 |
| 46 | 0.39 | 51 | 0.41 |
| 52 | 0.37 | 53 | 0.70 |
| 54 | 0.79 | 55 | 0.77 |
| 58 | 0.715 | 59 | 0.43 |
| 60 | 0.78 | 63 | 0.64 |
| 64 | 0.75 | 65 | 0.29 |
| 66 | 0.87 | 67 | 0.26 |
| 68 | 0.28 | 69 | 0.34 |
| 70 | 0.54 | 71 | 0.44 |
| 72 | 0.39 | 73 | 0.19 |
| 74 | 0.40 | 75 | 0.41 |

The IC$_{50}$ values in Table show average values.

TABLE 37

| Example No. | IC$_{50}$ (μM) | Example No. | IC$_{50}$ (μM) |
|---|---|---|---|
| 76 | 0.29 | 77 | 0.54 |
| 78 | 0.32 | 79 | 0.89 |
| 80 | 0.43 | 81 | 0.33 |
| 82 | 0.59 | 86 | 0.941 |
| 89 | 0.69 | 91 | 0.56 |
| 92 | 0.19 | 93 | 0.76 |
| 96 | 0.31 | 98 | 0.30 |
| 99 | 0.53 | 102 | 0.59 |
| 103 | 0.43 | 104 | 0.35 |
| 105 | 0.60 | 107 | 0.56 |
| 108 | 0.25 | 109 | 0.16 |
| 111 | 0.19 | 114 | 0.28 |
| 115 | 0.09 | 118 | 0.09 |
| 119 | 0.13 | 120 | 0.28 |
| 121 | 0.23 | 122 | 0.24 |
| 127 | 0.37 | 129 | 0.61 |
| 131 | 0.17 | 135 | 0.22 |
| 137 | 0.14 | 138 | 0.16 |
| 140 | 0.12 | 141 | 0.12 |
| 142 | 0.06 | 143 | 0.10 |

The IC$_{50}$ values in Table show average values.

Experimental Example 2

Inhibitory Effect Exo Vivo on CETP Activity in Total Plasma of Normal Hamster The compound of the present invention was suspended in 0.5% methyl cellulose solution and orally administered once to a healthy hamster with a plastic gavage needle. Blood was taken at 2 or 4 hr after the administration and CETP activity in plasma was measured according to the following method.

The donor lipoprotein obtained above was added to hamster plasma (100 μL) to prepare [$^3$H]CE-HDL$_3$-containing plasma (ca. 1,000 dpm/μL). The [$^3$H]CE-HDL$_3$-containing plasma was dispensed to two microtubes by 25 μL each, and one was incubated at 37° C. and the other was incubated at 4° C. for 4 hr each. After ice-cooling, TBS solution (50 μl) containing 1 mol/L magnesium chloride and 2% dextran sulfate was added to each microtube and the mixture was thoroughly stirred. After keeping at 41° C. for 30 min, the mixture was centrifuged (10,000×g, 4° C., 20 min), and the radioactivity in the obtained supernatant (HDL fraction) was measured with a liquid scintillation counter. The radioactivity of the [$^3$H]CE-HDL$_3$-containing plasma was measured with a liquid scintillation counter, and taken as the total radioactivity. The transfer rate of [$^3$H]CE was calculated from the following formula using the total radioactivity (Total count), radioactivity by 37° C. incubation (37° C. count) and radioactivity by 4° C. incubation (4° C. count) of the sample of each individual and taken as the CETP activity.

CETP activity(transfer ratio (%))={[(4° C. count)−(37° C. count)]/(Total count)}×100

The CETP activity inhibitory ratio of each compound administration group based on the CETP activity of the solvent administration group as 100% was calculated from the following formula and expressed in %.

CETP activity inhibitory ratio (%)=100−[(CETP activity of each compound administration group)/(CETP activity of solvent administration group)×100]

The results are shown in the following.

TABLE 38

| compound | Dose (mg/kg) | CETP activity (%) | |
|---|---|---|---|
| | | 2 (hr later) | 4 (hr later) |
| 35 | 30 | 37.8 | — |
| 36 | 30 | 33.3 | — |
| 37 | 30 | 45.4 | — |
| 38 | 30 | 79.4 | — |
| 39 | 30 | 49.6 | — |
| 40 | 30 | 59.5 | — |
| 41 | 30 | 36.0 | — |
| 89 | 10 | 77.7 | — |
| 91 | 10 | 44.7 | — |
| 92 | 10 | 46.9 | — |
| 96 | 10 | 41.1 | — |
| 98 | 10 | 43.3 | — |
| 107 | 10 | 41.9 | — |
| 108 | 10 | 53.8 | — |
| 109 | 10 | 42.8 | — |
| 115 | 3 | — | 62.1 |
| 118 | 3 | — | 55.4 |
| 142 | 3 | — | 71.6 |
| 143 | 3 | — | 42.2 |
| 154 | 3 | — | 64.2 |
| 157 | 3 | — | 80.4 |
| 158 | 3 | — | 55.6 |

The CETP activity inhibitory ratios in Table show average values.

Experimental Example 3

Blood HDL Cholesterol Increasing Effect in Normal Hamster

To the plasma (40 μL) obtained from the above-mentioned animal at 4 or 8 hr after the administration was added 15% polyethylene glycol solution (40 μL) and the mixture was thoroughly stirred. After keeping at room temperature for 10 min, the mixture was centrifuged (10,000×g, 4° C., 20 min) and the cholesterol content (HDL cholesterol content) of the obtained supernatant (HDL fraction) was measured. The increase ratio of the HDL cholesterol content of each compound administration group when the HDL cholesterol content of the solvent administration group as 100% was calculated from the following formula and expressed in %.

HDL cholesterol increase ratio(%)=[(HDL cholesterol content of each compound administration group/HDL cholesterol content of solvent administration group)×100]−100

The results are shown in the following.

TABLE 39

| compound | Dose (mg/kg) | HDL cholesterol increase content (%) | |
|---|---|---|---|
| | | 4 (hr later) | 8 (hr later) |
| 115 | 3 | 23.3 | 30.7 |
| 118 | 3 | 21.1 | 31.7 |
| 142 | 3 | 20.3 | 31.9 |
| 143 | 3 | 17.0 | 21.3 |
| 154 | 3 | 13.3 | 22.4 |
| 157 | 3 | 17.9 | 27.1 |
| 158 | 3 | 14.8 | 23.7 |

The HDL cholesterol increase ratios in Table show average values.

Experimental Example 4

Concomitant Use Test

For the experiment, 10-week-old male Japanese white rabbits (manufactured by KITAYAMA LABES Co., Ltd.) were used. The animal was acclimated on normal food (RC-4, manufactured by Oriental Bio-Service Co.) and fasted for 24 hr and a high cholesterol food (0.25% cholesterol-added RC-4, manufactured by Oriental Bio-Service Co.) was given by 100 g/day per rabbit (preliminary feeding) for 3 days. On the next day of day 3 of preliminary feeding, blood was taken from the auricular artery before feeding, and the animals were grouped by 6 rabbits per group based on the parameters (HDL cholesterol content, total cholesterol content, triglyceride content) of plasma and body weight.

Foods were prepared (manufactured by Oriental Bio-Service Co.) by adding simvastatin (0.002%), compound (0.2%) of Example 168, or simvastatin (0.002%)+compound (0.2%) of Example 168 to a high cholesterol food, and each food was given to the grouped animals by 100 g/day per rabbit for 15 days. At 8 hr after feeding on day 15, the total blood was taken from the carotid artery under anesthesia, HDL cholesterol content, total cholesterol content and ApoA-I content in plasma were measured. The arteriosclerosis index was calculated from [(total cholesterol content-HDL cholesterol content)/HDL cholesterol content]. Furthermore, the HDL$_3$ fraction was separated from plasma by ultracentrifugation and the cholesterol content of the fraction was measured. In Table, arteriosclerotic index, ApoA-1 content and HDL$_3$ cholesterol content are shown based on the value of the control group as 100%.

TABLE 40

| group | Arteriosclerotic index (%) | ApoA-I content (%) | HDL$_3$ cholesterol content (%) |
|---|---|---|---|
| control | 100 | 100 | 100 |
| simvastatin | 53 | 114 | 128 |
| compound of Example 168 | 82 | 114 | 141 |
| Simvastatin + compound of Example 168 | 37 | 150 | 170 |

INDUSTRIAL APPLICABILITY

From the foregoing test results and the like, the compound and a salt thereof of the present invention have superior CETP activity inhibitory effect. Therefore, they can decrease IDL, VLDL and LDL that promote arteriosclerosis and increase HDL that acts suppressively. As a result, they are useful as prophylactic or therapeutic agents for hyperlipidemia. In addition, they are useful as prophylactic or therapeutic agents for arteriosclerotic disease and the like.

Moreover, concurrent use of the compound of the present invention with a different therapeutic agent for hyperlipidemia (statin pharmaceutical agent) is expected to promote increase in HDL cholesterol, decrease arteriosclerotic index particularly remarkably, and show extremely superior synergistic effect. Therefore, it is clear that the compound of the present invention can be used concurrently with a different pharmaceutical agent, particularly other therapeutic agents for hyperlipidemia, arteriosclerosis, coronary artery disease, obesity, diabetes or hypertension.

The invention claimed is:

1. A dibenzylamine compound represented by the formula (1)

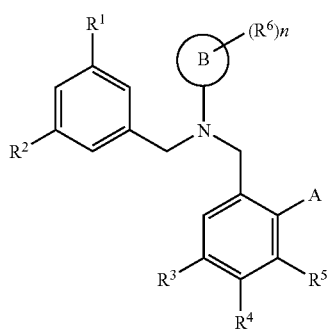

wherein
$R^1$ and $R^2$
are the same or different and each is a halogen atom, a nitro group, a cyano group or a $C_{1-6}$ alkyl group optionally substituted by halogen atoms;
$R^3$, $R^4$ and $R^5$
are the same or different and each is a hydrogen atom, a halogen atom, a $C_{1-6}$ alkyl group optionally substituted by halogen atoms, a $C_{1-6}$ alkylthio group optionally substituted by halogen atoms or a $C_{1-6}$ alkoxy group optionally substituted by halogen atoms, or $R^3$ and $R^4$ or $R^4$ and $R^5$ may form, together with a carbon atom bonded thereto, a homocyclic ring optionally having substituent(s) or a heterocyclic ring optionally having substituent(s);
A is
—C($R^{11}$)($R^{12}$)($R^{13}$)
(wherein $R^{11}$, $R^{12}$ and $R^{13}$ are the same or different and each is
a hydrogen atom,
a $C_{1-6}$ alkyl group (wherein $C_{1-6}$ alkyl group is optionally substituted by phenyl group or —COOR$^9$ (wherein $R^9$ is a hydrogen atom or a $C_{1-6}$ alkyl group)) or
a $C_{4-10}$ cycloalkylalkyl group (wherein $C_{4-10}$ cycloalkylalkyl group is optionally substituted by 1 to 3 substituents from halogen atom, nitro group, amino group, hydroxyl group, cyano group, acyl group, $C_{1-6}$ alkoxy group, $C_{1-6}$ alkyl group (wherein $C_{1-6}$ alkyl group is optionally substituted by hydroxyl group, $C_{1-6}$ alkoxy group or phosphono group), —(CH$_2$)$_q$—CON($R^{20}$)($R^{21}$) (wherein $R^{20}$ and $R^{21}$ are the same or different and each is hydrogen atom or $C_{1-6}$ alkyl group and q is 0 or an integer of 1 to 5) or —(CH$_2$)$_r$—COOR$^{10}$ (wherein $R^{10}$ is hydrogen atom or $C_{1-6}$ alkyl group and r is 0 or an integer of 1 to 5)))
or
—O—C($R^{11}$)($R^{12}$)($R^{13}$) (wherein $R^{11}$, $R^{12}$ and $R^{13}$ are as defined above);
Ring B is an aryl group or a hetercyclic residue;
$R^6$ is a hydrogen atom, a halogen atom, a nitro group, an amino group, a hydroxyl group, a cyano group, an acyl group, a $C_{1-6}$ alkoxy group, a $C_{2-6}$ alkenyl group or a $C_{1-6}$ alkyl group (wherein $C_{1-6}$ alkyl group is optionally substituted by hydroxyl group or —COOR$^{14}$ (wherein $R^{14}$ is a hydrogen atom or a $C_{1-6}$ alkyl group)); and
n is an integer of 1 to 3
or a pharmaceutically acceptable salt thereof.

2. The dibenzylamine compound of claim 1
wherein
$R^3$, $R^4$ and $R^5$
are the same or different and each is a hydrogen atom, a halogen atom, a $C_{1-6}$ alkyl group optionally substituted by halogen atoms or a $C_{1-6}$ alkoxy group optionally substituted by halogen atoms, or $R^3$ and $R^4$ or $R^4$ and $R^5$ may form, together with a carbon atom bonded thereto, a homocyclic ring optionally having substituent(s) or a heterocyclic ring optionally having substituent(s);
$R^{11}$, $R^{12}$ and $R^{13}$
are the same or different and each is a hydrogen atom, a $C_{1-6}$ alkyl group (wherein $C_{1-6}$ alkyl group is optionally substituted by phenyl group or —COOR$^9$ (wherein $R^9$ is a hydrogen atom or a $C_{1-6}$ alkyl group) or a $C_{4-10}$ cycloalkylalkyl group (wherein $C_{4-10}$ cycloalkylalkyl group is optionally substituted by 1 to 3 substituents from halogen atom, nitro group, amino group, hydroxyl group, cyano group, acyl group, $C_{1-6}$ alkoxy group, $C_{1-6}$ alkyl group or —COOR$^{10}$ (wherein $R^{10}$ a hydrogen atom or a $C_{1-6}$ alkyl group));
$R^6$ is
a hydrogen atom,
a halogen atom,
a nitro group,
an amino group,
a hydroxyl group,
a cyano group,
an acyl group,
a $C_{1-6}$ alkoxy group
or
a $C_{1-6}$ alkyl group (wherein $C_{1-6}$ alkyl group is optionally substituted by hydroxyl group or —COOR$^{14}$ (wherein $R^{14}$ is a hydrogen atom or a $C_{1-6}$ alkyl group)),
or a pharmaceutically acceptable salt thereof.

3. The dibenzylamine compound of claim 2, wherein $R^1$ is a $C_{1-6}$ alkyl group substituted by a halogen atom, or a pharmaceutically acceptable salt thereof.

4. The dibenzylamine compound of claim 3, wherein $R^1$ is a trifluoromethyl group, or a pharmaceutically acceptable salt thereof.

5. The dibenzylamine compound of claim 4, wherein ring B and ($R^6$)$_n$ are each

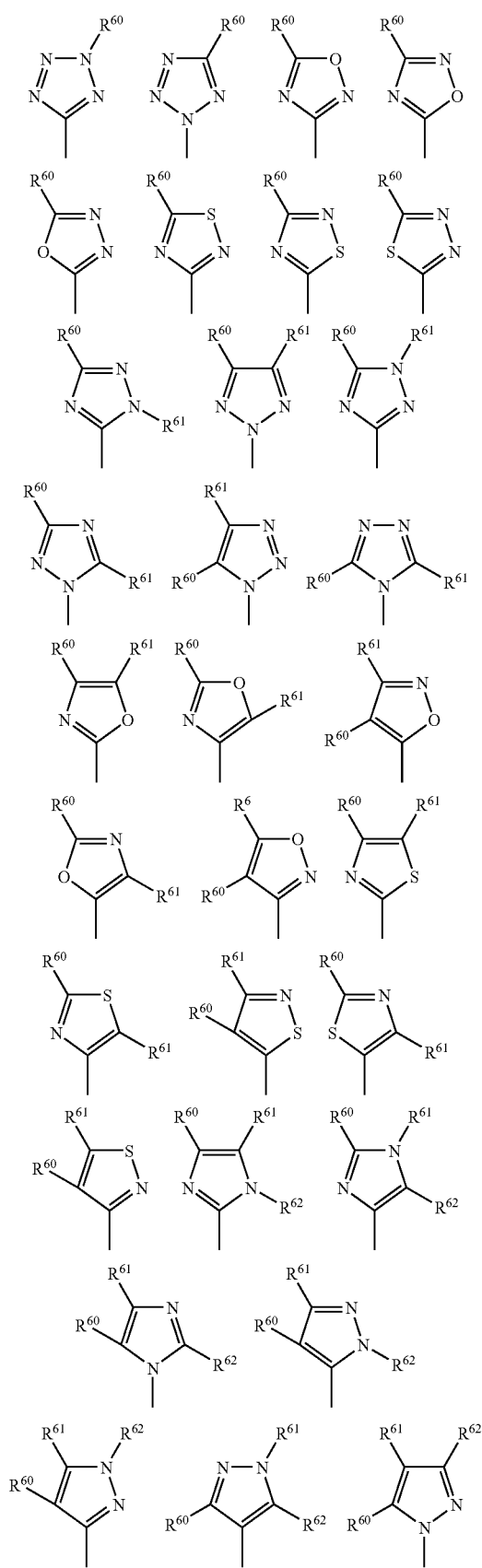

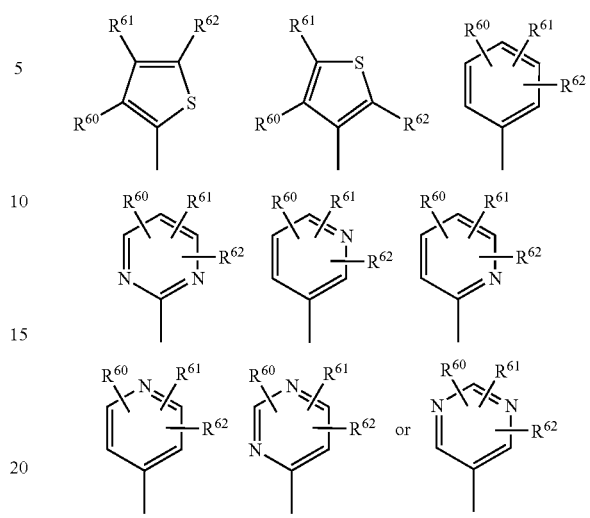

wherein $R^{60}$, $R^{61}$ and $R^{62}$ are the same or different and each is a hydrogen atom, a halogen atom, a nitro group, an amino group, a hydroxyl group, a cyano group, an acyl group, a $C_{1-6}$ alkoxy group, a $C_{2-6}$ alkenyl group or a $C_{1-6}$ alkyl group (wherein $C_{1-6}$ alkyl group is optionally substituted by hydroxyl group or —$COOR^{14}$ (wherein $R^{14}$ is as defined above)) or a pharmaceutically acceptable salt thereof.

6. The dibenzylamine compound of claim 5, wherein ring B and $(R^6)_n$ are each

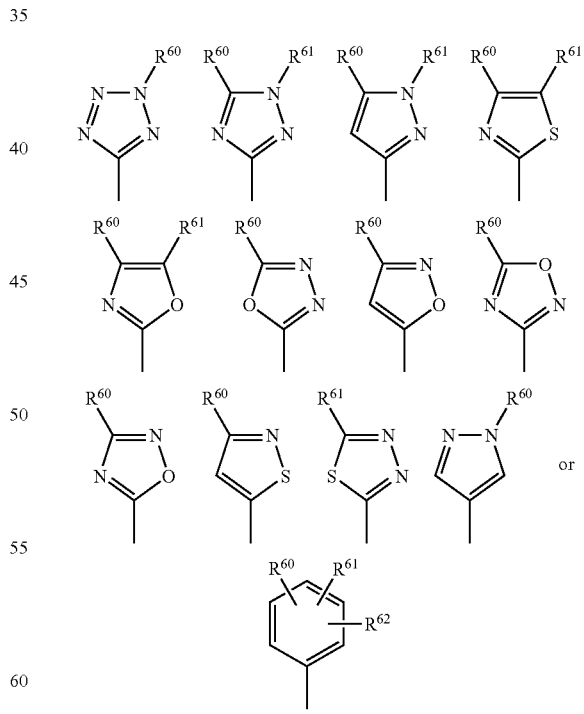

wherein $R^{60}$, $R^{61}$ and $R^{62}$ are as defined above or a pharmaceutically acceptable salt thereof.

7. The dibenzylamine compound of claim 6, wherein ring B and $(R^6)_n$ are each

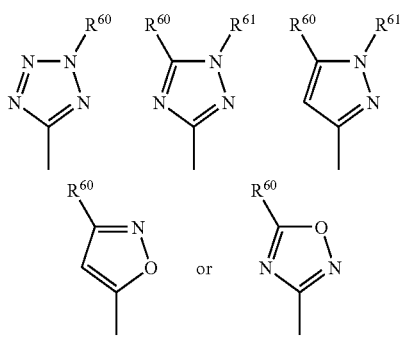

wherein $R^{60}$ and $R^{61}$ are as defined above or a pharmaceutically acceptable salt thereof.

8. A pharmaceutical composition comprising the dibenzylamine compound of claim 1 or a pharmaceutically acceptable salt thereof, and a pharmaceutically acceptable carrier.

9. A method for treating hyperlipidemia, which comprises administering a dibenzylamine compound of claim 1 or a pharmaceutically acceptable salt thereof to a mammal.

10. A method for treating arteriosclerosis, which comprises administering a dibenzylamine compound of claim 1 or a pharmaceutically acceptable salt thereof to a mammal.

11. The pharmaceutical composition of claim 8, which is used in combination with a different therapeutic agent for hyperlipidemia.

12. The pharmaceutical composition of claim 11, wherein the different therapeutic agent for hyperlipidemia is a statin pharmaceutical agent.

13. The pharmaceutical composition of claim 12, wherein the statin pharmaceutical agent is at least one pharmaceutical agent selected from the group consisting of lovastatin, simvastatin, pravastatin, fluvastatin, atorvastatin and cerivastatin.

14. The pharmaceutical composition of claim 8, which is used in combination with a different therapeutic agent for obesity.

15. The pharmaceutical composition of claim 14, wherein the different therapeutic agent for obesity is mazindol.

16. The pharmaceutical composition of claim 8, which is used in combination with a different therapeutic agent for diabetes.

17. The pharmaceutical composition of claim 16, wherein the different therapeutic agent for diabetes is at least one pharmaceutical agent selected from the group consisting of an insulin preparation, a sulfonylurea, an insulin secretagogue, a sulfonamide, a biguanide, an α glucosidase inhibitor and an insulin sensitizer.

18. The pharmaceutical composition of claim 17, wherein the different therapeutic agent for diabetes is at least one pharmaceutical agent selected from the group consisting of insulin, glibenclamide, tolbutamide, glyclopyramide, acetohexamide, glimepiride, tolazamide, gliclazide, nateglinide, glybuzole, metformin hydrochloride, buformin hydrochloride, voglibose, acarbose and pioglitazone hydrochloride.

19. The pharmaceutical composition of claim 8, which is used in combination with a different therapeutic agent for hypertension.

20. The pharmaceutical composition of claim 19, wherein the different therapeutic agent for hypertension is at least one pharmaceutical agent selected from the group consisting of a loop diuretic, an angiotensin converting enzyme inhibitor, an angiotensin II receptor antagonist, a Ca antagonist, a β blocker, an α,β blocker and an α blocker.

21. The pharmaceutical composition of claim 20, wherein the different therapeutic agent for hypertension is at least one pharmaceutical agent selected from the group consisting of a furosemide sustained-release preparation, captopril, a captopril sustained-release preparation, enalapril maleate, alacepril, delapril hydrochloride, cilazapril, lisinopril, benazepril hydrochloride, imidapril hydrochloride, temocapril hydrochloride, quinapril hydrochloride, trandrapril, perindopril erbumine, losartan potassium, candesartan cilexetil, nicardipine hydrochloride, a nicardipine hydrochloride sustained-release preparation, nilvadipine, nifedipine, a nifedipine sustained-release preparation, benidipine hydrochloride, diltiazem hydrochloride, a diltiazem hydrochloride sustained-release preparation, nisoldipine, nitrendipine, manidipine hydrochloride, barnidipine hydrochloride, efonidipine hydrochloride, amlodipine besylate, felodipine, cilnidipine, aranidipine, propranolol hydrochloride, a propranolol hydrochloride sustained-release preparation, pindolol, a pindolol sustained-release preparation, indenolol hydrochloride, carteolol hydrochloride, a carteolol hydrochloride sustained-release preparation, bunitrolol hydrochloride, a bunitrolol hydrochloride sustained-release preparation, atenolol, acebutolol hydrochloride, metoprolol tartrate, a metoprolol tartrate sustained-release preparation, nipradilol, penbutolol sulfate, tilisolol hydrochloride, carvedilol, bisoprolol fumarate, betaxolol hydrochloride, celiprolol hydrochloride, bopindolol malonate, bevantolol hydrochloride, labetalol hydrochloride, arotinolol hydrochloride, amosulalol hydrochloride, prazosin hydrochloride, terazosin hydrochloride, doxazosin mesylate, bunazosin hydrochloride, a bunazosin hydrochloride sustained-release preparation, urapidil and phentolamine mesylate.

22. The method of claim 9, which aims at the treatment of hyperlipidemia and which is used in combination with a different therapeutic agent for hyperlipidemia.

23. The method of claim 22, wherein the different therapeutic agent for hyperlipidemia is a statin pharmaceutical agent.

24. The method of claim 23, wherein the statin pharmaceutical agent is at least one pharmaceutical agent selected from the group consisting of lovastatin, simvastatin, pravastatin, fluvastatin, atorvastatin and cerivastatin.

25. The method of claim 9, which aims at the treatment of hyperlipidemia and which is used in combination with a different therapeutic agent for obesity.

26. The method of claim 25, wherein the different therapeutic agent for obesity is mazindol.

27. The method of claim 9, which aims at the treatment of hyperlipidemia and which is used in combination with a different therapeutic agent for diabetes.

28. The method of claim 27, wherein the different therapeutic agent for diabetes is at least one pharmaceutical agent selected from the group consisting of an insulin preparation, a sulfonylurea, an insulin secretagogue, a sulfonamide, a biguanide, an α glucosidase inhibitor and an insulin sensitizer.

29. The method of claim 28, wherein the different therapeutic agent for diabetes is at least one pharmaceutical agent selected from the group consisting of insulin, glibenclamide, tolbutamide, glyclopyramide, acetohexamide, glimepiride, tolazamide, gliclazide, nateglinide, glybuzole, metformin hydrochloride, buformin hydrochloride, voglibose, acarbose and pioglitazone hydrochloride.

30. The method of claim 9, which aims at the treatment of hyperlipidemia and which is used in combination with a different therapeutic agent for hypertension.

31. The method of claim 30, wherein the different therapeutic agent for hypertension is at least one pharmaceutical agent selected from the group consisting of a loop diuretic, an angiotensin converting enzyme inhibitor, an angiotensin II receptor antagonist, a Ca antagonist, a β blocker, an α,β blocker and an α blocker.

32. The method of claim 31, wherein the different therapeutic agent for hypertension is at least one pharmaceutical agent selected from the group consisting of a furosemide sustained-release preparation, captopril, a captopril sustained-release preparation, enalapril maleate, alacepril, delapril hydrochloride, cilazapril, lisinopril, benazepril hydrochloride, imidapril hydrochloride, temocapril hydrochloride, quinapril hydrochloride, trandrapril, perindopril erbumine, losartan potassium, candesartan cilexetil, nicardipine hydrochloride; a nicardipine hydrochloride sustained-release preparation, nilvadipine, nifedipine, a nifedipine sustained-release preparation, benidipine hydrochloride, diltiazem hydrochloride, a diltiazem hydrochloride sustained-release preparation, nisoldipine, nitrendipine, manidipine hydrochloride, barnidipine hydrochloride, efonidipine hydrochloride, amlodipine besylate, felodipine, cilnidipine, aranidipine, propranolol hydrochloride, a propranolol hydrochloride sustained-release preparation, pindolol, a pindolol sustained-release preparation, indenolol hydrochloride, carteolol hydrochloride, a carteolol hydrochloride sustained-release preparation, bunitrolol hydrochloride, a bunitrolol hydrochloride sustained-release preparation, atenolol, acebutolol hydrochloride, metoprolol tartrate, a metoprolol tartrate sustained-release preparation, nipradilol, penbutolol sulfate, tilisolol hydrochloride, carvedilol, bisoprolol fumarate, betaxolol hydrochloride, celiprolol hydrochloride, bopindolol malonate, bevantolol hydrochloride, labetalol hydrochloride, arotinolol hydrochloride, amosulalol hydrochloride, prazosin hydrochloride, terazosin hydrochloride, doxazosin mesylate, bunazosin hydrochloride, a bunazosin hydrochloride sustained-release preparation, urapidil and phentolamine mesylate.

33. The method of claim 10, which aims at the treatment of arteriosclerosis and which is used in combination with a different therapeutic agent for hyperlipidemia.

34. The method of claim 33, wherein the different therapeutic agent for hyperlipidemia is a statin pharmaceutical agent.

35. The method of claim 34, wherein the statin pharmaceutical agent is at least one pharmaceutical agent selected from the group consisting of lovastatin, simvastatin, pravastatin, fluvastatin, atorvastatin and cerivastatin.

36. The method of claim 10, which aims at the treatment of arteriosclerosis and which is used in combination with a different therapeutic agent for obesity.

37. The method of claim 36, wherein the different therapeutic agent for obesity is mazindol.

38. The method of claim 10, which aims at the treatment of arteriosclerosis and which is used in combination with a different therapeutic agent for diabetes.

39. The method of claim 38, wherein the different therapeutic agent for diabetes is at least one pharmaceutical agent selected from the group consisting of an insulin preparation, a sulfonylurea, an insulin secretagogue, a sulfonamide, a biguanide, an α glucosidase inhibitor and an insulin sensitizer.

40. The method of claim 39, wherein the different therapeutic agent for diabetes is at least one pharmaceutical agent selected from the group consisting of insulin, glibenclamide, tolbutamide, glycopyramide, acetohexamide, glimepiride, tolazamide, gliclazide, nateglinide, glybuzole, metformin hydrochloride, buformin hydrochloride, voglibose, acarbose and pioglitazone hydrochloride.

41. The method of claim 10, which aims at the treatment of arteriosclerosis and which is used in combination with a different therapeutic agent for hypertension.

42. The method of claim 41, wherein the different therapeutic agent for hypertension is at least one pharmaceutical agent selected from the group consisting of a loop diuretic, an angiotensin converting enzyme inhibitor, an angiotensin II receptor antagonist, a Ca antagonist, a β blocker, an α,β blocker and an α blocker.

43. The method of claim 42, wherein the different therapeutic agent for hypertension is at least one pharmaceutical agent selected from the group consisting of a furosemide sustained-release preparation, captopril, a captopril sustained-release preparation, enalapril maleate, alacepril, delapril hydrochloride, cilazapril, lisinopril, benazepril hydrochloride, imidapril hydrochloride, temocapril hydrochloride, quinapril hydrochloride, trandrapril, perindopril erbumine, losartan potassium, candesartan cilexetil, nicardipine hydrochloride, a nicardipine hydrochloride sustained-release preparation, nilvadipine, nifedipine, a nifedipine sustained-release preparation, benidipine hydrochloride, diltiazem hydrochloride, a diltiazem hydrochloride sustained-release preparation, nisoldipine, nitrendipine, manidipine hydrochloride, barnidipine hydrochloride, efonidipine hydrochloride, amlodipine besylate, felodipine, cilnidipine, aranidipine, propranolol hydrochloride, a propranolol hydrochloride sustained-release preparation, pindolol, a pindolol sustained-release preparation, indenolol hydrochloride, carteolol hydrochloride, a carteolol hydrochloride sustained-release preparation, bunitrolol hydrochloride, a bunitrolol hydrochloride sustained-release preparation, atenolol, acebutolol hydrochloride, metoprolol tartrate, a metoprolol tartrate sustained-release preparation, nipradilol, penbutolol sulfate, tilisolol hydrochloride, carvedilol, bisoprolol fumarate, betaxolol hydrochloride, celiprolol hydrochloride, bopindolol malonate, bevantolol hydrochloride, labetalol hydrochloride, arotinolol hydrochloride, amosulalol hydrochloride, prazosin hydrochloride, terazosin hydrochloride, doxazosin mesylate, bunazosin hydrochloride, a bunazosin hydrochloride sustained-release preparation, urapidil and phentolamine mesylate.

* * * * *